(12) United States Patent
Baker et al.

(10) Patent No.: US 7,550,569 B2
(45) Date of Patent: Jun. 23, 2009

(54) ANTIBODIES THAT SPECIFICALLY BIND TO GMAD

(75) Inventors: Kevin P. Baker, Darnestown, MD (US); Vivian R. Albert, Rockville, MD (US); Partha Chowdhury, Gaithersburg, MD (US)

(73) Assignee: Human Genome Science, Inc., Rockville, MD (US)

( * ) Notice: Subject to any disclaimer, the term of this patent is extended or adjusted under 35 U.S.C. 154(b) by 448 days.

(21) Appl. No.: 10/935,290

(22) Filed: Sep. 8, 2004

(65) Prior Publication Data

US 2005/0069542 A1 Mar. 31, 2005

Related U.S. Application Data

(63) Continuation-in-part of application No. PCT/US03/09625, filed on Mar. 28, 2003.

(60) Provisional application No. 60/368,813, filed on Apr. 1, 2002.

(51) Int. Cl.
C12P 21/08 (2006.01)
C07K 16/00 (2006.01)

(52) U.S. Cl. ............... 530/388.26; 530/387.9

(58) Field of Classification Search ............ None
See application file for complete search history.

(56) References Cited

OTHER PUBLICATIONS

Chen, C., et al. J. Exp. Med. Sep. 1992;176:855-866.*
De Pascalis, R., et al. J. Immunol. 2002;169:3076-3084.*
Lamminmaki, U., et al. J. Biol. Chem. 2001:276(39):36687-36694.*
Score alignment with WO200202641, Sequence 952, Oct. 13, 2007.*
MacCallum, R.M., et al. J. Mol. Bio. 1996;262:732-745.*

* cited by examiner

Primary Examiner—G. R Ewoldt
(74) Attorney, Agent, or Firm—Foley & Lardner LLP

(57) ABSTRACT

The present invention relates to antibodies and related molecules that immunospecifically bind to GMAD. Such antibodies have uses, for example, in the prevention and treatment of both insulin- and non insulin-dependent diabetes mellitus (i.e. Type I and Type II diabetes) and other related disorders. The invention also relates to nucleic acid molecules encoding anti-GMAD antibodies, vectors and host cells containing these nucleic acids, and methods for producing the same. The present invention relates to methods and compositions for preventing, detecting, diagnosing, treating or ameliorating a disease or disorder, especially diabetes and other related disorders, comprising administering to an animal, preferably a human, an effective amount of one or more antibodies or fragments or variants thereof, or related molecules, that immunospecifically bind to GMAD.

2 Claims, No Drawings

ANTIBODIES THAT SPECIFICALLY BIND TO GMAD

CROSS-REFERENCE TO RELATED APPLICATIONS

This application is a continuation-in-part of International Application No. PCT/US03/09625, filed Mar. 28, 2003, which claims benefit under 35 U.S.C. § 119(e) of U.S. Provisional Application No. 60/368,813, filed Apr. 1, 2002, each of which is hereby incorporated by reference in its entirety.

FIELD OF THE INVENTION

The present invention relates to antibodies and related molecules that immunospecifically bind to GMAD. Such antibodies have uses, for example, in the prevention and treatment of both insulin- and non insulin-dependent diabetes mellitus (i.e. Type I and Type II diabetes) and other related disorders. The invention also relates to nucleic acid molecules encoding anti-GMAD antibodies, vectors and host cells containing these nucleic acids, and methods for producing the same. The present invention relates to methods and compositions for preventing, detecting, diagnosing, treating or ameliorating a disease or disorder, especially diabetes and other related disorders, comprising administering to an animal, preferably a human, an effective amount of one or more antibodies or fragments or variants thereof, or related molecules, that immunospecifically bind to GMAD.

BACKGROUND OF THE INVENTION

Over the past few decades, an increasing percentage of the population has become diabetic. Diabetes mellitus is categorized into two types: Type I, known as Insulin-Dependent Diabetes Mellitus (IDDM), or Type II, known as Non-Insulin-Dependent Diabetes Mellitus (NIDDM). IDDM is an autoimmune disorder in which the insulin-secreting pancreatic beta cells of the islets of Langerhans are destroyed. In these individuals, recombinant insulin therapy is employed to maintain glucose homeostasis and normal energy metabolism. NIDDM, on the other hand, is a polygenic disorder with no one gene responsible for the progression of the disease.

In NIDDM, insulin resistance eventually leads to the abolishment of insulin secretion resulting in insulin deficiency. Insulin resistance, at least in part, ensues from a block at the level of glucose uptake and phosphorylation in humans. Diabetics demonstrate a decrease in expression in adipose tissue of insulin-receptor substrate 1 ("IRS5") (Carvalho et al., FASEB J 13(15):2173-8 (1999)), glucose transporter 4 ("GLUT4") (Garvey et al., Diabetes 41(4):465-75 (1992)), and the novel abundant protein M gene transcript 1 ("apM1") (Statnick et al., Int J Exp Diabetes 1(2): 81-8 (2000)), as well as other as of yet unidentified factors. Insulin deficiency in NIDDM leads to failure of normal pancreatic beta-cell function and eventually to pancreatic-beta cell death.

NIDDM is also characterized by target-tissue resistance to insulin, that cannot be overcome by beta cell hypersecretion. Insulin resistance is accompanied by increased adiposity, which in turn leads to obesity. A polypeptide known as GMAD (also known as Resistin) is specifically secreted by adipocytes, leading to a decrease in insulin action (e.g., glucose transport), and a subsequent increase in adiposity in animal models (Steppan et. al., Nature, vol 409, 18, 307-12 (2001)). In addition, secretion of the GMAD polypeptide has been shown to lead to increased insulin resistance by adipocytes, whereas an inhibition of GMAD leads to an increase in insulin action and thus an increase in cellular glucose uptake (Steppan et. al., Nature, vol 409, 18, 307-12 (2001)).

Insulin affects fat, muscle, and liver. Insulin is the major regulator of energy metabolism. Malfunctioning of any step(s) in insulin secretion and/or action can lead to many disorders, including for example the dysregulation of oxygen utilization, adipogenesis, glycogenesis, lipogenesis, glucose uptake, protein synthesis, thermogenesis, and maintenance of the basal metabolic rate. This malfunctioning results in diseases and/or disorders that include, but are not limited to, diabetes (e.g., Non-Insulin-Dependent Diabetes Mellitus (NIDDM)), insulin resistance, insulin deficiency, hyperinsulinemia, hyperglycemia, hyperlipidemia, hyperketonemia, dyslipidemia, hypertension, coronary artery disease, renal failure, neuropathy (e.g., autonomic neuropathy, parasympathetic neuropathy, and polyneuropathy), metabolic disorders (e.g., glucose metabolic disorders), endocrine disorders, obesity, weight loss, liver disorders (e.g., liver disease, cirrhosis of the liver, and disorders associated with liver transplant), stroke and conditions associated with these disorders.

Numerous debilitating diabetes-related secondary effects include, but are not limited to, obesity, forms of blindness (cataracts and diabetic retinopathy), limb amputations, kidney failure, fatty liver, coronary artery disease, stroke and neuropathy. Some of the current drugs used to treat insulin resistance and/or diabetes (e.g., insulin secratogogues such as sulfonylurea, insulin sensitizers such as thiazolidenediones and metformin, and α-glucosidase and lipase inhibitors) are inadequate due to the dosage amounts and frequency with which they have to be administered as a result of poor pharmacokinetic properties, the lack of effective control over blood sugar levels, and potential side effects, among other reasons. Diabetes therapeutic proteins, in their native state or when recombinantly produced, exhibit a rapid in vivo clearance. Typically, significant amounts of therapeutics are required to be effective during therapy. In addition, small molecules smaller than the 20 kDa range can be readily filtered through the renal tubules (glomerulus) leading to dose-dependent nephrotoxicity.

The discovery of a new composition that regulates glucose metabolism satisfies a need in the art by providing new compositions which are useful in the diagnosis, treatment, prevention and/or prognosis of diabetes, as well as endocrine disorders, hyperglycemia, liver disorders, inflammation, and aberrant cell growth. Furthermore, the identification of a new composition that regulates glucose metabolism permits the development of a range of derivatives, agonists and antagonists which in turn have applications in the diagnosis, treatment, prevention and/or prognosis of a range of conditions such as diabetes, musculoskeletal disorders, cartilage and bone growth disorders, liver disorders, inflammation, and aberrant cell growth.

SUMMARY OF THE INVENTION

The present invention encompasses antibodies (including molecules comprising, or alternatively consisting of, antibody fragments or variants thereof) that immunospecifically bind to a GMAD polypeptide or polypeptide fragment or variant of a GMAD. In particular, the invention encompasses antibodies (including molecules comprising, or alternatively consisting of, antibody fragments or variants thereof) that immunospecifically bind to a polypeptide or polypeptide fragment or variant of human GMAD such as those of SEQ ID NO:2.

The present invention relates to methods and compositions for preventing, treating or ameliorating a disease or disorder comprising administering to an animal, preferably a human, an effective amount of one or more antibodies or fragments or variants thereof, or related molecules, that specifically bind to a GMAD polypeptide or a fragment or variant thereof. In specific embodiments, the present invention relates to methods and compositions for preventing, treating or ameliorating a disease or disorder associated with GMAD function or aberrant GMAD expression, comprising administering to an animal, preferably a human, an effective amount of one or more antibodies or fragments or variants thereof, or related molecules, that immunospecifically bind to a GMAD polypeptide or a fragment or variant thereof. In highly preferred embodiments, the present invention relates to antibody-based methods and compositions for preventing, treating or ameliorating Non-Insulin Dependent Diabetes Mellitus (NIDDM) and/or conditions associated with NIDDM. Other diseases and disorders which can be treated, prevented or ameliorated with the antibodies of the invention include, but are not limited to, insulin resistance, insulin deficiency, hyperinsulinemia, hyperglycemia, hyperlipidemia, hyperketonemia, dyslipidemia, hypertension, coronary artery disease, renal failure, neuropathy (e.g., autonomic neuropathy, parasympathetic neuropathy, and polyneuropathy), metabolic disorders (e.g., glucose metabolic disorders), endocrine disorders, obesity, weight loss, liver disorders (e.g., liver disease, cirrhosis of the liver, and disorders associated with liver transplant), stroke and conditions associated with these disorders.

The present invention also encompasses methods and compositions for detecting, diagnosing, or prognosing diseases or disorders comprising administering to an animal, preferably a human, an effective amount of one or more antibodies or fragments or variants thereof, or related molecules, that specifically bind to GMAD or a fragment or variant thereof. In specific embodiments, the present invention also encompasses methods and compositions for detecting, diagnosing, or prognosing diseases or disorders associated with GMAD function or GMAD receptor function or aberrant GMAD or GMAD receptor expression, comprising administering to an animal, preferably a human, an effective amount of one or more antibodies or fragments or variants thereof, or related molecules, that specifically bind to GMAD or a fragment or variant thereof. In highly preferred embodiments, the present invention relates to antibody-based methods and compositions for detecting, diagnosing, or prognosing Non-Insulin Dependent Diabetes Mellitus (NIDDM) and/or conditions associated with NIDDM. Other diseases and disorders which can be detected, diagnosed, or prognosed with the antibodies of the invention include, but are not limited to, insulin resistance, insulin deficiency, hyperinsulinemia, hyperglycemia, hyperlipidemia, hyperketonemia, dyslipidemia, hypertension, coronary artery disease, renal failure, neuropathy (e.g., autonomic neuropathy, parasympathetic neuropathy, and polyneuropathy), metabolic disorders (e.g., glucose metabolic disorders), endocrine disorders, obesity, weight loss, liver disorders (e.g., liver disease, cirrhosis of the liver, and disorders associated with liver transplant), inflammatory disorders (e.g., asthma, allergic disorders) stroke and proliferative disorders.

Another embodiment of the present invention includes the use of the antibodies of the invention as a diagnostic tool to monitor the expression of GMAD expression on cells.

Single chain Fv's (scFvs) that specifically bind GMAD polypeptides (SEQ ID NO:2) have been generated. Thus, the invention encompasses these scFvs, listed in Table 1. In addition, the invention encompasses cell lines engineered to express antibodies corresponding to these scFvs which are deposited with the American Type Culture Collection ("ATCC") as of the dates listed in Table 1 and given the ATCC Deposit Numbers identified in Table 1. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

Further, the present invention encompasses polynucleotides encoding the scFvs, as well as the amino acid sequences of the scFvs. Molecules comprising, or alternatively consisting of, fragments or variants of these scFvs (e.g., VH domains, VH CDRs, VL domains, or VL CDRs having an amino acid sequence of any one of the scFvs referred to in Table 1), that specifically bind to GMAD polypeptides or fragments or variants thereof are also encompassed by the invention, as are nucleic acid molecules that encode these antibodies and/or molecules. In highly preferred embodiments, the present invention encompasses antibodies, or fragments or variants thereof, that bind to the mature form of the GMAD polypeptide (or fragments and variants thereof).

The present invention also provides anti-GMAD antibodies which are coupled to a detectable label, such as an enzyme, a fluorescent label, a luminescent label, or a bioluminescent label. The present invention also provides anti-GMAD antibodies which are coupled to a therapeutic or cytotoxic agent. The present invention also provides anti-GMAD antibodies which are coupled to a radioactive material.

The present invention further provides antibodies that inhibit or abolish GMAD activity. In highly preferred embodiments of the present invention, anti-GMAD antibodies of the present invention are used to treat, prevent or ameliorate NIDDM and/or conditions associated with NIDDM. In other highly preferred embodiments, anti-GMAD antibodies of the present invention are administered to an individual alone or in combination with other therapeutic compounds to treat, prevent or ameliorate NIDDM.

The present invention also provides antibodies that specifically bind one or more GMAD polypeptides and act as either GMAD agonists or GMAD antagonists. In specific embodiments, the antibodies of the invention inhibit the differentiation of GMAD or GMAD receptor expressing cells (e.g., adipocytes). In other specific embodiments, the antibodies of the invention downregulate or inhibit GMAD expression and thereby promote glucose uptake.

In further embodiments, the antibodies of the invention have a dissociation constant $(K_D)$ of $10^{-7}$ M or less. In preferred embodiments, the antibodies of the invention have a dissociation constant $(K_D)$ of $10^{-9}$ M or less.

In further embodiments, antibodies of the invention have an off rate $(k_{off})$ of $10^{-3}$/sec or less. In preferred embodiments, antibodies of the invention have an off rate $(k_{off})$ of $10^{-4}$/sec or less. In other preferred embodiments, antibodies of the invention have an off rate $(k_{off})$ of $10^{-5}$/sec or less.

The present invention also provides panels of antibodies (including molecules comprising, or alternatively consisting of, antibody fragments or variants) wherein the panel members correspond to one, two, three, four, five, ten, fifteen, twenty, or more different antibodies of the invention (e.g., whole antibodies, Fabs, F(ab')$_2$ fragments, Fd fragments, disulfide-linked Fvs (sdFvs), anti-idiotypic (anti-Id) antibodies, and scFvs).

The present invention further provides mixtures of antibodies, wherein the mixture corresponds to one, two, three, four, five, ten, fifteen, twenty, or more different antibodies of the invention (e.g., whole antibodies, Fabs, F(ab')$_2$ fragments, Fd fragments, disulfide-linked Fvs (sdFvs), anti-idiotypic (anti-Id) antibodies, and scFvs)). The present invention also provides for compositions comprising, or alternatively consisting of, one, two, three, four, five, ten, fifteen, twenty, or more antibodies of the present invention (including molecules comprising, or alternatively consisting of, antibody fragments or variants thereof). A composition of the invention may comprise, or alternatively consist of, one, two, three, four, five, ten, fifteen, twenty, or more amino acid sequences of one or more antibodies or fragments or variants thereof. Alternatively, a composition of the invention may comprise, or alternatively consist of, nucleic acid molecules encoding one or more antibodies of the invention.

The present invention also provides for fusion proteins comprising an antibody (including molecules comprising, or alternatively consisting of, antibody fragments or variants thereof) of the invention, and a heterologous polypeptide (i.e., a polypeptide unrelated to an antibody or antibody domain). Nucleic acid molecules encoding these fusion proteins are also encompassed by the invention. A composition of the present invention may comprise, or alternatively consist of, one, two, three, four, five, ten, fifteen, twenty or more fusion proteins of the invention. Alternatively, a composition of the invention may comprise, or alternatively consist of, nucleic acid molecules encoding one, two, three, four, five, ten, fifteen, twenty or more fusion proteins of the invention.

The present invention also provides for a nucleic acid molecule(s), generally isolated, encoding an antibody (including molecules, such as scFvs, VH domains, or VL domains, that comprise, or alternatively consist of, an antibody fragment or variant thereof) of the invention. The present invention also provides a host cell transformed with a nucleic acid molecule of the invention and progeny thereof. The present invention also provides a method for the production of an antibody (including a molecule comprising, or alternatively consisting of, an antibody fragment or variant thereof) of the invention. The present invention further provides a method of expressing an antibody (including a molecule comprising, or alternatively consisting of, an antibody fragment or variant thereof) of the invention from a nucleic acid molecule. These and other aspects of the invention are described in further detail below.

DETAILED DESCRIPTION OF THE INVENTION

Definitions

The term "antibody," as used herein, refers to immunoglobulin molecules and immunologically active portions of immunoglobulin molecules, i.e., molecules that contain an antigen binding site that specifically binds an antigen. As such, the term antibody encompasses not only whole antibody molecules, but also antibody multimers and antibody fragments as well as variants (including derivatives) of antibodies, antibody multimers and antibody fragments. Examples of molecules which are described by the term "antibody" herein include, but are not limited to: single chain Fvs (scFvs), Fab fragments, Fab' fragments, F(ab')$_2$, disulfide linked Fvs (sdFvs), Fvs, and fragments comprising or alternatively consisting of, either a VL or a VH domain. The term "single chain Fv" or "scFv" as used herein refers to a polypeptide comprising a VL domain of antibody linked to a VH domain of an antibody. Antibodies that specifically bind to GMAD may have cross-reactivity with other antigens. Preferably, antibodies that specifically bind to GMAD do not cross-react with other antigens. Antibodies that specifically bind to GMAD can be identified, for example, by immunoassays or other techniques known to those of skill in the art, e.g., the immunoassays described in the Examples below.

Antibodies of the invention include, but are not limited to, monoclonal, multispecific, human or chimeric antibodies, single chain antibodies, Fab fragments, F(ab') fragments, anti-idiotypic (anti-Id) antibodies (including, e.g., anti-Id antibodies to antibodies of the invention), intracellularly-made antibodies (i.e., intrabodies), and epitope-binding fragments of any of the above. The immunoglobulin molecules of the invention can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass of immunoglobulin molecule. Preferably, an antibody of the invention comprises, or alternatively consists of, a VH domain, VH CDR, VL domain, or VL CDR having an amino acid sequence of any one of those referred to in Table 1, or a fragment or variant thereof. In a preferred embodiment, the immunoglobulin is an IgG1 isotype. In another preferred embodiment, the immunoglobulin is an IgG4 isotype. Immunoglobulins may have both a heavy and light chain. An array of IgG, IgE, IgM, IgD, IgA, and IgY heavy chains may be paired with a light chain of the kappa or lambda forms.

Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of F(ab')$_2$ fragments are tetravalent, whereas dimers of Fab fragments or scFv molecules are bivalent. Individual monomers within an antibody multimer may be identical or different, i.e., they may be heteromeric or homomeric antibody multimers. For example, individual antibodies within a multimer may have the same or different binding specificities.

Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl)cyclohexane-1-carboxylate] and SATA [N-succinimidyl S-acethylthio-acetate] (available, for example, from Pierce Biotechnology, Inc. (Rockford, Ill.)) can be used to form antibody multimers. An exemplary protocol for the formation of antibody homodimers is given in Ghetie et al., Proceedings of the National Academy of Sciences USA (1997) 94:7509-7514, which is hereby incorporated by reference in its entirety. Antibody homodimers can be converted to Fab'2 homodimers through digestion with pepsin. Another way to form antibody homodimers is through the use of the autophilic T15 peptide described in Zhao and Kohler, The Journal of Immunology (2002) 25:396-404, which is hereby incorporated by reference in its entirety.

Alternatively, antibodies can be made to multimerize through recombinant DNA techniques. IgM and IgA naturally form antibody multimers through the interaction with the J chain polypeptide. Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) Clinical Immunology 101:21-31. and Frigerio et al., (2000) Plant Physiology 123:1483-94., both of which are hereby incorporated by reference in their entireties.) ScFv dimers can also be formed through recombinant techniques known in the art; an example of the construction of scFv dimers is given in Goel et al., (2000) Cancer Research 60:6964-6971 which is hereby incorporated by reference in its entirety. Antibody multimers may be purified using any suitable method known in the art, including, but not limited to, size exclusion chromatography.

By "isolated antibody" is intended an antibody removed from its native environment. Thus, an antibody produced by, purified from and/or contained within a hybridoma and/or a recombinant host cell is considered isolated for purposes of the present invention.

Unless otherwise defined in the specification, specific binding or immunospecifc binding by an anti-GMAD antibody means that the anti-GMAD antibody binds GMAD but does not significantly bind to (i.e., cross react with) proteins other than GMAD, such as other proteins in the same family of proteins). An antibody that binds GMAD protein and does not cross-react with other proteins is not necessarily an antibody that does not bind said other proteins in all conditions; rather, the GMAD-specific antibody of the invention preferentially binds GMAD compared to its ability to bind said other proteins such that it will be suitable for use in at least one type of assay or treatment, i.e., give low background levels or result in no unreasonable adverse effects in treatment. It is well known that the portion of a protein bound by an antibody is known as the epitope. An epitope may either be linear (i.e., comprised of sequential amino acids residues in a protein sequences) or conformational (i.e., comprised of one or more amino acid residues that are not contiguous in the primary structure of the protein but that are brought together by the secondary, tertiary or quaternary structure of a protein). Given that GMAD-specific antibodies bind to epitopes of GMAD, an antibody that specifically binds GMAD may or may not bind fragments of GMAD and/or variants of GMAD (e.g., proteins that are at least 90% identical to GMAD) depending on the presence or absence of the epitope bound by a given GMAD-specific antibody in the GMAD fragment or variant. Likewise, GMAD-specific antibodies of the invention may bind species orthologues of GMAD (including fragments thereof) depending on the presence or absence of the epitope recognized by the antibody in the orthologue. Additionally, GMAD-specific antibodies of the invention may bind modified forms of GMAD, for example, GMAD fusion proteins. In such a case when antibodies of the invention bind GMAD fusion proteins, the antibody must make binding contact with the GMAD moiety of the fusion protein in order for the binding to be specific. Antibodies that specifically bind to GMAD can be identified, for example, by immunoassays or other techniques known to those of skill in the art, e.g., the immunoassays described in the Examples below.

The term "variant" as used herein refers to a polypeptide that possesses a similar or identical amino acid sequence as a GMAD polypeptide, a fragment of a GMAD polypeptide, an anti-GMAD antibody and/or antibody fragment thereof. A variant having a similar amino acid sequence refers to a polypeptide that satisfies at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a GMAD polypeptide, or a fragment thereof, an anti-GMAD antibody or antibody fragment thereof (including a VH domain, VHCDR, VL domain, or VLCDR having an amino acid sequence of any one of those of one or more scFvs referred to in Table 1) described herein; (b) a polypeptide encoded by a nucleotide sequence, the complementary sequence of which hybridizes under stringent conditions to a nucleotide sequence encoding a GMAD polypeptide (e.g., SEQ ID NO:2), a fragment of a GMAD polypeptide, an anti-GMAD antibody or antibody fragment thereof (including a VH domain, VHCDR, VL domain, or VLCDR having an amino acid sequence of any one of those referred to in Table 1), described herein, of at least 5 amino acid residues, at least 10 amino acid residues, at least 15 amino acid residues, at least 20 amino acid residues, at least 25 amino acid residues, at least 30 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, or at least 150 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99%, identical to the nucleotide sequence encoding a GMAD polypeptide, a fragment of a GMAD polypeptide, an anti-GMAD antibody or antibody fragment thereof (including a VH domain, VHCDR, VL domain, or VLCDR having an amino acid sequence of any one of those of one or more scFvs referred to in Table 1), described herein. Preferably, a variant GMAD polypeptide, a variant fragment of a GMAD polypeptide, or a variant anti-GMAD antibody and/or antibody fragment possess similar or identical function and/or structure as the reference GMAD polypeptide, the reference fragment of a GMAD polypeptide, or the reference anti-GMAD antibody and/or antibody fragment, respectively.

A polypeptide with similar structure to a GMAD polypeptide, a fragment of a GMAD polypeptide, an anti-GMAD antibody or antibody fragment thereof, described herein refers to a polypeptide that has a similar secondary, tertiary or quaternary structure of a GMAD polypeptide, a fragment of a GMAD polypeptide, an anti-GMAD antibody, or antibody fragment thereof, described herein. The structure of a polypeptide can be determined by methods known to those skilled in the art, including but not limited to, X-ray crystallography, nuclear magnetic resonance, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can be accomplished using a mathematical algorithm known to those of skill in the art. An example of a mathematical algorithm for comparing two sequences is the algorithm of Karlin and Altschul *Proc. Natl. Acad. Sci. USA* 87:2264-2268(1990), modified as in Karlin and Altschul *Proc. Natl. Acad. Sci. USA* 90:5873-5877(1993). The BLASTn and BLASTx programs of Altschul, et al. *J. Mol. Biol.* 215:403-410(1990) have incorporated such an alogrithm. BLAST nucleotide searches can be performed with the BLASTn program (score=100, wordlength=12) to obtain nucleotide sequences homologous to a nucleic acid molecules of the invention. BLAST protein searches can be performed with the BLASTx program (score=50, wordlength=3) to obtain amino acid sequences homologous to a protein molecules of the invention. To obtain gapped alignments for comparison purposes, Gapped BLAST can be utilized as described in Altschul et al. *Nucleic Acids Res.* 25:3589-3402(1997). Alternatively, PSI-BLAST can be used to perform an iterated search which detects distant relationships between molecules (Id.). When utilizing BLAST, Gapped BLAST, and PSI-BLAST programs, the default parameters of the respective programs (e.g., BLASTx and BLASTn) can be used.

Another example of a mathematical algorithm utilized for the comparison of sequences is the algorithm of Myers and Miller, CABIOS (1989). The ALIGN program (version 2.0) which is part of the GCG sequence alignment software package has incorporated such an alogrithm. Other algorithms for sequence analysis known in the art include ADVANCE and ADAM as described in Torellis and Robotti *Comput. Appl. Biosci.*, 10 :3-5(1994); and FASTA described in Pearson and Lipman *Proc. Natl. Acad. Sci.* 85:2444-8(1988). Within FASTA, ktup is a control option that sets the sensitivity and speed of the search.

The term "derivative" as used herein, refers to a variant polypeptide of the invention that comprises, or alternatively consists of, an amino acid sequence of a GMAD polypeptide, a fragment of a GMAD polypeptide, or an antibody of the invention which has been altered by the introduction of amino acid residue substitutions, deletions or additions. The term "derivative" as used herein also refers to a GMAD polypeptide, a fragment of a GMAD polypeptide, or an antibody that specifically binds to a GMAD polypeptide which has been modified, e.g., by the covalent attachment of any type of molecule to the polypeptide. For example, but not by way of limitation, a GMAD polypeptide, a fragment of a GMAD polypeptide, or an anti-GMAD antibody, may be modified, e.g., by glycosylation, acetylation, pegylation, phosphorylation, amidation, derivatization by known protecting/blocking groups, proteolytic cleavage, linkage to a cellular ligand or other protein, etc. A derivative of a GMAD polypeptide, a fragment of a GMAD polypeptide, or an anti-GMAD antibody, may be modified by chemical modifications using techniques known to those of skill in the art, including, but not limited to, specific chemical cleavage, acetylation, formylation, metabolic synthesis of tunicamycin, etc. Further, a derivative of a GMAD polypeptide, a fragment of a GMAD polypeptide, or an anti-GMAD antibody, may contain one or more non-classical amino acids. A polypeptide derivative possesses a similar or identical function as a GMAD polypeptide, a fragment of a GMAD polypeptide, or an anti-GMAD receptor antibody, described herein.

The term "fragment" as used herein refers to a polypeptide comprising an amino acid sequence of at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino acid residues, at least 70 amino acid residues, at least 80 amino acid residues, at least 90 amino acid residues, or at least 100 amino acid residues of the amino acid sequence of GMAD, or an anti-GMAD antibody (including molecules such as scFv's, that comprise, or alternatively consist of, antibody fragments or variants thereof) that specifically binds to GMAD.

The term "host cell" as used herein refers to the particular subject cell transfected with a nucleic acid molecule and the progeny or potential progeny of such a cell. Progeny may not be identical to the parent cell transfected with the nucleic acid molecule due to mutations or environmental influences that may occur in succeeding generations or integration of the nucleic acid molecule into the host cell genome.

As used herein the phrase "splice variant" refers to cDNA molecules produced from a RNA molecules initially transcribed from the same genomic DNA sequence which have undergone alternative RNA splicing. Alternative RNA splicing occurs when a primary RNA transcript undergoes splicing, generally for the removal of introns, which results in the production of more than one mRNA molecule each of which may encode different amino acid sequences. The term "splice variant" also refers to the proteins encoded by the above cDNA molecules.

Unless indicated, "GMAD proteins" and "GMAD polypeptides" refer to all fragments and variants of the protein of SEQ ID NO:2, as well as to proteins resulting from the alternate splicing of the genomic DNA sequences encoding proteins having regions of amino acid sequence identity and GMAD activity which correspond to the protein of SEQ ID NO:2 as well as GMAD allellic variants.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. See generally, *Fundamental Immunology* Ch. 7 (Paul, W., ed., 2nd ed. Raven Press, N.Y. (1989) (incorporated by reference in its entirety for all purposes). The variable regions of each light/heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the heavy and the ligt chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J Mol. Biol.* 196: 901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. J

*Immunol.* 148:1547 1553 (1992). In addition, bispecific antibodies may be formed as "diabodies" (Holliger et al. "'Diabodies': small bivalent and bispecific antibody fragments" PNAS USA 90:6444-6448 (1993)) or "Janusins" (Traunecker et al. "Bispecific single chain molecules (Janusins) target cytotoxic lymphocytes on HIV infected cells" *EMBO J* 10:3655-3659 (1991) and Traunecker et al. "Janusin: new molecular design for bispecific reagents" *Int J Cancer Suppl* 7:51-52 (1992)).

Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Anti-GMAD Antibodies

Using phage display technology, single chain antibody molecules ("scFvs") that immunospecifically bind to GMAD polypeptides (or fragments or variants thereof) have been identified. Molecules comprising, or alternatively consisting of, fragments or variants of these scFvs (e.g., including VH domains, VH CDRs, VL domains, or VL CDRs having an amino acid sequence of any one of those referred to in Table 1), that immunospecifically bind to one or more GMAD polypeptides (or fragments or variants thereof) are also encompassed by the invention, as are nucleic acid molecules that encode these scFvs, and/or molecules.

In particular, the invention also relates to scFvs comprising, or alternatively consisting of, an amino acid sequence selected from the group consisting of SEQ ID NOS: 40-136 as referred to in Table 1 below. scFvs corresponding to SEQ ID NO:40-136 were selected for their ability to specifically bind GMAD polypeptide. Molecules comprising, or alternatively consisting of, fragments or variants of these scFvs (e.g., including VH domains, VH CDRs, VL domains, or VL CDRs having an amino acid sequence of any one of those referred to in Table 1), that specifically bind to one or more GMAD polypeptide are also encompassed by the invention, as are nucleic acid molecules that encode these scFvs, and/or molecules (e.g., SEQ ID NOS: 137-233).

The present invention provides antibodies (including molecules comprising, or alternatively consisting of, antibody fragments or variants thereof) that immunospecifically bind to a GMAD polypeptide or a polypeptide fragment or variants of GMAD. In particular, the invention provides antibodies corresponding to the scFvs referred to in Table 1, such scFvs may routinely be "converted" to immunoglobulin molecules by inserting, for example, the nucleotide sequences encoding the VH and/or VL domains of the scFv into an expression vector containing the constant domain sequences and engineered to direct the expression of the immunoglobulin molecule, as described in more detail in Example 2 below.

NS0 cell lines that express IgG1 antibodies that comprise the VH and VL domains of scfvs of the invention have been deposited with the American Type Culture Collection ("ATCC") on the dates listed in Table 1 and given the ATCC Deposit Numbers identified in Table 1. The ATCC is located at 10801 University Boulevard, Manassas, Va. 20110-2209, USA. The ATCC deposit was made pursuant to the terms of the Budapest Treaty on the International Recognition of the Deposit of Microorganisms for Purposes of Patent Procedure.

Accordingly, in one embodiment, the invention provides antibodies that comprise the VH and VL domains of scFvs of the invention.

TABLE 1

| scFv | scFv protein SEQ ID NO: | scFv DNA SEQ ID NO: | AAs of VH Domain | AAs of VH CDR1 | AAs of VH CDR2 | AAs of VH CDR3 | AAs of VL Domain | AAs of VL CDR1 | AAs of VL CDR2 | AAs of VL CDR3 | Cell Line Expressing antibody | ATCC Deposit Number | ATCC Deposit Date |
|---|---|---|---|---|---|---|---|---|---|---|---|---|---|
| GMBC603 | 40 | 137 | 1-123 | 31-35 | 50-66 | 99-112 | 139-249 | 161-174 | 190-196 | 229-238 | | | |
| GMBC604 | 41 | 138 | 1-117 | 31-35 | 50-66 | 99-106 | 133-243 | 155-168 | 184-190 | 223-232 | | | |
| GMBC605 | 42 | 139 | 1-121 | 31-35 | 50-68 | 101-110 | 137-247 | 159-172 | 188-194 | 227-236 | | | |
| GMBC606 | 43 | 140 | 1-119 | 31-35 | 50-66 | 99-108 | 135-242 | 156-166 | 182-188 | 221-231 | | | |
| GMBC607 | 44 | 141 | 1-121 | 31-35 | 50-68 | 101-110 | 137-247 | 159-172 | 188-194 | 227-236 | | | |
| GMBC608 | 45 | 142 | 1-123 | 31-35 | 50-66 | 99-112 | 139-246 | 160-170 | 186-192 | 225-235 | | | |
| GMBC609 | 46 | 143 | 1-121 | 31-35 | 50-68 | 101-110 | 137-247 | 159-171 | 187-193 | 226-236 | | | |
| GMBC610 | 47 | 144 | 1-118 | 31-35 | 50-66 | 99-107 | 134-241 | 155-165 | 181-187 | 220-230 | | | |
| GMBC612 | 48 | 145 | 1-116 | 31-35 | 50-66 | 99-105 | 132-239 | 155-165 | 181-187 | 220-229 | | | |
| GMBC613 | 49 | 146 | 1-122 | 31-35 | 50-66 | 99-111 | 138-245 | 159-169 | 185-191 | 224-234 | | | |
| GMBC614 | 50 | 147 | 1-121 | 31-35 | 50-68 | 101-110 | 137-247 | 159-172 | 188-194 | 227-236 | | | |
| GMBC615 | 51 | 148 | 1-121 | 31-35 | 50-68 | 101-110 | 137-247 | 159-172 | 188-194 | 227-236 | | | |
| GMBC616 | 52 | 149 | 1-121 | 31-35 | 50-68 | 101-110 | 137-247 | 159-172 | 188-194 | 227-236 | | | |
| GMBC617 | 53 | 150 | 1-117 | 31-35 | 50-65 | 98-106 | 133-243 | 155-168 | 184-190 | 223-232 | | | |
| GMBC618 | 54 | 151 | 1-121 | 31-35 | 50-68 | 101-110 | 137-247 | 159-171 | 187-193 | 226-236 | | | |
| GMBC619 | 55 | 152 | 1-121 | 31-35 | 50-66 | 99-110 | 137-244 | 158-168 | 184-190 | 223-233 | | | |
| GMBC620 | 56 | 153 | 1-121 | 31-35 | 50-68 | 101-110 | 137-247 | 159-172 | 188-194 | 227-236 | | | |
| GMBC621 | 57 | 154 | 1-118 | 31-35 | 50-66 | 99-107 | 134-241 | 155-165 | 181-187 | 220-230 | | | |
| GMBC625 | 58 | 155 | 1-121 | 31-35 | 50-68 | 101-110 | 137-247 | 159-172 | 188-194 | 227-236 | | | |
| GMBC626 | 59 | 156 | 1-121 | 31-35 | 50-68 | 101-110 | 137-247 | 159-172 | 188-194 | 227-236 | | | |
| GMBC627 | 60 | 157 | 1-118 | 31-35 | 50-66 | 99-107 | 134-244 | 156-169 | 185-191 | 224-233 | | | |
| GMBC628 | 61 | 158 | 1-126 | 31-35 | 50-66 | 99-115 | 142-249 | 163-173 | 189-195 | 228-238 | | | |
| GMBC629 | 62 | 159 | 1-121 | 31-35 | 50-68 | 101-110 | 137-244 | 158-168 | 184-190 | 223-233 | | | |
| GMBC630 | 63 | 160 | 1-119 | 31-35 | 50-66 | 99-108 | 135-242 | 156-166 | 182-188 | 221-231 | | | |
| GMBC632 | 64 | 161 | 1-121 | 31-35 | 50-68 | 101-110 | 137-244 | 158-168 | 184-190 | 223-233 | | | |
| GMBC634 | 65 | 162 | 1-121 | 31-35 | 50-68 | 101-110 | 137-247 | 159-172 | 188-194 | 227-236 | | | |
| GMBC635 | 66 | 163 | 1-121 | 31-35 | 50-68 | 101-110 | 137-244 | 158-168 | 184-190 | 223-233 | | | |
| GMBC638 | 67 | 164 | 1-121 | 31-35 | 50-68 | 101-110 | 137-247 | 159-172 | 188-194 | 227-236 | | | |
| GMBC639 | 68 | 165 | 1-130 | 31-35 | 50-66 | 99-119 | 146-253 | 167-177 | 193-199 | 232-242 | | | |
| GMBC641 | 69 | 166 | 1-120 | 31-35 | 50-66 | 99-109 | 136-243 | 157-167 | 183-189 | 222-232 | | | |
| GMBC642 | 70 | 167 | 1-120 | 31-35 | 50-66 | 99-109 | 136-243 | 157-167 | 183-189 | 222-232 | | | |

TABLE 1-continued

| scFv | scFv protein SEQ ID NO: | scFv DNA SEQ ID NO: | AAs of VH Domain | AAs of VH CDR1 | AAs of VH CDR2 | AAs of VH CDR3 | AAs of VL Domain | AAs of VL CDR1 | AAs of VL CDR2 | AAs of VL CDR3 | Cell Line Expressing antibody | ATCC Deposit Number | ATCC Deposit Date |
|---|---|---|---|---|---|---|---|---|---|---|---|---|---|
| GMBC645 | 71 | 168 | 1-121 | 31-35 | 50-68 | 101-110 | 137-247 | 159-172 | 188-194 | 227-236 | | | |
| GMBC646 | 72 | 169 | 1-118 | 31-35 | 50-66 | 99-107 | 134-241 | 157-167 | 183-189 | 222-231 | | | |
| GMBC647 | 73 | 170 | 1-121 | 31-35 | 50-68 | 101-110 | 137-247 | 159-172 | 188-194 | 227-236 | | | |
| GMBC648 | 74 | 171 | 1-121 | 31-35 | 50-68 | 101-110 | 137-244 | 158-168 | 184-190 | 223-233 | | | |
| GMBC649 | 75 | 172 | 1-121 | 31-35 | 50-68 | 101-110 | 137-247 | 159-172 | 188-194 | 227-236 | | | |
| GMBC651 | 76 | 173 | 1-121 | 31-35 | 50-68 | 101-110 | 137-247 | 159-172 | 188-194 | 227-236 | | | |
| GMBC652 | 77 | 174 | 1-121 | 31-35 | 50-68 | 101-110 | 137-247 | 159-172 | 188-194 | 227-236 | | | |
| GMBC653 | 78 | 175 | 1-119 | 31-35 | 50-66 | 99-108 | 135-246 | 157-169 | 185-191 | 224-235 | | | |
| GMBC654 | 79 | 176 | 1-121 | 31-35 | 50-68 | 101-110 | 137-247 | 159-172 | 188-194 | 227-236 | | | |
| GMBC655 | 80 | 177 | 1-116 | 31-35 | 50-66 | 99-105 | 132-239 | 155-165 | 181-187 | 220-229 | | | |
| GMBC657 | 81 | 178 | 1-121 | 31-35 | 50-68 | 101-110 | 137-244 | 158-168 | 184-190 | 223-233 | | | |
| GMBC658 | 82 | 179 | 1-121 | 31-35 | 50-68 | 101-110 | 137-247 | 159-172 | 188-194 | 227-236 | | | |
| GMBC659 | 83 | 180 | 1-121 | 31-35 | 50-68 | 101-110 | 137-247 | 159-172 | 188-194 | 227-236 | | | |
| GMBC660 | 84 | 181 | 1-121 | 31-35 | 50-68 | 101-110 | 137-247 | 159-172 | 188-194 | 227-236 | | | |
| GMBC662 | 85 | 182 | 1-117 | 31-35 | 50-66 | 99-106 | 133-243 | 155-168 | 184-190 | 223-232 | | | |
| GMBC664 | 86 | 183 | 1-121 | 31-35 | 50-68 | 101-110 | 137-247 | 159-172 | 188-194 | 227-236 | | | |
| GMBC665 | 87 | 184 | 1-121 | 31-35 | 50-68 | 101-110 | 137-244 | 158-168 | 184-190 | 223-233 | | | |
| GMBC666 | 88 | 185 | 1-121 | 31-35 | 50-68 | 101-110 | 137-247 | 159-171 | 187-193 | 226-236 | | | |
| GMBC667 | 89 | 186 | 1-121 | 31-35 | 50-68 | 101-110 | 137-247 | 159-172 | 188-194 | 227-236 | | | |
| GMBC668 | 90 | 187 | 1-121 | 31-35 | 50-68 | 101-110 | 137-244 | 158-168 | 184-190 | 223-233 | | | |
| GMBC669 | 91 | 188 | 1-121 | 31-35 | 50-68 | 101-110 | 137-247 | 159-172 | 188-194 | 227-236 | | | |
| GMBC670 | 92 | 189 | 1-121 | 31-35 | 50-68 | 101-110 | 137-247 | 159-172 | 188-194 | 227-236 | | | |
| GMBC672 | 93 | 190 | 1-121 | 31-35 | 50-68 | 101-110 | 137-247 | 159-172 | 188-194 | 227-236 | | | |
| GMBC673 | 94 | 191 | 1-122 | 31-35 | 50-66 | 99-111 | 138-243 | 159-169 | 185-191 | 224-232 | | | |
| GMBC676 | 95 | 192 | 1-121 | 31-35 | 50-68 | 101-110 | 137-247 | 159-172 | 188-194 | 227-236 | | | |
| GMBC678 | 96 | 193 | 1-121 | 31-35 | 50-68 | 101-110 | 137-247 | 159-172 | 188-194 | 227-236 | | | |
| GMBC679 | 97 | 194 | 1-121 | 31-35 | 50-68 | 101-110 | 137-247 | 159-172 | 188-194 | 227-236 | | | |
| GMBC681 | 98 | 195 | 1-117 | 31-35 | 50-66 | 99-106 | 133-240 | 156-166 | 182-188 | 221-230 | | | |
| GMBC682 | 99 | 196 | 1-121 | 31-35 | 50-68 | 101-110 | 137-244 | 158-168 | 184-190 | 223-233 | | | |
| GMBC683 | 100 | 197 | 1-118 | 31-35 | 50-66 | 99-107 | 134-241 | 155-165 | 181-187 | 220-230 | | | |
| GMBC684 | 101 | 198 | 1-121 | 31-35 | 50-68 | 101-110 | 137-247 | 159-172 | 188-194 | 227-236 | | | |
| GMBC685 | 102 | 199 | 1-121 | 31-35 | 50-68 | 101-110 | 137-244 | 158-168 | 184-190 | 223-233 | | | |
| GMBC686 | 103 | 200 | 1-121 | 31-35 | 50-68 | 101-110 | 137-247 | 159-172 | 188-194 | 227-236 | | | |
| GMBC687 | 104 | 201 | 1-124 | 31-35 | 50-66 | 99-113 | 140-247 | 163-173 | 189-195 | 228-237 | | | |
| GMBC689 | 105 | 202 | 1-121 | 31-35 | 50-68 | 101-110 | 137-247 | 159-172 | 188-194 | 227-236 | | | |
| GMBC690 | 106 | 203 | 1-121 | 31-35 | 50-68 | 101-110 | 137-247 | 159-172 | 188-194 | 227-236 | | | |
| GMBC691 | 107 | 204 | 1-130 | 31-35 | 50-66 | 99-119 | 146-253 | 167-177 | 193-199 | 232-242 | | | |
| GMBC692 | 108 | 205 | 1-121 | 31-35 | 50-68 | 101-110 | 137-247 | 159-172 | 188-194 | 227-236 | | | |
| GMBC693 | 109 | 206 | 1-121 | 31-35 | 50-68 | 101-110 | 137-247 | 159-172 | 188-194 | 227-236 | | | |
| GMBC696 | 110 | 207 | 1-118 | 31-35 | 50-66 | 99-107 | 134-241 | 155-165 | 181-187 | 220-230 | | | |
| GMBC725 | 111 | 208 | 1-119 | 31-35 | 50-66 | 99-108 | 135-242 | 156-166 | 182-188 | 221-231 | | | |
| GMBC727 | 112 | 209 | 1-121 | 31-35 | 50-68 | 101-110 | 137-247 | 159-172 | 188-194 | 227-236 | | | |
| GMBC729 | 113 | 210 | 1-121 | 31-35 | 50-68 | 101-110 | 137-244 | 158-168 | 184-190 | 223-233 | | | |
| GMBC730 | 114 | 211 | 1-121 | 31-35 | 50-68 | 101-110 | 137-247 | 159-172 | 188-194 | 227-236 | | | |
| GMCC101 | 115 | 212 | 1-118 | 31-35 | 50-66 | 99-107 | 134-245 | 157-169 | 185-191 | 224-234 | | | |
| GMCC102 | 116 | 213 | 1-133 | 31-35 | 50-66 | 99-122 | 149-260 | 172-184 | 200-206 | 239-249 | | | |
| GMCC105 | 117 | 214 | 1-123 | 31-35 | 50-66 | 99-112 | 139-250 | 163-173 | 189-195 | 228-239 | | | |
| GMCC106 | 118 | 215 | 1-118 | 31-36 | 51-66 | 99-107 | 134-245 | 157-169 | 185-191 | 224-234 | | | |
| GMCC107 | 119 | 216 | 1-122 | 31-35 | 50-66 | 99-111 | 138-250 | 161-174 | 190-196 | 229-239 | | | |
| GMCC108 | 120 | 217 | 1-128 | 31-35 | 50-66 | 99-117 | 144-255 | 167-177 | 193-199 | 232-244 | | | |
| GMCC109 | 121 | 218 | 1-122 | 31-35 | 50-66 | 99-111 | 138-244 | 161-171 | 187-193 | 226-233 | | | |
| GMCC110 | 122 | 219 | 1-125 | 31-37 | 52-67 | 100-114 | 141-250 | 165-175 | 191-197 | 230-239 | | | |
| GMCC112 | 123 | 220 | 1-120 | 31-35 | 50-65 | 98-109 | 136-245 | 161-172 | 188-194 | 227-235 | | | |
| GMCC114 | 124 | 221 | 1-124 | 31-36 | 51-67 | 100-113 | 140-250 | 164-174 | 190-196 | 229-239 | | | |
| GMCC118 | 125 | 222 | 1-127 | 31-35 | 50-68 | 101-116 | 143-251 | 166-176 | 192-198 | 231-240 | | | |
| GMCC119 | 126 | 223 | 1-125 | 31-35 | 50-66 | 99-114 | 141-252 | 164-177 | 193-199 | 232-241 | | | |
| GMCC124 | 127 | 224 | 1-124 | 31-35 | 50-66 | 99-113 | 140-251 | 163-175 | 191-197 | 230-240 | | | |
| GMCC125 | 128 | 225 | 1-120 | 31-35 | 50-66 | 99-109 | 136-247 | 160-170 | 186-192 | 225-236 | | | |
| GMCC126 | 129 | 226 | 1-123 | 31-36 | 51-66 | 99-112 | 139-246 | 162-172 | 188-194 | 227-235 | | | |
| GMCC127 | 130 | 227 | 1-116 | 31-35 | 50-66 | 99-105 | 132-242 | 156-166 | 182-188 | 221-231 | | | |
| GMCC129 | 131 | 228 | 1-119 | 31-35 | 50-66 | 99-108 | 135-246 | 159-169 | 185-191 | 224-235 | | | |
| GMCC131 | 132 | 229 | 1-120 | 31-35 | 50-65 | 98-109 | 136-248 | 159-172 | 188-194 | 227-237 | | | |
| GMCC136 | 133 | 230 | 1-120 | 31-35 | 50-66 | 99-109 | 136-245 | 161-171 | 187-193 | 226-235 | | | |
| GMCC138 | 134 | 231 | 1-122 | 31-37 | 52-67 | 100-111 | 138-248 | 162-172 | 188-194 | 227-237 | | | |
| GMCC142 | 135 | 232 | 1-121 | 31-35 | 50-66 | 99-110 | 137-246 | 161-171 | 187-193 | 226-235 | | | |
| GMCC151 | 136 | 233 | 1-123 | 31-35 | 50-66 | 99-112 | 139-250 | 163-173 | 189-195 | 228-239 | | | |

The present invention encompasses antibodies (including molecules comprising, or alternatively consisting of, antibody fragments or variants thereof) that specifically bind to a GMAD polypeptide or a fragment, variant, or fusion protein thereof. A GMAD polypeptide includes, but is not limited to, GMAD (SEQ ID NO:2) or the polypeptide encoded by the GMAD cDNA contained in ATCC Deposit No. 209215 on Aug. 21, 1997. GMAD may be produced through recombinant expression of nucleic acids encoding the polypeptide of SEQ ID NO:2 (e.g., the GMAD cDNA in the ATCC Deposit Number 209215). Antibodies of the invention may specifically bind GMAD as well as fragments and variants thereof, and are described in more detail below.

GMAD Polypeptides

In certain embodiments of the present invention, the antibodies of the present invention bind GMAD polypeptide, or fragments or variants thereof. The following section describes the GMAD polypeptides, fragments and variants that the antibodies of the invention may bind in more detail.

In certain embodiments, the antibodies of the present invention specifically bind GMAD polypeptide. An antibody that specifically binds GMAD may, in some embodiments, bind fragments, variants (including species orthologs and allelic variants of GMAD), multimers or modified forms of GMAD. For example, an antibody specific for GMAD may bind the GMAD moiety of a fusion protein comprising all or a portion of GMAD.

GMAD proteins may be found as homodimers. Accordingly, the present invention relates to antibodies that bind GMAD proteins found as homodimers. In specific embodiments, antibodies of the invention bind GMAD homodimers.

GMAD proteins may also be found as monomers or multimers (i.e., dimers, trimers, tetramers, and higher multimers). Accordingly, the present invention relates to antibodies that bind GMAD proteins found as monomers or as part of multimers. In specific embodiments, antibodies of the invention bind GMAD monomers, dimers, trimers or tetramers. In additional embodiments, antibodies of the invention bind at least dimers, at least trimers, or at least tetramers containing one or more GMAD polypeptides.

Antibodies of the invention may bind GMAD homomers or heteromers. As used herein, the term homomer, refers to a multimer containing only GMAD proteins of the invention (including GMAD fragments, variants, and fusion proteins, as described herein). These homomers may contain GMAD proteins having identical or different polypeptide sequences. In a specific embodiment, a homomer of the invention is a multimer containing only GMAD proteins having an identical polypeptide sequence. In another specific embodiment, antibodies of the invention bind GMAD homomers containing GMAD proteins having different polypeptide sequences. In specific embodiments, antibodies of the invention bind a GMAD homodimer (e.g., containing GMAD proteins having identical or different polypeptide sequences) or a homotrimer (e.g., containing GMAD proteins having identical or different polypeptide sequences). In additional embodiments, antibodies of the invention bind at least a homodimer, at least a homotrimer, or at least a homotetramer of GMAD.

As used herein, the term heteromer refers to a multimer containing heterologous proteins (i.e., proteins containing polypeptide sequences that do not correspond to GMAD polypeptide sequences) in addition to the GMAD proteins of the invention. In a specific embodiment, antibodies of the invention bind a heterodimer, a heterotrimer, or a heterotetramer. In additional embodiments, the antibodies of the invention bind at least a homodimer, at least a homotrimer, or at least a homotetramer containing one or more GMAD polypeptides.

Antibodies of the invention may bind GMAD protein multimers that are the result of hydrophobic, hydrophilic, ionic and/or covalent associations and/or may be indirectly linked, by for example, liposome formation. Thus, in one embodiment, antibodies of the invention may bind multimers, such as, for example, homodimers or homotrimers, that are formed when GMAD proteins contact one another in solution. In another embodiment, antibodies of the invention may bind heteromultimers, such as, for example, heterotrimers or heterotetramers, that are formed when proteins of the invention contact antibodies to GMAD polypeptides (or antibodies to the heterologous polypeptide sequence in a fusion protein) in solution. In other embodiments, multimers that one or more antibodies of the invention may bind are formed by covalent associations with and/or between the GMAD proteins of the invention. Such covalent associations may involve one or more amino acid residues contained in the polypeptide sequence of the protein (e.g., the polypeptide sequence recited in SEQ ID NO:2 or the polypeptide encoded by the deposited GMAD cDNA clone of ATCC Deposit 209215). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a GMAD fusion protein. In one example, covalent associations are between the heterologous sequence contained in a fusion protein (see, e.g., U.S. Pat. No. 5,478,925). In a specific example, the covalent associations are between the heterologous sequence contained in a GMAD-Fc fusion protein (as described herein). In another specific example, covalent associations of fusion proteins are between heterologous polypeptide sequences from another GMAD-related polypeptides (e.g., other FIZZ, RELM family) that are capable of forming covalently associated multimers, such as for example, oseteoprotegerin (see, e.g., International Publication No. WO 98/49305, the contents of which are herein incorporated by reference in its entirety).

Antibodies of the invention may bind GMAD protein multimers that were generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers that may be bound by one or more antibodies of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins that may be bound by one or more antibodies of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer that one or more antibodies of the invention may bind (see, e.g., U.S. Pat. No. 5,478,925, which is herein incorporated by reference in its entirety).

Alternatively, antibodies of the invention may bind GMAD protein multimers that were generated using genetic engineering techniques known in the art. In one embodiment, proteins contained in multimers that may be bound by one or more antibodies of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer that may be bound by one or more antibodies of the invention are generated by ligating a polynucleotide sequence encoding a GMAD polypeptide to a sequence encoding a linker polypeptide and then further to a synthetic polynucleotide encoding the translated product of the polypeptide in the reverse orientation from the original C-terminus to the N-terminus (see, e.g., U.S. Pat. No. 5,478,925, which is herein incorporated by reference in its entirety). In another embodiment, recombinant techniques described herein or otherwise known in the art are applied to generate recombinant GMAD polypeptides which contain a transmembrane domain and which can be incorporated by membrane reconstitution techniques into liposomes (see, e.g., U.S. Pat. No. 5,478,925, which is herein incorporated by reference in its entirety). In another embodiment, two or more GMAD polypeptides are joined through synthetic linkers (e.g., peptide, carbohydrate or soluble polymer linkers). Examples include those peptide linkers described in U.S. Pat. No. 5,073,627 (hereby incorporated by reference). Proteins comprising multiple GMAD polypeptides separated by peptide linkers may be produced using conventional recombinant DNA technology. In specific embodiments, antibodies of the invention bind proteins comprising multiple GMAD polypeptides separated by peptide linkers.

Another method for preparing multimer GMAD polypeptides involves use of GMAD polypeptides fused to a leucine zipper or isoleucine polypeptide sequence. Leucine zipper domains and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric GMAD proteins are those described in PCT application WO 94/10308, hereby incorporated by reference. Recombinant fusion proteins comprising a soluble GMAD polypeptide fused to a peptide that dimerizes or trimerizes in solution are expressed in suitable host cells, and the resulting soluble multimeric GMAD is recovered from the culture supernatant using techniques known in the art. In specific embodiments, antibodies of the invention bind GMAD-leucine zipper fusion protein monomers and/or GMAD-leucine zipper fusion protein multimers.

Other peptides derived from naturally occurring trimeric proteins may be employed in preparing trimeric GMAD. In specific embodiments, antibodies of the invention bind GMAD-fusion protein monomers and/or GMAD fusion protein trimers.

Antibodies that bind GMAD polypeptides may bind them as isolated polypeptides or in their naturally occurring state. For, example antibodies of the present invention may bind recombinantly produced GMAD polypeptides. In a specific embodiment, antibodies of the present invention bind a GMAD polypeptide purified from a cell culture wherein cells in said cell culture comprise a polynucleotide encoding amino acids 1 to 108 of SEQ ID NO:2 operably associated with a regulatory sequence that controls expression of said polynucleotide. Antibodies of the present invention may bind GMAD polypeptide fragments comprising or alternatively, consisting of, the amino acid sequence of SEQ ID NO:2, encoded by the GMAD cDNA contained in ATCC Deposit Number 209215, or encoded by nucleic acids which hybridize (e.g., under stringent hybridization conditions) to the GMAD nucleotide sequence contained in ATCC Deposit Number 209215, or the complementary strand thereto. Protein fragments may be "free-standing," or comprised within a larger polypeptide of which the fragment forms a part or region, most preferably as a single continuous region. Antibodies of the present invention may bind polypeptide fragments, including, for example, fragments that comprise or alternatively, consist of from about amino acid residues: 1 to 23, 24 to 43, 44 to 63, 64 to 83 and/or 84 to 108, of SEQ ID NO:2. In this context "about" includes the particularly recited value, larger or smaller by several (5, 4, 3, 2, or 1) amino acids, at either extreme or at both extremes. Moreover, polypeptide fragments that antibodies of the invention may bind can be at least about 10, 20, 30, 40, 50, 60, 70, 80, 90, or 100 amino acids in length. In this context "about" includes the particularly recited value, larger or smaller by several (5, 4, 3, 2, or 1) amino acids, at either extreme or at both extremes.

Preferably, antibodies of the present invention bind polypeptide fragments selected from the group: a polypeptide comprising or alternatively, consisting of, a fragment of the predicted mature GMAD polypeptide, wherein the fragment has a GMAD functional activity (e.g., antigenic activity or biological acitivity); or a polypeptide comprising, or alternatively, consisting of, one, two, three, four or more, epitope bearing portions of the GMAD protein. The amino acid residues constituting the preferred epitopes have been predicted by computer analysis. Thus, as one of ordinary skill would appreciate, the amino acid residues constituting these domains may vary slightly (e.g., by about 1 to about 15 amino acid residues) depending on the criteria used to define each epitope. Polynucleotides encoding these polypeptides are also encompassed by the invention.

In another preferred embodiment, antibodies of the present invention bind GMAD polypeptides comprising, or alternatively consisting of, the expressed and/or mature polypeptide of GMAD (amino acid residues 21-108 of SEQ ID NO:2). In highly preferred embodiments, the antibodies of the invention that bind all or a portion of the mature GMAD polypeptide and inhibit GMAD-induced insulin resistance (i.e. gradual reduction in insulin uptake) in cells expressing GMAD (e.g., adipocytes). In other highly preferred embodiments, the antibodies of the invention that bind all or a portion of the mature GMAD polypeptide and inhibit GMAD-induced glucose resistance (i.e. gradual reduction in insulin-mediated glucose uptake) in cells expressing GMAD (e.g., adipocytes).

Antibodies of the invention may also bind fragments comprising, or alternatively, consisting of, structural or functional attributes of GMAD. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) GMAD. Certain preferred regions are those set out in Table 2 and include, but are not limited to, regions of the aforementioned types identified by analysis of the amino acid sequence depicted in (SEQ ID NO:2), such preferred regions include; Garnier-Robson predicted alpha-regions, beta-regions, turn-regions, and coil-regions; Chou- Fasman predicted alpha-regions, beta-regions, and turn-regions; Kyte-Doolittle predicted hydrophilic regions; Eisenberg alpha and beta amphipathic regions; Emini surface-forming regions; and Jameson-Wolf high antigenic index regions, as predicted using the default parameters of these computer programs.

The data representing the structural or functional attributes of GMAD set forth in Table 2, as described above, was generated using the various modules and algorithms of the DNA*STAR set on default parameters. Column I represents the results of a Garnier-Robson analysis of alpha helical regions; Column II represents the results of a Chou-Fasman analysis of alpha helical regions; Column III represents the results of a Garnier Robson analysis of beta sheet regions; Column IV represents the results of a Chou-Fasman analysis of beta sheet regions; Column V represents the results of a Garnier Robson analysis of turn regions; Column VI represents the results of a Chou-Fasman analysis of turn regions; Column VII represents the results of a Garnier Robson analysis of coil regions; Column VIII represents a Kyte-Doolittle hydrophilicity plot; Column; Column IX represents a Hopp-Woods hydrophobicity plot; Column X represents the results of an Eisenberg analysis of alpha amphipathic regions; Column XI represents the results of an Eisenberg analysis of beta amphipathic regions; Column XII represents the results of a Karplus-Schultz analysis of flexible regions; Column XIII represents the Jameson-Wolf antigenic index score; and Column XIV represents the Emini surface probability plot.

In a preferred embodiment, the data presented in columns VIII, XIII, and XIV of Table 2 can be used to determine regions of GMAD which exhibit a high degree of potential for antigenicity. Regions of high antigenicity are determined from the data presented in columns VIII, XIII, and/or XIV by choosing values which represent regions of the polypeptide which are likely to be exposed on the surface of the polypeptide in an environment in which antigen recognition may occur in the process of initiation of an immune response.

The above-mentioned preferred regions set out in Table 2 include, but are not limited to, regions of the aforementioned types identified by analysis of the amino acid sequence set out in SEQ ID NO:2. As set out in Table 2, such preferred regions include Garnier-Robson alpha-regions, beta-regions, turn-regions, and coil-regions, Chou-Fasman alpha-regions, beta-regions, and turn-regions, Kyte-Doolittle hydrophilic regions, Eisenberg alpha- and beta-amphipathic regions, Karplus-Schulz flexible regions, Jameson-Wolf regions of high antigenic index and Emini surface-forming regions. Among preferred polypeptide fragments that one or more antibodies of the invention may bind are those that comprise regions of GMAD that combine several structural features, such as several (e.g., 1, 2, 3, or 4) of the same or different region features set out above and in Table 2.

TABLE 2

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | A | . | . | . | . | . | −0.68 | 0.09 | . | . | . | −0.30 | 0.62 |
| Lys | 2 | A | A | . | . | . | . | . | −1.10 | 0.23 | . | . | . | −0.30 | 0.26 |
| Ala | 3 | A | A | . | . | . | . | . | −1.52 | 0.49 | * | . | . | −0.60 | 0.17 |
| Leu | 4 | A | A | . | . | . | . | . | −1.94 | 0.74 | . | . | . | −0.60 | 0.14 |
| Cys | 5 | A | A | . | . | . | . | . | −2.37 | 0.81 | . | . | . | −0.60 | 0.06 |
| Leu | 6 | A | A | . | . | . | . | . | −1.98 | 1.50 | * | . | . | −0.60 | 0.05 |
| Leu | 7 | . | A | B | . | . | . | . | −2.88 | 1.43 | . | . | . | −0.60 | 0.09 |
| Leu | 8 | . | A | B | . | . | . | . | −3.10 | 1.39 | . | . | . | −0.60 | 0.12 |
| Leu | 9 | . | A | B | . | . | . | . | −2.63 | 1.50 | . | . | . | −0.60 | 0.12 |
| Pro | 10 | . | A | B | . | . | . | . | −2.78 | 1.24 | . | . | . | −0.60 | 0.15 |
| Val | 11 | . | A | B | . | . | . | . | −2.78 | 1.24 | . | . | . | −0.60 | 0.15 |
| Leu | 12 | . | A | B | . | . | . | . | −2.82 | 1.24 | . | . | . | −0.60 | 0.15 |
| Gly | 13 | . | A | B | . | . | . | . | −2.31 | 1.20 | . | . | . | −0.60 | 0.07 |
| Leu | 14 | . | A | B | . | . | . | . | −1.80 | 1.16 | . | . | . | −0.60 | 0.13 |
| Leu | 15 | . | A | B | . | . | . | . | −1.54 | 0.90 | . | . | . | −0.60 | 0.21 |
| Val | 16 | . | . | B | . | . | T | . | −1.00 | 0.21 | . | . | . | 0.10 | 0.42 |
| Ser | 17 | . | . | B | . | . | T | . | −1.00 | 0.27 | . | . | F | 0.25 | 0.73 |
| Ser | 18 | A | . | . | . | . | T | . | −1.32 | 0.27 | . | . | F | 0.25 | 0.73 |
| Lys | 19 | A | . | . | . | . | T | . | −0.81 | 0.16 | . | . | F | 0.25 | 0.53 |
| Thr | 20 | A | . | . | B | . | . | . | −0.60 | −0.10 | . | . | F | 0.45 | 0.53 |
| Leu | 21 | A | . | . | B | . | . | . | 0.26 | 0.13 | . | . | . | −0.30 | 0.39 |
| Cys | 22 | A | . | . | B | . | . | . | 0.56 | −0.26 | * | . | . | 0.30 | 0.34 |
| Ser | 23 | A | . | . | B | . | . | . | 0.27 | −0.26 | * | . | . | 0.30 | 0.40 |
| Met | 24 | A | A | . | . | . | . | . | −0.67 | −0.24 | * | . | . | 0.30 | 0.49 |
| Glu | 25 | A | A | . | . | . | . | . | −0.36 | −0.24 | * | . | . | 0.30 | 0.65 |
| Glu | 26 | A | A | . | . | . | . | . | 0.46 | −0.41 | . | * | . | 0.30 | 0.77 |
| Ala | 27 | A | A | . | . | . | . | . | 1.23 | −0.80 | . | * | . | 0.75 | 1.36 |
| Ile | 28 | A | A | . | . | . | . | . | 0.64 | −1.41 | * | * | . | 0.75 | 1.53 |
| Asn | 29 | A | A | . | . | . | . | . | 1.24 | −0.73 | * | * | . | 0.60 | 0.62 |
| Glu | 30 | A | A | . | . | . | . | . | 1.24 | −0.33 | * | * | F | 0.60 | 1.06 |
| Arg | 31 | A | A | . | . | . | . | . | 0.39 | −0.83 | * | * | F | 0.90 | 2.63 |
| Ile | 32 | A | A | . | . | . | . | . | 0.39 | −0.87 | * | * | F | 0.90 | 1.21 |
| Gln | 33 | A | A | . | . | . | . | . | 0.93 | −0.77 | * | * | F | 0.75 | 0.71 |
| Glu | 34 | A | A | . | . | . | . | . | 0.63 | −0.34 | * | * | . | 0.30 | 0.36 |
| Val | 35 | A | A | . | . | . | . | . | −0.18 | 0.04 | * | . | . | −0.30 | 0.68 |
| Ala | 36 | A | A | . | . | . | . | . | −1.18 | 0.04 | * | * | . | −0.30 | 0.33 |
| Gly | 37 | A | A | . | B | . | . | . | −0.99 | 0.33 | * | * | . | −0.30 | 0.13 |
| Ser | 38 | A | A | . | B | . | . | . | −0.88 | 1.11 | * | * | . | −0.60 | 0.15 |
| Leu | 39 | A | A | . | B | . | . | . | −1.47 | 0.47 | * | * | . | −0.60 | 0.30 |
| Ile | 40 | . | A | B | B | . | . | . | −1.50 | 0.47 | * | * | . | −0.60 | 0.30 |
| Phe | 41 | . | A | B | B | . | . | . | −1.21 | 0.73 | * | . | . | −0.60 | 0.16 |
| Arg | 42 | . | A | B | B | . | . | . | −1.17 | 0.73 | * | * | . | −0.60 | 0.26 |
| Ala | 43 | . | A | B | B | . | . | . | −1.76 | 0.43 | * | * | . | −0.60 | 0.49 |

TABLE 2-continued

| Res | Position | I | II | III | IV | V | VI | VII | VIII | IX | X | XI | XII | XIII | XIV |
|-----|----------|---|----|----|----|----|----|-----|------|----|---|----|-----|------|-----|
| Ile | 44 | . | A | B | B | . | . | . | −1.29 | 0.43 | * | * | . | −0.60 | 0.40 |
| Ser | 45 | . | A | B | B | . | . | . | −0.29 | 0.07 | * | . | . | −0.30 | 0.20 |
| Ser | 46 | . | . | . | B | . | . | C | 0.07 | 0.07 | * | * | F | 0.05 | 0.39 |
| Ile | 47 | . | . | . | B | . | . | C | −0.34 | 0.00 | * | . | F | 0.05 | 0.55 |
| Gly | 48 | . | . | . | . | . | T | C | 0.24 | −0.30 | * | . | F | 1.05 | 0.55 |
| Arg | 49 | . | . | . | . | . | T | C | 0.83 | −0.69 | * | * | F | 1.35 | 0.72 |
| Gly | 50 | . | . | . | . | . | T | C | 0.28 | −0.69 | * | . | F | 1.50 | 1.37 |
| Ser | 51 | . | . | . | . | . | T | C | 0.27 | −0.73 | * | . | F | 1.50 | 1.03 |
| Glu | 52 | . | . | B | B | . | . | . | 0.86 | −0.67 | * | * | F | 1.09 | 0.76 |
| Ser | 53 | . | . | B | B | . | . | . | 1.31 | −0.29 | * | * | F | 1.28 | 1.02 |
| Val | 54 | . | . | B | B | . | . | . | 0.86 | −0.71 | * | * | F | 1.92 | 1.50 |
| Thr | 55 | . | . | B | B | . | . | . | 1.20 | −0.67 | . | * | F | 2.11 | 0.85 |
| Ser | 56 | . | . | . | . | T | T | . | 0.69 | −0.67 | . | * | F | 3.40 | 1.07 |
| Arg | 57 | . | . | . | . | T | T | . | 0.10 | −0.37 | . | * | F | 2.76 | 1.18 |
| Gly | 58 | . | . | . | . | T | T | . | 0.09 | −0.51 | . | * | F | 2.57 | 0.83 |
| Asp | 59 | . | . | . | . | T | T | . | 0.28 | −0.51 | . | * | F | 2.23 | 0.89 |
| Leu | 60 | . | . | B | . | . | . | . | 0.38 | −0.33 | . | * | F | 0.99 | 0.24 |
| Ala | 61 | . | . | B | . | . | . | . | 0.79 | 0.10 | . | * | . | −0.10 | 0.38 |
| Thr | 62 | . | . | B | . | . | . | . | 0.33 | −0.33 | * | * | . | 0.50 | 0.45 |
| Cys | 63 | . | . | B | . | . | T | . | −0.02 | 0.10 | * | * | . | 0.10 | 0.54 |
| Pro | 64 | . | . | . | . | . | T | T | . | −0.61 | 0.20 | * | . | F | 0.65 | 0.46 |
| Arg | 65 | . | . | . | . | . | T | T | . | −0.66 | 0.20 | * | . | F | 0.65 | 0.32 |
| Gly | 66 | . | . | . | . | . | T | T | . | −0.38 | 0.36 | . | . | . | 0.50 | 0.45 |
| Phe | 67 | . | . | B | B | . | . | . | −0.41 | 0.27 | . | . | . | −0.30 | 0.42 |
| Ala | 68 | . | . | B | B | . | . | . | −0.41 | 0.27 | . | . | . | −0.30 | 0.21 |
| Val | 69 | . | . | B | B | . | . | . | −0.51 | 0.84 | . | . | . | −0.60 | 0.11 |
| Thr | 70 | . | . | B | B | . | . | . | −1.29 | 0.90 | . | . | . | −0.60 | 0.19 |
| Gly | 71 | . | . | B | B | . | . | . | −1.29 | 0.69 | . | . | . | −0.60 | 0.10 |
| Cys | 72 | . | . | . | . | T | T | . | −0.89 | 0.61 | . | . | . | 0.20 | 0.13 |
| Thr | 73 | . | . | . | . | T | T | . | −0.89 | 0.36 | . | . | . | 0.50 | 0.12 |
| Cys | 74 | . | . | . | . | T | T | . | −0.70 | 0.37 | . | . | . | 0.50 | 0.13 |
| Gly | 75 | . | . | . | . | T | T | . | −0.73 | 0.51 | . | . | . | 0.20 | 0.13 |
| Ser | 76 | . | . | . | . | T | . | . | −0.69 | 0.37 | . | . | . | 0.30 | 0.09 |
| Ala | 77 | . | . | . | . | T | . | . | −0.31 | 0.27 | . | . | . | 0.30 | 0.22 |
| Cys | 78 | . | . | . | . | T | T | . | 0.00 | 0.61 | . | * | . | 0.20 | 0.23 |
| Gly | 79 | . | . | . | . | T | T | . | −0.19 | 0.19 | . | * | . | 0.50 | 0.29 |
| Ser | 80 | . | . | . | . | T | T | . | 0.27 | 0.44 | . | * | . | 0.20 | 0.21 |
| Trp | 81 | . | . | B | . | . | T | . | −0.02 | −0.06 | . | * | . | 0.70 | 0.78 |
| Asp | 82 | . | A | B | B | . | . | . | 0.57 | −0.13 | . | * | . | 0.30 | 0.79 |
| Val | 83 | A | A | . | B | . | . | . | 0.92 | −0.56 | . | * | . | 0.75 | 1.02 |
| Arg | 84 | A | A | . | B | . | . | . | 0.96 | −0.46 | . | * | . | 0.45 | 1.41 |
| Ala | 85 | A | A | . | . | . | . | . | 0.59 | −0.89 | . | * | F | 0.90 | 1.21 |
| Glu | 86 | . | A | . | . | T | . | . | 0.84 | −0.31 | . | * | F | 0.85 | 0.88 |
| Thr | 87 | . | A | . | . | T | . | . | 0.18 | −0.46 | . | * | F | 0.85 | 0.61 |
| Thr | 88 | . | A | . | . | T | . | . | 1.03 | 0.11 | . | * | . | 0.10 | 0.32 |
| Cys | 89 | . | . | . | . | T | T | . | 0.26 | 0.01 | . | * | . | 0.50 | 0.32 |
| His | 90 | . | . | . | . | T | T | . | 0.26 | 0.59 | . | . | . | 0.20 | 0.12 |
| Cys | 91 | . | . | B | . | . | T | . | −0.09 | 0.60 | . | . | . | −0.20 | 0.08 |
| Gln | 92 | . | . | B | . | . | T | . | −0.38 | 0.54 | . | . | . | −0.20 | 0.16 |
| Cys | 93 | . | . | . | . | T | . | . | −0.07 | 0.59 | . | . | . | 0.00 | 0.11 |
| Ala | 94 | . | . | . | . | T | . | . | 0.31 | 0.09 | . | . | . | 0.30 | 0.35 |
| Gly | 95 | . | . | . | . | T | T | . | 0.03 | 0.43 | . | . | . | 0.20 | 0.21 |
| Met | 96 | . | . | . | . | T | T | . | 0.36 | 0.51 | . | . | . | 0.42 | 0.57 |
| Asp | 97 | . | . | . | . | T | T | . | −0.23 | 0.37 | . | . | . | 0.94 | 0.56 |
| Trp | 98 | . | . | . | . | T | T | . | 0.54 | 0.37 | . | . | . | 1.16 | 0.57 |
| Thr | 99 | . | . | . | . | T | . | . | 0.47 | −0.06 | . | . | . | 1.93 | 1.14 |
| Gly | 100 | . | . | . | . | T | T | . | 0.14 | −0.10 | * | . | . | 2.20 | 0.37 |
| Ala | 101 | . | . | . | . | T | T | . | 0.86 | 0.47 | * | . | . | 1.08 | 0.19 |
| Arg | 102 | . | . | . | . | T | T | . | 0.00 | −0.44 | . | . | . | 1.76 | 0.25 |
| Cys | 103 | . | . | . | . | T | T | . | 0.29 | −0.29 | . | . | . | 1.54 | 0.19 |
| Cys | 104 | . | . | . | . | T | . | . | 0.39 | −0.31 | * | . | . | 1.12 | 0.32 |
| Arg | 105 | . | . | B | . | . | . | . | 0.34 | −0.39 | * | . | . | 0.50 | 0.26 |
| Val | 106 | . | . | B | . | . | . | . | 0.54 | 0.04 | * | . | . | −0.10 | 0.61 |
| Gln | 107 | . | . | B | . | . | . | . | 0.04 | −0.10 | * | . | . | 0.65 | 1.46 |
| Pro | 108 | . | . | B | . | . | . | . | 0.32 | −0.24 | . | * | . | 0.50 | 0.95 |

In another aspect, the invention provides an antibody that binds a peptide or polypeptide comprising an epitope-bearing portion of a polypeptide described herein. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660-666. Peptides capable of eliciting protein-reactive sera are frequently represented in the primary sequence of a protein, can be characterized by a set of simple chemical rules, and are confined neither to immunodominant regions of intact proteins nor to the amino or carboxyl terminals.

Antigenic epitope-bearing peptides and polypeptides are therefore useful to raise antibodies, including monoclonal antibodies, that bind to a GMAD polypeptide of the invention. See, for instance, Wilson et al., Cell 37:767-778 (1984) at 777. Antigenic epitope-bearing peptides and polypeptides preferably contain a sequence of at least seven, more preferably at least nine and most preferably between at least about 15 to about 30 amino acids contained within the amino acid sequence of SEQ ID NO:2.

Antibodies of the invention may bind one or more antigenic GMAD polypeptides or peptides including, but not limited to: a polypeptide comprising amino acid residues from about 54 to about 59 of SEQ ID NO:2. In this context "about" includes the particularly recited range, larger or smaller by several (5, 4, 3, 2, or 1) amino acids, at either terminus or at both termini. As indicated above, the inventors have determined that the above polypeptide fragments are antigenic regions of the GMAD protein. Epitope-bearing GMAD peptides and polypeptides may be produced by any conventional means. Houghten, R. A., "General method for the rapid solid-phase synthesis of large numbers of peptides: specificity of antigen-antibody interaction at the level of individual amino acids," Proc. Natl. Acad. Sci. USA 82:5131-5135 (1985). This "Simultaneous Multiple Peptide Synthesis (SMPS)" process is further described in U.S. Pat. No. 4,631,211 to Houghten et al. (1986).

As one of skill in the art will appreciate, GMAD polypeptides and the epitope-bearing fragments thereof described herein can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84-86 (1988)). Fusion proteins that have a disulfide-linked dimeric structure due to the IgG part can also be more efficient in binding and neutralizing other molecules than the monomeric GMAD protein or protein fragment alone (Fountoulakis et al., J Biochem 270:3958-3964 (1995)). Thus, antibodies of the invention may bind fusion proteins that comprise all or a portion of a GMAD polypeptide.

Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may also bind such modified GMAD polypeptides or GMAD polypeptide fragments or variants.

For instance, for many proteins, including the extracellular domain of a membrane associated protein or the mature form(s) of a secreted protein, it is known in the art that one or more amino acids may be deleted from the N-terminus or C-terminus without substantial loss of biological function, or loss of the ability to be bound by a specific antibody. For instance, Ron et al., *J. Biol. Chem.,* 268:2984-2988 (1993) reported modified KGF proteins that had heparin binding activity even if 3, 8, or 27 amino-terminal amino acid residues were missing.

However, even if deletion of one or more amino acids from the N-terminus of a protein results in modification or loss of one or more biological functions of the protein, other functional activities (e.g., biological activities, ability to multimerize, ability to reduce insulin and/or cellular glucose uptake) may still be retained. For example, the ability of shortened GMAD polypeptides to induce and/or bind to antibodies which recognize the complete or mature forms of the GMAD polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a GMAD polypeptide with a large number of deleted N-terminal amino acid residues may retain some biological or immunogenic activities. In fact, peptides composed of as few as six GMAD amino acid residues may often evoke an immune response.

Accordingly, the present invention further provides antibodies that bind polypeptides having one or more residues deleted from the amino terminus of the GMAD amino acid sequence of SEQ ID NO:2 up to the arginine residue at position number 102 and polynucleotides encoding such polypeptides. In particular, the present invention provides antibodies that bind polypeptides comprising the amino acid sequence of residues $n^1$-108 of SEQ ID NO:2, where $n^1$ is an integer from 2 to 103 corresponding to the position of the amino acid residue in SEQ ID NO:2.

More in particular, the invention provides antibodies that bind polypeptides comprising, or alternatively consisting of, the amino acid sequence of residues of K-2 to P-108; A-3 to P-108; L-4 to P-108; C-5 to P-108; L-6 to P-108; L-7 to P-108; L-8 to P-108; L-9 to P-108; P-10 to P-108; V-11 to P-108; L-12 to P-108; G-13 to P-108; L-14 to P-108; L-15 to P-108; V-16 to P-108; S-17 to P-108; S-18 to P-108; K-19 to P-108; T-20 to P-108; L-21 to P-108; C-22 to P-108; S-23 to P-108; M-24 to P-108; E-25 to P-108; E-26 to P-108; A-27 to P-108; I-28 to P-108; N-29 to P-108; E-30 to P-108; R-31 to P-108; 1-32 to P-108; Q-33 to P-108; E-34 to P-108; V-35 to P-108; A-36 to P-108; G-37 to P-108; S-38 to P-108; L-39 to P-108; 1-40 to P-108; F-41 to P-108; R-42 to P-108; A-43 to P-108; I-44 to P-108; S-45 to P-108; S-46 to P-108; I-47 to P-108; G-48 to P-108; R-49 to P-108; G-50 to P-108; S-51 to P-108; E-52 to P-108; S-53 to P-108; V-54 to P-108; T-55 to P-108; S-56 to P-108; R-57 to P-108; G-58 to P-108; D-59 to P-108; L-60 to P-108; A-61 to P-108; T-62 to P-108; C-63 to P-108; P-64 to P-108; R-65 to P-108; G-66 to P-108; F-67 to P-108; A-68 to P-108; V-69 to P-108; T-70 to P-108; G-71 to P-108; C-72 to P-108; T-73 to P-108; C-74 to P-108; G-75 to P-108; S-76 to P-108; A-77 to P-108; C-78 to P-108; G-79 to P-108; S-80 to P-108; W-81 to P-108; D-82 to P-108; V-83 to P-108; R-84 to P-108;A-85 to P-108; E-86 to P-108; T-87 to P-108; T-88 to P-108; C-89 to P-108; H-90 to P-108; C-91 to P-108; Q-92 to P-108; C-93 to P-108; A-94 to P-108; G-95 to P-108; M-96 to P-108; D-97 to P-108; W-98 to P-108; T-99 to P-108; G-100 to P-108; A-101 to P-108; R-102 to P-108; C-103 to P-108; of the GMAD sequence of SEQ ID NO:2.

As mentioned above, even if deletion of one or more amino acids from the C-terminus of a protein results in modification of loss of one or more biological functions of the protein, other functional activities (e.g., biological activities such as the ability to induce resistance to cellular insulin and/or glucose uptake) may still be retained. For example the ability of the shortened GMAD polypeptide to induce and/or bind to antibodies which recognize the complete or mature forms of the GMAD polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a GMAD polypeptide with a large number of deleted C-terminal amino acid residues may retain some biological or immunogenic activities. In fact, peptides composed of as few as six GMAD amino acid residues may often evoke an immune response.

In another embodiment, antibodies of the invention bind C-terminal deletions of the GMAD polypeptide that can be described by the general formula 1-$m^1$ where $m^1$ is a number from 7 to 102 corresponding to the amino acid sequence identified of SEQ ID NO:2. In specific embodiments, the invention provides antibodies that bind GMAD polypeptides comprising, or alternatively consisting of, the amino acid sequence of residues: M-1 to R-102; M-1 to A-101; M-1 to G-100; M-1 to T-99; M-1 to W-98; M-1 to D-97; M-1 to M-96; M-1 to G-95; M-1 to A-94; M-1 to C-93; M-1 to Q-92; M-1 to C-91; M-1 to H-90; M-1 to C-89; M-1 to T-88; M-1 to T-87; M-1 to E-86; M-1 to A-85; M-1 to R-84; M-1 to V-83; M-1 to D-82; M-1 to W-81; M-1 to S-80; M-1 to G-79; M-1 to C-78; M-1 to A-77; M-1 to S-76; M-1 to G-75; M-1 to C-74; M-1 to T-73; M-1 to C-72; M-1 to G-71; M-1 to T-70; M-1 to V-69; M-1 to A-68; M-1 to F-67; M-1 to G-66; M-1 to R-65; M-1 to P-64; M-1 to C-63; M-1 to T-62; M-1 to A-61; M-1 L-60; M-1 to D-59; M-1 to G-58; M-1 to R-57; M-1 to S-56; M-1 to T-55; M-1 to V-54; M-1 to S-53; M-1 to E-52; M-1 to S-51; M-1 to G-50; M-1 to R-49; M-1 to G-48; M-1 to I-47; M-1 to S-46; M-1 to S-45; M-1 to I-44; M-1 to A-43; M-1 to R-42; M-1 to F-41; M-1 to I-40; M-1 to L-39; M-1 to S-38; M-1 to G-37; M-1 to A-36; M-1 to V-35; M-1 to E-34; M-1 to Q-33; M-1 to I-32; M-1 to R-31; M-1 to E-30; M-1 to N-29; M-1 to I-28; M-1 to A-27; M-1 to E-26; M-1 to E-25; M-1 to M-24; M-1 to S-23; M-1 to C-22; M-1 to L-21; M-1 to T-20; M-1 to K-19; M-1 to S-18; M-1 to S-17; M-1 to V-16; M-1 to L-15; M-1 to L-14; M-1 to G-13; M-1 to L-12; M-1 to V-11; M-1 to P-10; M-1 to L-9; M-1 to L-8; M-1 to L-7; of the GMAD sequence of SEQ ID NO:2.

The invention also provides antibodies that bind polypeptides having one or more amino acids deleted from both the amino and the carboxyl termini of a GMAD polypeptide, which may be described generally as having residues $n^1$-$m^1$ of SEQ ID NO:2, where $n^1$, and $m^1$ are integers as described above.

Preferably, antibodies of the present invention bind fragments of GMAD comprising a portion of the secreted protein; i.e., within residues 21-108 of SEQ ID NO:2, since any portion therein is expected to be expressed, and secreted.

It will be recognized in the art that some amino acid sequence of GMAD can be varied without significant effect of the structure or function of the protein. If such differences in sequence are contemplated, it should be remembered that there will be critical areas on the protein which determine activity. Such areas will usually comprise residues which make up the ligand binding site or which form tertiary structures which affect these domains.

Thus, the invention further includes antibodies that bind variations of the GMAD protein which show substantial GMAD protein activity or which include regions of GMAD such as the protein fragments discussed below. Such mutants include deletions, insertions, inversions, repeats, and type substitution. Guidance concerning which amino acid changes are likely to be phenotypically silent can be found in Bowie, J. U. et al., *Science* 247:1306-1310 (1990).

Thus, antibodies of the present invention may bind a fragment, derivative, or analog of the polypeptide of SEQ ID NO:2, or that encoded by the GMAD cDNA in ATCC deposit 209215. Such fragments, variants or derivatives may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the GMAD protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

In addition, antibodies of the present invention may bind a GMAD polypeptide that contains one or more amino acid substitutions, deletions or additions, either from natural mutations or human manipulation.

As indicated, changes are preferably of a minor nature, such as conservative amino acid substitutions that do not significantly affect the folding or activity of the protein (see Table 3).

TABLE 3

| Conservative Amino Acid Substitutions. | |
|---|---|
| Aromatic | Phenylalanine<br>Tryptophan<br>Tyrosine |
| Hydrophobic | Leucine<br>Isoleucine<br>Valine |
| Polar | Glutamine<br>Asparagine |
| Basic | Arginine<br>Lysine<br>Histidine |
| Acidic | Aspartic Acid<br>Glutamic Acid |
| Small | Alanine<br>Serine |

TABLE 3-continued

| Conservative Amino Acid Substitutions. | |
|---|---|
| | Threonine<br>Methionine<br>Glycine |

In specific embodiments, the number of substitutions, additions or deletions in the amino acid sequence of SEQ ID NO:2 and/or any of the polypeptide fragments described herein is 75, 70, 60, 50, 40, 35, 30, 25, 20, 15, 10, 9, 8, 7, 6, 5, 4, 3, 2, 1 or 30-20, 20-15, 20-10, 15-10, 10-1,5-10, 1-5,1-3 or 1-2.

In specific embodiments, the antibodies of the invention bind GMAD polypeptides or fragments or variants thereof (especially a fragment comprising or alternatively consisting of, the secreted, mature form of GMAD), that contains any one or more of the following conservative mutations in GMAD: Ml replaced with A, G, I, L, S, T, or V; K2 replaced with H, or R; A3 replaced with G, I, L, S, T, M, or V; L4 replaced with A, G, I, S, T, M, or V; L6 replaced with A, G, I, S, T, M, or V; L7 replaced with A, G, I, S, T, M, or V; L8 replaced with A, G, I, S, T, M, or V; L9 replaced with A, G, I, S, T, M, or V; V11 replaced with A, G, I, L, S, T, or M; L12 replaced with A, G, I, S, T, M, or V; G13 replaced with A, I, L, S, T, M, or V; L14 replaced with A, G, I, S, T, M, or V; L15 replaced with A, G, I, S, T, M, or V; V16 replaced with A, G, I, L, S, T, or M; S17 replaced with A, G, I, L, T, M, or V; S18 replaced with A, G, I, L, T, M, or V; K19 replaced with H, or R; T20 replaced with A, G, I, L, S, M, or V; L21 replaced with A, G, I, S, T, M, or V; S23 replaced with A, G, I, L, T, M, or V; M24 replaced with A, G, I, L, S, T, or V; E25 replaced with D; E26 replaced with D; A27 replaced with G, I, L, S, T, M, or V; I28 replaced with A, G, L, S, T, M, or V; N29 replaced with Q; E30 replaced with D; R31 replaced with H, or K; I32 replaced with A, G, L, S, T, M, or V; Q33 replaced with N; E34 replaced with D; V35 replaced with A, G, I, L, S, T, or M; A36 replaced with G, I, L, S, T, M, or V; G37 replaced with A, I, L, S, T, M, or V; S38 replaced with A, G, I, L, T, M, or V; L39 replaced with A, G, I, S, T, M, or V; I40 replaced with A, G, L, S, T, M, or V; F41 replaced with W, or Y; R42 replaced with H, or K; A43 replaced with G, I, L, S, T, M, or V; I44 replaced with A, G, L, S, T, M, or V; S45 replaced with A, G, I, L, T, M, or V; S46 replaced with A, G, I, L, T, M, or V; I47 replaced with A, G, L, S, T, M, or V; G48 replaced with A, I, L, S, T, M, or V; R49 replaced with H, or K; G50 replaced with A, I, L, S, T, M, or V; S51 replaced with A, G, I, L, T, M, or V; E52 replaced with D; S53 replaced with A, G, I, L, T, M, or V; V54 replaced with A, G, I, L, S, T, or M; T55 replaced with A, G, I, L, S, M, or V; S56 replaced with A, G, I, L, T, M, or V; R57 replaced with H, or K; G58 replaced with A, I, L, S, T, M, or V; D59 replaced with E; L60 replaced with A, G, I, S, T, M, or V; A61 replaced with G, I, L, S, T, M, or V; T62 replaced with A, G, I, L, S, M, or V; R65 replaced with H, or K; G66 replaced with A, I, L, S, T, M, or V; F67 replaced with W, or Y; A68 replaced with G, I, L, S, T, M, or V; V69 replaced with A, G, I, L, S, T, or M; T70 replaced with A, G, I, L, S, M, or V; G71 replaced with A, I, L, S, T, M, or V; T73 replaced with A, G, I, L, S, M, or V; G75 replaced with A, I, L, S, T, M, or V; S76 replaced with A, G, I, L, T, M, or V; A77 replaced with G, I, L, S, T, M, or V; G79 replaced with A, I, L, S, T, M, or V; S80 replaced with A, G, I, L, T, M, or V; W81 replaced with F, or Y; D82 replaced with E; V83 replaced with A, G, I, L, S, T, or M; R84 replaced with H, or K; A85 replaced with G, I, L, S, T, M, or V; E86 replaced with D; T87 replaced with A, G, I, L, S, M, or V; T88 replaced with A, G, I, L, S, M, or V; H90 replaced with K, or R; Q92 replaced with N; A94 replaced with G, I, L, S, T, M, or V; G95 replaced with A, I, L, S, T, M, or V; M96 replaced with A, G, I, L, S, T, or V; D97 replaced with E; W98 replaced with F, or Y; T99 replaced with A, G, I, L, S, M, or V; G100 replaced with A, I, L, S, T, M, or V; A101 replaced with G, I, L, S, T, M, or V; R102 replaced with H, or K; R105 replaced with H, or K; V106 replaced with A, G, I, L, S, T, or M; and/or Q107 replaced with N; of SEQ ID NO:2.

In specific embodiments, the antibodies of the invention bind GMAD polypeptides or fragments or variants thereof (especially a fragment comprising or alternatively consisting of, the secreted, mature form of GMAD), that contains any one or more of the following non-conservative mutations in GMAD: M1 replaced with D, E, H, K, R, N, Q, F, W, Y, P, or C; K2 replaced with D, E, A, G, I, L, S, T, M, V, N, Q, F, W, Y, P, or C; A3 replaced with D, E, H, K, R, N, Q, F, W, Y, P, or C; L4 replaced with D, E, H, K, R, N, Q, F, W, Y, P, or C; C5 replaced with D, E, H, K, R, A, G, I, L, S, T, M, V, N, Q, F, W, Y, or P; L6 replaced with D, E, H, K, R, N, Q, F, W, Y, P, or C; L7 replaced with D, E, H, K, R, N, Q, F, W, Y, P, or C; L8 replaced with D, E, H, K, R, N, Q, F, W, Y, P, or C; L9 replaced with D, E, H, K, R, N, Q, F, W, Y, P, or C; P10 replaced with D, E, H, K, R, A, G, I, L, S, T, M, V, N, Q, F, W, Y, or C; V11 replaced with D, E, H, K, R, N, Q, F, W, Y, P, or C; L12 replaced with D, E, H, K, R, N, Q, F, W, Y, P, or C; G13 replaced with D, E, H, K, R, N, Q, F, W, Y, P, or C; L14 replaced with D, E, H, K, R, N, Q, F, W, Y, P, or C; L15 replaced with D, E, H, K, R, N, Q, F, W, Y, P, or C; V16 replaced with D, E, H, K, R, N, Q, F, W, Y, P, or C; S17 replaced with D, E, H, K, R, N, Q, F, W, Y, P, or C; S18 replaced with D, E, H, K, R, N, Q, F, W, Y, P, or C; K19 replaced with D, E, A, G, I, L, S, T, M, V, N, Q, F, W, Y, P, or C; T20 replaced with D, E, H, K, R, N, Q, F, W, Y, P, or C; L21 replaced with D, E, H, K, R, N, Q, F, W, Y, P, or C; C22 replaced with D, E, H, K, R, A, G, I, L, S, T, M, V, N, Q, F, W, Y, or P; S23 replaced with D, E, H, K, R, N, Q, F, W, Y, P, or C; M24 replaced with D, E, H, K, R, N, Q, F, W, Y, P, or C; E25 replaced with H, K, R, A, G, I, L, S, T, M, V, N, Q, F, W, Y, P, or C; E26 replaced with H, K, R, A, G, I, L, S, T, M, V, N, Q, F, W, Y, P, or C; A27 replaced with D, E, H, K, R, N, Q, F, W, Y, P, or C; 128 replaced with D, E, H, K, R, N, Q, F, W, Y, P, or C; N29 replaced with D, E, H, K, R, A, G, I, L, S, T, M, V, F, W, Y, P, or C; E30 replaced with H, K, R, A, G, I, L, S, T, M, V, N, Q, F, W, Y, P, or C; R31 replaced with D, E, A, G, I, L, S, T, M, V, N, Q, F, W, Y, P, or C; I32 replaced with D, E, H, K, R, N, Q, F, W, Y, P, or C; Q33 replaced with D, E, H, K, R, A, G, I, L, S, T, M, V, F, W, Y, P, or C; E34 replaced with H, K, R, A, G, I, L, S, T, M, V, N, Q, F, W, Y, P, or C; V35 replaced with D, E, H, K, R, N, Q, F, W, Y, P, or C; A36 replaced with D, E, H, K, R, N, Q, F, W, Y, P, or C; G37 replaced with D, E, H, K, R, N, Q, F, W, Y, P, or C; S38 replaced with D, E, H, K, R, N, Q, F, W, Y, P, or C; L39 replaced with D, E, H, K, R, N, Q, F, W, Y, P, or C; I40 replaced with D, E, H, K, R, N, Q, F, W, Y, P, or C; F41 replaced with D, E, H, K, R, N, Q, A, G, I, L, S, T, M, V, P, or C; R42 replaced with D, E, A, G, I, L, S, T, M, V, N, Q, F, W, Y, P, or C; A43 replaced with D, E, H, K, R, N, Q, F, W, Y, P, or C; I44 replaced with D, E, H, K, R, N, Q, F, W, Y, P, or C; S45 replaced with D, E, H, K, R, N, Q, F, W, Y, P, or C; S46 replaced with D, E, H, K, R, N, Q, F, W, Y, P, or C; 147 replaced with D, E, H, K, R, N, Q, F, W, Y, P, or C; G48 replaced with D, E, H, K, R, N, Q, F, W, Y, P, or C; R49 replaced with D, E, A, G, I, L, S, T, M, V, N, Q, F, W, Y, P, or C; G50 replaced with D, E, H, K, R, N, Q, F, W, Y, P, or C; S51 replaced with D, E, H, K, R, N, Q, F, W, Y, P, or C; E52 replaced with H, K, R, A, G, I, L, S, T, M, V, N, Q, F, W, Y, P, or C; S53 replaced with D, E, H, K, R, N, Q, F, W, Y, P, or C;

V54 replaced with D, E, H, K, R, N, Q, F, W, Y, P, or C; T55 replaced with D, E, H, K, R, N, Q, F, W, Y, P, or C; S56 replaced with D, E, H, K, R, N, Q, F, W, Y, P, or C; R57 replaced with D, E, A, G, I, L, S, T, M, V, N, Q, F, W, Y, P, or C; G58 replaced with D, E, H, K, R, N, Q, F, W, Y, P, or C; D59 replaced with H, K, R, A, G, I, L, S, T, M, V, N, Q, F, W, Y, P, or C; L60 replaced with D, E, H, K, R, N, Q, F, W, Y, P, or C; A61 replaced with D, E, H, K, R, N, Q, F, W, Y, P, or C; T62 replaced with D, E, H, K, R, N, Q, F, W, Y, P, or C; C63 replaced with D, E, H, K, R, A, G, I, L, S, T, M, V, N, Q, F, W, Y, or P; P64 replaced with D, E, H, K, R, A, G, I, L, S, T, M, V, N, Q, F, W, Y, or C; R65 replaced with D, E, A, G, I, L, S, T, M, V, N, Q, F, W, Y, P, or C; G66 replaced with D, E, H, K, R, N, Q, F, W, Y, P, or C; F67 replaced with D, E, H, K, R, N, Q, A, G, I, L, S, T, M, V, P, or C; A68 replaced with D, E, H, K, R, N, Q, F, W, Y, P, or C; V69 replaced with D, E, H, K, R, N, Q, F, W, Y, P, or C; T70 replaced with D, E, H, K, R, N, Q, F, W, Y, P, or C; G71 replaced with D, E, H, K, R, N, Q, F, W, Y, P, or C; C72 replaced with D, E, H, K, R, A, G, I, L, S, T, M, V, N, Q, F, W, Y, or P; T73 replaced with D, E, H, K, R, N, Q, F, W, Y, P, or C; C74 replaced with D, E, H, K, R, A, G, I, L, S, T, M, V, N, Q, F, W, Y, or P; G75 replaced with D, E, H, K, R, N, Q, F, W, Y, P, or C; S76 replaced with D, E, H, K, R, N, Q, F, W, Y, P, or C; A77 replaced with D, E, H, K, R, N, Q, F, W, Y, P, or C; C78 replaced with D, E, H, K, R, A, G, I, L, S, T, M, V, N, Q, F, W, Y, or P; G79 replaced with D, E, H, K, R, N, Q, F, W, Y, P, or C; S80 replaced with D, E, H, K, R, N, Q, F, W, Y, P, or C; W81 replaced with D, E, H, K, R, N, Q, A, G, I, L, S, T, M, V, P, or C; D82 replaced with H, K, R, A, G, I, L, S, T, M, V, N, Q, F, W, Y, P, or C; V83 replaced with D, E, H, K, R, N, Q, F, W, Y, P, or C; R84 replaced with D, E, A, G, I, L, S, T, M, V, N, Q, F, W, Y, P, or C; A85 replaced with D, E, H, K, R, N, Q, F, W, Y, P, or C; E86 replaced with H, K, R, A, G, I, L, S, T, M, V, N, Q, F, W, Y, P, or C; T87 replaced with D, E, H, K, R, N, Q, F, W, Y, P, or C; T88 replaced with D, E, H, K, R, N, Q, F, W, Y, P, or C; C89 replaced with D, E, H, K, R, A, G, I, L, S, T, M, V, N, Q, F, W, Y, or P; H90 replaced with D, E, A, G, I, L, S, T, M, V, N, Q, F, W, Y, P, or C; C91 replaced with D, E, H, K, R, A, G, I, L, S, T, M, V, N, Q, F, W, Y, or P; Q92 replaced with D, E, H, K, R, A, G, I, L, S, T, M, V, F, W, Y, P, or C; C93 replaced with D, E, H, K, R, A, G, I, L, S, T, M, V, N, Q, F, W, Y, or P; A94 replaced with D, E, H, K, R, N, Q, F, W, Y, P, or C; G95 replaced with D, E, H, K, R, N, Q, F, W, Y, P, or C; M96 replaced with D, E, H, K, R, N, Q, F, W, Y, P, or C; D97 replaced with H, K, R, A, G, I, L, S, T, M, V, N, Q, F, W, Y, P, or C; W98 replaced with D, E, H, K, R, N, Q, A, G, I, L, S, T, M, V, P, or C; T99 replaced with D, E, H, K, R, N, Q, F, W, Y, P, or C; G100 replaced with D, E, H, K, R, N, Q, F, W, Y, P, or C; A101 replaced with D, E, H, K, R, N, Q, F, W, Y, P, or C; R102 replaced with D, E, A, G, I, L, S, T, M, V, N, Q, F, W, Y, P, or C; C103 replaced with D, E, H, K, R, A, G, I, L, S, T, M, V, N, Q, F, W, Y, or P; C104 replaced with D, E, H, K, R, A, G, I, L, S, T, M, V, N, Q, F, W, Y, or P; R105 replaced with D, E, A, G, I, L, S, T, M, V, N, Q, F, W, Y, P, or C; V106 replaced with D, E, H, K, R, N, Q, F, W, Y, P, or C; Q107 replaced with D, E, H, K, R, A, G, I, L, S, T, M, V, F, W, Y, P, or C; P108 replaced with D, E, H, K, R, A, G, I, L, S, T, M, V, N, Q, F, W, Y, or C; of SEQ ID NO:2.

Amino acids in the GMAD protein of the present invention that are essential for function can be identified by methods known in the art, such as site-directed mutagenesis or alanine-scanning mutagenesis (Cunningham and Wells, *Science* 244: 1081-1085 (1989)). The latter procedure introduces single alanine mutations at every residue in the molecule. The resulting mutant molecules are then tested for biological activity such as receptor binding or in vitro, or in vivo proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)). In preferred embodiments, antibodies of the present invention bind regions of GMAD that are essential for GMAD function. In other preferred embodiments, antibodies of the present invention bind regions of GMAD that are essential for GMAD function and inhibit or abolish GMAD function. In other preferred embodiments, antibodies of the present invention bind regions of GMAD that are essential for GMAD function and enhance GMAD function.

Additionally, protein engineering may be employed to improve or alter the characteristics of GMAD polypeptides. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may bind such modified GMAD polypeptides.

Non-naturally occurring variants of GMAD may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), restriction selection mutagenesis (see e.g., Wells et al., *Philos. Trans. R. Soc. London SerA* 317:415 (1986)).

Thus, the invention also encompasses antibodies that bind GMAD derivatives and analogs that have one or more amino acid residues deleted, added, and/or substituted to generate GMAD polypeptides that are better suited for binding activity, therapeutic activity or expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognition sequences in the GMAD polypeptides and/or an amino acid deletion at the second position of any one or more such recognition sequences will prevent glycosylation of GMAD at the modified tripeptide sequence (see, e.g., Miyajimo et al., EMBO J. 5(6):1193-1197). Additionally, one or more of the amino acid residues of GMAD polypeptides (e.g., arginine and lysine residues) may be deleted or substituted with another residue to eliminate undesired processing by proteases such as, for example, furins or kexins.

The antibodies of the present invention also include antibodies that bind a polypeptide comprising, or alternatively, consisting of, the polypeptide encoded by the deposited GMAD cDNA (the deposit having ATCC Accession Number 209215); a polypeptide comprising, or alternatively, consisting of, the polypeptide of SEQ ID NO:2 minus the amino terminal methionine; a polypeptide comprising, or alternatively, consisting of the secreted form of GMAD; a polypeptide comprising, or alternatively, consisting of, the mature form of GMAD; as well as polypeptides which are at least 80% identical, more preferably at least 90% or 95% identical, still more preferably at least 96%, 97%, 98% or 99% identical to the polypeptides described above (e.g., the polypeptide encoded by the deposited GMAD cDNA clone (the deposit having ATCC Accession Number 209215), the polypeptide of SEQ ID NO:2, and portions of such polypeptides with at least 30 amino acids and more preferably at least 50 amino acids.

By a polypeptide having an amino acid sequence at least, for example, 95% "identical" to a reference amino acid sequence of a GMAD polypeptide is intended that the amino acid sequence of the polypeptide is identical to the reference sequence except that the polypeptide sequence may include up to five amino acid alterations per each 100 amino acids of the reference amino acid of the GMAD polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present application is also directed to antibodies that bind proteins containing polypeptides at least 90%, 95%, 96%, 97%, 98% or 99% identical to the GMAD polypeptide sequence set forth herein as $n^1$-$m^1$. In preferred embodiments, the application is directed to antibodies that bind proteins containing polypeptides at least 90%, 95%, 96%, 97%, 98% or 99% identical to polypeptides having the amino acid sequence of the specific GMAD N- and C-terminal deletions recited herein.

In certain preferred embodiments, antibodies of the invention bind GMAD fusion proteins as described above wherein the GMAD portion of the fusion protein are those described as $n^1$-$m^1$ herein.

Antibodies of the Invention may Bind Modified GMAD Polypeptides

It is specifically contemplated that antibodies of the present invention may bind modified forms of the GMAD protein (SEQ ID NO:2)

In specific embodiments, antibodies of the present invention bind GMAD polypeptides (such as those described above) including, but not limited to naturally purified GMAD polypeptides, GMAD polypeptides produced by chemical synthetic procedures, and GMAD polypeptides produced by recombinant techniques from a prokaryotic or eukaryotic host, including, for example, bacterial, yeast, higher plant, insect and mammalian cells using, for example, the recombinant compositions and methods described above. Depending upon the host employed in a recombinant production procedure, the polypeptides may be glycosylated or non-glycosylated. In addition, GMAD polypeptides may also include an initial modified methionine residue, in some cases as a result of host-mediated processes.

In addition, GMAD proteins that antibodies of the present invention may bind can be chemically synthesized using techniques known in the art (e.g., see Creighton, Proteins: Structures and Molecular Principles, W.H. Freeman & Co., N.Y. (1983), and Hunkapiller, et al., *Nature* 310:105-111 (1984)). For example, a peptide corresponding to a fragment of a GMAD polypeptide can be synthesized by use of a peptide synthesizer. Furthermore, if desired, nonclassical amino acids or chemical amino acid analogs can be introduced as a substitution or addition into the GMAD polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention additionally, encompasses antibodies that bind GMAD polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications to GMAD polypeptides for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are antibodies that bind chemically modified derivatives of GMAD polypeptide which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a protein via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249-304 (1992); Francis et al., *Intern. J of Hematol.* 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each GMAD polypeptide (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

As mentioned the antibodies of the present invention may bind GMAD polypeptides that are modified by either natural processes, such as posttranslational processing, or by chemical modification techniques which are well known in the art. It will be appreciated that the same type of modification may be present in the same or varying degrees at several sites in a given GMAD polypeptide. GMAD polypeptides may be branched, for example, as a result of ubiquitination, and they may be cyclic, with or without branching. Cyclic, branched, and branched cyclic GMAD polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

Anti-GMAD Antibodies:

In one embodiment, the invention provides antibodies (e.g., antibodies comprising two heavy chains and two light chains linked together by disulfide bridges) that specifically bind a GMAD polypeptide (e.g., SEQ ID NO:2) or fragments or variants thereof, wherein the amino acid sequence of the heavy chain and the amino acid sequence of the light chain are the same as the amino acid sequence of a heavy chain and a light chain of one or more scFvs referred to in Table 1. In another embodiment, the invention provides antibodies (each consisting of two heavy chains and two light chains linked together by disulfide bridges to form an antibody) that specifically bind a GMAD polypeptide (e.g., SEQ ID NO:2) or fragments or variants thereof, wherein the amino acid sequence of the heavy chain or the amino acid sequence of the light chain are the same as the amino acid sequence of a heavy chain or a light chain of one or more scFvs referred to in Table 1. Specific binding to GMAD polypeptides may be determined by immunoassays known in the art or described herein for assaying specific antibody-antigen binding. Molecules comprising, or alternatively consisting of, fragments or variants of these antibodies that specifically bind to GMAD are also encompassed by the invention, as are nucleic acid molecules encoding these antibodies molecules, fragments and/or variants (e.g., SEQ ID NOS:137-233).

In one embodiment of the present invention, antibodies that specifically bind to GMAD or a fragment or variant thereof, comprise a polypeptide having the amino acid sequence of any one of the heavy chains of at least one of the scFvs referred to in Table 1 and/or any one of the light chains of at least one of the scFvs referred to in Table 1.

In another embodiment of the present invention, antibodies that specifically bind to GMAD or a fragment or variant thereof, comprise a polypeptide having the amino acid sequence of any one of the VH domains of at least one of the scFvs referred to in Table 1 and/or any one of the VL domains of at least one of the scFvs referred to in Table 1. In preferred embodiments, antibodies of the present invention comprise the amino acid sequence of a VH domain and VL domain from a single scFv referred to in Table 1. In alternative embodiments, antibodies of the present invention comprise the amino acid sequence of a VH domain and a VL domain from different scFvs referred to in Table 1. Molecules comprising, or alternatively consisting of, antibody fragments or variants of the VH and/or VL domains of at least one of the scFvs referred to in Table 1 that specifically bind to GMAD are also encompassed by the invention, as are nucleic acid molecules encoding these VH and VL domains, molecules, fragments and/or variants.

The present invention also provides antibodies that specifically bind to a polypeptide, or polypeptide fragment or variant of GMAD, wherein said antibodies comprise, or alternatively consist of, a polypeptide having an amino acid sequence of any one, two, three, or more of the VH CDRs contained in a VH domain of one or more scFvs referred to in Table 1. In particular, the invention provides antibodies that specifically bind GMAD, comprising, or alternatively consisting of, a polypeptide having the amino acid sequence of a VH CDR1 contained in a VH domain of one or more scFvs referred to in Table 1. In another embodiment, antibodies that specifically bind GMAD, comprise, or alternatively consist of, a polypeptide having the amino acid sequence of a VH CDR2 contained in a VH domain of one or more scFvs referred to in Table 1. In a preferred embodiment, antibodies that specifically bind GMAD, comprise, or alternatively consist of, a polypeptide having the amino acid sequence of a VH CDR3 contained in a VH domain of one or more scFvs referred to in Table 1. Molecules comprising, or alternatively consisting of, these antibodies, or antibody fragments or variants thereof, that specifically bind to GMAD or a GMAD fragment or variant thereof are also encompassed by the invention, as are nucleic acid molecules encoding these antibodies, molecules, fragments and/or variants (e.g., SEQ ID NOS:137-233).

The present invention also provides antibodies that specifically bind to a polypeptide, or polypeptide fragment or variant of GMAD, wherein said antibodies comprise, or alternatively consist of, a polypeptide having an amino acid sequence of any one, two, three, or more of the VL CDRs contained in a VL domain of one or more scFvs referred to in Table 1. In particular, the invention provides antibodies that specifically bind GMAD, comprising, or alternatively consisting of, a polypeptide having the amino acid sequence of a VL CDR1 contained in a VL domain of one or more scFvs referred to in Table 1. In another embodiment, antibodies that specifically bind GMAD, comprise, or alternatively consist of, a polypeptide having the amino acid sequence of a VL CDR2 contained in a VL domain of one or more scFvs referred to in Table 1. In a preferred embodiment, antibodies that specifically bind GMAD, comprise, or alternatively consist of, a polypeptide having the amino acid sequence of a VL CDR3 contained in a VL domain of one or more scFvs referred to in Table 1. Molecules comprising, or alternatively consisting of, these antibodies, or antibody fragments or variants thereof, that specifically bind to GMAD or a GMAD fragment or variant are also encompassed by the invention, as are nucleic acid molecules encoding these antibodies, molecules, fragments and/or variants (e.g., SEQ ID NOS:137-233).

The present invention also provides antibodies (including molecules comprising, or alternatively consisting of, antibody fragments or variants) that specifically bind to a GMAD polypeptide or polypeptide fragment or variant of GMAD, wherein said antibodies comprise, or alternatively consist of, one, two, three, or more VH CDRs and one, two, three or more VL CDRs, as contained in a VH domain or VL domain of one or more scFvs referred to in Table 1. In particular, the invention provides for antibodies that specifically bind to a polypeptide or polypeptide fragment or variant of GMAD, wherein said antibodies comprise, or alternatively consist of, a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof, of the VH CDRs and VL CDRs contained in a VH domain or VL domain of one or more scFvs referred to in Table 1. In a preferred embodiment, one or more of these combinations are from the same antibody as disclosed in Table 1. Molecules comprising, or alternatively consisting of, fragments or variants of these antibodies, that specifically bind to GMAD are also encompassed by the invention, as are nucleic acid molecules encoding these antibodies, molecules, fragments or variants (e.g., SEQ ID NOS:137-233).

Nucleic Acid Molecules Encoding anti-GMAD Antibodies

The present invention also provides for nucleic acid molecules, generally isolated, encoding an antibody of the invention (including molecules comprising, or alternatively consisting of, antibody fragments or variants thereof). In specific embodiments, the nucleic acid molecules encoding an antibody of the invention comprise, or alternatively consist of SEQ ID NOS:137-233 or fragments or variants thereof.

In a specific embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of at least one of the scFvs referred to in Table 1 and a VL domain having an amino acid sequence of VL domain of at least one of the scFvs referred to in Table 1. In another embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of at least one of the scFvs referred to in Table 1 or a VL domain having an amino acid sequence of a VL domain of at least one of the scFvs referred to in Table 1.

The present invention also provides antibodies that comprise, or alternatively consist of, variants (including derivatives) of the antibody molecules (e.g., the VH domains and/or VL domains) described herein, which antibodies specifically bind to GMAD or fragment or variant thereof. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid subsitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to induce resistance to cellular insulin and/or glucose uptake).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybriodma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g, improvements in antigen binding activity or change in antibody specificity). Following mutagenesis, the encoded protein may routinely be expressed and the functional and/or biological activity of the encoded protein, (e.g., ability to specifically bind GMAD) can be determined using techniques described herein or by routinely modifying techniques known in the art.

In a specific embodiment, an antibody of the invention (including a molecule comprising, or alternatively consisting of, an antibody fragment or variant thereof), that specifically binds GMAD polypeptides or fragments or variants thereof, comprises, or alternatively consists of, an amino acid sequence encoded by a nucleotide sequence that hybridizes to a nucleotide sequence that is complementary to that encoding one of the VH or VL domains of one or more scFvs referred to in Table 1, under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989*, Current Protocols in Molecular Biology*, Vol. I, Green Publishing Associates, Inc. and John Wiley & Sons, Inc., New York at pages 6.3.1-6.3.6 and 2.10.3). Nucleic acid molecules encoding these antibodies are also encompassed by the invention.

It is well known within the art that polypeptides, or fragments or variants thereof, with similar amino acid sequences often have similar structure and many of the same biological activities. Thus, in one embodiment, an antibody (including a molecule comprising, or alternatively consisting of, an antibody fragment or variant thereof), that specifically binds to a GMAD polypeptide or a fragment or variant of a GMAD polypeptide, comprises, or alternatively consists of, a VH domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VH domain of at least one of the scFvs referred to in Table 1.

In another embodiment, an antibody (including a molecule comprising, or alternatively consisting of, an antibody fragment or variant thereof), that specifically binds to a GMAD polypeptide or a fragment or variant of a GMAD polypeptide, comprises, or alternatively consists of, a VL domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VL domain of at least one of the scFvs referred to in Table 1.

Methods of Producing Antibodies

Antibodies in accordance with the invention are preferably prepared using a phage scFv display library. Technologies utilized for achieving the same are disclosed in the patents, applications, and references disclosed herein.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues) or synthetic cDNA libraries. The DNA encoding the VH and VL domains are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to an antigen of interest (i.e., a GMAD polypeptide or a fragment thereof) can be selected or identified with antigen, e.g., using labeled antigen or antigen bound or captured to a solid surface or bead. Examples of phage display methods that can be used to make the antibodies of the present invention include, but are not limited to, those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280(1994); PCT application No. PCT/GB91/O1 134; PCT publications WO 90/02809; WO 91/10737; WO 92/01047; WO 92/18719; WO 93/1 1236; WO 95/15982; WO 95/20401; WO97/13844; and U.S. Pat. Nos. 5,698,426; 5,223,409; 5,403,484; 5,580,717; 5,427,908; 5,750,753; 5,821,047; 5,571,698; 5,427,908; 5,516,717; 5,780,225; 5,658,727; 5,735,743 and 5,969,108; each of which is incorporated herein by reference in its entirety.

For some uses, such as for in vitro affinity maturation of an antibody of the invention, it may be useful to express the VH and VL domains of one or more scFvs referred to in Table 1 as single chain antibodies or Fab fragments in a phage display library. For example, the cDNAs encoding the VH and VL domains of the scFvs referred to in Table 1 may be expressed in all possible combinations using a phage display library, allowing for the selection of VH/VL combinations that bind a GMAD polypeptide with preferred binding characteristics such as improved affinity or improved off rates. Additionally, VH and VL segments—the CDR regions of the VH and VL domains of the scFvs referred to in Table 1, in particular, may be mutated in vitro. Expression of VH and VL domains with "mutant" CDRs in a phage display library allows for the selection of VH/VL combinations that bind a GMAD polypeptides with preferred binding characteristics such as improved affinity or improved off rates.

Additional Methods of Producing Antibodies

Antibodies of the invention (including antibody fragments or variants) can be produced by any method known in the art. For example, it will be appreciated that antibodies in accordance with the present invention can be expressed in cell lines including but not limited to myeloma cell lines and hybridoma cell lines. Sequences encoding the cDNAs or genomic clones for the particular antibodies can be used for transformation of a suitable mammalian or nonmammalian host cells or to generate phage display libraries, for example. Additionally, polypeptide antibodies of the invention may be chemically synthesized or produced through the use of recombinant expression systems.

One way to produce the antibodies of the invention would be to clone the VH and/or VL domains of the scFvs referred to in Table 1. In order to isolate the VH and VL domains from bacteria transfected with a vector containing the scFv, PCR primers complementary to VH or VL nucleotide sequences (See Example 2), may be used to amplify the VH and VL sequences. The PCR products may then be cloned using vectors, for example, which have a PCR product cloning site consisting of a 5' and 3' single T nucleotide overhang, that is complementary to the overhanging single adenine nucleotide added onto the 5' and 3' end of PCR products by many DNA polymerases used for PCR reactions. The VH and VL domains can then be sequenced using conventional methods known in the art. Alternatively, the VH and VL domains may be amplified using vector specific primers designed to amplify the entire scFv, (i.e. the VH domain, linker and VL domain.)

The cloned VH and VL genes may be placed into one or more suitable expression vectors. By way of non-limiting example, PCR primers including VH or VL nucleotide sequences, a restriction site, and a flanking sequence to protect the restriction site may be used to amplify the VH or VL sequences. Utilizing cloning techniques known to those of skill in the art, the PCR amplified VH domains may be cloned into vectors expressing the appropriate immunoglobulin constant region, e.g., the human IgG1 or IgG4 constant region for VH domains, and the human kappa or lambda constant regions for kappa and lambda VL domains, respectively. Preferably, the vectors for expressing the VH or VL domains comprise a promoter suitable to direct expression of the heavy and light chains in the chosen expression system, a secretion signal, a cloning site for the immunoglobulin variable domain, immunoglobulin constant domains, and a selection marker such as neomycin. The VH and VL domains may also be cloned into a single vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art (See, for example, Guo et al., J. Clin. Endocrinol. Metab. 82:925-31 (1997), and Ames et al., J. Immunol. Methods 184:177-86 (1995) which are herein incorporated in their entireties by reference).

The invention provides polynucleotides comprising, or alternatively consisting of, a nucleotide sequence encoding an antibody of the invention (including molecules comprising, or alternatively consisting of, antibody fragments or variants thereof). The invention also encompasses polynucleotides that hybridize under high stringency, or alternatively, under intermediate or lower stringency hybridization conditions, e.g., as defined supra, to polynucleotides complementary to nucleic acids having a polynucleotide sequence that encodes an antibody of the invention or a fragment or variant thereof.

The polynucleotides may be obtained, and the nucleotide sequence of the polynucleotides determined, by any method known in the art. If the amino acid sequences of the VH domains, VL domains and CDRs thereof, are known, nucleotide sequences encoding these antibodies can be determined using methods well known in the art, i.e., the nucleotide codons known to encode the particular amino acids are assembled in such a way to generate a nucleic acid that encodes the antibody, of the invention. Such a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody (including molecules comprising, or alternatively consisting of, antibody fragments or variants thereof) may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells or Epstein Barr virus transformed B cell lines that express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody (including molecules comprising, or alternatively consisting of, antibody fragments or variants thereof) is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, VH and VL domains of heavy and light chains of one or more scFvs referred to in Table 1, or fragments or variants thereof, are inserted within framework regions using recombinant DNA techniques known in the art. In a specific embodiment, one, two, three, four, five, six, or more of the CDRs of heavy and light chains of one or more scFvs referred to in Table 1, or fragments or variants thereof, is inserted within framework regions using recombinant DNA techniques known in the art. The framework regions may be naturally occurring or consensus framework regions, and preferably are human framework regions (see, e.g., Chothia et al., J. Mol. Biol. 278: 457-479 (1998) for a listing of human framework regions, the contents of which are hereby incorporated by reference in its entirety). Preferably, the polynucleotides generated by the combination of the framework regions and CDRs encode an antibody (including molecules comprising, or alternatively consisting of, antibody fragments or variants thereof) that specifically binds to GMAD. Preferably, as discussed supra, polynucleotides encoding variants of antibodies or antibody fragments having one or more amino acid substitutions may be made within the framework regions, and, preferably, the amino acid substitutions do not significantly alter binding of the antibody to its antigen. Additionally, such methods may be used to make amino acid substitutions or deletions of one or more variable region cysteine residues participating in an intrachain disulfide bond to generate antibody molecules, or antibody fragments or variants, lacking one or more intrachain disulfide bonds. Other alterations to the polynucleotide are encompassed by the present invention and fall within the ordinary skill of the art.

XenoMouse Technology

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B cell development. Furthermore, such a strategy could provide an ideal source for production of fully human monoclonal antibodies (Mabs) an important milestone towards fulfilling the promise of antibody therapy in human disease.

Fully human antibodies are expected to minimize the immunogenic and allergic responses intrinsic to mouse or mouse-derivatized Monoclonal antibodies and thus to increase the efficacy and safety of the administered antibodies. The use of fully human antibodies can be expected to provide a substantial advantage in the treatment of chronic and recurring human diseases, such as cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Monoclonal antibodies with the desired specificity could be readily produced and selected.

This general strategy was demonstrated in connection with the generation of the first XenoMouse™ strains as published in 1994. See Green et al. *Nature Genetics* 7:13-21 (1994). The XenoMouse™ strains were engineered with yeast artificial chromosomes (YACS) containing 245 kb and 10 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human monoclonal antibodies. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. *Nature Genetics* 15:146-156 (1997), Green and Jakobovits *J Exp. Med.* 188: 483-495 (1998), Green, *Journal of Immunological Methods* 231:11-23 (1999) and U.S. patent application Ser. No. 08/759,620, filed Dec. 3, 1996, the disclosures of which are hereby incorporated by reference.

Such approach is further discussed and delineated in U.S. patent application Ser. No. 07/466,008, filed Jan. 12, 1990, Ser. No. 07/710,515, filed Nov. 8, 1990, Ser. No. 07/919,297, filed Jul. 24, 1992, Ser. No. 07/922,649, filed Jul. 30, 1992, filed No. 08/031,801, filed Mar. 15, 1993, Ser. No. 08/112, 848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/471, 191, filed Jun. 5, 1995, Ser. No. 08/462,837, filed Jun. 5, 1995, Ser. No. 08/486,853, filed Jun. 5, 1995, Ser. No. 08/486, 857, filed Jun. 5, 1995, Ser. No. 08/486,859, filed Jun. 5, 1995, Ser. No. 08/462,513, filed Jun. 5, 1995, Ser. No. 08/724, 752, filed Oct. 2, 1996, and Ser. No. 08/759,620, filed Dec. 3, 1996. See also Mendez et al. *Nature Genetics* 15:146-156 (1997) and Green and Jakobovits *J Exp. Med.* 188:483 495 (1998). See also European Patent No., EP 0 471 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against GMAD polypeptides in order to vitiate concerns and/or effects of HAMA or HACA responses.

Monoclonal antibodies specific for GMAD polypeptides may be prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 571-681 (1981)). Briefly, mice such as XenoMouse™ mice may be immunized with GMAD polypeptides. After immunization, the splenocytes of such mice may be extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones which secrete antibodies capable of binding the GMAD polypetides.

For some uses, including in vivo use of antibodies in humans and in vitro detection assays, it may be preferable to use human or chimeric antibodies. Completely human antibodies are particularly desirable for therapeutic treatment of human patients. See also, U.S. Pat. Nos. 4,444,887 and 4,716,111; and PCT publications WO 98/46645, WO 98/50435, WO 98/24893, WO98/16654, WO 96/34096, WO 96/35735, and WO 91/10741; each of which is incorporated herein by reference in its entirety. In a specific embodiment, antibodies of the present invention comprise one or more VH and VL domains of the invention and constant regions from another immunoglobulin molecule, preferably a human immunoglobulin molecule. In a specific embodiment, antibodies of the present invention comprise one or more CDRs corresponding to the VH and VL domains of the invention and framework regions from another immunoglobulin molecule, preferably a human immunoglobulin molecule. In other embodiments, an antibody of the present invention comprises one, two, three, four, five, six or more VL CDRs or VH CDRs corresponding to one or more of the VH or VL domains of one or more scFvs referred to in Table 1, or fragments or variants thereof, and framework regions (and, optionally one or more CDRs not present in the scFvs referred to in Table 1) from a human immunoglobulin molecule. In a preferred embodiment, an antibody of the present invention comprises a VH CDR3, VL CDR3, or both, corresponding to the same scFv, or different scFvs selected from the scFvs referred to in Table 1, or fragments or variants thereof, and framework regions from a human immunoglobulin.

A chimeric antibody is a molecule in which different portions of the antibody are derived from different immunoglobulin molecules such as antibodies having a human variable region and a non-human (e.g., murine) immunoglobulin constant region or vice versa. Methods for producing chimeric antibodies are known in the art. See e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397, which are incorporated herein by reference in their entirety. Chimeric antibodies comprising one or more CDRs from human species and framework regions from a non-human immunoglobulin molecule (e.g., framework regions from a murine, canine or feline immunoglobulin molecule) (or vice versa) can be produced using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,352). In a preferred embodiment, chimeric antibodies comprise a human CDR3 having an amino acid sequence of any one of the VH CDR3s or VL CDR3s of a VH or VL domain of one or more of the scFvs referred to in Table 1, or a variant thereof, and non-human framework regions or human framework regions different from those of the frameworks in the corresponding scFvs disclosed in Table 1. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 352:323 (1988), which are incorporated herein by reference in their entireties.)

Intrabodies are antibodies, often scFvs, that are expressed from a recombinant nucleic aicd molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies of the invention can be produced using methods known in the art, such as those disclosed and reviewed in Chen et al., Hum. Gene Ther. 5:595-601 (1994); Marasco, W. A., Gene Ther. 4:11-15 (1997); Rondon and Marasco, Annu. Rev. Microbiol. 51:257-283 (1997); Proba et al., J. Mol. Biol. 275:245-253 (1998); Cohen et al., Oncogene 17:2445-2456 (1998); Ohage and Steipe, J. Mol. Biol. 291:1119-1128 (1999); Ohage et al., J. Mol. Biol. 291:1129-1134 (1999); Wirtz and Steipe, Protein Sci. 8:2245-2250 (1999); Zhu et al., J. Immunol. Methods 231:207-222 (1999); and references cited therein.

Recombinant expression of an antibody of the invention (including antibody fragments or variants thereof (e.g., a heavy or light chain of an antibody of the invention), requires construction of an expression vector(s) containing a polynucleotide that encodes the antibody. Once a polynucleotide encoding an antibody molecule (e.g., a whole antibody, a heavy or light chain of an antibody, or portion thereof (preferably, but not necessarily, containing the heavy or light chain variable domain)), of the invention has been obtained, the vector(s) for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464, the contents of each of which are hereby incorporated by reference in its entirety) and the variable domain of the antibody may be cloned into such a vector for expression of the entire heavy chain, the entire light chain, or both the entire heavy and light chains.

The expression vector(s) is(are) transferred to a host cell by conventional techniques and the transfected cells are then cultured by conventional techniques to produce an antibody of the invention. Thus, the invention includes host cells containing polynucleotide(s) encoding an antibody of the invention (e.g., whole antibody, a heavy or light chain thereof, or portion thereof, or a single chain antibody, or a fragment or variant thereof), operably linked to a heterologous promoter.

In preferred embodiments, for the expression of entire antibody molecules, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include, but are not limited to, bacteriophage particles engineered to express antibody fragments or variants teherof (single chain antibodies), microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990); Bebbington et al., Bio/Techniques 10:169 (1992); Keen and Hale, Cytotechnology 18:207 (1996)). These references are incorporated in their entirities by reference herein.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., EMBO 1. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) may be used as a vector to express foreign genes. The virus grows in *Spodoptera frugiperda* cells. Antibody coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, Proc. Natl. Acad. Sci. USA 8 1:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, NSO, MDCK, 293, 3T3, and W138.

For long-term, high-yield production of recombinant proteins, stable expression is preferred. For example, cell lines which stably express the antibody may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., Cell 11:223 (1977)), hypoxanthineguanine phosphoribosyltransferase (Szybalska & Szybalski, Proc. Natl. Acad. Sci. USA 48:202 (1992)), and adenine phosphoribosyltransferase (Lowy et al., Cell 22:8 17 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260: 926-932 (1993); and Morgan and Anderson, Ann. Rev. Biochem. 62: 191-217 (1993); TIB TECH 11(5):155-2 15 (May, 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells" in *DNA Cloning, Vol.*3. (Academic Press, New York, 1987)). When a marker in the vector system expressing antibody is amplifiable, increase in the level of inhibitor present in culture of host cell will increase the number of copies of the marker gene. Since the amplified region is associated with the coding sequence of the antibody, production of the antibody will also increase (Crouse et al., Mol. Cell. Biol. 3:257 (1983)).

Vectors which use glutamine synthase (GS) or DHFR as the selectable markers can be amplified in the presence of the drugs methionine sulphoximine or methotrexate, respectively. An advantage of glutamine synthase based vectors are the availabilty of cell lines (e.g., the murine myeloma cell line, NSO) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are incorporated in their entireties by reference herein. Additionally, glutamine synthase expression vectors that may be used according to the present invention are commercially available from supliers, including, for example Lonza Biologics, Inc. (Portsmouth, N.H.). Expression and production of monoclonal antibodies using a GS expression system in murine myeloma cells is described in Bebbington et al., Bio/technology 10:169(1992) and in Biblia and Robinson Biotechnol. Prog. 11:1 (1995) which are incorporated in their entirities by reference herein.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain (Proudfoot, Nature 322:52 (1986); Kohler, Proc. Natl. Acad. Sci. USA 77:2 197 (1980)). The coding sequences for the heavy and light chains may comprise cDNA or genomic DNA.

Once an antibody molecule of the invention (including molecules comprising, or alternatively consisting of, antibody fragments or variants thereof) has been chemically synthesized or recombinantly expressed, it may be purified by any method known in the art for purification of an immunoglobulin molecule, or more generally, a protein molecule, such as, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art, to facilitate purification.

Antibodies of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the antibodies of the present invention may be glycosylated or may be non-glycosylated. In addition, antibodies of the invention may also include an initial modified methionine residue, in some cases as a result of host-mediated processes.

Antibodies of the invention can be chemically synthesized using techniques known in the art (e.g., see Creighton, 1983, Proteins: Structures and Molecular Principles, W.H. Freeman & Co., N.Y., and Hunkapiller, M., et al., 1984, Nature 310: 105-111). For example, a peptide corresponding to a fragment of an antibody of the invention can be synthesized by use of a peptide synthesizer. Furthermore, if desired, nonclassical amino acids or chemical amino acid analogs can be introduced as a substitution or addition into the antibody polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses antibodies which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The antibodies may also be modified with a detectable label, such as an enzymatic, fluorescent, radioisotopic or affinity label to allow for detection and isolation of the antibody.

Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters such as, for example, $^{213}$Bi, or other radioisotopes such as, for example, iodine ($^{131}$I, $^{125}$I, $^{123}$I, $^{121}$I), carbon ($^{14}$C), sulfur ($^{35}$S), tritium ($^3$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin.

In specific embodiments, antibodies of the invention may be labeled with Europium. For example, antibodies of the invention may be labelled with Europium using the DELFIA Eu-labeling kit (catalog# 1244-302, Perkin Elmer Life Sciences, Boston, Mass.) following manufacturer's instructions.

In specific embodiments, antibodies of the invention are attached to macrocyclic chelators useful for conjugating radiometal ions, including but not limited to, $^{111}$In, $^{177}$Lu, $^{90}$Y, $^{166}$Ho, $^{153}$Sm, $^{215}$Bi and $^{225}$Ac to polypeptides. In a preferred embodiment, the radiometal ion associated with the macrocyclic chelators attached to antibodies of the invention is $^{111}$In. In another preferred embodiment, the radiometal ion associated with the macrocyclic chelator attached to antibodies polypeptides of the invention is $^{90}$Y. In specific embodiments, the macrocyclic chelator is 1,4,7,10-tetraazacyclododecane-N,N',N'',N'''-tetraacetic acid (DOTA). In specific embodiments, the macrocyclic chelator is α-(5-isothiocyanato-2-methoxyphenyl)-1,4,7,10-tetraazacyclododecane-1,4,7,10-tetraacetic acid. In other specific embodiments, the DOTA is attached to the antibody of the invention via a linker molecule. Examples of linker molecules useful for conjugating a macrocyclic chelator such as DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

In one embodiment, antibodies of the invention are labeled with biotin. In other related embodiments, biotinylated antibodies of the invention may be used, for example, as an imaging agent or as a means of identifying one or more TRAIL receptor coreceptor or ligand molecules.

Also provided by the invention are chemically modified derivatives of antibodies of the invention which may provide additional advantages such as increased solubility, stability and in vivo or in vitro circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The antibodies may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the antibody with consideration of effects on functional or antigenic domains of the antibody. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins, e.g., antibodies, via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire antibodies chemically modified at the N-terminus of either the heavy chain or the light chain or both. Using polyethylene glycol as an illustration, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective chemical modification at the N-terminus may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the antibodies of the invention may be accomplished by any number of means. For example, polyethylene glycol may be attached to the antibody either directly or by an intervening linker. Linkerless systems for attaching polyethylene glycol to proteins are described in Delgado et al., Crit. Rev. Thera. Drug Carrier Sys. 9:249-304 (1992); Francis et al., Intern. J. of Hematol. 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of antibodies without an intervening linker employs tresylated MPEG, which is produced by the modification of monmethoxy polyethylene glycol (MPEG) using tresylchloride (C1SO2CH2CF3). Upon reaction of protein with tresylated MPEG, polyethylene glycol is directly attached to amine groups of the protein. Thus, the invention includes antibody-polyethylene glycol conjugates produced by reacting antibodies of the invention with a polyethylene glycol molecule having a 2,2,2-trifluoreothane sulphonyl group.

Polyethylene glycol can also be attached to antibodies using a number of different intervening linkers. For example, U.S. Pat. No. 5,612,460, the entire disclosure of which is incorporated herein by reference, discloses urethane linkers for connecting polyethylene glycol to proteins. Antibody-polyethylene glycol conjugates wherein the polyethylene glycol is attached to the antibody by a linker can also be produced by reaction of antibodies with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference.

Pegylated antibody products produced using the reaction chemistries set out herein are included within the scope of the invention.

The number of polyethylene glycol moieties attached to each antibody of the invention (i.e., the degree of substitution) may also vary. For example, the pegylated antibodies of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per antibody molecule. Methods for determining the degree of substitution are discussed, for example, in Delgado et al., Crit. Rev. Thera. Drug Carrier Sys. 9:249-304 (1992).

Characterization of Anti-GMAD Antibodies

Antibodies of the present invention (including molecules comprising, or alternatively consisting of, antibody fragments or variants thereof) may also be described or specified in terms of their binding to GMAD polypeptides or fragments or variants of GMAD polypeptides. In specific embodiments, antibodies of the invention bind GMAD polypeptides, or fragments or variants thereof, with a dissociation constant or $K_D$ of less than or equal to $5\times10^{-2}$ M, $10^{-2}$ M, $5\times10^{-3}$ M, $10^{-3}$ M, $5\times10^{4}$ M, $10^{4}$ M, $5\times10^{-5}$ M, or $10^{-5}$ M. More preferably, antibodies of the invention bind GMAD polypeptides or fragments or variants thereof with a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, antibodies of the invention bind GMAD polypeptides or fragments or variants thereof with a dissociation constant or $K_D$ less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. The invention encompasses antibodies that bind GMAD polypeptides with a dissociation constant or $K_D$ that is within any one of the ranges that are between each of the individual recited values.

In specific embodiments, antibodies of the invention bind GMAD polypeptides or fragments or variants thereof with an off rate ($k_{off}$) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. More preferably, antibodies of the invention bind GMAD polypeptides or fragments or variants thereof with an off rate ($k_{off}$) less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$. The invention encompasses antibodies that bind GMAD polypeptides with an off rate ($k_{off}$) that is within any one of the ranges that are between each of the individual recited values.

In other embodiments, antibodies of the invention bind GMAD polypeptides or fragments or variants thereof with an on rate ($k_{on}$) of greater than or equal to $10^{3}$ M$^{-1}$ sec$^{-1}$, $5\times10^{3}$ M$^{-1}$ sec$^{31}$, $10^{4}$ M$^{-1}$ sec$^{-1}$ or $5\times10^{4}$ M$^{-1}$ sec$^{-1}$. More preferably, antibodies of the invention bind GMAD polypeptides or fragments or variants thereof with an on rate ($k_{on}$) greater than or equal to $10^{5}$ M$^{-1}$ sec$^{-1}$, $5\times10^{5}$ M$^{-1}$ sec$^{-1}$, $10^{6}$ M$^{-1}$ sec$^{-1}$, or $5\times10^{6}$ M$^{-1}$ sec$^{-1}$ or $10^{7}$ M$^{-1}$ sec$^{-1}$. The invention encompasses antibodies that bind GMAD polypeptides with on rate ($k_{on}$) that is within any one of the ranges that are between each of the individual recited values.

The antibodies of the invention (including molecules comprising, or alternatively consisting of, antibody fragments or variants thereof) specifically bind to a polypeptide or polypeptide fragment or variant of a human GMAD polypeptide (SEQ ID NO:2). In another embodiment, the antibodies of the invention specifically bind to a polypeptide or polypeptide fragment or variant of a simian GMAD polypeptide. In yet another embodiment, the antibodies of the invention specifically bind to a polypeptide or polypeptide fragment or variant of a murine GMAD polypeptide. In one embodiment, the antibodies of the invention bind specifically to human and simian GMAD polypeptides. In another embodiment, the antibodies of the invention bind specifically to human GMAD polypeptides and murine GMAD polypeptides. More preferably, antibodies of the invention, preferentially bind to human GMAD polypeptides compared to murine GMAD polypeptides.

In preferred embodiments, the antibodies of the present invention (including molecules comprising, or alternatively consisting of, antibody fragments or variants thereof), specifically bind to GMAD polypeptides and do not cross-react with any other antigens. In preferred embodiments, the antibodies of the invention specifically bind to GMAD polypeptides (e.g., SEQ ID NO:2 or fragments or variants thereof) and do not cross-react with one or more GMAD-related (e.g., other FIZZ or RELM family) polypeptides.

By way of non-limiting example, an antibody may be considered to bind a first antigen preferentially if it binds said first antigen with a dissociation constant ($K_D$) that is less than the antibody's $K_D$ for the second antigen. In another non-limiting embodiment, an antibody may be considered to bind a first antigen preferentially if it binds said first antigen with an affinity (i.e., $K_D$) that is at least one order of magnitude less than the antibody's $K_D$ for the second antigen. In another non-limiting embodiment, an antibody may be considered to bind a first antigen preferentially if it binds said first antigen with an affinity (i.e., $K_D$) that is at least two orders of magnitude less than the antibody's $K_D$ for the second antigen.

In another non-limiting embodiment, an antibody may be considered to bind a first antigen preferentially if it binds said first antigen with an off rate ($k_{off}$) that is less than the antibody's $k_{off}$ for the second antigen. In another non-limiting embodiment, an antibody may be considered to bind a first antigen preferentially if it binds said first antigen with a $k_{off}$ that is at least one order of magnitude less than the antibody's $k_{off}$ for the second antigen. In another non-limiting embodiment, an antibody may be considered to bind a first antigen preferentially if it binds said first antigen with a $k_{off}$ that is at least two orders of magnitude less than the antibody's $k_{off}$ for the second antigen.

The invention also encompasses antibodies (including molecules comprising, or alternatively consisting of, antibody fragments or variants thereof) that have one or more of the same biological characteristics as one or more of the antibodies described herein. By "biological characteristics" is meant, the in vitro or in vivo activities or properties of the antibodies, such as, for example, the ablity to antagonize GMAD action (see, e.g., Example 3), the ability to increase insulin action, the ability to increase cellular uptake of insulin, the ability increase cellular uptake of glucose (e.g. glucose transport), the ability to inhibit cell-specific (e.g., adipocytes) GMAD secretion, and/or the ability to inhibit differentiation of GMAD or GMAD receptor expressing cells (e.g., adipocytes). Other biological activities that anti-GMAD antibodies may have, include, but are not limited to, the ability to stimulate GMAD mediated biological activity (e.g., the ability to decrease insulin action.) Optionally, the antibodies of the invention will bind to the same epitope as at least one of the antibodies specifically referred to herein. Such epitope binding can be routinely determined using assays known in the art.

The present invention provides for antibodies (including molecules comprising, or alternatively consisting of, antibody fragments or variants thereof), that inhibit one or more GMAD polypeptide mediated biological activities. In one embodiment, an antibody that inhibits one or more GMAD polypeptide mediated biological activities comprises, or alternatively consists of, a VH and/or a VL domain of at least one of the scFvs referred to in Table 1, or fragment or variant thereof. In a specific embodiment, an antibody that inhibits one or more GMAD polypeptide mediated biological activities comprises, or alternatively consists of, a VH and a VL domain of any one of the scFvs referred to in Table 1, or fragment or variant thereof. Nucleic acid molecules encoding these antibodies are also encompassed by the invention.

The present invention also provides for antibodies (including molecules comprising, or alternatively consisting of, antibody fragments or variants thereof), that increase insulin action. In one embodiment, an antibody that increases insulin action comprises, or alternatively consists of, a VH and/or a VL domain of any one of the scFvs referred to in Table 1, or fragment or variant thereof. In a specific embodiment, an antibody that increases insulin action comprises, or alternatively consists of, a VH and a VL domain of any one of the scFvs referred to in Table 1, or fragment or variant thereof. Nucleic acid molecules encoding these antibodies are also encompassed by the invention.

The present invention also provides for antibodies (including molecules comprising, or alternatively consisting of, antibody fragments or variants thereof), that increase cellular glucose uptake. In one embodiment, an antibody that increases cellular glucose uptake comprises, or alternatively consists of, a VH and/or a VL domain of any one of the scFvs referred to in Table 1, or fragment or variant thereof. In a specific embodiment, an antibody that increases cellular glucose uptake comprises, or alternatively consists of, a VH and a VL domain of any one of the scFvs referred to in Table 1, or fragment or variant thereof. Nucleic acid molecules encoding these antibodies are also encompassed by the invention.

The present invention also provides for antibodies (including molecules comprising, or alternatively consisting of, antibody fragments or variants thereof) that decrease cell-specific (e.g., adipocytes) GMAD expression. In one embodiment, an antibody that decreases cell-specific (e.g., adipocyte) GMAD expression, or alternatively consists of, a VH and/or a VL domain of any one of the scFvs referred to in Table 1, or fragment or variant thereof. In a specific embodiment, an antibody that decreases cell-specific (e.g., adipocyte) GMAD expression comprises, or alternatively consists of, a VH and a VL domain of any one of the scFvs referred to in Table 1, or fragment or variant thereof. Nucleic acid molecules encoding these antibodies are also encompassed by the invention.

The present invention also provides for antibodies (including molecules comprising, or alternatively consisting of, antibody fragments or variants thereof), that inhibit differentiation of GMAD or GMAD receptor expressing cells (e.g., adipocyte). In one embodiment, an antibody that inhibits differentiation of GMAD or GMAD receptor expressing cells comprises, or alternatively consists of, a VH and/or a VL domain of any one of the scFvs referred to in Table 1, or fragment or variant thereof. In a specific embodiment, an antibody that inhibits differentiation of GMAD or GMAD receptor expressing cells comprises, or alternatively consists of, a VH and a VL domain of any one of the scFvs referred to in Table 1, or fragment or variant thereof. Nucleic acid molecules encoding these antibodies are also encompassed by the invention.

The present invention also provides for antibodies (including molecules comprising, or alternatively consisting of, antibody fragments or variants thereof), which decrease insulin action. In one embodiment, an antibody that decreases insulin action comprises, or alternatively consists of, a VH and/or a VL domain of any one of the scFvs referred to in Table 1, or fragment or variant thereof. In a specific embodiment, an antibody that decreases insulin action comprises, or alternatively consists of, a VH and a VL domain of any one of the scFvs referred to in Table 1, or fragment or variant thereof. Nucleic acid molecules encoding these antibodies are also encompassed by the invention.

Antibodies of the present invention (including antibody fragments or variants thereof) may be characterized in a variety of ways. In particular, antibodies and related molecules of the invention may be assayed for the ability to specifically bind to GMAD polypeptides or a fragment or variant of a GMAD polypeptide using techniques described herein or routinely modifying techniques known in the art. Assays for the ability of the antibodies of the invention to specifically bind GMAD polypeptides or a fragment of GMAD polypeptides may be performed in solution (e.g., Houghten, Bio/Techniques 13:412-421(1992)), on beads (e.g., Lam, Nature 354:82-84 (1991)), on chips (e.g., Fodor, Nature 364:555-556 (1993)), on bacteria (e.g., U.S. Pat. No. 5,223,409), on spores (e.g., U.S. Pat. Nos. 5,571,698; 5,403,484; and 5,223,409), on plasmids (e.g., Cull et al., Proc. Natl. Acad. Sci. USA 89:1865-1869 (1992)) or on phage (e.g., Scott and Smith, Science 249:386-390 (1990); Devlin, Science 249:404-406 (1990); Cwirla et al., Proc. Natl. Acad. Sci. USA 87:7178-7182 (1990); and Felici, J. Mol. Biol. 222:301-310 (1991)) (each of these references is incorporated herein in its entirety by reference). Such assays may be used to identify antibodies that specifically bind to GMAD polypeptides or a fragment or variant of a GMAD polypeptide.

The antibodies of the invention may be assayed for specific binding to GMAD polypeptides and cross-reactivity with other antigens by any method known in the art. Immunoassays which can be used to analyze specific binding and cross-reactivity include, but are not limited to, competitive and non-competitive assay systems using techniques such as BIAcore analysis, FACS (fluorescence activated cell sorter) analysis, immunofluorescence, immunocytochemistry, radioimmunoassays, ELISA (enzyme linked immunosorbent assay), "sandwich" immunoassays, immunoprecipitation assays, western blots, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

ELISAs comprise preparing antigen, coating the well of a 96-well microtiter plate with the antigen, washing away antigen that did not bind the wells, adding the antibody of interest conjugated to a detectable compound such as an enzymatic substrate (e.g., horseradish peroxidase or alkaline phosphatase) to the wells and incubating for a period of time, washing away unbound antibodies or non-specifically bound antibodies, and detecting the presence of the antibodies specifically bound to the antigen coating the well. In ELISAs, the antibody of interest does not have to be conjugated to a detectable compound; instead, a second antibody (which recognizes the antibody of interest) conjugated to a detectable compound may be added to the well. Alternatively, the antigen need not be directly coated to the well; instead the ELISA plates may be coated with an anti-Ig Fc antibody, and the antigen, in the form of a GMAD-Fc fusion protein, may be bound to the anti-Ig Fc coated to the plate. This may be desirable so as to maintain the antigen protein (e.g., a GMAD polypeptide) in a more native conformation than it may have when it is directly coated to a plate. In another alternative, instead of coating the well with the antigen, the antibody may be coated to the well. In this case, the detectable molecule could be the antigen conjugated to a detectable compound such as an enzymatic substrate (e.g., horseradish peroxidase or alkaline phosphatase). One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody (including an scFv or other molecule comprising, or alternatively consisting of, antibody fragments or variants thereof) to an antigen and the off-rate of an antibody-antigen interaction can be determined by competitive binding assays. One example of a competitive binding assay is a radioimmunoassay comprising the incubation of labeled antigen (e.g., antigen labeled with $^3$H or $^{125}$I), or fragment or variant thereof with the antibody of interest in the presence of increasing amounts of unlabeled antigen, and the detection of the antibody bound to the labeled antigen. The affinity of the antibody of the present invention for GMAD and the binding off-rates can be determined from the data by Scatchard plot analysis. Competition with a second antibody can also be determined using radioimmunoassays. In this case, GMAD polypeptide is incubated with an antibody of the present invention conjugated to a labeled compound (e.g., compound labeled with $^3$H or $^{125}$I) in the presence of increasing amounts of an unlabeled second anti-GMAD antibody. This kind of competitive assay between two antibodies, may also be used to determine if two antibodies bind the same, closely associated (e.g, overlapping), or different epitopes.

In a preferred embodiment, BIAcore kinetic analysis is used to determine the binding on and off rates of antibodies (including antibody fragments or variants thereof) to GMAD, or fragments of GMAD. BIAcore kinetic analysis comprises analyzing the binding and dissociation of antibodies from chips with immobilized GMAD on their surface.

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40 degrees C., adding protein A and/or protein G sepharose beads to the cell lysate, incubating for about an hour or more at 40 degrees C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

Antibody Conjugates

The present invention encompasses antibodies (including antibody fragments or variants thereof), recombinantly fused or chemically conjugated (including both covalent and non-covalent conjugations) to a heterologous polypeptide (or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. For example, antibodies of the invention may be used to target heterologous polypeptides to particular cell types (e.g., cancer cells), either in vitro or in vivo, by fusing or conjugating the heterologous polypeptides to antibodies of the invention that are specific for particular cell surface antigens or which bind antigens that bind particular cell surface receptors. Antibodies of the invention may also be fused to albumin (including but not limited to recombinant human serum albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention. Such fusion proteins may, for example, facilitate purification and may increase half-life in vivo. Antibodies fused or conjugated to heterologous polypeptides may also be used in in vitro immunoassays and purification methods using methods known in the art. See e.g., Harbor et al., supra, and PCT publication WO 93/2 1232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising, or alternatively consisting of, heterologous polypeptides fused or conjugated to antibody fragments. For example, the heterologous polypeptides may be fused or conjugated to a Fab fragment, Fd fragment, Fv fragment, F(ab)$_2$ fragment, or a portion thereof. Methods for fusing or conjugating polypeptides to antibody portions are known in the art. See, e.g., U.S. Pat. Nos. 5,356,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88: 10535-10539 (1991); Zheng et al., J. Immunol. 154:5590-5600 (1995); and Vil et al., Proc. Natl. Acad. Sci. USA 89:11357-11341 (1992) (said references incorporated by reference in their entireties).

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of antibodies (including molecules comprising, or alternatively consisting of, antibody fragments or variants thereof), such methods can be used to generate antibodies with altered activity (e.g., antibodies with higher affinities and lower dissociation rates). See, generally, U.S. Pat. Nos. 5,605,793; 5,811,238; 5,830,721; 5,834,252; and 5,837,458, and Patten et al., Curr. Opinion Biotechnol. 8:724-35 (1997); Harayama, Trends Biotechnol. 16(2):76-82 (1998); Hansson, et al., J. Mol. Biol. 287: 265-76 (1999); and Lorenzo and Blasco, Biotechniques 24(2):308-13 (1998) (each of these patents and publications are hereby incorporated by reference in its entirety). In one embodiment, polynucleotides encoding antibodies of the invention may be altered by being subjected to random mutagenesis by error-prone PCR, random nucleotide insertion or other methods prior to recombination. In another embodiment, one or more portions of a polynucleotide encoding an antibody which portions specifically bind to GMAD may be recombined with one or more components, motifs, sections, parts, domains, fragments, etc. of one or more heterologous molecules.

Moreover, the antibodies of the present invention (including antibody fragments or variants thereof) can be fused to marker sequences, such as a polypeptides to facilitate purification. In preferred embodiments, the marker amino acid sequence is a hexa-histidine polypeptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., Cell 37:767 (1984)) and the FLAG® tag (Stratagene, La Jolla, Calif.).

The present invention further encompasses antibodies (including antibody fragments or variants thereof), conjugated to a diagnostic or therapeutic agent. The antibodies can be used diagnostically to, for example, monitor or prognose the development or progression of a tumor as part of a clinical testing procedure or monitor or prognose type II diabetes to, e.g., determine the efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include, but are not limited to, horseradish peroxidase, alkaline phosphatase, beta-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not Imited to, luciferase, luciferin, and aequorin; and examples of suitable radioactive material include, but are not limited to, iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{135}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh and $^{97}$Ru.

Further, an antibody of the invention (including antibody fragments or variants thereof), may be coupled or conjugated to a therapeutic moiety such as a cytotoxin, e.g., a cytostatic or cytocidal agent, a therapeutic agent or a radioactive metal ion, e.g., alpha-emitters such as, for example, $^{213}$Bi, or other radioisotopes such as, for example, $^{103}$Pd, $^{135}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Y, $^{117}$Tin, $^{186}$Re, $^{188}$Re and $^{166}$Ho. In specific embodiments, an antibody or fragment thereof is attached to macrocyclic chelators that chelate radiometal ions, including but not limited to, $^{177}$Lu, $^{90}$Y, $^{166}$Ho, and $^{153}$Sm, to polypeptides. In specific embodiments, the macrocyclic chelator is 1,4,7,10-tetraazacyclododecane-N,N',N",N'''-tetraacetic acid (DOTA). In other specific embodiments, the DOTA is attached to the an antibody of the invention or fragment thereof via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al., Nucl. Med. Biol. 26(8):943-50, 1999 which are hereby incorporated by reference in their entirety.

A cytotoxin or cytotoxic agent includes any agent that is detrimental to cells. Examples include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, thymidine kinase, endonuclease, RNAse, and puromycin and fragments, variants or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques known in the art may be applied to label antibodies of the invention. Such techniques include, but are not limited to, the use of bifunctional conjugating agents (see e.g., U.S. Pat. Nos. 5,756,065; 5,714,711; 5,696,239; 5,652,371; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

The antibodies of the invention which are conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, but are not limited to, for example, a toxin such as abrin, ricin A, alpha toxin, pseudomonas exotoxin, or diphtheria toxin, saporin, momordin, gelonin, pokeweed antiviral protein, alpha-sarcin and cholera toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (see, International Publication No. WO 97/35899), Fas Ligand (Takahashi et al., Int. Immunol., 6:1567-1574 (1994)), VEGI (see, International Publication No. WO 99/23105), a thrombotic agent or an anti-angiogenic agent, e.g., angiostatin or endostatin; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

Antibodies of the invention (including antibody fragments or variants thereof), may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating a therapeutic moiety to antibodies are well known, see, e.g., Arnon et al., "Monoclonal Antibodies For immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody of the invention can be conjugated to a second antibody to form an antibody heteroconjugate as described by Segal in U.S. Pat. No. 4,676,980, which is incorporated herein by reference in its entirety.

An antibody of the invention (including an other molecules comprising, or alternatively consisting of, an antibody fragment or variant thereof), with or without a therapeutic moiety conjugated to it, administered alone or in combination with cytotoxic factor(s) and/or cytokine(s) can be used as a therapeutic.

Uses of Antibodies of the Invention

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of GMAD polypeptides in biological samples. See, e.g., Harlow et al., Antibodies: A Laboratory Manual, (Cold Spring Harbor Laboratory Press, 2nd ed. 1988) (incorporated by reference herein in its entirety).

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types, particularly of adipose cells. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell,* 96:737-49 (1999)).

These techniques allow for the screening of particular populations of cells, such as adipocytes (e.g., in Type I or II diabetes patients). Alternatively, these techniques allow for the screening of mast cells, eosinophils, lymphocytes and bronchial tissue for the expression of GMAD.

Epitope Mapping

The present invention provides antibodies (including antibody fragments or variants thereof), which can be used to identify epitopes of a GMAD polypeptide. In particular, the antibodies of the present invention can be used to identify epitopes of a human GMAD polypeptide (e.g., SEQ ID NO:2) or a GMAD polypeptide expressed on human cells; a murine GMAD or a GMAD polypeptide expressed on murine cells; a rat GMAD polypeptide or a GMAD polypeptide expressed on rat cells; or a monkey GMAD polypeptide or a GMAD polypeptide expressed on monkey cells, using techniques described herein or otherwise known in the art. Fragments which function as epitopes may be produced by any conventional means. (See, e.g., Houghten, Proc. Natl. Acad. Sci. USA 82:5131-5135 (1985), further described in U.S. Pat. No. 4,711,211.) Identified epitopes of antibodies of the present invention may, for example, be used as vaccine candidates, i.e., to immunize an individual to elicit antibodies against the naturally occurring forms of GMAD polypeptides.

Diagnostic Uses of Antibodies

Labeled antibodies of the invention (including molecules comprising, or alternatively consisting of, antibody fragments or variants thereof) which specifically bind to a GMAD polypeptide can be used for diagnostic purposes to detect, diagnose, prognose, or monitor diseases and/or disorders. In specific embodiments, labeled antibodies of the invention (including molecules comprising, or alternatively consisting of, antibody fragments or variants thereof) which specifically bind to a GMAD polypeptide can be used for diagnostic purposes to detect, diagnose, prognose, or monitor diseases and/or disorders associated with the aberrant expression and/or activity of a GMAD polypeptide.

Thus, the invention provides a diagnostic method of a disorder, which involves (a) assaying the expression level of a polypeptide of the present invention in cells or body fluid of an individual; and (b) comparing the assayed polypeptide expression level with a standard polypeptide expression level, whereby an increase or decrease in the assayed polypeptide expression level compared to the standard expression level is indicative of a disorder. In certain embodiments, the disorder diagnosed according to a method of the invention is selected from the group: diabetes (e.g., Non-Insulin-Dependent Diabetes Mellitus (NIDDM)), insulin insensitivity (i.e, insulin resistance), hyperinsulinemia, hyperglycemia, dyslipidemia, hypertension, coronary artery disease, renal failure, neuropathy (e.g., autonomic neuropathy, parasympathetic neuropathy, and polyneuropathy), a metabolic disorder (e.g., a glucose metabolic disorder), an endocrine disorder, obesity, weight loss, a liver disorder (e.g., liver disease, cirrhosis of the liver, and a disorder associated with liver transplant), and/or a condition associated with one or more of these disorders.

In particular embodiments, the invention provides a diagnostic method of a metabolic disorder, which involves (a) assaying the expression level of a polypeptide of the present invention in cells or body fluid of an individual; and (b) comparing the assayed polypeptide expression level with a standard polypeptide expression level, whereby an increase or decrease in the assayed polypeptide expression level compared to the standard expression level is indicative of a metabolic disorder.

In other embodiments, the invention provides a diagnostic method useful for diagnosis of insulin responsiveness, which involves (a) assaying the expression level of a polypeptide of the present invention in cells or body fluid of an individual; and (b) comparing the assayed polypeptide expression level with a standard polypeptide expression level, whereby an increase in the assayed polypeptide expression level compared to the standard expression level is indicative of an insulin responsiveness disorder (e.g., insulin resistance).

In other embodiments, the invention provides a diagnostic method useful for diagnosis of diabetes, which involves (a) assaying the expression level of a polypeptide of the present invention in cells or body fluid of an individual; and (b) comparing the assayed polypeptide expression level with a standard polypeptide expression level, whereby an increase in the assayed polypeptide expression level compared to the standard expression level is indicative of diabetes.

In other embodiments, the invention provides a diagnostic method useful for diagnosis and/or prognosis of a predisposition for diabetes, which involves (a) assaying the expression level of a polypeptide of the present invention in cells or body fluid of an individual; and (b) comparing the assayed polypeptide expression level with a standard polypeptide expression level, whereby a decrease in the assayed polypeptide expression level compared to the standard expression level is indicative of a predisposition for diabetes.

The invention provides for the detection of expression of a GMAD polypeptide comprising: (a) assaying the expression of a GMAD polypeptide in a biological sample from an individual using one or more antibodies of the invention that specifically binds to a GMAD polypeptide; and (b) comparing the level of a GMAD polypeptide with a standard level of a GMAD polypeptide, (e.g., the level in normal biological samples).

The invention provides for the detection of aberrant expression of a GMAD polypeptide comprising: (a) assaying the expression of a GMAD polypeptide in a biological sample from an individual using one or more antibodies of the invention that specifically binds to a GMAD polypeptide; and (b) comparing the level of a GMAD polypeptide with a standard level of a GMAD polypeptide, e.g., in normal biological samples, whereby an increase or decrease in the assayed level of a GMAD polypeptide compared to the standard level of a GMAD polypeptide is indicative of aberrant expression.

By "biological sample" is intended any fluids and/or cells obtained from an individual, body fluid, body tissue, body cell, cell line, tissue culture, or other source that may contain a GMAD polypeptide protein or mRNA. Body fluids include, but are not limited to, sera, plasma, urine, synovial fluid, spinal fluid, saliva, and mucous. Tissues samples may be taken from virtually any tissue in the body. Tissue samples may also be obtained from autopsy material. Methods for obtaining tissue biopsies and body fluids from mammals are well known in the art. Where the biological sample is to include mRNA, a tissue biopsy is the preferred source.

One aspect of the invention is the detection and diagnosis of a disease or disorder associated with aberrant expression of a GMAD polypeptide or a GMAD polypeptide receptor in an animal, preferably a mammal and most preferably a human. In one embodiment, diagnosis comprises: a) administering (for example, parenterally, subcutaneously, or intraperitoneally) to a subject an effective amount of a labeled antibody of the invention (including molecules comprising, or alternatively consisting of, antibody fragments or variants thereof) that specifically binds to a GMAD polypeptide; b) waiting for a time interval following the administering for permitting the labeled antibody to preferentially concentrate at sites in the subject where GMAD polypeptide is expressed (and for unbound labeled molecule to be cleared to background level); c) determining background level; and d) detecting the labeled antibody in the subject, such that detection of labeled antibody or fragment thereof above the background level and above or below the level observed in a person without the disease or disorder indicates that the subject has a particular disease or disorder associated with aberrant expression of a GMAD polypeptide or a GMAD polypeptide receptor. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of the disease or disorder is carried out by repeating the method for diagnosing the disease or disorder, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Therapeutic Uses of Antibodies

One or more antibodies of the present invention (including molecules comprising, or alternatively consisting of, antibody fragments or variants thereof) that specifically bind to GMAD may be used locally or systemically in the body as a therapeutic. The present invention is further directed to antibody-based therapies which involve administering antibodies of the invention (including molecules comprising, or alternatively consisting of, antibody fragments or variants thereof) to an animal, preferably a mammal, and most preferably a human, for preventing or treating one or more of the disclosed diseases, disorders, or conditions. Therapeutic compounds of the invention include, but are not limited to, antibodies of the invention and nucleic acids encoding antibodies (and anti-idiotypic antibodies) of the invention as described herein. In one embodiment, the antibodies of the invention can be used to treat, ameliorate or prevent diseases, disorders or conditions, including, but not limited to, any one or more of the diseases, disorders, or conditions described herein. The treatment and/or prevention of diseases, disorders, or conditions includes, but is not limited to, alleviating symptoms associated with those diseases, disorders or conditions. Antibodies of the invention may be provided in pharmaceutically acceptable compositions as known in the art or as described herein. In certain embodiments, properties of the antibodies of the present invention, as detailed in the Examples below, make the antibodies better therapeutic agents than previously described GMAD binding antibodies.

Type I and Type II Diabetes Mellitus

In highly preferred embodiments, the antibodies of the invention (including fragments, variants, and fusion proteins thereof, especially neutralizing or antagonistic antibodies) may be used to diagnose, prognose, treat, prevent, or ameliorate diabetes mellitus (type I and type II) as well as conditions associated with diabetes mellitus (type I and type II), including, but not limited to, diabetic ketoacidosis, diabetic coma, nonketotic hyperglycemic-hyperosmolar coma, seizures, mental confusion, drowsiness, cardiovascular disease (e.g., heart disease, atherosclerosis, microvascular disease, hypertension, stroke, and other cardiovascular diseases and disorders), dyslipidemia, kidney disease (e.g., renal failure, nephropathy other renal disorders), nerve damage, neuropathy, vision impairment (e.g., diabetic retinopathy and blindness), ulcers and impaired wound healing, infections (e.g., infectious diseases and infectious diseases, especially of the urinary tract and skin), carpal tunnel syndrome and Dupuytren's contracture.

In highly preferred embodiments, the antibodies of the invention (including fragments, variants, and fusion proteins thereof) are administered to a patient (preferably a human) to treat or prevent an insulin related disease, disorder, or condition. In specific embodiments, the compositions of the invention are administered to treat or prevent a disorder characterized by a state of insulin resistance. Disorders characterized by insulin resistance that may be treated (e.g., ameliorated), prevented, diagnosed, and/or prognosed using the compositions of the invention include, but are not limited to, NIDDM, obesity, hypertension, renal failure, androgen excess, and liver cirrhosis or liver disease, injury and/or complications associated with transplantation. In further, specific embodiments, the compositions of the invention are administered to treat or prevent hyperinsulinemia or a disorder or condition associated therewith.

In highly preferred embodiments, the antibodies of the invention (including fragments, variants, and fusion proteins thereof) may be used to diagnose, prognose, treat, prevent, or ameliorate diseases and disorders associated with aberrant glucose metabolism or glucose uptake into cells.

In other highly preferred embodiments, the antibodies of the invention (including fragments, variants, and fusion proteins thereof) are administered to an animal, preferably a mammal, and most preferably a human, in order to regulate the animal's weight. In specific embodiments, the antibodies, polynucleotides and/or polypeptides corresponding to this gene and/or agonists or antagonists thereof are administered to an animal, preferably a mammal, and most preferably a human, in order to control the animal's weight by modulating a biochemical pathway involving insulin. In still other embodiments the antibodies polynucleotides and/or polypeptides corresponding to this gene and/or agonists or antagonists thereof are administered to an animal, preferably a mammal, and most preferably a human, in order to control the animal's weight by modulating a biochemical pathway involving insulin-like growth factor.

In highly preferred embodiments, the antibodies of the invention (including fragments, variants, and fusion proteins thereof) are used to diagnose, treat, prevent, or prognose or monitor non-insulin dependent diabetes (NIDDM) or a condition associated with NIDDM.

In highly preferred embodiments, the antibodies of the invention (including fragments, variants, and fusion proteins thereof) are administered to a patient (preferably a human) to treat or prevent non-insulin dependent diabetes (NIDDM) or a condition associated with NIDDM.

In other preferred embodiments, the antibodies of the invention (including fragments, variants, and fusion proteins thereof) are used to diagnose, treat, prevent, or prognose or monitor insulin dependent diabetes (IDDM) or a condition associated with IDDM.

In other preferred embodiments, the antibodies of the invention (including fragments, variants, and fusion proteins thereof) are administered to a patient (preferably a human) to treat or prevent insulin dependent diabetes (IDDM) or a condition associated with IDDM.

In highly preferred embodiments, the antibodies of the invention (including fragments, variants, and fusion proteins thereof) are used to treat, prevent, ameliorate, diagnose and/or prognose diseases and disorders associated with aberrant glucose metabolism or glucose uptake into cells. In other preferred embodiments, the antibodies of the invention (including fragments, variants, and fusion proteins thereof) are used to treat, prevent, ameliorate, diagnose and/or prognose diseases and disorders associated with aberrant glucose metabolism or glucose uptake into cells.

In other highly preferred embodiments, the antibodies of the invention (including fragments, variants, and fusion proteins thereof) are administered to a patient (preferably a human) to regulate glucose metabolism. In highly preferred embodiments, the antibodies of the invention (including fragments, variants, and fusion proteins thereof) are administered to a patient (preferably a human) to increase glucose metabolism.

In other highly preferred embodiments, the antibodies of the invention (including fragments, variants, and fusion proteins thereof) are used treat, prevent, ameliorate, diagnose and/or prognose hyperglycemia.

In other highly preferred embodiments, the antibodies of the invention (including fragments, variants, and fusion proteins thereof) are used to diagnose, treat, prevent, or prognose or monitor dyslipidemia or a condition associated with dyslipidemia.

Additionally, in highly preferred embodiments, the antibodies of the invention (including fragments, variants, and fusion proteins thereof) are used to diagnose, treat, prognose or monitor obesity.

In other highly preferred embodiments, the antibodies of the invention (including fragments, variants, and fusion proteins thereof) are administered to a patient (preferably a human) to treat obesity or a condition associated with obesity.

In other highly preferred embodiments, the antibodies of the invention (including fragments, variants, and fusion proteins thereof) are administered to a patient (preferably a human) to limit weight gain.

In other highly preferred embodiments, the antibodies of the invention (including fragments, variants, and fusion proteins thereof) to suppress appetite.

In other preferred embodiments, the antibodies of the invention (including fragments, variants, and fusion proteins thereof) are administered to a patient (preferably a human) to increase appetite.

In other preferred embodiments, the antibodies of the invention (including fragments, variants, and fusion proteins thereof) are administered to a patient (preferably a human) to alter or regulate nutritional partitioning in the patient. In one embodiment, the antibodies of the invention (including fragments, variants, and fusion proteins thereof) are administered according to this method to reduce fat mass. In another embodiment, the antibodies of the invention (including fragments, variants, and fusion proteins thereof) are administered according to this method to increase muscle mass.

In other preferred embodiments, the antibodies of the invention (including fragments, variants, and fusion proteins thereof) are administered to a patient (preferably a human) to promote weight gain.

In other embodiments, the antibodies of the invention (including fragments, variants, and fusion proteins thereof) are used to diagnose, treat, prevent, or prognose or monitor hypertension or a condition associated with hypertension.

In other embodiments, the antibodies of the invention (including fragments, variants, and fusion proteins thereof) are used to diagnose, treat, prevent, or prognose or monitor coronary artery disease or a condition associated with coronary artery disease.

In other embodiments, the antibodies of the invention (including fragments, variants, and fusion proteins thereof) are used to diagnose, treat, prevent, or prognose or monitor a neuropathy, neural injury, or a condition associated with a neuropathy or neural injury. Neuropathies that can be diagnosed, treated, prevented, or prognosed using the compositions of the invention include, but are not limited to, autonomic neuropathy, parasympathetic neuropathy, and polyneuropathy. In preferred embodiments, the compositions of the invention are used to diagnose, treat, prevent, or prognose parasympathetic neuropathy or parasympathetic neural injury or conditions associated with parasympathetic neuropathy or parasympathetic neural injury. In highly preferred embodiments, the compositions of the invention are used to diagnose, treat, prevent, or prognose hepatic parasympathetic neuropathy or hepatic parasympathetic neural injury, and/or conditions associated with hepatic parasympathetic neuropathy or hepatic parasympathetic neural injury.

In one embodiment, the antibodies of the invention (including fragments, variants, and fusion proteins thereof) are administered to a patient (preferably a human) to increase glucose production in adipocytes and/or other cells.

Additionally, in one embodiment, the antibodies of the invention (including fragments, variants, and fusion proteins thereof) are administered to a patient (preferably a human) to increase gluconeogenesis in adipocytes and/or other cells.

In a highly preferred embodiment, the antibodies of the invention (including fragments, variants, and fusion proteins thereof) are administered to a patient (preferably a human) to modulate (e.g., increase) the effect of insulin on blood glucose levels.

A highly preferred embodiment of the invention is a method of increasing glucose uptake of a cell comprising contacting a cell with one or more GMAD polypeptides of the invention. A specific embodiment is this method performed in vitro. A specific embodiment is this method performed in vivo. A specific embodiment is where the cell is a liver cell, or where the cell is an adipocyte, or where the cell is a kidney cell, or where the cell is a muscle cell.

In one embodiment, the invention provides a method of increasing glucose production of a cell comprising contacting a cell with a GMAD antibody. In one embodiment, this method is performed in vitro. In another embodiment this method is performed in vivo. In specific embodiments, the cell contacted according to this method is a liver cell, an adipocyte, a kidney cell, or a muscle cell.

In another embodiment, the invention provides a method of decreasing glucose uptake by a cell comprising contacting a cell with a GMAD antibody of the invention (including fragments, variants, and fusion proteins as described herein). In one embodiment, this method is performed in vitro. In another embodiment this method is performed in vivo. In specific embodiments, the cell contacted according to this method is a liver cell, an adipocyte, a kidney cell, a skin cell, a bone cell, or a skeletal muscle cell.

In another embodiment, the invention provides a method of increasing the sensitivity of a cell to insulin comprising contacting a cell with a GMAD antibody of the invention (including fragments, variants, and fusion proteins as described herein). In one embodiment, this method is performed in vitro. In another embodiment this method is performed in vivo. In specific embodiments, the cell contacted according to this method is a liver cell, an adipocyte, a kidney cell, a skin cell, a bone cell, or a skeletal muscle cell.

In another highly preferred embodiment, the antibodies of the invention are used to treat, prevent, diagnose, or ameliorate cardiovascular disease.

In another highly preferred embodiment, the antibodies of the invention are used to treat, prevent, diagnose, or ameliorate complications associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, infection (e.g., an infectious disease or disorder as described in the "Infectious Diseases" section below, especially of the urinary tract and skin), carpal tunnel syndrome and Dupuytren's contracture).

In another highly preferred embodiment, the antibodies of the invention are used to treat, prevent, diagnose, or ameliorate obesity and/or complications associated with obesity.

In additional highly preferred embodiments, the antibodies of the invention are used to treat, prevent, diagnose, or ameliorate weight loss or alternatively, weight gain.

In additional highly preferred embodiments, the antibodies of the invention are used to treat, prevent, diagnose, or ameliorate complications associated with insulin resistance.

In additional highly preferred embodiments, the antibodies of the invention are used to treat, prevent, diagnose, or ameliorate complications associated with hyperglycemia.

In additional highly preferred embodiments, the antibodies of the invention are used to treat, prevent, diagnose, or ameliorate complications associated with obesity.

In additional preferred embodiments, the antibodies of the invention are used to treat, prevent, diagnose, or ameliorate Fragile X Syndrome.

In additional preferred embodiments, the antibodies of the invention are used to treat, prevent, diagnose, or ameliorate disorders of the musculoskeletal systems including myopathies, muscular dystrophy, and/or as described herein.

In additional highly preferred embodiments, the antibodies of the invention are used to treat, prevent, diagnose, or ameliorate glycogen storage disease (e.g., glycogenoses), hepatitis, gallstones, cirrhosis of the liver, degenerative or necrotic liver disease, alcoholic liver diseases, fibrosis, liver regeneration, metabolic disease, dyslipidemia and cholesterol metabolism, and hepatocarcinomas.

In additional preferred embodiments, the antibodies of the invention are used to treat, prevent, diagnose, or ameliorate liver disorders, including, but not limited to, cirrhosis, hepatoblastoma, hepatocarcinoma, jaundice, hepatitis, liver metabolic diseases, and conditions that are attributable to the differentiation of hepatocyte progenitor cells.

Endocrine Disorders

In preferred embodiments, antibodies of the present invention, are used to treat, prevent, diagnose, and/or prognose disorders and/or diseases related to hormone imbalance, and/or disorders or diseases of the endocrine system.

Hormones secreted by the glands of the endocrine system control physical growth, sexual function, metabolism, and other functions. Disorders may be classified in two ways: disturbances in the production of hormones, and the inability of tissues to respond to hormones. The etiology of these hormone imbalance or endocrine system diseases, disorders or conditions may be genetic, somatic, such as cancer and some autoimmune diseases, acquired (e.g., by chemotherapy, injury or toxins), or infectious. Moreover, polynucleotides, polypeptides, antibodies, and/or agonists or antagonists of the present invention can be used as a marker or detector of a particular disease or disorder related to the endocrine system and/or hormone imbalance.

Endocrine system and/or hormone imbalance and/or diseases encompass disorders of uterine motility including, but not limited to: complications with pregnancy and labor (e.g., pre-term labor, post-term pregnancy, spontaneous abortion, and slow or stopped labor); and disorders and/or diseases of the menstrual cycle (e.g., dysmenorrhea and endometriosis).

Endocrine system and/or hormone imbalance disorders and/or diseases include disorders and/or diseases of the pancreas, such as, for example, diabetes mellitus, diabetes insipidus, congenital pancreatic agenesis, pheochromocytoma—islet cell tumor syndrome; disorders and/or diseases of the adrenal glands such as, for example, Addison's Disease, corticosteroid deficiency, virilizing disease, hirsutism, Cushing's Syndrome, hyperaldosteronism, pheochromocytoma; disorders and/or diseases of the pituitary gland, such as, for example, hyperpituitarism, hypopituitarism, pituitary dwarfism, pituitary adenoma, panhypopituitarism, acromegaly, gigantism; disorders and/or diseases of the thyroid, including but not limited to, hyperthyroidism, hypothyroidism, Plummer's disease, Graves' disease (toxic diffuse goiter), toxic nodular goiter, thyroiditis (Hashimoto's thyroiditis, subacute granulomatous thyroiditis, and silent lymphocytic thyroiditis), Pendred's syndrome, myxedema, cretinism, thyrotoxicosis, thyroid hormone coupling defect, thymic aplasia, Hurthle cell tumours of the thyroid, thyroid cancer, thyroid carcinoma, Medullary thyroid carcinoma; disorders and/or diseases of the parathyroid, such as, for example, hyperparathyroidism, hypoparathyroidism; disorders and/or diseases of the hypothalamus.

In addition, endocrine system and/or hormone imbalance disorders and/or diseases may also include disorders and/or diseases of the testes or ovaries, including cancer. Other disorders and/or diseases of the testes or ovaries further include, for example, ovarian cancer, polycystic ovary syndrome, Klinefelter's syndrome, vanishing testes syndrome (bilateral anorchia), congenital absence of Leydig's cells, cryptorchidism, Noonan's syndrome, myotonic dystrophy, capillary haemangioma of the testis (benign), neoplasias of the testis and neo-testis.

Moreover, endocrine system and/or hormone imbalance disorders and/or diseases may also include disorders and/or diseases such as, for example, polyglandular deficiency syndromes, pheochromocytoma, neuroblastoma, multiple Endocrine neoplasia, and disorders and/or cancers of endocrine tissues.

Inflammation and Inflammatory Disorders

In other embodiments, the antibodies of the invention (including fragments and variants thereof) may be used in the diagnosis, prognosis, prevention, and/or treatment of inflammatory disorders, as described herein.

In highly preferred embodiments, allergic reactions and conditions, such as asthma (particularly allergic asthma) or other respiratory problems, may also be treated, prevented, and/or diagnosed using polypeptides, antibodies, or polynucleotides of the invention, and/or agonists or antagonists thereof. Moreover, these molecules can be used to treat, prevent, and/or diagnose anaphylaxis, hypersensitivity to an antigenic molecule, or blood group incompatibility.

Allergic reactions and conditions, such as asthma (particularly allergic asthma) or other respiratory problems, may also be treated, prevented, and/or diagnosed using antibodies of the invention. Moreover, these molecules can be used to treat, prevent, and/or diagnose anaphylaxis, hypersensitivity to an antigenic molecule, or blood group incompatibility.

Additionally, antibodies of the invention, may be used to treat or prevent IgE-mediated allergic reactions. Such allergic reactions include, but are not limited to, asthma, rhinitis, and eczema. In specific embodiments, polynucleotides, polypeptides, antibodies, and/or agonists or antagonists of the present invention may be used to modulate IgE concentrations in vitro or in vivo.

Moreover, antibodies of the present invention have uses in the diagnosis, prognosis, prevention, and/or treatment of inflammatory conditions. For example, since polypeptides, antibodies, or polynucleotides of the invention, and/or agonists or antagonists of the invention may inhibit the activation, proliferation and/or differentiation of cells involved in an inflammatory response, these molecules can be used to diagnose, prognose, prevent, and/or treat chronic and acute inflammatory conditions. Such inflammatory conditions include, but are not limited to, for example, inflammation associated with infection (e.g., septic shock, sepsis, or systemic inflammatory response syndrome), ischemia-reperfusion injury, endotoxin lethality, complement-mediated hyperacute rejection, nephritis, cytokine or chemokine induced lung injury, inflammatory bowel disease, Crohn's disease, over production of cytokines (e.g., TNF or IL-1.), respiratory disorders (such as, e.g., asthma and allergy); gastrointestinal disorders (such as, e.g., inflammatory bowel disease); cancers (such as, e.g., gastric, ovarian, lung, bladder, liver, and breast); CNS disorders (such as, e.g., multiple sclerosis; ischemic brain injury and/or stroke; traumatic brain injury; neurodegenerative disorders, such as, e.g., Parkinson's disease and Alzheimer's disease; AIDS-related dementia; and prion disease); cardiovascular disorders (such as, e.g., atherosclerosis, myocarditis, cardiovascular disease, and cardiopulmonary bypass complications); as well as many additional diseases, conditions, and disorders that are characterized by inflammation (such as, e.g., hepatitis, rheumatoid arthritis, gout, trauma, pancreatitis, sarcoidosis, dermatitis, renal ischemia-reperfusion injury, Grave's disease, systemic lupus erythematosis, diabetes mellitus, and allogenic transplant rejection).

Because inflammation is a fundamental defense mechanism, inflammatory disorders can effect virtually any tissue of the body. Accordingly, antibodies of the invention have uses in the treatment of tissue-specific inflammatory disorders, including, but not limited to, adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myosititis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, sclerochoroiditis, scrotitis, sinusitis, sponylitis, steatitis, stomatitis, synovitis, syringitis, tendonitis, tonsillitis, urethritis, and vaginitis.

In specific embodiments, antibodies of the invention, are useful to treat, diagnose, and/or prevent organ transplant rejections and graft-versus-host disease. Organ rejection occurs by host immune cell destruction of the transplanted tissue through an immune response. Similarly, an immune response is also involved in GVHD, but, in this case, the foreign transplanted immune cells destroy the host tissues.

Polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing organ rejection or GVHD. In specific embodiments, polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing experimental allergic and hyperacute xenograft rejection.

In another specific embodiment, antibodies of the invention are used as an agent to induce higher affinity antibodies.

In another specific embodiment, antibodies of the invention are used as an agent to increase serum immunoglobulin concentrations.

Cardiovascular Disorders

Antibodies of the invention may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Antibodies of the invention are especially effective for the treatment of critical limb ischemia and coronary disease.

Antibodies of the invention may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides may be administered as part of a Therapeutic, described in more detail below. Methods of delivering polynucleotides are described in more detail herein.

Additional Therapeutic Uses of Antibodies

The present invention is directed to a method for inhibiting GMAD-mediated insulin resistance, which involves administering to a cell (which expresses a GMAD polypeptide in vitro or in vivo), an effective amount of an antibody of the invention, capable of decreasing GMAD mediated signaling (through a GMAD receptor). Preferably, GMAD mediated signaling is decreased to treat a disease wherein increased GMAD expression is exhibited.

The antibodies of the invention can be used to treat, ameliorate or prevent diseases, disorders or conditions associated with aberrant expression and/or activity of GMAD, including, but not limited to, any one or more of the diseases, disorders, or conditions described herein. The treatment and/or prevention of diseases, disorders, or conditions associated with aberrant GMAD expression and/or activity includes, but is not limited to, alleviating symptoms associated with those diseases, disorders or conditions. Antibodies of the invention may be provided in pharmaceutically acceptable compositions as known in the art or as described herein.

Further, antibodies of the present invention (including molecules comprising, or alternatively consisting of, antibody fragments or variants thereof) which inhibit GMAD-mediated biological activities (e.g., the inhibition of insulin action) can be administered to an animal to treat, prevent or ameliorate a disease or disorder described herein, particularly Type I and II Diabetes Mellitus and inflammatory disorders. These antibodies may diminish either all or a subset of the biological activities of GMAD, for example, by inducing a conformational change in GMAD. In a specific embodiment, an antibody of the present invention that inhibits GMAD activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to GMAD activity in absence of the antibody is administered to an animal to treat, prevent or ameliorate a disease or disorder. In another embodiment, a combination of antibodies, a combination of antibody fragments, a combination of antibody variants, or a combination of antibodies, antibody fragments and/or antibody variants that inhibit GMAD activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to GMAD activity in absence of the said antibodies or antibody fragments and/or antibody variants is administered to an animal to treat, prevent or ameliorate a disease or disorder.

Further, antibodies of the present invention (including molecules comprising, or alternatively consisting of, antibody fragments or variants thereof) which inhibit GMAD-mediated biological activities (e.g., the inhibition of insulin action) can be administered to an animal to treat, prevent or ameliorate a disease or disorder associated with aberrant GMAD expression, excess or aberrant GMAD function, or aberrant GMAD receptor expression. These antibodies may diminish either all or a subset of the biological activities of GMAD, for example, by preventing GMAD interaction with its receptor. In a specific embodiment, an antibody of the present invention that diminishes GMAD activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to GMAD activity in absence of the antibody is administered to an animal to treat, prevent or ameliorate a disease or disorder associated with aberrant GMAD expression, excess GMAD function, or aberrant GMAD receptor expression. In another embodiment, a combination of antibodies, a combination of antibody fragments, a combination of antibody variants, or a combination of antibodies, antibody fragments and/or antibody variants that diminish GMAD activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to GMAD activity in absence of the said antibodies or antibody fragments and/or antibody variants is administered to an animal to treat, prevent or ameliorate a disease or disorder associated with aberrant GMAD expression or excess GMAD function or aberrant GMAD receptor expression.

Antibodies of the present invention (including molecules comprising, or alternatively consisting of, antibody fragments or variants thereof) that function as agonists or antagonists of GMAD, preferably of GMAD signal transduction, can be administered to an animal to treat, prevent or ameliorate a disease or disorder associated with aberrant GMAD expression, lack of GMAD function, or aberrant GMAD receptor expression. For example, antibodies of the invention that act as GMAD agonists may be administered to an animal to treat, prevent or ameliorate a disease or disorder associated with aberrant GMAD expression, lack of GMAD function, or aberrant GMAD receptor expression. As an alternative example, antibodies of the invention which disrupt or prevent the interaction between GMAD and its receptor or inhibit, reduce, or prevent signal transduction through one or more GMADs, may be administered to an animal to treat, prevent or ameliorate a disease or disorder associated with aberrant GMAD expression, lack of GMAD function, or aberrant GMAD receptor expression. Antibodies of the invention which do not prevent GMAD from binding its receptor but inhibit or downregulate GMAD signal transduction can be administered to an animal to treat, prevent or ameliorate a disease or disorder associated with aberrant GMAD expression, lack of GMAD function or aberrant GMAD receptor expression. The ability of an antibody of the invention to enhance, inhibit, upregulate or downregulate GMAD signal transduction may be determined by techniques described herein or otherwise known in the art. For example, GMAD-induced receptor activation and the activation of signaling molecules can be determined by detecting the association of adaptor proteins with the GMAD receptors, by immunoprecipitation followed by western blot analysis (for example, as described herein).

Further, antibodies of the present invention (including molecules comprising, or alternatively consisting of, antibody fragments or variants thereof) which activate GMAD-mediated biological activities (e.g., the inhibition of insulin action) can be administered to an animal to treat, prevent or ameliorate a disease or disorder associated with aberrant GMAD expression, or aberrant GMAD receptor expression. These antibodies may potentiate or activate either all or a subset of the biological activities of GMAD, for example, by inducing a conformational change in GMAD. In a specific embodiment, an antibody of the present invention that increases GMAD activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to GMAD activity in absence of the antibody is administered to an animal to treat, prevent or ameliorate a disease or disorder associated with aberrant GMAD expression, lack of GMAD function, or aberrant GMAD receptor expression. In another embodiment, a combination of antibodies, a combination of antibody fragments, a combination of antibody variants, or a combination of antibodies, antibody fragments and/or antibody variants that increase GMAD activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to GMAD activity in absence of the said antibodies or antibody fragments and/or antibody variants is administered to an animal to treat, prevent or ameliorate a disease or disorder associated with aberrant GMAD expression or lack of GMAD function or aberrant GMAD receptor expression.

In a specific embodiment, an antibody of the present invention (including molecules comprising, or alternatively consisting of, antibody fragments or variants thereof) that inhibits or downregulates, in full or in part, GMAD activity (e.g., inhibition of insulin action) by at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to GMAD activity in absence of the antibody is administered to an animal to treat, prevent or ameliorate a disease or disorder associated with aberrant GMAD expression, excessive GMAD function, aberrant GMAD receptor expression, or excessive GMAD receptor function. In another embodiment, a combination of antibodies, a combination of antibody fragments, a combination of antibody variants, or a combination of antibodies, antibody fragments, and/or variants that inhibit or downregulate GMAD activity by at least 95%, at least 90%, at least 85%, at least 80%, at least 75%, at least 70%, at least 65%, at least 60%, at least 55%, at least 50%, at least 45%, at least 40%, at least 45%, at least 35%, at least 30%, at least 25%, at least 20%, or at least 10% relative to GMAD activity in absence of said antibodies, antibody fragments, and/or antibody variants are administered to an animal to treat, prevent or ameliorate a disease or disorder associated with aberrant GMAD expression, excessive GMAD function, aberrant GMAD receptor expression, or excessive GMAD receptor function.

Therapeutic/Prophylactic Compositions and Administration

The invention provides methods of treatment, inhibition and prophylaxis by administration to a subject of an effective amount of antibody (or fragment or variant thereof) or pharmaceutical composition of the invention, preferably an antibody of the invention. In a preferred aspect, an antibody or fragment or variant thereof is substantially purified (i.e., substantially free from substances that limit its effect or produce undesired side-effects). The subject is preferably an animal, including but not limited to, animals such as cows, pigs, horses, chickens, cats, dogs, etc., and is preferably a mammal, and most preferably a human.

Formulations and methods of administration that can be employed when the compound comprises a nucleic acid or an immunoglobulin are described above; additional appropriate formulations and routes of administration can be selected from among those described herein below.

Various delivery systems are known and can be used to administer an antibody of the invention or a fragment or variant thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of introduction include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the composition can be delivered in a vesicle, in particular a liposome (see Langer, Science 249:1527-1535 (1990); Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid.).

In yet another embodiment, the composition can be delivered in a controlled release system. In one embodiment, a pump may be used (see Langer, supra; Sefton, CRC Crit. Ref.

Biomed. Eng. 14:20 1 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:71 (1983); see also Levy et al., Science 228: 190 (1985); During et al., Ann. Neurol. 25:35 1 (1989); Howard et al., J.Neurosurg. 7 1:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1535 (1990)).

In a specific embodiment where the composition of the invention is a nucleic acid encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of therapeutic or pharmaceutical compositions of the invention may be reduced by enhancing uptake and tissue penetration (e.g., into the brain) of the antibodies by modifications such as, for example, lipidation.

Generally, administration of products of a species origin or species reactivity (in the case of antibodies) that is the same species as that of the patient is preferred. Thus, in a preferred embodiment, human antibodies, fragments, or variants, (e.g., derivatives), or nucleic acids, are administered to a human patient for therapy or prophylaxis.

It is preferred to use high affinity and/or potent in vivo inhibiting and/or neutralizing antibodies of the invention (including molecules comprising, or alternatively consisting of, antibody fragments or variants thereof) that specifically bind to one or more GMAD polypeptides, or polynucleotides encoding antibodies that specifically bind to one or more GMAD polypeptides, for both immunoassays and therapy of disorders related to GMAD polynucleotides or polypeptides, including fragments thereof. Such antibodies will preferably have an affinity for GMAD polypeptides and/or GMAD polypeptide fragments. Preferred binding affinities include those with a dissociation constant or $K_D$ of less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, antibodies of the invention bind GMAD polypeptides or fragments or variants thereof with a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, antibodies of the invention bind GMAD polypeptides or fragments or variants thereof with a dissociation constant or $K_D$ less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. In a preferred embodiment, antibodies of the invention inhibit proliferation, differentiation, and/or apoptosis of GMAD receptor expressing cells. In an additional preferred embodiment, antibodies of the invention induce differentiation of GMAD receptor expressing cells.

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibody and antibody compositions of the invention may be administered alone or in combination with other therapeutic agents, including but not limited to anti-diabetic agents, chemotherapeutic agents, antibiotics, antivirals, anti-retroviral agents, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

Combination Therapies with Anti-GMAD Antibodies, Anti-Diabetic Drugs, and/or Immunomodulatory Agents, Anti-GMAD antibodies may be administered in combination with other anti-GMAD antibodies, GMAD, and/or antidiabetic drugs.

In specific embodiments, an antibody of the invention that specifically binds GMAD is used or administered in combination with a second antibody that specifically binds GMAD. In another embodiment, the antibodies specific for GMAD are antagonistic antibodies that inhibit GMAD secretion and/ or GMAD biological activity (e.g., inhibition of insulin action, inhibition of glucose uptake). In a specific embodiment, the combination of anti-GMAD treatment inhibits more GMAD biological activity than either anti-GMAD antibody treatment alone.

In another embodiment, the antibodies specific for GMAD are agonistic antibodies that stimulate cellular insulin resistance. In a specific embodiment, the combination of anti-GMAD treatment sitmulates more insulin resistance than either anti-GMAD antibody treatment alone. The anti-GMAD antibodies can be administered either simultaneously, sequentially, or a combination of simultaneous or sequential administration throughout the dosage regimen. In another specific embodiment anti-GMAD antibodies are used or administered in combination with a chemotherapeutic drug, antidiabetic drug, and/or immunomodulatory drug. In a particular embodiment, the synergistic inhibition of insulin resistance from anti-GMAD antibody treatment, is more evident or more pronounced when the anti-GMAD antibodies are used or administered in combination with an antidiabetic drug, a chemotherapeutic agent, immunomodulatory drug, and/or a cross-linking reagent.

In one embodiment, the compositions of the invention are administered in combination with other antidiabetic drugs, including, but not limited to Thiazolidinediones, or TZDs including but not limited to, rosiglitazone, piogliatazone, and troglitazone. In another specific embodiment, compositions of the invention are used in combination with oral hypoglycemic sulfonylurea drugs including, but not limited to, acarbose, acetohexamide, chlorpropamide, glimepiride, glipizide, glyburide, metformin, tolazamide, and/or tolbutamide. In another specific embodiment, compositions of the invention are used in combination with insulin, insulin derivatives, and/or insulin substitutes, In still other embodiments, compositions of the invention are administered in combination with one or more of the following, Acenorm™; Acenorm™ Cor™; Acepress™; Acepril™; Aceten™; Adocor™; Alopresin™; Angiopril™; Apuzin™; Asisten™; Capace™; Capoten™; Capotena™; Capril™; Captensin™; Captoflux™; Captolane™; Captolong™; Captopress™; Captopril™; Captoprilan™; Captoril™; Captral™; Cardipril™; Cesplon™; Cryopril™; Debax™; Dexacap™; Ecapres™; Ecaten™; Epicordin™; Epsitron™; Farcopril™; Farmoten™; Hiperil™; Hypotensor™; Inhibace™; Isopresol™; Katopil™; Lopirin ™; Lopril™; Medepres™; Mereprine ™; Minitent™; Praten™; Precaptil™; Rilcapton™; Ropril™; Smarten™; Tensicap™; Tensiomen™; Tensobon™; Tenzib™; and Zorkaptil™. In still other embodiments, compositions of the invention are administered in combination with one or more of the following: a biguanide antidiabetic agent, a glitazone antidiabetic agent, and a sulfonylurea antidiabetic agent.

In other embodiments, antibody compositions of the invention may be administered in combination with anti-opportunistic infection agents. Anti-opportunistic agents that may be administered in combination with the albumin fusion proteins and/or polynucleotides of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF).

In a specific embodiment, antibody and antibody compositions of the invention are administered in combination with steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells. Other immunosuppressive agents that may be administered in combination with the compositions of the invention include, but are not limited to, prednisolone, methotrexate, thalidomide, methoxsalen, rapamycin, leflunomide, mizoribine (BREDININ™), brequinar, deoxyspergualin, and azaspirane (SKF 105685), ORTHOCLONE OKT® 3 (muromonab-CD3), SANDIMMUNE™, NEORAL™, SANGDYA™ (cyclosporine), PROGRAF® (FK506, tacrolimus), CELLCEPT® (mycophenolate motefil, of which the active metabolite is mycophenolic acid), IMURAN™ (azathioprine), glucocorticosteroids, adrenocortical steroids such as DELTASONE™ (prednisone) and HYDELTRASOL™ (prednisolone), FOLEX™ and MEXATE™ (methotrxate), OXSORALEN-ULTRA™ (methoxsalen) and RAPAMUNE™ (sirolimus). In a specific embodiment, immunosuppressants may be used to prevent rejection of organ or bone marrow transplantation.

In an additional embodiment, the antibody and antibody compositions of the invention are administered alone or in combination with an anti-inflammatory agent. Anti-inflammatory agents that may be administered with the antibody and antibody compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

Additional Combination Therapies

The antibodies of the invention (including molecules comprising, or alternatively consisting of, antibody fragments or variants thereof) may be administered alone or in combination with other therapeutic or prophylactic regimens (e.g., radiation therapy, chemotherapy, hormonal therapy, immunotherapy, anti-tumor agents, anti-angiogenesis and anti-inflammatory agents). Such combinatorial therapy may be administered sequentially and/or concomitantly.

The invention also encompasses combining the polynucleotides and/or antibodies of the invention with other proposed or conventional diabetic therapies. Thus, for example, the polynucleotides and/or antibodies of the invention can be combined with compounds that singly exhibit insulin stimulatory effects, and or glucose-transport action.

The antibodies and/or antibody compositions of the invention and/or agonists or antagonists thereof is administered to the patient by any suitable technique, including but not limited to, parenteral, sublingual, topical, intrapulmonary and intranasal, and those techniques further discussed herein.

In an additional embodiment, the antibody and antibody compositions of the invention are administered alone or in combination with an anti-angiogenic agent(s). Anti-angiogenic agents that may be administered with the antibody and antibody compositions of the invention include, but are not limited to, Angiostatin (Entremed, Rockville, Md.), Troponin-1 (Boston Life Sciences, Boston, Mass.), anti-Invasive Factor, retinoic acid and derivatives thereof, paclitaxel (Taxol), Suramin, Tissue Inhibitor of Metalloproteinase-1, Tissue Inhibitor of Metalloproteinase-2, VEGI, Plasminogen Activator Inhibitor-1, Plasminogen Activator Inhibitor-2, and various forms of the lighter "d group" transition metals. Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates. Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include, but are not limited to, platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d, L-3,4-dehydroproline, Thiaproline, alpha, alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or "CCA"; (Takeuchi et al., Agents Actions 36:312-316, 1992); and metalloproteinase inhibitors such as BB94.

Additional anti-angiogenic factors that may also be utilized within the context of the present invention include Thalidomide, (Celgene, Warren, N.J.); Angiostatic steroid; AGM-1470 (H. Brem and J. Folkman *J Pediatr. Surg.* 28:445-51 (1993)); an integrin alpha v beta 3 antagonist (C. Storgard et al., *J Clin. Invest.* 103:47-54 (1999)); carboxynaminolmidazole; Carboxyamidotriazole (CAI) (National Cancer Institute, Bethesda, Md.); Conbretastatin A-4 (CA4P) (OXiGENE, Boston, Mass.); Squalamine (Magainin Pharmaceuticals, Plymouth Meeting, Pa.); TNP-470, (Tap Pharmaceuticals, Deerfield, Ill.); ZD-0101 AstraZeneca (London, UK); APRA (CT2584); Benefin, Byrostatin-1 (SC359555); CGP-41251 (PKC 412); CM101; Dexrazoxane (ICRF187); DMXAA; Endostatin; Flavopridiol; Genestein; GTE; ImmTher; Iressa (ZD1839); Octreotide (Somatostatin); Panretin; Penacillamine; Photopoint; PI-88; Prinomastat (AG-3540) Purlytin; Suradista (FCE26644); Tamoxifen (Nolvadex); Tazarotene; Tetrathiomolybdate; Xeloda (Capecitabine); and 5-Fluorouracil.

Anti-angiogenic agents that may be administered in combination with the antibodies and/or the compositions of the invention may work through a variety of mechanisms including, but not limited to, inhibiting proteolysis of the extracellular matrix, blocking the function of endothelial cell-extracellular matrix adhesion molecules, by antagonizing the function of angiogenesis inducers such as growth factors, and inhibiting integrin receptors expressed on proliferating endothelial cells. Examples of anti-angiogenic inhibitors that interfere with extracellular matrix proteolysis and which may be administered in combination with the antibody and antibody compositions of the invention include, but are not limited to, AG-3540 (Agouron, La Jolla, Calif.), BAY-12-9566 (Bayer, West Haven, Conn.), BMS-275291 (Bristol Myers Squibb, Princeton, N.J.), CGS-27032A (Novartis, East Hanover, N.J.), Marimastat (British Biotech, Oxford, UK), and Metastat (Aetema, St-Foy, Quebec). Examples of anti-angiogenic inhibitors that act by blocking the function of endothelial cell-extracellular matrix adhesion molecules and which may be administered in combination with the antibody and antibody compositions of the invention include, but are not limited to, EMD-121974 (Merck KcgaA Darmstadt, Germany) and Vitaxin (lxsys, La Jolla, Calif./Medimmune, Gaithersburg, Md.). Examples of anti-angiogenic agents that act by directly antagonizing or inhibiting angiogenesis inducers and which may be administered in combination with the antibody and antibody compositions of the invention include, but are not limited to, Angiozyme (Ribozyme, Boulder, Colo.), Anti-VEGF antibody (Genentech, S. San Francisco, Calif.), PTK-787/ZK-225846 (Novartis, Basel, Switzerland), SU-101 (Sugen, S. San Francisco, Calif.), SU-5416 (Sugen, Pharmacia Upjohn, Bridgewater, N.J.), and SU-6668 (Sugen). Other anti-angiogenic agents act to indirectly inhibit angiogenesis. Examples of indirect inhibitors of angiogenesis which may be administered in combination with the antibody and antibody compositions of the invention include, but are not limited to, IM-862 (Cytran, Kirkland, Wash.), Interferon-alpha, IL-12 (Roche, Nutley, N.J.), and Pentosan polysulfate (Georgetown University, Washington, D.C.).

In a further embodiment, the antibody and antibody compositions of the invention are administered in combination with an antibiotic agent. Antibiotic agents that may be administered with the antibody and antibody compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

In a preferred embodiment, the antibody and antibody compositions of the invention are administered in combination with steroid therapy. Steroids that may be administered in combination with the antibody and antibody compositions of the invention, include, but are not limited to, oral corticosteroids, prednisone, and methylprednisolone (e.g., IV methylprednisolone). In a specific embodiment, antibody and antibody compositions of the invention are administered in combination with prednisone.

The antibodies and antibody compositions of the invention may be administered alone or in combination with other adjuvants. Adjuvants that may be administered with the antibody and antibody compositions of the invention include, but are not limited to, alum, alum plus deoxycholate (ImmunoAg), MTP-PE (Biocine Corp.), QS21 (Genentech, Inc.), BCG, and MPL. In a specific embodiment, antibody and antibody compositions of the invention are administered in combination with alum. In another specific embodiment, antibody and antibody compositions of the invention are administered in combination with QS-21. Further adjuvants that may be administered with the antibody and antibody compositions of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the antibody and antibody compositions of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In another specific embodiment, antibody and antibody compositions of the invention are used in combination with PNEUMOVAX-23™ to treat, prevent, and/or diagnose infection and/or any disease, disorder, and/or condition associated therewith. In one embodiment, antibody and antibody compositions of the invention are used in combination with PNEUMOVAX-23™ to treat, prevent, and/or diagnose any Gram positive bacterial infection and/or any disease, disorder, and/or condition associated therewith. In another embodiment, antibody and antibody compositions of the invention are used in combination with PNEUMOVAX-23™ to treat, prevent, and/or diagnose infection and/or any disease, disorder, and/or condition associated with one or more members of the genus *Enterococcus* and/or the genus *Streptococcus*. In another embodiment, antibody and antibody compositions of the invention are used in any combination with PNEUMOVAX-23™ to treat, prevent, and/or diagnose infection and/or any disease, disorder, and/or condition associated with one or more members of the Group B streptococci. In another embodiment, antibody and antibody compositions of the invention are used in combination with PNEUMOVAX-23™ to treat, prevent, and/or diagnose infection and/or any disease, disorder, and/or condition associated with *Streptococcus pneumoniae*.

In a preferred embodiment, the antibody and antibody compositions of the invention are administered in combination with CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In a nonexclusive embodiment, the antibody and antibody compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-714 (Toyama), pemetrexed disodium (Eli Lilly), atreleuton (Abbott), valdecoxib (Monsanto), eltenac (Byk Gulden), campath, AGM-1470 (Takeda), CDP-571 (Celitech Chiroscience), CM-101 (CarboMed), ML-3000 (Merckle), CB-2431 (KS Biomedix), CBF-BS2 (KS Biomedix), IL-IRa gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-671 (Merck), ST-1482 (Sigma-Tau), and butixocort propionate (WarnerLambert).

In a preferred embodiment, the antibody and antibody compositions of the invention are administered in combination with one, two, three, four, five or more of the following drugs: methotrexate, sulfasalazine, sodium aurothiomalate, auranofin, cyclosporine, penicillamine, azathioprine, an antimalarial drug, cyclophosphamide, chlorambucil, gold, ENBREL™ (Etanercept), anti-TNF antibody, LJP 394 (La Jolla Pharmaceutical Company, San Diego, Calif.) and prednisolone.

In an additional embodiment, antibody and antibody compositions of the invention are administered alone or in combination with one or more intravenous immune globulin preparations. Intravenous immune globulin preparations that may be administered with the antibody and antibody compositions of the invention include, but not limited to, GAMMAR™, IVEEGAM™, SANDOGLOBULIN™, GAMMAGARD S/D™, and GAMIMUNE™. In a specific embodiment, antibody and antibody compositions of the invention are administered in combination with intravenous immune globulin preparations in transplantation therapy (e.g., bone marrow transplant).

In an additional embodiment, the antibody and antibody compositions of the invention are administered in combination with other polypeptides, polynucleotides or antibodies used to treat diagnose or ameliorate diabetes, including, but not limited to RELM and/or other FIZZ family polpeptides, Apo-lipoprotein, Insulin, Interferon Alpha, M-CSF, Platelet factor 4, IL-2, Resistin, AC2 Inhibitor, Leptin, IL-1 Receptor Agonist, HLDOU18, HCE-IP80, GLP-1, ABC1, Adiposin, CNTF, CTLA4, Decorin, GGF-2, Glucagon, IL-10, IL2-Diptheria Toxin Chimera, IL-4, Microsomal Transfer Protein, NGF, NT-3, PAF acetyl hydrolase, PDGF, Prosaptide, TGF Beta 2, Troponin 1, Lp-PLA2, Fas, FasL, TR6, HNHFE71, HLWCF05, Preproapolipoprotein, BMP-1, BMP-2B, BMP-4, BMP-5, BMP-6, Osteogenic protein-2, GDF-1, BMP-9, BMP-10, BMP-12, BMP-15, BMP-17, BMP-18, APM-1, ACRP-30, Calpain 10a, Calpain-10b, Calpain-10c, and VEGF-1.

Demonstration of Therapeutic or Prophylactic Utility of a Composition

The compounds of the invention are preferably tested in vitro, and then in vivo for the desired therapeutic or prophylactic activity, prior to use in humans. For example, in vitro assays which can be used to determine whether administration of a specific antibody or composition of the present invention is indicated, include in vitro cell culture assays in which a patient tissue sample is grown in culture, and exposed to or otherwise administered an antibody or composition of the present invention, and the effect of such an antibody or composition of the present invention upon the tissue sample is observed. In various specific embodiments, in vitro assays can be carried out with representative cells of cell types involved in a patient's disorder, to determine if an antibody or composition of the present invention has a desired effect upon such cell types. Preferably, the antibodies or compositions of the invention are also tested in in vitro assays and animal model systems prior to administration to humans (See, e.g., Examples 6 and 9).

Antibodies or compositions of the present invention for use in therapy can be tested for their toxicity in suitable animal model systems, including but not limited to rats, mice, chicken, cows, monkeys, and rabbits. For in vivo testing of an antibody or composition's toxicity any animal model system known in the art may be used.

Antibodies or compositions of the invention can be tested for their ability to reduce tumor formation in in vitro, ex vivo and in vivo assays. Antibodies or compositions of the invention can also be tested for their ability to inhibit viral replication or reduce viral load in in vitro and in vivo assays. Antibodies or compositions of the invention can also be tested for their ability to reduce bacterial numbers in in vitro and in vivo assays known to those of skill in the art. Antibodies or compositions of the invention can also be tested for their ability to alleviate of one or more symptoms associated with diabetes (e.g., insulin resistance). Antibodies or compositions of the invention can also be tested for their ability to decrease the time course of the infectious disease. Further, antibodies or compositions of the invention can be tested for their ability to increase the survival period of animals suffering from disease or disorder, including cancer, an immune disorder or an infectious disease. Techniques known to those of skill in the art can be used to analyze the function of the antibodies or compositions of the invention in vivo.

Antigen expression can be assayed, for example, by immunoassays including, but not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs). In a preferred embodiment, the ability of an antibody or composition of the invention to induce B-cell proliferation is measured. In another preferred embodiment, the ability of an antibody or composition of the invention to modulate immunoglobulin expression is measured.

Panels/Mixtures

The present invention also provides for mixtures of antibodies (including scFvs and other molecules comprising, or alternatively consisting of, antibody fragments or variants thereof) that specifically bind to GMAD or a fragment or variant thereof, wherein the mixture has at least one, two, three, four, five or more different antibodies of the invention. In specific embodiments, the invention provides mixtures of at least 2, preferably at least 4, at least 6, at least 8, at least 10, at least 12, at least 15, at least 20, or at least 25 different antibodies that specifically bind to GMAD or fragments or variants thereof, wherein at least 1, at least 2, at least 4, at least 6, or at least 10, antibodies of the mixture is an antibody of the invention. In a specific embodiment, each antibody of the mixture is an antibody of the invention.

The present invention also provides for panels of antibodies (including scFvs and other molecules comprising, or alternatively consisting of, antibody fragments or variants thereof) that specifically bind to GMAD or a fragment or variant thereof, wherein the panel has at least one, two, three, four, five or more different antibodies of the invention. In specific embodiments, the invention provides for panels of antibodies that have different affinities for GMAD, different specificities for GMAD, or different dissociation rates. The invention provides panels of at least 10, preferably at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, or at least 1000, antibodies. Panels of antibodies can be used, for example, in 96 well plates for assays such as ELISAs.

The present invention further provides for compositions comprising, one or more antibodies (including molecules comprising, or alternatively consisting of, antibody fragments or variants of the invention). In one embodiment, a composition of the present invention comprises, one, two, three, four, five, or more antibodies that comprise or alternatively consist of, a polypeptide having an amino acid sequence of any one or more of the VH domains of a heavy chain of one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VH CDR1s of a heavy chain of one or more of the scFvs referred to in Table 1, or a variant thereof. In another embodiment, a composition of the present invention comprises, one, two, three, four, five or more antibodies that comprise, or alternatively consist of, a polypeptide having an amino acid sequence of any one or more of the VH CDR2s of a heavy chain of of one or more of the scFvs referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VH CDR3s as of a heavy chain of of one or more of the scFvs referred to in Table 1, or a variant thereof.

Other embodiments of the present invention providing for compositions comprising, one or more antibodies (including molecules comprising, or alternatively consisting of, antibody fragments or variants of the invention) are listed below. In another embodiment, a composition of the present invention comprises, one, two, three, four, five, or more antibodies that comprise, or alternative consist of, a polypeptide having an amino acid sequence of any one or more of the VL domains of a light chain of one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR1s domains of a light chain of one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR2s of a light chain of one or more of the scFvs referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VL CDR3s domains of a light chain of one or more of the scFvs referred to in Table 1, or a variant thereof.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises an antibody of the invention, preferably a purified antibody, in one or more containers. In an alterative embodiment, a kit comprises an antibody fragment that specifically binds to GMAD polypeptides or fragments or variants thereof. In a specific embodiment, the kits of the present invention contain a substantially isolated GMAD polypeptide or fragment or variant thereof as a control. Preferably, the kits of the present invention further comprise a control antibody which does not react with any, some or all GMAD. In another specific embodiment, the kits of the present invention contain a means for detecting the binding of an antibody to GMAD polypeptides (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized GMAD. The GMAD provided in the kit may also be attached to a solid support. In a more specific embodiment the detecting means of the above-described kit includes a solid support to which GMAD is attached. Such a kit may also include a non-attached reporter-labeled anti-human antibody. In this embodiment, binding of the antibody to GMAD can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with GMAD, and means for detecting the binding of GMAD polypeptides to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having surface-bound GMAD obtained by the methods of the present invention. After GMAD polypeptides bind to a specific antibody, the unbound serum components are removed by washing, reporter-labeled anti-human antibody is added, unbound anti-human antibody is removed by washing, and a reagent is reacted with reporter-labeled anti-human antibody to bind reporter to the reagent in proportion to the amount of bound anti-GMAD antibody on the solid support. Typically, the reporter is an enzyme which is detected by incubating the solid phase in the presence of a suitable fluorometric, luminescent or calorimetric substrate.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant GMAD, and a reporter-labeled anti-human antibody for detecting surface-bound anti-GMAD antibody.

Gene Therapy

In a specific embodiment, nucleic acids comprising sequences encoding antibodies or functional derivatives thereof, are administered to treat, inhibit or prevent a disease or disorder associated with aberrant expression and/or activity of GMAD and/or its receptors, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 1 1(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, a composition of the invention comprises, or alternatively consists of, nucleic acids encoding an antibody, said nucleic acids being part of an expression vector that expresses the antibody or fragments or chimeric proteins or heavy or light chains thereof in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is an scFv; alternatively, the nucleic acid sequences include sequences encoding both the heavy and light chains, or fragments or variants thereof, of an antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06 180; WO 92/22715; WO92/203 16; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention or fragments or variants thereof are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:29 1-302 (1994), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., J. Clin. Invest. 93:644-651(1994); Klein et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-

155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-718 (1993); Cohen et al., Meth. Enzymol. 217:718-644 (1993); Clin. Pharma. Ther. 29:69-92m (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody or fragment thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 7 1:973-985 (1992); Rheinwald, Meth. Cell Bio. 21A:229 (1980); and Pittelkow and Scott, Mayo Clinic Proc. 71:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

EXAMPLES

Example 1

Isolation of scFvs that Specifically Bind GMAD

General Methods

Rescue of the Library.

A library of scFvs is constructed from the RNA of human PBLs as described in WO92/01047 (which is hereby incorporated by reference in its entirety). To rescue phage displaying antibody fragments, approximately $10^9$ E. coli harboring the phagemid are used to inoculate 50 ml of 2×TY containing 1% glucose and 100 micrograms/ml of ampicillin (2×TY-AMP-GLU) and grown to an O.D. of 0.8 with shaking. Five ml of this culture is used to inoculate 50 ml of 2×TY-AMP-GLU, $2×10^8$ TU of delta gene 3 helper (M13 delta gene III, see WO92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 micrograms/ml ampicillin and 50 micrograms/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells were spun down (IEC-Centra 8, 4000 revs/min for 10 min), resuspended in 300 ml 2×TY broth containing 100 micrograms ampicillin/ml and 25 micrograms kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 micrometer filter (Minisart NML; Sartorius) to give a final concentration of approximately $10^{13}$ transducing units/ml (ampicillin-resistant clones).

Panning the Library.

Immunotubes (Nunc) are coated overnight in PBS with 4 ml of either 100 micrograms/ml or 10 micrograms/ml of a polypeptide of the present invention. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 micrograms/ml ampicillin. The resulting bacterial library is then rescued with delta gene 3 helper phage as described above to prepare phage for a subsequent round of selection. This process is usually repeated for a total of 2-4 rounds of affinity purification.

Characterization of Binders.

Eluted phage from the final rounds of selection are used to infect *E. coli* HB 2151 and soluble scFv is produced (Marks, et al., 1991) from single colonies for assay. ELISAs are performed with microtiter plates coated with either 10 picograms/ml of the polypeptide of the present invention in 50 mM bicarbonate pH 9.6. Clones positive in ELISA are further characterized by PCR fingerprinting (see e.g., WO92/01047) and then by sequencing.

Isolation of scFvs Referred to in Table 1

The scFvs presented in Table 1 were isolated using a methods similar to those described above. Briefly, Flag-tagged recombinant human GMAD was immobilized in Immuno tubes. Three phage display libraries from Cambridge Antibody Technology (Cambridgeshire, United Kingdom) were screened for GMAD binding scFvs. Prior to panning the phage libraries on FLAG tagged GMAD, the phage libraries were each incubated with Flag peptide (SEQ ID NO:39) for deselection. Three rounds of selection for phage expressing scFv that bind GMAD were performed by panning the phage libraries on flag-tagged GMAD.

After the first and second round of panning, bound phages were eluted and amplified in *E. coli* for the subsequent pannings. After round two of panning, four 96-well plates of single bacterial colonies (each infected with an scFv expressing phage particle) were isolated and grown. Similarly, eight 96-well plates of single bacterial colonies were isolated and grown up after round three of panning. The scFvs contained in each of the bacterial colonies were then sequenced. Certain of the scFvs had identical sequences, so a panel of phage expressing unique scFv sequences was created and further characterized.

The individual phage isolates in the panel of phage, each phage expressing a unique scFv that bound to flag-tagged GMAD, were tested to ensure specificity for GMAD using an ELISA assay. The scFvs were tested in an ELISA for their ability to bind a heterologous flag-tagged protein, in this case—immobilized soluble TL3 (amino acids 105-251 of SEQ ID NO:234, GenBank Accesion Number NP_003799, also described in International Patent Application Publication Number WO97/33902 and WO2001/96528 which are herein incorporated by reference in their entireties). ScFvs specific for GMAD (i.e., that bind flag tagged GMAD but not flagged tagged TL-3 and/or flag-tagged TR2) in this ELISA assay were identified and resequenced for confirmation. The scFvs that specifically bind GMAD identified in this manner are listed in Table 1 and the sequences of these scFvs are shown in SEQ ID NOS:40-136 (amino acid sequences) and SEQ ID NOS: 136-233 (nucleotide sequences).

Example 2

Identification and Cloning of VH and VL Domains

One method to identfy and clone VH and VL domains from cell lines expressing a particular antibody is to perform PCR with VH and VL specific primers on cDNA made from the antibody expressing cell lines. Briefly, RNA is isolated from the cell lines and used as a template for RT-PCR designed to amplify the VH and VL domains of the antibodies of the EBV cell lines. Cells may lysed in the TRIzol® reagent (Life Technologies, Rockville. MD) and extracted with one fifth volume of chloroform. After addition of chloroform, the solution is allowed to incubate at room temperature for 10 minutes, and the centrifuged at 14,000 rpm for 15 minutes at 4° C. in a tabletop centrifuge. The supernatant is collected and RNA is precipitated using an equal volume of isopropanol. Precipitated RNA is pelleted by centrifuging at 14,000 rpm for 15 minutes at 4° C. in a tabletop centrifuge. Following centrifugation, the supernatant is discarded and washed with 75% ethanol. Following washing, the RNA is centrifuged again at 800 rpm for 5 minutes at 4° C. The supernatant is discarded and the pellet allowed to air dry. RNA is the dissolved in DEPC water and heated to 60° C. for 10 minutes. Quantities of RNA can determined using optical density measurements.

cDNA may be synthesized, according to methods well-known in the art, from 1.5-2.5 micrograms of RNA using reverse transcriptase and random hexamer primers. cDNA is then used as a template for PCR amplification of VH and VL domains. Primers used to amplify VH and VL genes are shown in Table 8. Typically a PCR reaction makes use of a single 5' primer and a single 3' primer. Sometimes, when the amount of available RNA template is limiting, or for greater efficiency, groups of 5' and/or 3' primers may be used. For example, sometimes all five VH-5' primers and all JH3' primers are used in a single PCR reaction. The PCR reaction is carried out in a 50 microliter volume containing 1× PCR buffer, 2 mM of each dNTP, 0.7 units of High Fidelity Taq polymerse, 5' primer mix, 3' primer mix and 7.5 microliters of cDNA. The 5' and 3' primer mix of both VH and VL can be made by pooling together 22 pmole and 28 pmole, respectively, of each of the individual primers. PCR conditions are: 96° C. for 5 minutes; followed by 25 cycles of 94° C. for 1 minute, 50° C. for 1 minute, and 72° C. for 1 minute; followed by an extension cycle of 72° C. for 10 minutes. After the reaction is completed, sample tubes were stored 4° C.

TABLE 6

Primer Sequences Used to Amplify VH and VL domains.

| Primer name | SEQ ID NO | Primer Sequence (5'-3') |
|---|---|---|
| VH Primers | | |
| Hu VH1-5' | 3 | CAGGTGCAGCTGGTGCAGTCTGG |
| Hu VH2-5' | 4 | CAGGTCAACTTAAGGGAGTCTGG |
| Hu VH3-5' | 5 | GAGGTGCAGCTGGTGGAGTCTGG |
| Hu VH4-5' | 6 | CAGGTGCAGCTGCAGGAGTCGGG |
| Hu VH5-5' | 7 | GAGGTGCAGCTGTTGCAGTCTGC |
| Hu VH6-5' | 8 | CAGGTAGAGCTGCAGCAGTCAGG |
| Hu JH1,2-5' | 9 | TGAGGAGACGGTGACCAGGGTGCC |
| Hu JH3-5' | 10 | TGAAGAGACGGTGACCATTGTCCC |
| Hu 3H4,5-5' | 11 | TGAGGAGACGGTGACCAGGGTTCC |
| Hu 3H6-5' | 12 | TGAGGAGACGGTGACCGTGGTCCC |
| VL Primers | | |
| Hu Vkappa1-5' | 13 | GACATCCAGATGACCCAGTCTCC |
| Hu Vkappa2a-5' | 14 | GATGTTGTGATGACTCAGTCTCC |
| Hu Vkappa2b-5' | 15 | GATATTGTGATGACTCAGTCTCC |

TABLE 6-continued

Primer Sequences Used to Amplify VH and VL domains.

| Primer name | SEQ ID NO | Primer Sequence (5'-3') |
|---|---|---|
| Hu Vkappa3-5' | 16 | GAAATTGTGTTGACGCAGTCTCC |
| Hu Vkappa4-5' | 17 | GACATCGTGATGACCCAGTCTCC |
| Hu Vkappa5-5' | 18 | GAAACGACACTCACGCAGTCTCC |
| Hu Vkappa6-5' | 19 | GAAATTGTGCTGACTCAGTCTCC |
| Hu Vlambda1-5' | 20 | CAGTCTGTGTTGACGGAGGCGCC |
| Hu Vlambda2-5' | 21 | CAGTCTGCCCTGACTCAGGCTGC |
| Hu Vlambda3-5' | 22 | TCGTATGTGCTGACTCAGCGACC |
| Hu Vlambda3b-5' | 23 | TCITCTGAGCTGACTCAGGACCC |
| Hu Vlambda4-5' | 24 | CACGTTATACTGACTCAACCGCC |
| Hu Vlambda5-5' | 25 | CAGGGTGTGCTCACTCAGCCGTC |
| Hu Vlambda6-5' | 26 | AATTTTATGCTGACTCAGCCCCA |
| Hu Jkappa1-3' | 27 | ACGTTTGATTTCCACCTTGGTCCC |
| Hu Jkappa2-3' | 28 | ACGTTTGATCTCCAGCTTGGTCCC |
| Hu Jkappa3-3' | 29 | ACGTTTGATATCCACTTTGGTCCC |
| Hu Jkappa4-3' | 30 | ACGTTTGATGTCCACCTTGGTCCG |
| Hu Jkappa5-3' | 31 | ACGTTTAATCTCCAGTCGTGTCCC |
| Hu Jlambda1-3' | 32 | CAGTCTGTGTTGACGCAGCCGCC |
| Hu Jlambda2-3' | 33 | CAGTCTGCCCTGACTGAGGCTGC |
| Hu Jlambda3-3' | 34 | TCCTATGTGGTGACTCAGCCACC |
| Hu Jlambda3b-3' | 35 | TCTTCTGAGCTGACTCAGGACCC |
| Hu Jlambda4-3' | 36 | CACGTTATACTGACTCAACCGCC |
| Hu Jlambda5-3' | 37 | GAGGCTGTGCTCACTCAGCGGTC |
| Hu Jlambda6-3' | 38 | AATTTTATGCTGACTCAGCCCCA |

PCR samples are then electrophoresed on a 1.3% agarose gel. DNA bands of the expected sizes (~506 base pairs for VH domains, and 344 base pairs for VL domains) can be cut out of the gel and purified using methods well known in the art. Purified PCR products can be ligated into a PCR cloning vector (TA vector from Invitrogen Inc., Carlsbad, Calif.). Individual cloned PCR products can be isolated after transfection of E. coli and blue/white color selection. Cloned PCR products may then be sequenced using methods commonly known in the art.

Example 3

[$^3$H]-2-Deoxyglucose Uptake Assay

Adipose, skeletal muscle, and liver are insulin-sensitive tissues. Insulin can stimulate glucose uptake/transport into these tissues. In the case of adipose and skeletal muscle, insulin initiates the signal transduction that eventually leads to the translocation of the glucose transporter 4 molecule, GLUT4, from a specialized intracellular compartment to the cell surface. Once on the cell surface, GLUT4 allows for glucose uptake/transport.

A number of adipose and muscle related cell-lines can be used to test for glucose uptake/transport activity in the absence or presence of a combination of any one or more of the therapeutic drugs listed for the treatment of diabetes mellitus. In particular, the 3T3-L1 murine fibroblast cells and the L6 murine skeletal muscle cells can be differentiated into 3T3-L1 adipocytes and into myotubes, respectively, to serve as appropriate in vitro models for the [$^3$H]-2-deoxyglucose uptake assay (Garcia de Herreros et al., J. Biol. Chem. 264 (33):19994-19999 (1989); Urso et al., J Biol Chem, 274(43): 30864-73 (1999); Wang et al., J Mol Endocrinol, 19(3): 241-8 (1997); Haspel et al., J Membr Biol, 169 (1): 45-53 (1999); Tsakiridis et al., Endocrinology, 136(10): 4315-22 (1995)).

Differentiation of 3T3L-1

Murine 3T3-L1 fibroblast are induced to differentiate into adipocytes according to the protocol described in Garcia de Herreros et al., J. Biol. Chem. 264(33):19994-19999 (1989) which is hereby incorporated by reference in its entirety. Alternatively, human adipocytes can be purchased from Zen-Bio, INC (# SA-1096).

[$^3$H]-2-Deoxyglucose Uptake

Briefly, 2×10$^5$ cells/100 µL of adipocytes or differentiated 3T3-L1 cells are transferred to 96-well Tissue-Culture, "TC", treated, i.e., coated with 50 microgramr/mL of poly-L-lysine, plates in (DMEM+10% FBS) and are incubated overnight at 37° C. in 5% CO$_2$. The cells are first washed once with serum free low glucose DMEM medium and are then placed into 100 microliter/well of the same serum free low glucose DMEM medium containing anti-GMAD antibodies of the invention, and/or fragments and variants thereof (e.g. 250 ng/ml, 500 ng/ml or Imicrogram/ml), for 16 hours at 37° C. in the absence or presence GMAD (e.g., 500 ng/microliter). The plates are then washed three times with HEPES buffered saline. Insulin is added at 1-100 nM in HEPES buffered saline for 30 min at 37° C. The cells are again washed three times with HEPES buffered saline. 10 µM labeled [$^3$H]-2-deoxyglucose (Amersham, #TRK672) and 10 µM unlabeled 2-deoxyglucose (SIGMA, D-3179) are added and allowed to incubate at room temperature for 10 minutes. Next, the cells are washed threes times in cold PBS. As controls, the same conditions are carried out except in the absence of insulin or GMAD. The cells are lysed upon the addition of 150 microliter/well of 0.2 N NaOH and subsequent incubation with shaking for 20 minutes at room temperature. Samples are then transferred to a scintillation vial to which is added 5 mL of scintillation fluid. The vials are counted in a Beta-Scintillation counter. Uptake in duplicate conditions, the difference being the absence or presence of insulin, is determined with the following equation: [(Insulin counts per minute "cpm"–Non-Specific cpm)/(No Insulin cpm–Non-Specific cpm)]. Non-specific uptake was measured in the presence of 10 micromolar cytochalasin B (SIGMA, C6762). Average responses fall within the limits of about 5-fold and 3-fold that of controls for adipocytes and myotubes, respectively.

Example 4

Assaying for Glycosuria

Glycosuria (i.e., excess sugar in the urine), can be readily assayed to provide an index of the disease state of diabetes mellitus. Excess sugar in the urine of a patient as compared with a normal patient is symptomatic of IDDM and NIDDM.

Efficacy of treatment of such a patient having IDDM and NIDDM is indicated by a resulting decrease in the amount of excess glucose in the urine. In a preferred embodiment for IDDM and NIDDM monitoring, urine samples from patients are assayed for the presence of glucose using techniques known in the art. Glycosuria in humans is defined by a urinary glucose concentration exceeding 100 mg per 100 ml. Excess sugar levels in those patients exhibiting glycosuria can be measured even more precisely by obtaining blood samples and assaying serum glucose.

Example 5

Occurrence of Diabetes in NOD Mice

Female NOD (non-obese diabetic) mice are characterized by displaying IDDM with a course which is similar to that found in humans, although the disease is more pronounced in female than male NOD mice. Hereinafter, unless otherwise stated, the term "NOD mouse" refers to a female NOD mouse. NOD mice have a progressive destruction of beta cells which is caused by a chronic autoimmune disease. Thus, NOD mice begin life with euglycemia, or normal blood glucose levels. By about 15 to 16 weeks of age, however, NOD mice start becoming hyperglycemic, indicating the destruction of the majority of their pancreatic beta cells and the corresponding inability of the pancreas to produce sufficient insulin. Thus, both the cause and the progression of the disease are similar to human IDDM patients.

In vivo assays of efficacy of anti-GMAD antibody therapy can be assessed in female NOD/LtJ mice (commercially available from The Jackson Laboratory, Bar Harbor, Me.). In the literature, it's reported that 80% of female mice develop diabetes by 24 weeks of age and onset of insulitis begins between 6-8 weeks age. NOD mice are inbred and highly responsive to a variety of immunoregulatory strategies. Adult NOD mice (6-8 weeks of age) have an average mass of 20-25 g.

These mice can be either untreated (control), treated with the therapeutics of the subject invention (e.g., specific GMAD antibodies and/or fragments and variants thereof), alone or in combination with other therapeutic compounds stated above. The effect of these various treatments on the progression of diabetes can be measured as follows:

At 14 weeks of age, the female NOD mice can be phenotyped according to glucose tolerance. Glucose tolerance can be measured with the intraperitoneal glucose tolerance test (IPGTT). Briefly, blood is drawn from the paraorbital plexus at 0 minutes and 60 minutes after the intraperitoneal injection of glucose (1 g/kg body weight). Normal tolerance is defined as plasma glucose at 0 minutes of less than 144 mg %, or at 60 minutes of less than 160 mg %. Blood glucose levels are determined with a Glucometer Elite apparatus.

Based upon this phenotypic analysis, animals can be allocated to the different experimental groups. In particular, animals with more elevated blood glucose levels can be assigned to the impaired glucose tolerance group. The mice can be fed ad libitum and can be supplied with acidified water (pH 2.3).

The glucose tolerant and intolerant mice can be further subdivided into control, and treatment groups (e.g. with anti-GMAD antibodies of the invention) in the presence or absence of other anti-diabetic drugs. Mice in the control group can receive an interperitoneal injection of vehicle daily, six times per week. Mice in the treatment group can receive an interperitoneal injection of the specific anti-GMAD antibodies and fragments and variants thereof, in vehicle daily, six times per week.

The level of urine glucose in the NOD mice can be determined on a bi-weekly basis using Labstix (Bayer Diagnostics, Hampshire, England). Weight and fluid intake can also be determined on a bi-weekly basis. The onset of diabetes is defined after the appearance of glucosuria on two consecutive determinations. After 10 weeks of treatment, an additional IPGTT can be performed and animals can be sacrificed the following day.

Over the 10 week course of treatment, control animals in both the glucose tolerant and glucose intolerant groups develop diabetes at a rate of 60% and 86%, respectively (see U.S. Pat. No. 5,866,546, Gross et al.). Thus, high rates of diabetes occur even in NOD mice which are initially glucose tolerant if no intervention is made.

Results can be confirmed by the measurement of blood glucose levels in NOD mice, before and after treatment. Blood glucose levels are measured as described above in both glucose tolerant and intolerant mice in all groups described.

Additionally, the therapeutics of the subject invention (e.g., specific GMAD antibodies and fragments and variants thereof) can be quantified using spectrometric analysis and appropriate protein quantities can be resuspended prior to injection in 50 microliter phosphate buffered saline (PBS) per dose. Two injections, one week apart, can be administered subcutaneously under the dorsal skin of each mouse. Monitoring can be performed on two separate occasions prior to immunization and can be performed weekly throughout the treatment and continued thereafter. Urine can be tested for glucose every week (Keto-Diastix.RTM.; Miles Inc., Kankakee, Ill.) and glycosuric mice can be checked for serum glucose (ExacTech.RTM., MediSense, Inc., Waltham, Mass.). Diabetes is diagnosed when fasting glycemia is greater than 2.5 g/L.

Example 6

Histological Examination of NOD Mice

Histological examination of tissue samples from NOD mice can demonstrate the ability of the compositions of the present invention, and/or a combination of the compositions of the present invention with other therapeutic agents for diabetes, to increase the relative concentration of beta cells in the pancreas. The experimental method is as follows:

The mice from Example 6 can be sacrificed at the end of the treatment period and tissue samples can be taken from the pancreas. The samples can be fixed in 10% formalin in 0.9% saline and embedded in wax. Two sets of 5 serial 5 micron sections can be cut for immunolabelling at a cutting interval of 150 microns. Sections can be immunolabelled for insulin (guinea pig anti-insulin antisera dilution 1:1000, ICN Thames U.K.) and glucagon (rabbit anti-pancreatic glucagon antisera dilution 1:2000) and detected with peroxidase conjugated anti-guinea pig (Dako, High Wycombe, U.K.) or peroxidase conjugated anti-rabbit antisera (dilution 1:50, Dako).

The composition of the present invention may or may not have as strong an effect on the visible mass of beta cells as it does on the clinical manifestations of diabetes in glucose tolerant and glucose intolerant animals.

Example 7

In vivo Mouse Model of NIDDM

Male C57BL/6J mice from Jackson Laboratory (Bar Harbor, Me.) can be obtained at 3 weeks of age and fed on conventional chow or diets enriched in either fat (35.5% wt/wt; Bioserv.Frenchtown, N.J.) or fructose (60% wt/wt; Harlan Teklad, Madison, Wis.). The regular chow is composed of 4.5% wt/wt fat, 23% wt/wt protein, 31.9% wt/wt starch, 3.7% wt/wt fructose, and 5.3% wt/wt fiber. The high-fat (lard) diet is composed of 35.5% wt/wt fat, 20% wt/wt protein, 36.4% wt/wt starch, 0.0% wt/wt fructose, and 0.1% wt/wt fiber. The high-fructose diet is composed of 5% wt/wt fat, 20% wt/wt protein, 0.0% wt/wt starch, 60% wt/wt fructose, and 9.4% wt/wt fiber. The mice may be housed no more than five per cage at 22°+/−3° C. temperature- and 50%+/− 20% humidity-controlled room with a 12-hour light (6 am to 6 pm)/dark cycle (Luo et al., Metabolism 47(6): 663-8 (1998), "Nongenetic mouse models of non-insulin-dependent diabetes mellitus"; Larsen et al., Diabetes 50(11): 2530-9 (2001), "Systemic administration of the long-acting GLP-1 derivative NN2211 induces lasting and reversible weight loss in both normal and obese rats"). After exposure to the respective diets for 3 weeks, mice can be injected intraperitoneally with either streptozotocin, "STZ" (Sigma, St. Louis, Mo.), at 100 mg/kg body weight or vehicle (0.05 mol/L citric acid, pH 4.5) and kept on the same diet for the next 4 weeks. Under nonfasting conditions, blood is obtained 1, 2, and 4 weeks post-STZ by nipping the distal part of the tail. Samples are used to measure nonfasting plasma glucose and insulin concentrations. Body weight and food intake are recorded weekly.

To directly determine the effect of the high-fat diet on the ability of insulin to stimulate glucose disposal, the experiments can be initiated on three groups of mice, fat-fed, chow-fed injected with vehicle, and fat-fed injected with STZ at the end of the 7-week period described above. Mice can be fasted for 4 hours before the experiments. In the first series of experiments, mice can be anesthetized with methoxyflurane (Pitman-Moor, Mundelein, Ill.) inhalation. Regular insulin (Sigma) can be injected intravenously ([IV] 0.1 U/kg body weight) through a tail vein, and blood can be collected 3, 6, 9, 12, and 15 minutes after the injection from a different tail vein. Plasma glucose concentrations can be determined on these samples, and the half-life (t½) of glucose disappearance from plasma can be calculated using WinNonlin (Scientific Consulting, Apex, N.C.), a pharmacokinetics/pharmacodynamics software program.

In the second series of experiments, mice can be anesthetized with intraperitoneal sodium pentobarbital (Sigma). The abdominal cavity is opened, and the main abdominal vein is exposed and catheterized with a 24-gauge IV catheter (Johnson-Johnson Medical, Arlington, Tex.). The catheter is secured to muscle tissue adjacent to the abdominal vein, cut on the bottom of the syringe connection, and hooked to a prefilled PE50 plastic tube, which in turn is connected to a syringe with infusion solution. The abdominal cavity is then sutured closed. With this approach, there would be no blockage of backflow of the blood from the lower part of the body. Mice can be infused continuously with glucose (24.1 mg/kg/min) and insulin (10 mU/kg/min) at an infusion volume of 10 µL/min. Retro-orbital blood samples (70 µL each) can be taken 90, 105, 120, and 135 minutes after the start of infusion for measurement of plasma glucose and insulin concentrations. The mean of these four samples is used to estimate steady-state plasma glucose (SSPG) and insulin (SSPI) concentrations for each animal.

Finally, experiments to evaluate the ability of the antibody of the present application, either alone or in combination with any one or more of the therapeutic drugs listed for the treatment of diabetes mellitus, to decrease plasma glucose can be performed in the following two groups of "NIDDM" mice models that are STZ-injected: (1) fat-fed C57BL/6J, and (2) fructose-fed C57BL/6J. Plasma glucose concentrations of the mice for these studies may range from 255 to 555 mg/dL. Mice are randomly assigned to treatment with either vehicle, antibodies of the present invention either alone or in combination with any one or more of the therapeutic drugs listed for the treatment of diabetes mellitus. A total of three doses may be administered. Tail vein blood samples can be taken for measurement of the plasma glucose concentration before the first dose and 3 hours after the final dose.

Plasma glucose concentrations can be determined using the Glucose Diagnostic Kit from Sigma (Sigma No. 315), an enzyme calorimetric assay. Plasma insulin levels can be determined using the Rat Insulin RIA Kit from Linco Research (#RI-13K; St. Charles, Mo.).

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith, in both computer and paper forms, is hereby incorporated by reference in its entirety.

The entire disclosures (including the specification, sequence listing, and drawings) of International Application No. PCT/US03/09625, filed Mar. 28, 2003, and U.S. Provisional Application No. 60/368,813 filed Apr. 1, 2002 are herein incorporated by reference in their entirety:

What is claimed is:

1. An isolated antibody or fragment thereof comprising the amino acid sequence of the VHCDR1, VHCDR2, VHCDR3, VLCDR1, VLCDR2, and VLCDR3 of SEQ ID NO: 43, wherein said antibody or fragment thereof specifically binds a GMAD polypeptide.

2. The antibody or fragment thereof of claim 1 that binds a GMAD polypeptide purified from a cell culture wherein said GMAD polypeptide is encoded by a polynucleotide encoding amino acids 1 to 108 of SEQ ID NO:2.

* * * * *

UNITED STATES PATENT AND TRADEMARK OFFICE
CERTIFICATE OF CORRECTION

PATENT NO. : 7,550,569 B2 Page 1 of 1
APPLICATION NO. : 10/935290
DATED : June 23, 2009
INVENTOR(S) : Baker et al.

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 448 days Delete the phrase "by 448 days" and insert -- by 951 days --

Signed and Sealed this

Sixth Day of April, 2010

David J. Kappos
*Director of the United States Patent and Trademark Office*

SEQUENCE LISTING

```
<160> NUMBER OF SEQ ID NOS: 234

<210> SEQ ID NO 1
<211> LENGTH: 553
<212> TYPE: DNA
<213> ORGANISM: homo sapiens
<220> FEATURE:
<221> NAME/KEY: CDS
<222> LOCATION: (47)..(373)
<223> OTHER INFORMATION:

<400> SEQUENCE: 1
gtgtgccgga tttggttagc tgagcccacc gagaggcgcc tgcagg atg aaa gct      55
```

```
                                    Met Lys Ala
                                     1 ctc tgt ctc ctc ctc ctc cct gtc ctg ggg ctg ttg gtg tct agc aag       103
Leu Cys Leu Leu Leu Leu Pro Val Leu Gly Leu Leu Val Ser Ser Lys
    5               10                  15 acc ctg tgc tcc atg gaa gaa gcc atc aat gag agg atc cag gag gtc       151
Thr Leu Cys Ser Met Glu Glu Ala Ile Asn Glu Arg Ile Gln Glu Val
20              25                  30                  35 gcc ggc tcc cta ata ttt agg gca ata agc agc att ggc ctg gag tgc       199
Ala Gly Ser Leu Ile Phe Arg Ala Ile Ser Ser Ile Gly Leu Glu Cys
                40                  45                  50 cag agc gtc acc tcc agg ggg gac ctg gct act tgc ccc cga ggc ttc       247
Gln Ser Val Thr Ser Arg Gly Asp Leu Ala Thr Cys Pro Arg Gly Phe
            55                  60                  65 gcc gtc acc ggc tgc act tgt ggc tcc gcc tgt ggc tcg tgg gat gtg       295
Ala Val Thr Gly Cys Thr Cys Gly Ser Ala Cys Gly Ser Trp Asp Val
        70                  75                  80 cgc gcc gag acc aca tgt cac tgc cag tgc gcg ggc atg gac tgg acc       343
Arg Ala Glu Thr Thr Cys His Cys Gln Cys Ala Gly Met Asp Trp Thr
    85                  90                  95 gga gcg cgc tgc tgt cgt gtg cag ccc tga ggtcgcgcgc agtggcaaca        393
Gly Ala Arg Cys Cys Arg Val Gln Pro
100             105 gcgcgggcgg aggcggctcc aggtccggag ggttgcgggg gagctggaaa taaacctgga    453
gatgatgatg atgatgatga tggaaaaaaa aaaaaaaaaa aaaaaaaaaa aaaaaaaaa     513 aaaaaaaaaa aaaaaaaaaa aaaaaaaaaa aaaaaaaaa                          553

<210> SEQ ID NO 2
<211> LENGTH: 108
<212> TYPE: PRT
<213> ORGANISM: homo sapiens

<400> SEQUENCE: 2

Met Lys Ala Leu Cys Leu Leu Leu Pro Val Leu Gly Leu Leu Val
1               5                   10                  15

Ser Ser Lys Thr Leu Cys Ser Met Glu Glu Ala Ile Asn Glu Arg Ile
            20                  25                  30

Gln Glu Val Ala Gly Ser Leu Ile Phe Arg Ala Ile Ser Ser Ile Gly
        35                  40                  45

Leu Glu Cys Gln Ser Val Thr Ser Arg Gly Asp Leu Ala Thr Cys Pro
    50                  55                  60

Arg Gly Phe Ala Val Thr Gly Cys Thr Cys Gly Ser Ala Cys Gly Ser
65                  70                  75                  80

Trp Asp Val Arg Ala Glu Thr Thr Cys His Cys Gln Cys Ala Gly Met
                85                  90                  95

Asp Trp Thr Gly Ala Arg Cys Cys Arg Val Gln Pro
            100                 105

<210> SEQ ID NO 3
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 3
caggtgcagc tggtgcagtc tgg                                            23
```

```
<210> SEQ ID NO 4
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 4
caggtcaact taagggagtc tgg                                              23

<210> SEQ ID NO 5
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 5
gaggtgcagc tggtggagtc tgg                                              23

<210> SEQ ID NO 6
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 6
caggtgcagc tgcaggagtc ggg                                              23

<210> SEQ ID NO 7
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 7
gaggtgcagc tgttgcagtc tgc                                              23

<210> SEQ ID NO 8
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 8
caggtacagc tgcagcagtc agg                                              23

<210> SEQ ID NO 9
<211> LENGTH: 24
<212> TYPE: DNA
<213> ORGANISM: Artificial sequence
<220> FEATURE:
<223> OTHER INFORMATION: primer useful to amplify VH and VL domains

<400> SEQUENCE: 9
tgaggagacg gtgaccaggg tgcc                                             24

<210> SEQ ID NO 10
<211> LENGTH: 24
<212> TYPE: DNA
<213> ORGANISM: Artificial sequence
<220> FEATURE:
<223> OTHER INFORMATION: primer useful to amplify VH and VL domains
```

<400> SEQUENCE: 10
tgaagagacg gtgaccattg tccc  24

<210> SEQ ID NO 11
<211> LENGTH: 24
<212> TYPE: DNA
<213> ORGANISM: Artificial sequence
<220> FEATURE:
<223> OTHER INFORMATION: primer useful to amplify VH and VL domains

<400> SEQUENCE: 11
tgaggagacg gtgaccaggg ttcc  24

<210> SEQ ID NO 12
<211> LENGTH: 24
<212> TYPE: DNA
<213> ORGANISM: Artificial sequence
<220> FEATURE:
<223> OTHER INFORMATION: primer useful to amplify VH and VL domains

<400> SEQUENCE: 12
tgaggagacg gtgaccgtgg tccc  24

<210> SEQ ID NO 13
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 13
gacatccaga tgacccagtc tcc  23

<210> SEQ ID NO 14
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 14
gatgttgtga tgactcagtc tcc  23

<210> SEQ ID NO 15
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 15
gatattgtga tgactcagtc tcc  23

<210> SEQ ID NO 16
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 16
gaaattgtgt tgacgcagtc tcc  23

<210> SEQ ID NO 17
<211> LENGTH: 23

```
<212> TYPE: DNA
<213> ORGANISM: Artificial sequence
<220> FEATURE:
<223> OTHER INFORMATION: primer useful to amplify VH and VL domains

<400> SEQUENCE: 17
gacatcgtga tgacccagtc tcc                                               23

<210> SEQ ID NO 18
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 18
gaaacgacac tcacgcagtc tcc                                               23

<210> SEQ ID NO 19
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 19
gaaattgtgc tgactcagtc tcc                                               23

<210> SEQ ID NO 20
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 20
cagtctgtgt tgacgcagcc gcc                                               23

<210> SEQ ID NO 21
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 21
cagtctgccc tgactcagcc tgc                                               23

<210> SEQ ID NO 22
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 22
tcctatgtgc tgactcagcc acc                                               23

<210> SEQ ID NO 23
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 23
```

-continued

```
tcttctgagc tgactcagga ccc                                           23

<210> SEQ ID NO 24
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 24
cacgttatac tgactcaacc gcc                                           23

<210> SEQ ID NO 25
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 25
caggctgtgc tcactcagcc gtc                                           23

<210> SEQ ID NO 26
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 26
aattttatgc tgactcagcc cca                                           23

<210> SEQ ID NO 27
<211> LENGTH: 24
<212> TYPE: DNA
<213> ORGANISM: Artificial sequence
<220> FEATURE:
<223> OTHER INFORMATION: primer useful to amplify VH and VL domains

<400> SEQUENCE: 27
acgtttgatt tccaccttgg tccc                                          24

<210> SEQ ID NO 28
<211> LENGTH: 24
<212> TYPE: DNA
<213> ORGANISM: Artificial sequence
<220> FEATURE:
<223> OTHER INFORMATION: primer useful to amplify VH and VL domains

<400> SEQUENCE: 28
acgtttgatc tccagcttgg tccc                                          24

<210> SEQ ID NO 29
<211> LENGTH: 24
<212> TYPE: DNA
<213> ORGANISM: Artificial sequence
<220> FEATURE:
<223> OTHER INFORMATION: primer useful to amplify VH and VL domains

<400> SEQUENCE: 29
acgtttgata tccactttgg tccc                                          24

<210> SEQ ID NO 30
<211> LENGTH: 24
<212> TYPE: DNA
<213> ORGANISM: Artificial sequence
```

```
<220> FEATURE:
<223> OTHER INFORMATION: primer useful to amplify VH and VL domains

<400> SEQUENCE: 30
acgtttgatc tccaccttgg tccc                                          24

<210> SEQ ID NO 31
<211> LENGTH: 24
<212> TYPE: DNA
<213> ORGANISM: Artificial sequence
<220> FEATURE:
<223> OTHER INFORMATION: primer useful to amplify VH and VL domains

<400> SEQUENCE: 31
acgtttaatc tccagtcgtg tccc                                          24

<210> SEQ ID NO 32
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 32
cagtctgtgt tgacgcagcc gcc                                           23

<210> SEQ ID NO 33
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 33
cagtctgccc tgactcagcc tgc                                           23

<210> SEQ ID NO 34
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 34
tcctatgtgc tgactcagcc acc                                           23

<210> SEQ ID NO 35
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 35
tcttctgagc tgactcagga ccc                                           23

<210> SEQ ID NO 36
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 36
cacgttatac tgactcaacc gcc                                           23
```

<210> SEQ ID NO 37
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 37
caggctgtgc tcactcagcc gtc          23

<210> SEQ ID NO 38
<211> LENGTH: 23
<212> TYPE: DNA
<213> ORGANISM: Artificial sequence
<220> FEATURE:
<223> OTHER INFORMATION: primer useful to amplify VH and VL domains

<400> SEQUENCE: 38
aattttatgc tgactcagcc cca          23

<210> SEQ ID NO 39
<211> LENGTH: 8
<212> TYPE: PRT
<213> ORGANISM: Artificial sequence
<220> FEATURE:
<223> OTHER INFORMATION: Flag peptide

<400> SEQUENCE: 39

Asp Tyr Lys Asp Asp Asp Asp Lys
1               5

<210> SEQ ID NO 40
<211> LENGTH: 249
<212> TYPE: PRT
<213> ORGANISM: Artificial sequence
<220> FEATURE:
<223> OTHER INFORMATION: scFv protein GMBC603

<400> SEQUENCE: 40

Gln Val Gln Leu Val Gln Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
            35                  40                  45

Ser Gly Ile Asn Trp Asn Gly Ser Thr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Leu Asn Tyr Asp Phe Trp Ser Gly Ser Gly Met Asp Val
                100                 105                 110

Trp Gly Arg Gly Thr Leu Val Thr Val Ser Ser Gly Gly Gly Ser
            115                 120                 125

Gly Gly Gly Gly Ser Gly Gly Gly Ser Gln Ser Val Leu Thr Gln
        130                 135                 140

Pro Ala Ser Val Ser Gly Ser Pro Gly Gln Ser Ile Thr Ile Ser Cys
145                 150                 155                 160

Thr Gly Thr Ser Ser Asp Val Gly Gly Tyr Asn Tyr Val Ser Trp Tyr
                165                 170                 175

Gln Gln His Pro Gly Lys Ala Pro Lys Leu Met Ile Tyr Glu Gly Ser
                180                 185                 190

Lys Arg Pro Ser Gly Val Ser Asn Arg Phe Ser Gly Ser Lys Ser Gly
            195                 200                 205

Asn Thr Ala Ser Leu Thr Ile Ser Gly Leu Gln Ala Glu Asp Glu Ala
            210                 215                 220

Asp Tyr Tyr Cys Ser Ser Tyr Thr Thr Arg Ser Thr Arg Val Phe Gly
225                 230                 235                 240

Gly Gly Thr Lys Leu Thr Val Leu Gly
                245

<210> SEQ ID NO 41
<211> LENGTH: 243
<212> TYPE: PRT
<213> ORGANISM: Artificial sequence
<220> FEATURE:
<223> OTHER INFORMATION: scFv protein GMBC604

<400> SEQUENCE: 41

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Asn Tyr
            20                  25                  30

Trp Ile Asn Trp Val Arg Gln Val Pro Gly Lys Gly Leu Glu Trp Met
        35                  40                  45

Gly Met Ile Asp Pro Thr Asp Ser Tyr Ala Lys Tyr Ser Pro Ser Phe
    50                  55                  60

Gln Gly His Val Thr Ile Ser Thr Asp Lys Ser Val Ser Thr Ala Tyr
65                  70                  75                  80

Leu Gln Trp Arg Ser Leu Gln Ala Ser Asp Ser Ala Ile Tyr Tyr Cys
                85                  90                  95

Val Arg Gly Tyr Ser Tyr Asp Leu Asp Tyr Trp Gly Lys Gly Thr Leu
            100                 105                 110

Val Thr Val Ser Ser Gly Gly Gly Gly Ser Gly Gly Gly Ser Gly
            115                 120                 125

Gly Gly Gly Ser Gln Ser Val Leu Thr Gln Pro Ala Ser Val Ser Gly
        130                 135                 140

Ser Pro Gly Gln Ser Ile Thr Ile Ser Cys Thr Gly Thr Ser Ser Asp
145                 150                 155                 160

Val Gly Gly Tyr Asn Tyr Val Ser Trp Tyr Gln Gln His Pro Gly Lys
                165                 170                 175

Ala Pro Lys Leu Met Ile Tyr Glu Gly Ser Lys Arg Pro Ser Gly Val
            180                 185                 190

Ser Asn Arg Phe Ser Gly Ser Lys Ser Gly Asn Thr Ala Ser Leu Thr
        195                 200                 205

Ile Ser Gly Leu Gln Ala Glu Asp Glu Ala Asp Tyr Tyr Cys Ser Ser
    210                 215                 220

Tyr Thr Thr Arg Ser Thr Arg Val Phe Gly Gly Gly Thr Lys Leu Thr
225                 230                 235                 240

Val Leu Gly

<210> SEQ ID NO 42
<211> LENGTH: 247
<212> TYPE: PRT
<213> ORGANISM: Artificial sequence
<220> FEATURE:

<223> OTHER INFORMATION: scFv protein GMBC605

<400> SEQUENCE: 42

```
Gln Val Gln Leu Val Gln Ser Gly Gly Gly Leu Val Lys Pro Gly Gly
1               5                   10                  15

Ser Leu Arg Leu Ser Cys Glu Thr Ser Gly Phe Lys Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Thr Ile Asp Tyr Ala Ala
    50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Arg Gly Thr Leu Val Thr Val Ser Ser Gly Gly Gly Ser Gly Gly
        115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly
225                 230                 235                 240

Thr Lys Leu Thr Val Leu Gly
                245
```

<210> SEQ ID NO 43
<211> LENGTH: 242
<212> TYPE: PRT
<213> ORGANISM: Artificial sequence
<220> FEATURE:
<223> OTHER INFORMATION: scFv protein GMBC606

<400> SEQUENCE: 43

```
Glu Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Ser Ser Ser Phe Ala Asn Ala Phe Asp Ile Trp Gly Gln Gly
            100                 105                 110

Thr Thr Val Thr Val Ser Ser Gly Gly Gly Ser Gly Gly Gly Gly
            115                 120                 125

Ser Gly Gly Gly Ser Ser Glu Leu Thr Gln Asp Pro Ala Val Ser
130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
                180                 185                 190

Arg Phe Ser Gly Ser Ser Ser Gly Asn Thr Ala Ser Leu Thr Ile Thr
                195                 200                 205

Gly Ala Gln Ala Glu Asp Glu Ala Asp Tyr Tyr Cys Asn Ser Arg Asp
210                 215                 220

Ser Ser Gly Asn His Val Val Phe Gly Gly Gly Thr Lys Leu Thr Val
225                 230                 235                 240

Leu Gly

<210> SEQ ID NO 44
<211> LENGTH: 247
<212> TYPE: PRT
<213> ORGANISM: Artificial sequence
<220> FEATURE:
<223> OTHER INFORMATION: scFv protein GMBC607

<400> SEQUENCE: 44

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
    50                  55                  60

Pro Val Lys Asp Arg Phe Thr Ile Ser Arg Asp Asp Ser Lys Asn Met
65                  70                  75                  80

Leu Tyr Leu Glu Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Gln Gly Thr Met Val Thr Val Ser Ser Gly Gly Gly Ser Gly Gly
        115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Asp Tyr Asn Tyr Val Ser Trp Tyr Gln Gln
                165                 170                 175

His Pro Gly Lys Ala Pro Lys Leu Met Ile Tyr Glu Gly Ser Lys Arg
                180                 185                 190

Pro Ser Gly Val Ser Asn Arg Phe Ser Gly Ser Lys Ser Gly Asn Thr
                195                 200                 205
```

```
Ala Ser Leu Thr Ile Ser Gly Leu Gln Ala Glu Asp Glu Ala Asp Tyr
    210                 215                 220
Tyr Cys Ser Ser Tyr Thr Thr Arg Ser Thr Arg Val Phe Gly Gly Gly
225                 230                 235                 240
Thr Lys Leu Thr Val Leu Gly
                245

<210> SEQ ID NO 45
<211> LENGTH: 246
<212> TYPE: PRT
<213> ORGANISM: Artificial sequence
<220> FEATURE:
<223> OTHER INFORMATION: scFv protein GMBC608

<400> SEQUENCE: 45

Glu Val Gln Leu Val Gln Ser Gly Gly Gly Leu Val Gln Pro Gly Arg
1               5                   10                  15
Ser Leu Arg Leu Ser Cys Ala Ala Ser Gly Phe Thr Phe Ser Asp Ser
            20                  25                  30
Tyr Met Thr Trp Ile Arg Gln Ala Pro Gly Glu Gly Leu Glu Phe Val
        35                  40                  45
Ser Tyr Ile Ser Ser Gly Ser Ser Thr Thr Tyr Tyr Thr Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Pro Glu Asp Thr Ala Val Tyr Tyr Cys
                85                  90                  95
Ala Arg Arg Ser Ile Ser Ser Asp Tyr Tyr Ser Tyr Tyr Leu Asp Val
            100                 105                 110
Trp Gly Lys Gly Thr Leu Val Thr Val Ser Ser Gly Gly Gly Gly Ser
        115                 120                 125
Gly Gly Gly Gly Ser Gly Gly Gly Ser Ser Glu Leu Thr Gln Asp
    130                 135                 140
Pro Ala Val Ser Val Ala Leu Gly Gln Thr Val Arg Ile Thr Cys Gln
145                 150                 155                 160
Gly Asp Ser Leu Arg Ser Tyr Tyr Ala Ser Trp Tyr Gln Gln Lys Pro
                165                 170                 175
Gly Gln Ala Pro Val Leu Val Ile Tyr Gly Lys Asn Asn Arg Pro Ser
            180                 185                 190
Gly Ile Pro Asp Arg Phe Ser Gly Ser Ser Ser Gly Asn Thr Ala Ser
        195                 200                 205
Leu Thr Ile Thr Gly Ala Gln Ala Glu Asp Glu Ala Asp Tyr Tyr Cys
    210                 215                 220
Asn Ser Arg Asp Ser Ser Gly Asn His Val Val Phe Gly Gly Gly Thr
225                 230                 235                 240
Lys Leu Thr Val Leu Gly
                245

<210> SEQ ID NO 46
<211> LENGTH: 247
<212> TYPE: PRT
<213> ORGANISM: Artificial sequence
<220> FEATURE:
<223> OTHER INFORMATION: scFv protein GMBC609

<400> SEQUENCE: 46

Gln Val Gln Leu Val Glu Ser Gly Gly Gly Leu Val Lys Pro Gly Glu
1               5                   10                  15
```

Ser Leu Arg Leu Ser Cys Glu Ala Ser Gly Phe Glu Phe Asn Tyr Ala
            20                  25                  30

Trp Met Ser Trp Val Arg Gln Ala Pro Gly Lys Gly Leu Glu Trp Val
        35                  40                  45

Gly Arg Ser Arg Ser Glu Ala Ser Gly Gly Thr Thr Asp Tyr Ala Ala
    50                  55                  60

Pro Leu Gln Asp Arg Phe Thr Ile Ser Arg Asp Asp Ser Lys Asn Thr
65                  70                  75                  80

Leu Tyr Leu Gln Val Asn Ser Leu Lys Ile Glu Asp Thr Gly Val Tyr
                85                  90                  95

Phe Cys Lys Trp Glu Lys Ser Glu Tyr Tyr Gly Met Asp Val Trp Gly
            100                 105                 110

Arg Gly Thr Pro Val Thr Val Ser Gly Gly Gly Ser Gly Gly
        115                 120                 125

Gly Gly Ser Gly Gly Gly Ser Gln Ser Val Leu Thr Gln Pro Pro
    130                 135                 140

Ser Val Ser Ala Ala Pro Gly Gln Lys Val Thr Ile Ser Cys Ser Gly
145                 150                 155                 160

Ser Thr Ser Asn Ile Gly Asn Asn Tyr Val Ser Trp Tyr Gln Gln His
                165                 170                 175

Pro Gly Lys Ala Pro Lys Leu Met Ile Tyr Asp Val Ser Lys Arg Pro
            180                 185                 190

Ser Gly Val Pro Asp Arg Phe Ser Gly Ser Lys Ser Gly Asn Ser Ala
        195                 200                 205

Ser Leu Asp Ile Ser Gly Leu Gln Ser Glu Asp Glu Ala Asp Tyr Tyr
    210                 215                 220

Cys Ala Ala Trp Asp Asp Ser Leu Ser Glu Phe Leu Phe Gly Thr Gly
225                 230                 235                 240

Thr Lys Leu Thr Val Leu Gly
                245

<210> SEQ ID NO 47
<211> LENGTH: 241
<212> TYPE: PRT
<213> ORGANISM: Artificial sequence
<220> FEATURE:
<223> OTHER INFORMATION: scFv protein GMBC610

<400> SEQUENCE: 47

Gln Val Thr Leu Lys Glu Ser Gly Ala Glu Val Lys Lys Pro Gly Ala
1               5                   10                  15

Ser Val Lys Val Ser Cys Lys Thr Ser Gly Phe Thr Phe Gly Ala Tyr
            20                  25                  30

Tyr Ile His Trp Val Arg Gln Val Pro Gly Gln Gly Leu Glu Trp Met
        35                  40                  45

Gly Trp Ile Asp Pro Asn Asn Gly Gly Thr Asn Tyr Ala Gln Lys Phe
    50                  55                  60

Gln Gly Arg Val Thr Met Thr Arg Asp Met Ser Thr Thr Thr Thr Tyr
65                  70                  75                  80

Met Glu Val Ser Gly Leu His Ser Asp Asp Thr Ala Val Tyr Tyr Cys
                85                  90                  95

Ala Arg Ala Arg Val Ala Thr Ile Leu Glu Tyr Trp Gly Arg Gly Thr
            100                 105                 110

Leu Val Thr Val Ser Ser Gly Gly Gly Gly Ser Gly Gly Gly Gly Ser
        115                 120                 125

```
Gly Gly Gly Gly Ser Pro Glu Leu Thr Gln Asp Pro Ala Val Ser Val
        130                 135                 140
Ala Leu Gly Gln Thr Val Arg Ile Thr Cys Gln Gly Asp Ser Leu Arg
145                 150                 155                 160
Ser Tyr Tyr Ala Ser Trp Tyr Gln Gln Lys Pro Gly Gln Ala Pro Val
                165                 170                 175
Leu Val Ile Tyr Gly Lys Asn Asn Arg Pro Ser Gly Ile Pro Asp Arg
            180                 185                 190
Phe Ser Gly Ser Ser Ser Gly Asn Thr Ala Ser Leu Thr Ile Thr Gly
        195                 200                 205
Ala Gln Ala Glu Asp Glu Ala Asp Tyr Tyr Cys Asn Ser Arg Asp Ser
    210                 215                 220
Ser Gly Asn His Val Val Phe Gly Gly Gly Thr Lys Leu Thr Val Leu
225                 230                 235                 240
Gly

<210> SEQ ID NO 48
<211> LENGTH: 239
<212> TYPE: PRT
<213> ORGANISM: Artificial sequence
<220> FEATURE:
<223> OTHER INFORMATION: scFv protein GMBC612

<400> SEQUENCE: 48

Glu Val Gln Leu Val Glu Ser Gly Gly Val Val Gln Pro Gly Gly
1               5                   10                  15
Ser Leu Arg Leu Ser Cys Ala Ala Ser Gly Phe Ser Phe Ser Ser Tyr
            20                  25                  30
Gly Met Gln Trp Val Arg Gln Ala Pro Gly Lys Gly Leu Glu Trp Val
        35                  40                  45
Ala Phe Ile Arg Tyr Asp Gly Ser Ile Lys Tyr Tyr Ala Asp Ser Val
    50                  55                  60
Lys Gly Arg Phe Thr Val Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Tyr Arg Ile Val Asp Tyr Trp Gly Gln Gly Thr Leu Val
            100                 105                 110
Thr Val Ser Ser Gly Gly Gly Gly Ser Gly Gly Gly Gly Ser Gly Gly
        115                 120                 125
Gly Gly Ser Asp Ile Gln Met Thr Gln Ser Pro Ser Thr Leu Ser Pro
    130                 135                 140
Ser Ile Gly Asp Arg Val Thr Ile Thr Cys Arg Ala Ser Glu Gly Ile
145                 150                 155                 160
Tyr His Trp Leu Ala Trp Tyr Gln Gln Lys Pro Gly Lys Ala Pro Lys
                165                 170                 175
Leu Leu Ile Tyr Lys Ala Ser Ser Leu Ala Ser Gly Ala Pro Ser Arg
            180                 185                 190
Phe Ser Gly Ser Gly Ser Gly Thr Asp Phe Thr Leu Thr Ile Ser Ser
        195                 200                 205
Leu Gln Pro Asp Asp Phe Ala Thr Tyr Tyr Cys Gln Gln Tyr Ser Asn
    210                 215                 220
Tyr Pro Leu Thr Phe Gly Gly Gly Thr Lys Leu Glu Ile Lys Arg
225                 230                 235
```

<210> SEQ ID NO 49
<211> LENGTH: 245
<212> TYPE: PRT
<213> ORGANISM: Artificial sequence
<220> FEATURE:
<223> OTHER INFORMATION: scFv protein GMBC613

<400> SEQUENCE: 49

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser His
            20                  25                  30

Trp Met Ser Trp Val Arg Gln Ala Pro Gly Lys Gly Leu Glu Trp Val
        35                  40                  45

Ala Ser Ile Lys Gln Asp Gly Arg Glu Lys His Phe Val Asp Ser Val
    50                  55                  60

Lys Gly Arg Phe Ser Ile Ser Arg Asp Asn Ala Lys Asn Ser Leu Tyr
65                  70                  75                  80

Leu Gln Met Asn Ser Leu Arg Thr Glu Asp Thr Ala Val Tyr Tyr Cys
                85                  90                  95

Ala Arg Glu Thr Tyr Gly Gly Tyr Tyr Tyr Phe Met Asp Val Trp
            100                 105                 110

Gly Lys Gly Thr Leu Val Thr Val Ser Ser Gly Gly Gly Ser Gly
            115                 120                 125

Gly Gly Gly Ser Gly Gly Gly Ser Ser Glu Leu Thr Gln Asp Pro
        130                 135                 140

Ala Val Ser Val Ala Leu Gly Gln Thr Val Arg Ile Thr Cys Gln Gly
145                 150                 155                 160

Asp Ser Leu Arg Ser Tyr Tyr Ala Ser Trp Tyr Gln Gln Lys Pro Gly
                165                 170                 175

Gln Ala Pro Val Leu Val Ile Tyr Gly Lys Asn Asn Arg Pro Ser Gly
            180                 185                 190

Ile Pro Asp Arg Phe Ser Gly Ser Ser Ser Gly Asn Thr Ala Ser Leu
        195                 200                 205

Thr Ile Thr Gly Ala Gln Ala Glu Asp Glu Ala Asp Tyr Tyr Cys Asn
    210                 215                 220

Ser Arg Asp Ser Ser Gly Asn His Val Val Phe Gly Gly Gly Thr Lys
225                 230                 235                 240

Leu Thr Val Leu Gly
                245

<210> SEQ ID NO 50
<211> LENGTH: 247
<212> TYPE: PRT
<213> ORGANISM: Artificial sequence
<220> FEATURE:
<223> OTHER INFORMATION: scFv protein GMBC614

<400> SEQUENCE: 50

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
    50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
            85                  90                  95

Tyr Cys Thr Trp Asp Trp Asp Phe Tyr Tyr Gly Met Asn Val Trp Gly
                100                 105                 110

Arg Gly Thr Met Val Thr Val Ser Ser Gly Gly Gly Ser Gly Gly
            115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
            195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly Gly
225                 230                 235                 240

Thr Lys Leu Thr Val Leu Gly
                245

<210> SEQ ID NO 51
<211> LENGTH: 247
<212> TYPE: PRT
<213> ORGANISM: Artificial sequence
<220> FEATURE:
<223> OTHER INFORMATION: scFv protein GMBC615

<400> SEQUENCE: 51

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Lys Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Thr Ile Asp Tyr Ala Ala
    50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
            85                  90                  95

Tyr Cys Thr Trp Asp Trp Asp Phe Tyr Tyr Gly Met Asn Val Trp Gly
                100                 105                 110

Lys Gly Thr Leu Val Ala Val Ser Ser Gly Gly Gly Gly Ser Gly Gly
            115                 120                 125

Gly Gly Ser Gly Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

-continued

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly Gly
225                 230                 235                 240

Thr Lys Leu Thr Val Leu Gly
                245

<210> SEQ ID NO 52
<211> LENGTH: 247
<212> TYPE: PRT
<213> ORGANISM: Artificial sequence
<220> FEATURE:
<223> OTHER INFORMATION: scFv protein GMBC616

<400> SEQUENCE: 52

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Thr Asp Tyr Ala Ala
    50                  55                  60

Pro Val Lys Asp Arg Phe Thr Ile Ser Arg Asp Asp Ser Glu Asn Thr
65                  70                  75                  80

Leu Tyr Leu Gln Met Asn Ser Leu Lys Thr Glu Asp Thr Ala Val Tyr
                85                  90                  95

Tyr Cys Thr Trp Asp His Ser Tyr Tyr Tyr Asp Met Ala Val Trp Gly
            100                 105                 110

Arg Gly Thr Leu Val Thr Val Ser Ser Gly Gly Gly Ser Gly Gly
        115                 120                 125

Gly Gly Ser Gly Gly Gly Gly Ser Gln Ser Val Leu Thr Gln Pro Pro
    130                 135                 140

Phe Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly Gly
225                 230                 235                 240

Thr Lys Leu Thr Val Leu Gly
                245

<210> SEQ ID NO 53
<211> LENGTH: 243
<212> TYPE: PRT
<213> ORGANISM: Artificial sequence

```
<220> FEATURE:
<223> OTHER INFORMATION: scFv protein GMBC617

<400> SEQUENCE: 53

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Leu Trp Phe Gly Leu Leu Tyr Trp Gly Gln Gly Thr Leu
            100                 105                 110

Val Thr Val Ser Ser Gly Gly Gly Ser Gly Gly Gly Gly Ser Gly
            115                 120                 125

Gly Gly Gly Ser Gln Ser Ala Leu Thr Gln Pro Ala Ser Val Ser Gly
        130                 135                 140

Ser Arg Gly Gln Ser Ile Thr Ile Ser Cys Thr Gly Thr Thr Gly Asp
145                 150                 155                 160

Val Gly Gly Tyr Asp Tyr Val Ser Trp Tyr Gln Gln His Pro Gly Lys
                165                 170                 175

Ala Pro Lys Leu Leu Ile Tyr Gly Asn Ser Asn Arg Pro Ser Gly Val
            180                 185                 190

Pro Asp Arg Phe Ser Ala Ser Lys Ser Gly Asn Thr Ala Ser Leu Thr
        195                 200                 205

Ile Ser Gly Leu Gln Ala Glu Asp Glu Ala Asp Tyr Phe Cys Ser Thr
    210                 215                 220

Tyr Ala Pro Pro Gly Ile Ile Met Phe Gly Gly Thr Lys Leu Thr
225                 230                 235                 240

Val Leu Gly

<210> SEQ ID NO 54
<211> LENGTH: 247
<212> TYPE: PRT
<213> ORGANISM: Artificial sequence
<220> FEATURE:
<223> OTHER INFORMATION: scFv protein GMBC618

<400> SEQUENCE: 54

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Lys Phe Asp Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Arg Ser Gly Gly Thr Ile Asp Tyr Ala Ala
    50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Arg Thr Glu Asp Thr Ala Leu Tyr
                85                  90                  95
```

```
Tyr Cys Thr Trp Asp Trp Asp Phe Tyr Tyr Gly Met Asn Val Trp Gly
            100                 105                 110

Arg Gly Thr Leu Val Thr Val Ser Ser Gly Gly Gly Ser Gly Gly
        115                 120                 125

Gly Gly Ser Gly Gly Gly Ser Gln Ser Val Leu Thr Gln Pro Pro
    130                 135                 140

Ser Ala Ser Gly Thr Pro Gly Gln Arg Val Thr Ile Ser Cys Ser Gly
145                 150                 155                 160

Ser Ser Ser Asn Ile Gly Ser Asn Thr Val Asn Trp Tyr Gln Arg Leu
                165                 170                 175

Pro Gly Ala Ala Pro Gln Leu Leu Ile Tyr Asn Asn Asp Gln Arg Pro
            180                 185                 190

Ser Gly Ile Pro Asp Arg Phe Ser Gly Ser Lys Ser Gly Thr Ser Gly
            195                 200                 205

Ser Leu Val Ile Ser Gly Leu Gln Ser Glu Asp Glu Ala Asp Tyr Tyr
        210                 215                 220

Cys Ala Ser Trp Asp Asp Ser Leu Asn Gly Arg Val Phe Gly Gly Gly
225                 230                 235                 240

Thr Lys Leu Thr Val Leu Gly
                245
```

```
<210> SEQ ID NO 55
<211> LENGTH: 244
<212> TYPE: PRT
<213> ORGANISM: Artificial sequence
<220> FEATURE:
<223> OTHER INFORMATION: scFv protein GMBC619

<400> SEQUENCE: 55

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Thr Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Gly Gly Trp Tyr His Pro Arg Leu Asp Tyr Trp Gly
            100                 105                 110

Gln Gly Thr Met Val Thr Val Ser Ser Gly Gly Gly Gly Ser Gly Gly
        115                 120                 125

Gly Gly Ser Gly Gly Gly Gly Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Ser Gly Asn Thr Ala Ser Leu Thr
            195                 200                 205
```

```
Ile Thr Gly Ala Gln Ala Glu Asp Glu Ala Asp Tyr Tyr Cys Asn Ser
    210                 215                 220
Arg Asp Ser Ser Gly Asn His Val Val Phe Gly Gly Thr Lys Leu
225                 230                 235                 240
Thr Val Leu Gly

<210> SEQ ID NO 56
<211> LENGTH: 247
<212> TYPE: PRT
<213> ORGANISM: Artificial sequence
<220> FEATURE:
<223> OTHER INFORMATION: scFv protein GMBC620

<400> SEQUENCE: 56

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Ala
                20                  25                  30
Trp Met Asn Trp Val Arg Gln Ala Pro Gly Lys Gly Leu Glu Trp Val
            35                  40                  45
Gly Arg Ile Lys Ser Lys Gly Ser Gly Thr Ile Asp Tyr Ala Ala
        50                  55                  60
Pro Val Lys Asp Arg Phe Thr Ile Ser Arg Asp Ser Lys Asn Thr
65                  70                  75                  80
Leu Tyr Leu Gln Met Asn Ser Leu Lys Thr Glu Asp Thr Ala Leu Tyr
                85                  90                  95
Tyr Cys Thr Trp Asp Trp Asp Phe Tyr Tyr Gly Met Asn Val Trp Gly
            100                 105                 110
Arg Gly Thr Met Val Thr Val Ser Gly Gly Gly Ser Gly Gly
        115                 120                 125
Gly Gly Ser Gly Gly Gly Ser Gln Ser Val Leu Thr Gln Pro Ala
    130                 135                 140
Ser Val Ser Gly Ser Pro Gly Gln Ser Ile Thr Ile Ser Cys Thr Gly
145                 150                 155                 160
Thr Ser Ser Asp Val Gly Gly Tyr Asn Tyr Val Ser Trp Tyr Gln Gln
                165                 170                 175
His Pro Gly Lys Ala Pro Lys Leu Met Ile Tyr Glu Gly Ser Lys Arg
            180                 185                 190
Pro Ser Gly Val Ser Asn Arg Phe Ser Gly Ser Lys Ser Gly Asn Thr
        195                 200                 205
Ala Ser Leu Thr Ile Ser Gly Leu Gln Ala Glu Asp Glu Ala Asp Tyr
    210                 215                 220
Tyr Cys Ser Ser Tyr Thr Thr Arg Ser Thr Arg Val Phe Gly Gly Gly
225                 230                 235                 240
Thr Lys Leu Thr Val Leu Gly
                245

<210> SEQ ID NO 57
<211> LENGTH: 241
<212> TYPE: PRT
<213> ORGANISM: Artificial sequence
<220> FEATURE:
<223> OTHER INFORMATION: scFv protein GMBC621

<400> SEQUENCE: 57

Glu Val Gln Leu Val Gln Ser Gly Gly Gly Val Val Gln Pro Gly Arg
1               5                   10                  15
```

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                    85                  90                  95

Ala Lys Arg Gly Leu Trp Thr Pro Ile Asp Tyr Trp Gly Lys Gly Thr
                100                 105                 110

Leu Val Thr Val Ser Ser Gly Gly Gly Gly Ser Gly Gly Gly Gly Ser
            115                 120                 125

Gly Gly Gly Gly Ser Ser Glu Leu Thr Gln Asp Pro Ala Val Ser Val
        130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
                180                 185                 190

Phe Ser Gly Ser Asn Ser Gly Asn Thr Ala Ser Leu Thr Ile Thr Gly
            195                 200                 205

Ala Gln Ala Glu Asp Glu Ala Asp Tyr Tyr Cys Asn Ser Arg Asp Ser
        210                 215                 220

Ser Gly Asn His Val Val Phe Gly Gly Gly Thr Lys Leu Thr Val Leu
225                 230                 235                 240

Gly

<210> SEQ ID NO 58
<211> LENGTH: 247
<212> TYPE: PRT
<213> ORGANISM: Artificial sequence
<220> FEATURE:
<223> OTHER INFORMATION: scFv protein GMBC625

<400> SEQUENCE: 58

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
            35                  40                  45

Gly Arg Ile Lys Ser Lys Arg Ser Gly Gly Thr Ile Asp Tyr Ala Ala
        50                  55                  60

Pro Val Lys Asp Arg Phe Thr Ile Ser Arg Asp Asp Ser Lys Asp Thr
65                  70                  75                  80

Met Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
                100                 105                 110

Gln Gly Thr Met Val Thr Val Ser Ser Gly Gly Gly Gly Ser Gly Gly
            115                 120                 125

```
Gly Gly Ser Gly Gly Gly Ser Gln Ser Val Leu Thr Gln Pro Ala
        130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Phe Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly Gly
225                 230                 235                 240

Thr Lys Leu Thr Val Leu Gly
                245

<210> SEQ ID NO 59
<211> LENGTH: 247
<212> TYPE: PRT
<213> ORGANISM: Artificial sequence
<220> FEATURE:
<223> OTHER INFORMATION: scFv protein GMBC626

<400> SEQUENCE: 59

Glu Val Gln Leu Val Gln Ser Gly Gly Gly Leu Val Lys Pro Gly Glu
1               5                   10                  15

Ser Leu Arg Leu Ser Cys Glu Ala Ser Gly Phe Glu Phe Asn Tyr Ala
            20                  25                  30

Trp Met Ser Trp Val Arg Gln Ala Pro Gly Lys Gly Leu Glu Trp Val
        35                  40                  45

Gly Arg Ser Arg Ser Glu Ala Ser Gly Gly Thr Thr Asp Tyr Ala Ala
    50                  55                  60

Pro Leu Gln Asp Arg Phe Thr Ile Ser Arg Asp Asp Ser Lys Asn Thr
65                  70                  75                  80

Leu Tyr Leu Gln Val Asn Ser Leu Lys Ile Glu Asp Thr Gly Val Tyr
                85                  90                  95

Phe Cys Lys Trp Glu Lys Ser Glu Tyr Tyr Gly Met Asp Val Trp Gly
            100                 105                 110

Arg Gly Thr Pro Val Thr Val Ser Ser Gly Gly Gly Ser Gly Gly
        115                 120                 125

Gly Gly Ser Gly Gly Gly Gly Ser Gln Ser Val Leu Thr Gln Pro Ala
        130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Arg Ala Glu Asp Glu Ala Asp Tyr
    210                 215                 220

Tyr Cys Ser Ser Tyr Thr Thr Lys Ser Thr Gln Val Phe Gly Gly Gly
225                 230                 235                 240
```

Thr Lys Leu Thr Val Leu Gly
            245

<210> SEQ ID NO 60
<211> LENGTH: 244
<212> TYPE: PRT
<213> ORGANISM: Artificial sequence
<220> FEATURE:
<223> OTHER INFORMATION: scFv protein GMBC627

<400> SEQUENCE: 60

Gly Val Gln Leu Val Gln Ser Gly Gly Glu Val Lys Lys Pro Gly Ala
1               5                   10                  15

Ser Val Arg Val Ser Cys Lys Ala Ser Arg Tyr Ile Phe Ser Asn Tyr
            20                  25                  30

Gly Phe Ser Trp Val Arg Gln Ala Pro Gly Gln Gly Leu Glu Trp Met
        35                  40                  45

Gly Ser Ile Arg Asn Asp Lys Gly Ser Thr Asn Tyr Ala Gln Gly Phe
    50                  55                  60

Gln Asp Arg Leu Thr Met Thr Thr Asp Thr Ser Thr Asn Thr Val Phe
65                  70                  75                  80

Met Glu Leu Arg Ser Leu Ser Ser Asp Asp Thr Ala Val Tyr Tyr Cys
                85                  90                  95

Ala Ser Ala Pro Tyr Tyr Gly Met Gly Ile Trp Gly Lys Gly Thr
            100                 105                 110

Leu Val Thr Val Ser Ser Gly Gly Gly Ser Gly Gly Gly Gly Ser
            115                 120                 125

Gly Gly Gly Gly Ser Gln Ser Val Leu Thr Gln Pro Ala Ser Val Ser
    130                 135                 140

Gly Ser Ser Gly Gln Ser Ile Thr Ile Ser Cys Thr Gly Thr Ser Ser
145                 150                 155                 160

Asp Val Gly Gly Tyr Asn Tyr Val Ser Trp Tyr Gln Gln His Pro Gly
                165                 170                 175

Lys Ala Pro Lys Leu Met Ile Tyr Glu Val Gly Asn Arg Pro Ser Gly
            180                 185                 190

Val Ser Asn Arg Phe Ser Gly Ser Lys Ser Gly Asn Thr Ala Ser Leu
        195                 200                 205

Thr Ile Ser Gly Leu Gln Ala Glu Asp Glu Ala Asp Tyr Tyr Cys Ser
    210                 215                 220

Ser Tyr Thr Thr Arg Ser Thr Arg Val Phe Gly Gly Gly Thr Lys Leu
225                 230                 235                 240

Thr Val Leu Gly

<210> SEQ ID NO 61
<211> LENGTH: 249
<212> TYPE: PRT
<213> ORGANISM: Artificial sequence
<220> FEATURE:
<223> OTHER INFORMATION: scFv protein GMBC628

<400> SEQUENCE: 61

Gln Val Gln Leu Gln Gln Ser Gly Ala Glu Val Lys Lys Pro Gly Ala
1               5                   10                  15

Ser Val Arg Val Ser Cys Lys Ala Ser Gly Tyr Thr Phe Thr Ser Tyr
            20                  25                  30

Gly Phe Ser Trp Val Arg Gln Ala Pro Gly Gln Arg Leu Glu Trp Met
        35                  40                  45

-continued

Gly Trp Ile Ser Ala Tyr Lys Gly Asn Ala Asn Tyr Ala Glu Lys Phe
            50                  55                  60

Gln Gly Arg Val Thr Met Thr Thr Asp Thr Ser Thr Asn Thr Ala Tyr
 65                  70                  75                  80

Met Glu Leu Arg Ser Leu Arg Ser Asp Asp Thr Ala Val Tyr Tyr Cys
                85                  90                  95

Ala Arg Thr Arg Ile Ser Val Ala Gly Leu Asp Tyr Tyr Tyr Gly
                    100                 105                 110

Leu Asp Val Trp Gly Arg Gly Thr Leu Val Thr Val Ser Ser Gly Gly
                115                 120                 125

Gly Gly Ser Gly Gly Gly Ser Gly Gly Gly Ser Ser Glu Leu
        130                 135                 140

Thr Gln Asp Pro Ala Val Ser Val Ala Leu Gly Gln Thr Val Arg Ile
145                 150                 155                 160

Thr Cys Gln Gly Asp Ser Leu Arg Ser Tyr Tyr Thr Asn Trp Phe Gln
                    165                 170                 175

Gln Lys Pro Gly Gln Ala Pro Leu Leu Val Val Tyr Ala Lys Asn Asn
                180                 185                 190

Arg Pro Ser Gly Ile Pro Asp Arg Phe Ser Gly Ser Ser Ser Gly Asn
                195                 200                 205

Thr Ala Ser Leu Thr Ile Thr Gly Ala Gln Ala Glu Asp Glu Ala Asp
        210                 215                 220

Tyr Tyr Cys Asn Ser Arg Asp Ser Ser Gly Asn His Val Val Phe Gly
225                 230                 235                 240

Gly Gly Thr Lys Leu Thr Val Leu Gly
                    245

<210> SEQ ID NO 62
<211> LENGTH: 244
<212> TYPE: PRT
<213> ORGANISM: Artificial sequence
<220> FEATURE:
<223> OTHER INFORMATION: scFv protein GMBC629

<400> SEQUENCE: 62

Gln Val Gln Leu Val Glu Ser Gly Gly Gly Leu Val Lys Pro Gly Gly
 1               5                   10                  15

Ser Leu Arg Leu Ser Cys Ala Gly Ser Gly Phe Lys Phe Ser Asp Ala
                20                  25                  30

Trp Met Asn Trp Val Arg Gln Ala Pro Gly Lys Gly Leu Glu Trp Val
                35                  40                  45

Gly Arg Ile Lys Ser Lys Gly Ser Gly Gly Thr Ile Glu Tyr Ala Val
            50                  55                  60

Pro Val Lys Asp Arg Phe Ile Ile Ser Arg Asp Asp Ser Lys Asp Thr
 65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
                    100                 105                 110

Gln Gly Thr Leu Val Thr Val Ser Ser Gly Gly Gly Ser Gly Gly
                115                 120                 125

Gly Gly Ser Gly Gly Gly Gly Ser Ser Glu Leu Thr Gln Asp Pro Ala
        130                 135                 140

Val Ser Val Ala Leu Gly Gln Thr Val Arg Ile Thr Cys Gln Gly Asp
145                 150                 155                 160

```
Ser Leu Arg Ser Tyr Tyr Thr Asn Trp Phe Gln Gln Lys Pro Gly Gln
            165                 170                 175

Ala Pro Leu Leu Val Val Tyr Ala Lys Asn Lys Arg Pro Ser Gly Ile
            180                 185                 190

Pro Asp Arg Phe Ser Gly Ser Ser Ser Gly Asn Thr Ala Ser Leu Thr
            195                 200                 205

Ile Thr Gly Ala Gln Ala Glu Asp Glu Ala Asp Tyr Tyr Cys His Ser
            210                 215                 220

Arg Asp Ser Ser Gly Asn His Val Leu Phe Gly Gly Thr Lys Leu
225             230                 235                 240

Thr Val Leu Gly

<210> SEQ ID NO 63
<211> LENGTH: 242
<212> TYPE: PRT
<213> ORGANISM: Artificial sequence
<220> FEATURE:
<223> OTHER INFORMATION: scFv protein GMBC630

<400> SEQUENCE: 63

Gln Val Gln Leu Val Glu Ser Gly Gly Gly Leu Val Gln Pro Gly Arg
1               5                   10                  15

Ser Leu Arg Leu Pro Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
            85                  90                  95

Ala Lys Ala Thr Ser Leu Leu Asn Ala Phe Asp Ile Trp Gly Arg Gly
            100                 105                 110

Thr Met Val Thr Val Ser Ser Gly Gly Gly Gly Ser Gly Gly Gly Gly
            115                 120                 125

Ser Gly Gly Gly Gly Ser Ser Glu Leu Thr Gln Asp Pro Ala Val Ser
            130                 135                 140

Val Ala Leu Gly Gln Thr Val Arg Ile Thr Cys Gln Gly Asp Ser Leu
145             150                 155                 160

Arg Ser Tyr Tyr Ala Ser Trp Tyr Gln Gln Lys Pro Gly Gln Ala Pro
            165                 170                 175

Val Leu Val Ile Tyr Gly Lys Asn Asn Arg Pro Ser Gly Ile Pro Asp
            180                 185                 190

Arg Phe Ser Gly Ser Ser Ser Gly Asn Thr Ala Ser Leu Thr Ile Thr
            195                 200                 205

Gly Ala Gln Ala Glu Asp Glu Ala Asp Tyr Tyr Cys Asn Ser Arg Asp
            210                 215                 220

Ser Ser Gly Asn His Val Val Phe Gly Gly Thr Lys Leu Thr Val
225             230                 235                 240

Leu Gly

<210> SEQ ID NO 64
<211> LENGTH: 244
<212> TYPE: PRT
<213> ORGANISM: Artificial sequence
```

```
<220> FEATURE:
<223> OTHER INFORMATION: scFv protein GMBC632

<400> SEQUENCE: 64

Gln Val Gln Leu Val Gln Ser Gly Gly Gly Leu Val Lys Pro Gly Gly
1               5                   10                  15

Ser Leu Arg Leu Ser Cys Ala Gly Ser Gly Phe Lys Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Glu Tyr Ala Ala
    50                  55                  60

Pro Val Lys Asp Arg Phe Ile Ile Ser Arg Asp Asp Ser Lys Asp Thr
65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Asp Met Asn Val Trp Gly
            100                 105                 110

Gln Gly Thr Met Val Thr Val Ser Ser Gly Gly Gly Ser Gly Gly
        115                 120                 125

Gly Gly Ser Gly Gly Gly Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Phe Gly Ser Ser Gly Asn Thr Ala Ser Leu Thr
        195                 200                 205

Ile Thr Gly Ala Gln Ala Glu Asp Glu Ala Asp Tyr Tyr Cys Asn Ser
    210                 215                 220

Arg Asp Ser Ser Gly Asn His Val Val Phe Gly Gly Gly Thr Lys Leu
225                 230                 235                 240

Thr Val Leu Gly

<210> SEQ ID NO 65
<211> LENGTH: 247
<212> TYPE: PRT
<213> ORGANISM: Artificial sequence
<220> FEATURE:
<223> OTHER INFORMATION: scFv protein GMBC634

<400> SEQUENCE: 65

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
    50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
                85                  90                  95
```

-continued

Tyr Cys Thr Trp Asp Trp Asp Phe Tyr Tyr Gly Met Asn Val Trp Gly
                100                 105                 110

Gln Gly Thr Leu Val Thr Val Ser Ser Gly Gly Gly Ser Gly Gly
            115                 120                 125

Gly Gly Ser Gly Gly Gly Ser Gln Ser Val Leu Thr Gln Pro Ala
        130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly
225                 230                 235                 240

Thr Lys Leu Thr Val Leu Gly
                245

<210> SEQ ID NO 66
<211> LENGTH: 244
<212> TYPE: PRT
<213> ORGANISM: Artificial sequence
<220> FEATURE:
<223> OTHER INFORMATION: scFv protein GMBC635

<400> SEQUENCE: 66

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
    50                  55                  60

Pro Val Lys Asp Arg Tyr Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Lys Gly Thr Met Val Thr Val Ser Ser Gly Gly Gly Gly Ser Gly Gly
        115                 120                 125

Gly Gly Ser Gly Gly Gly Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Gly Asn Thr Ala Ser Leu Thr
        195                 200                 205

```
Ile Thr Gly Ala Gln Ala Glu Asp Glu Ala Asp Tyr Tyr Cys Asn Ser
    210                 215                 220
Arg Asp Ser Ser Gly Asn His Val Val Phe Gly Gly Thr Lys Leu
225                 230                 235                 240
Thr Val Leu Gly

<210> SEQ ID NO 67
<211> LENGTH: 247
<212> TYPE: PRT
<213> ORGANISM: Artificial sequence
<220> FEATURE:
<223> OTHER INFORMATION: scFv protein GMBC638

<400> SEQUENCE: 67

Gln Val Gln Leu Val Gln Ser Gly Gly Gly Leu Val Lys Pro Gly Glu
1               5                   10                  15
Ser Leu Arg Leu Ser Cys Glu Ala Ser Gly Phe Glu Phe Asn Tyr Ala
                20                  25                  30
Trp Met Ser Trp Val Arg Gln Ala Pro Gly Lys Gly Leu Glu Trp Val
            35                  40                  45
Gly Arg Ser Arg Ser Val Ala Ser Gly Gly Thr Thr Asp Tyr Ala Ala
        50                  55                  60
Pro Leu Gln Asp Arg Phe Thr Ile Ser Arg Asp Asp Ser Lys Asn Thr
65                  70                  75                  80
Leu Tyr Leu Gln Val Asn Ser Leu Lys Ile Glu Asp Thr Gly Val Tyr
                85                  90                  95
Phe Cys Lys Trp Glu Lys Ser Glu Tyr Tyr Gly Met Asp Val Trp Gly
            100                 105                 110
Arg Gly Thr Met Val Thr Val Ser Gly Gly Gly Gly Ser Gly Gly
        115                 120                 125
Gly Gly Ser Gly Gly Gly Ser Gln Ser Val Leu Thr Gln Pro Ala
    130                 135                 140
Ser Val Ser Gly Ser Pro Gly Gln Ser Ile Thr Ile Ser Cys Thr Gly
145                 150                 155                 160
Thr Ser Ser Asp Val Gly Gly Tyr Asn Tyr Val Ser Trp Tyr Gln Gln
                165                 170                 175
His Pro Gly Lys Ala Pro Lys Leu Met Ile Tyr Glu Gly Ser Lys Arg
            180                 185                 190
Pro Ser Gly Val Ser Asn Arg Phe Ser Gly Ser Lys Ser Gly Asn Thr
        195                 200                 205
Ala Ser Leu Thr Ile Ser Gly Leu Gln Ala Glu Asp Glu Ala Asp Tyr
    210                 215                 220
Tyr Cys Ser Ser Tyr Thr Thr Arg Ser Thr Arg Val Phe Gly Gly Gly
225                 230                 235                 240
Thr Lys Leu Thr Val Leu Gly
                245

<210> SEQ ID NO 68
<211> LENGTH: 253
<212> TYPE: PRT
<213> ORGANISM: Artificial sequence
<220> FEATURE:
<223> OTHER INFORMATION: scFv protein GMBC639

<400> SEQUENCE: 68

Gly Val Gln Leu Val Gln Ser Gly Ala Glu Val Lys Thr Pro Gly Ala
1               5                   10                  15
```

```
Ser Val Lys Val Ser Cys Lys Ala Ser Gly Tyr Thr Phe Thr Asn His
            20                  25                  30

Tyr Met His Trp Val Arg Gln Ala Pro Gly Gln Gly Ile Glu Trp Val
            35                  40                  45

Gly Val Ile Asn Pro Ser Gly Asp Ser Ser Tyr Ala Gln Thr Phe
 50                  55                  60

Gln Gly Arg Val Thr Met Thr Arg Asp Thr Ser Thr Ser Thr Val Tyr
 65                  70                  75                  80

Met Glu Leu Arg Ser Leu Arg Ser Asp Asp Thr Ala Val Tyr Tyr Cys
            85                  90                  95

Ala Arg Asp Leu Phe Tyr Asp Phe Trp Ser Asp Tyr Tyr Arg Asn Asp
            100                 105                 110

Gln Tyr Tyr Tyr Met Asp Val Trp Gly Lys Gly Thr Leu Val Thr Val
            115                 120                 125

Ser Ser Gly Gly Gly Gly Ser Gly Gly Gly Ser Gly Gly Gly Gly
            130                 135                 140

Ser Ser Glu Leu Thr Gln Asp Pro Ala Val Ser Val Ala Leu Gly Gln
145                 150                 155                 160

Ala Val Arg Ile Thr Cys Gln Gly Asp Ser Leu Arg Ser Tyr Tyr Ala
            165                 170                 175

Ser Trp Tyr Gln Gln Lys Pro Gly Gln Ala Pro Val Leu Val Ile Tyr
            180                 185                 190

Gly Lys Asn Asn Arg Pro Ser Gly Ile Pro Asp Arg Phe Ser Gly Ser
            195                 200                 205

Ser Ser Gly Asn Thr Ala Ser Leu Thr Ile Thr Gly Ala Gln Ala Glu
            210                 215                 220

Asp Glu Ala Asp Tyr Tyr Cys Asn Ser Arg Asp Ser Ser Gly Asn His
225                 230                 235                 240

Val Val Phe Gly Gly Gly Thr Lys Leu Thr Val Leu Gly
            245                 250

<210> SEQ ID NO 69
<211> LENGTH: 243
<212> TYPE: PRT
<213> ORGANISM: Artificial sequence
<220> FEATURE:
<223> OTHER INFORMATION: scFv protein GMBC641

<400> SEQUENCE: 69

Glu Val Gln Leu Val Glu Ser Gly Gly Gly Val Val Arg Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
            85                  90                  95

Ala Lys Gly Gly Asp Arg Ser Phe Arg Ala Phe Asp Phe Trp Gly Gln
            100                 105                 110

Gly Thr Met Val Thr Val Ser Ser Gly Gly Gly Ser Gly Gly Gly
            115                 120                 125
```

```
Gly Ser Gly Gly Gly Ser Ser Glu Leu Thr Gln Asp Pro Ala Val
        130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Gln Lys Pro Gly Gln Ala
                165                 170                 175

Pro Val Leu Val Ile Tyr Gly Lys Asn Asn Arg Pro Ser Gly Ile Pro
            180                 185                 190

Asp Arg Phe Ser Gly Ser Ser Gly Asn Thr Ala Ser Leu Thr Ile
            195                 200                 205

Thr Gly Ala Gln Ala Glu Asp Glu Ala Asp Tyr Tyr Cys Asn Ser Arg
        210                 215                 220

Asp Ser Ser Gly Asn His Val Val Phe Gly Gly Gly Thr Lys Leu Thr
225                 230                 235                 240

Val Leu Gly

<210> SEQ ID NO 70
<211> LENGTH: 243
<212> TYPE: PRT
<213> ORGANISM: Artificial sequence
<220> FEATURE:
<223> OTHER INFORMATION: scFv protein GMBC642

<400> SEQUENCE: 70

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ile His
            20                  25                  30

Tyr Met His Trp Val Arg Gln Ala Pro Gly Gln Gly Leu Glu Trp Met
        35                  40                  45

Gly Ile Ile Asn Pro Gly Asp Gly Ser Thr Ser Tyr Ala Gln Asn Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Gly Arg Thr Val Thr Ser His Phe Asp Tyr Trp Gly Arg
            100                 105                 110

Gly Thr Leu Ala Thr Val Ser Ser Gly Gly Gly Gly Ser Gly Gly Gly
        115                 120                 125

Gly Ser Gly Gly Gly Gly Ser Ser Glu Leu Thr Gln Asp Pro Ala Val
    130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Gln Lys Pro Gly Gln Ala
                165                 170                 175

Pro Val Leu Val Ile Tyr Gly Lys Asn Asn Arg Pro Ser Gly Ile Pro
            180                 185                 190

Asp Arg Phe Ser Gly Ser Ser Gly Asn Thr Ala Ser Leu Thr Ile
            195                 200                 205

Thr Gly Ala Gln Ala Glu Asp Glu Ala Asp Tyr Tyr Cys Asn Ser Arg
        210                 215                 220

Asp Ser Ser Gly Asn His Val Val Phe Gly Gly Gly Thr Lys Leu Thr
225                 230                 235                 240
```

Val Leu Gly

<210> SEQ ID NO 71
<211> LENGTH: 247
<212> TYPE: PRT
<213> ORGANISM: Artificial sequence
<220> FEATURE:
<223> OTHER INFORMATION: scFv protein GMBC645

<400> SEQUENCE: 71

```
Glu Val Gln Leu Val Glu Ser Gly Gly Gly Leu Val Lys Pro Gly Gly
1               5                   10                  15

Ser Leu Arg Leu Ser Cys Ala Gly Ser Gly Phe Lys Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Glu Tyr Ala Ala
    50                  55                  60

Pro Val Lys Asp Arg Phe Ile Ile Ser Arg Asp Asp Ser Lys Asp Thr
65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Arg Gly Thr Leu Val Thr Val Ser Ser Gly Gly Gly Ser Gly Gly
        115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly
225                 230                 235                 240

Thr Glu Leu Thr Val Leu Gly
                245
```

<210> SEQ ID NO 72
<211> LENGTH: 241
<212> TYPE: PRT
<213> ORGANISM: Artificial sequence
<220> FEATURE:
<223> OTHER INFORMATION: scFv protein GMBC646

<400> SEQUENCE: 72

```
Gly Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45
```

```
Gly Ile Ile Asn Pro Ser Gly Gly Thr Thr Ser Tyr Ala Gln Lys Phe
            50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Met Tyr Tyr Cys
                85                  90                  95

Ala Arg Glu Arg Phe Leu Arg Gly Met Asp Val Trp Gly Arg Gly Thr
            100                 105                 110

Met Val Thr Val Ser Ser Gly Gly Gly Gly Ser Gly Gly Gly Gly Ser
            115                 120                 125

Gly Gly Gly Gly Ser Asp Ile Val Met Thr Gln Ser Pro Ser Thr Leu
130                 135                 140

Ser Ala Ser Val Gly Asp Arg Val Thr Ile Thr Cys Arg Ala Ser Gln
145                 150                 155                 160

Gly Ile Ser Ser Trp Leu Ala Trp Tyr Gln Gln Lys Pro Gly Arg Ala
            165                 170                 175

Pro Lys Val Leu Ile Tyr Lys Ala Ser Thr Leu Glu Ser Gly Val Pro
            180                 185                 190

Ser Arg Phe Ser Gly Ser Gly Ser Gly Thr Asp Phe Thr Leu Thr Ile
            195                 200                 205

Ser Ser Leu Gln Pro Glu Asp Phe Ala Thr Tyr Tyr Cys Gln Gln Ser
210                 215                 220

Tyr Ser Thr Pro Trp Thr Phe Gly Gln Gly Thr Lys Leu Glu Ile Lys
225                 230                 235                 240

Arg

<210> SEQ ID NO 73
<211> LENGTH: 247
<212> TYPE: PRT
<213> ORGANISM: Artificial sequence
<220> FEATURE:
<223> OTHER INFORMATION: scFv protein GMBC647

<400> SEQUENCE: 73

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
 50                  55                  60

Pro Val Lys Asp Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Gln Gly Thr Thr Val Thr Val Ser Ser Gly Gly Gly Gly Ser Gly Gly
            115                 120                 125

Gly Gly Ser Gly Gly Gly Gly Ser Gln Ser Val Leu Thr Gln Pro Ala
130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
```

```
                165                 170                 175
His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
            195                 200                 205

Ala Ser Leu Thr Ile Ser Gly Leu Gln Ala Glu Asp Glu Ala Asp Tyr
            210                 215                 220

Tyr Cys Ser Ser Tyr Thr Thr Arg Ser Thr Arg Val Phe Gly Gly Gly
225                 230                 235                 240

Thr Lys Leu Thr Val Leu Gly
                245

<210> SEQ ID NO 74
<211> LENGTH: 244
<212> TYPE: PRT
<213> ORGANISM: Artificial sequence
<220> FEATURE:
<223> OTHER INFORMATION: scFv protein GMBC648

<400> SEQUENCE: 74

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
            35                  40                  45

Gly Arg Ile Lys Ser Lys Arg Ser Gly Gly Thr Ile Asp Tyr Ala Ala
        50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Gln Gly Thr Met Val Thr Val Ser Ser Gly Gly Gly Ser Gly Gly
            115                 120                 125

Gly Gly Ser Gly Gly Gly Gly Ser Ser Glu Leu Thr Gln Asp Pro Thr
        130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Ser Gly Asn Thr Ala Ser Leu Thr
            195                 200                 205

Ile Thr Gly Ala Gln Ala Glu Asp Glu Ala Asp Tyr Tyr Cys Asn Ser
            210                 215                 220

Arg Asp Ser Ser Gly Asn His Val Val Phe Gly Gly Gly Thr Lys Leu
225                 230                 235                 240

Thr Val Leu Gly

<210> SEQ ID NO 75
<211> LENGTH: 247
<212> TYPE: PRT
<213> ORGANISM: Artificial sequence
```

```
<220> FEATURE:
<223> OTHER INFORMATION: scFv protein GMBC649

<400> SEQUENCE: 75

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
    50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Arg Gly Thr Leu Val Thr Val Ser Ser Gly Gly Gly Ser Gly Gly
        115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly Gly
225                 230                 235                 240

Thr Lys Leu Thr Val Leu Gly
                245

<210> SEQ ID NO 76
<211> LENGTH: 247
<212> TYPE: PRT
<213> ORGANISM: Artificial sequence
<220> FEATURE:
<223> OTHER INFORMATION: scFv protein GMBC651

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
    50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
```

```
                    85                  90                  95
Tyr Cys Thr Trp Asp Trp Asp Phe Tyr Tyr Gly Met Asn Val Trp Gly
                100                 105                 110
Arg Gly Thr Met Val Thr Val Ser Ser Gly Gly Gly Ser Gly Gly
            115                 120                 125
Gly Gly Ser Gly Gly Gly Ser Gln Ser Val Leu Thr Gln Pro Ala
        130                 135                 140
Ser Val Ser Gly Ser Pro Gly Gln Ser Ile Thr Ile Ser Cys Thr Gly
145                 150                 155                 160
Thr Ser Ser Asp Val Gly Gly Tyr Asn Tyr Val Ser Trp Tyr Gln Gln
                165                 170                 175
His Pro Gly Lys Ala Pro Lys Leu Met Ile Tyr Glu Gly Ser Lys Arg
            180                 185                 190
Pro Ser Gly Val Ser Asn Arg Phe Ser Gly Ser Lys Ser Gly Asn Thr
        195                 200                 205
Ala Ser Leu Thr Ile Ser Gly Leu Gln Ala Glu Asp Glu Ala Asp Tyr
        210                 215                 220
Tyr Cys Ser Ser Tyr Thr Thr Arg Ser Thr Arg Val Phe Gly Gly Gly
225                 230                 235                 240
Thr Lys Leu Thr Val Leu Gly
                245

<210> SEQ ID NO 77
<211> LENGTH: 247
<212> TYPE: PRT
<213> ORGANISM: Artificial sequence
<220> FEATURE:
<223> OTHER INFORMATION: scFv protein GMBC652

<400> SEQUENCE: 77

Gly Val Gln Leu Val Gln Ser Gly Gly Val Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Thr Asp Tyr Ala Ala
    50                  55                  60

Pro Val Lys Gly Arg Phe Thr Ile Ser Arg Asp Asp Ser Glu Asn Thr
65                  70                  75                  80

Leu Tyr Leu Gln Met Asn Ser Leu Lys Thr Glu Asp Thr Ala Val Tyr
                85                  90                  95

Tyr Cys Thr Trp Asp His Ser Tyr Tyr Tyr Asp Met Ala Val Trp Gly
                100                 105                 110

Arg Gly Thr Met Val Thr Ala Ser Ser Gly Gly Gly Gly Ser Gly Gly
            115                 120                 125

Gly Gly Ser Gly Gly Gly Gly Ser Gln Ser Val Leu Thr Gln Pro Ala
        130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Phe Met Ile Tyr Asp Val Ser Lys Arg
            180                 185                 190

Pro Ser Gly Val Ser Asn Arg Phe Ser Gly Ser Lys Ser Gly Asn Thr
```

```
                195                 200                 205
Ala Ser Leu Thr Ile Ser Gly Val Gln Ala Glu Asp Glu Ala Asp Tyr
    210                 215                 220

Tyr Cys Ser Ser Tyr Thr Ser Ala Ser Thr Val Ile Phe Gly Gly Gly
225                 230                 235                 240

Thr Lys Leu Thr Val Leu Gly
                245

<210> SEQ ID NO 78
<211> LENGTH: 246
<212> TYPE: PRT
<213> ORGANISM: Artificial sequence
<220> FEATURE:
<223> OTHER INFORMATION: scFv protein GMBC653

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Ser Arg Tyr Tyr Gly Met Asp Val Trp Ser Arg Gly
            100                 105                 110

Thr Leu Val Thr Val Ser Ser Gly Gly Gly Ser Gly Gly Gly Gly
        115                 120                 125

Ser Gly Gly Gly Gly Ser Ser Tyr Val Leu Thr Gln Pro Pro Ser Val
    130                 135                 140

Ser Gly Thr Pro Gly Gln Arg Val Thr Ile Ser Cys Ser Gly Gly Arg
145                 150                 155                 160

Ser Asn Ile Gly Ser Asn Thr Val Lys Trp Tyr Gln Gln Leu Pro Gly
                165                 170                 175

Ala Ala Pro Lys Leu Leu Ile Tyr Gly Asn Asp Gln Arg Pro Ser Gly
            180                 185                 190

Val Pro Asp Arg Phe Ser Gly Ser Lys Ser Gly Thr Ser Ala Ser Leu
        195                 200                 205

Ala Ile Thr Gly Val Gln Ala Glu Asp Glu Ala Asp Tyr Tyr Cys Gln
    210                 215                 220

Ser Tyr Asp Ser Ser Leu Arg Gly Ser Arg Val Phe Gly Thr Gly Thr
225                 230                 235                 240

Lys Val Thr Val Leu Gly
                245

<210> SEQ ID NO 79
<211> LENGTH: 247
<212> TYPE: PRT
<213> ORGANISM: Artificial sequence
<220> FEATURE:
<223> OTHER INFORMATION: scFv protein GMBC654

<400> SEQUENCE: 79
```

```
Glu Val Gln Leu Val Glu Thr Gly Gly Gly Leu Val Glu Pro Gly Gly
1               5                   10                  15

Ser Leu Arg Leu Ser Cys Ala Ala Ser Gly Phe Thr Phe Ser Asp Ala
                20                  25                  30

Trp Met Asn Trp Val Arg Gln Ala Pro Gly Lys Gly Leu Glu Trp Val
            35                  40                  45

Gly Arg Ile Lys Ser Lys Arg Ser Gly Gly Thr Ile Asp Tyr Ala Ala
    50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Lys Ile Glu Asp Thr Ala Leu Tyr
                85                  90                  95

Tyr Cys Thr Trp Asp Trp Asp Phe Tyr Tyr Gly Met Asn Val Trp Gly
            100                 105                 110

Lys Gly Thr Thr Val Thr Val Ser Gly Gly Gly Ser Gly Gly
                115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
            195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly Gly
225                 230                 235                 240

Thr Lys Leu Thr Val Leu Gly
                245

<210> SEQ ID NO 80
<211> LENGTH: 239
<212> TYPE: PRT
<213> ORGANISM: Artificial sequence
<220> FEATURE:
<223> OTHER INFORMATION: scFv protein GMBC655

<400> SEQUENCE: 80

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Gly Met Ser Trp Ile Arg Gln Ala Pro Gly Lys Gly Gln Glu Trp Val
            35                  40                  45

Ser Ala Ile Ser Gly Ser Gly Gly Ser Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Tyr Ser Ser Glu Asp Tyr Trp Gly Arg Gly Thr Met Val
            100                 105                 110
```

```
Thr Val Ser Ser Gly Gly Gly Ser Gly Gly Gly Ser Gly Gly
        115                 120                 125

Gly Gly Ser Asn Ile Gln Met Thr Gln Ser Pro Ser Phe Leu Ser Ala
    130                 135                 140

Ser Val Gly Asp Arg Val Thr Ile Thr Cys Arg Ala Ser Gln Gly Ile
145                 150                 155                 160

Asn Asn Tyr Leu Ala Trp Tyr Gln Gln Lys Pro Gly Arg Ala Pro Lys
                165                 170                 175

Leu Leu Ile Tyr Ala Ala Ser Ser Leu Gln Ser Gly Val Pro Ser Arg
            180                 185                 190

Phe Ser Gly Ser Gly Ser Gly Thr Asp Phe Thr Leu Thr Ile Ser Ser
            195                 200                 205

Leu Gln Pro Asp Asp Phe Ala Thr Tyr Tyr Cys Gln Gln Tyr Ser Asn
    210                 215                 220

Tyr Pro Leu Thr Phe Gly Gly Gly Thr Lys Leu Glu Ile Lys Arg
225                 230                 235

<210> SEQ ID NO 81
<211> LENGTH: 244
<212> TYPE: PRT
<213> ORGANISM: Artificial sequence
<220> FEATURE:
<223> OTHER INFORMATION: scFv protein GMBC657

<400> SEQUENCE: 81

Gln Met Gln Leu Met Gln Ser Gly Gly Gly Leu Val Lys Pro Gly Gly
1               5                   10                  15

Ser Leu Arg Leu Ser Cys Ala Gly Ser Gly Phe Lys Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Glu Tyr Ala Ala
    50                  55                  60

Pro Val Lys Asp Arg Phe Ile Ile Ser Arg Asp Asp Ser Lys Asp Thr
65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Gly Asn Thr Ala Ser Leu Thr
            195                 200                 205

Ile Thr Gly Ala Gln Ala Glu Asp Glu Ala Asp Tyr Tyr Cys Asn Ser
    210                 215                 220

Arg Asp Ser Ser Gly Asn His Val Val Phe Gly Gly Gly Thr Lys Leu
225                 230                 235                 240
```

-continued

Thr Val Leu Gly

<210> SEQ ID NO 82
<211> LENGTH: 247
<212> TYPE: PRT
<213> ORGANISM: Artificial sequence
<220> FEATURE:
<223> OTHER INFORMATION: scFv protein GMBC658

<400> SEQUENCE: 82

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Ala
                20                  25                  30

Trp Met Asn Trp Val Arg Gln Ala Pro Gly Lys Gly Leu Glu Trp Val
            35                  40                  45

Gly Arg Ile Lys Ser Lys Gly Ser Gly Gly Thr Ile Asp Tyr Ala Ala
        50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Arg Gly Thr Thr Val Thr Val Ser Ser Gly Gly Gly Ser Gly Gly
        115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly
225                 230                 235                 240

Thr Lys Leu Thr Val Leu Gly
            245

<210> SEQ ID NO 83
<211> LENGTH: 247
<212> TYPE: PRT
<213> ORGANISM: Artificial sequence
<220> FEATURE:
<223> OTHER INFORMATION: scFv protein GMBC659

<400> SEQUENCE: 83

Gln Val Gln Leu Val Glu Ser Gly Gly Gly Leu Val Lys Pro Gly Glu
1               5                   10                  15

Ser Leu Arg Leu Ser Cys Glu Ala Ser Gly Phe Glu Phe Asn Tyr Ala
                20                  25                  30

Trp Met Ser Trp Val Arg Gln Ala Pro Gly Lys Gly Leu Glu Trp Val
            35                  40                  45

-continued

Gly Arg Ser Arg Ser Glu Ala Ser Gly Gly Thr Thr Asp Tyr Ala Ala
    50                  55                  60

Pro Leu Gln Asp Arg Phe Thr Ile Ser Arg Asp Asp Ser Lys Asn Thr
 65                  70                  75                  80

Leu Tyr Leu Gln Val Asn Ser Leu Lys Ile Glu Asp Thr Gly Val Tyr
                 85                  90                  95

Phe Cys Lys Trp Glu Lys Ser Glu Tyr Tyr Gly Met Asp Val Trp Gly
            100                 105                 110

Arg Gly Thr Leu Val Thr Val Ser Gly Gly Gly Ser Gly Gly
            115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
            195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly
225                 230                 235                 240

Thr Lys Leu Thr Val Leu Gly
                245

<210> SEQ ID NO 84
<211> LENGTH: 247
<212> TYPE: PRT
<213> ORGANISM: Artificial sequence
<220> FEATURE:
<223> OTHER INFORMATION: scFv protein GMBC660

<400> SEQUENCE: 84

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Ile Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
    50                  55                  60

Pro Val Lys Asp Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Leu Tyr
                 85                  90                  95

Tyr Cys Thr Trp Asp Trp Asp Phe Tyr Tyr Gly Met Asn Val Trp Gly
            100                 105                 110

Gln Gly Thr Pro Val Thr Val Ser Gly Gly Gly Ser Gly Gly
            115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

-continued

```
Thr Ser Ser Asp Val Gly Gly Tyr Asn Tyr Val Ser Trp Tyr Gln Gln
            165                 170                 175
His Pro Gly Lys Ala Pro Lys Leu Met Ile Tyr Glu Gly Ser Lys Arg
            180                 185                 190
Pro Ser Gly Val Ser Asn Arg Phe Ser Gly Ser Lys Ser Gly Asn Thr
            195                 200                 205
Ala Ser Leu Thr Ile Ser Gly Leu Gln Ala Glu Asp Glu Ala Asp Tyr
        210                 215                 220
Tyr Cys Ser Ser Tyr Thr Thr Arg Ser Thr Arg Val Phe Gly Gly Gly
225                 230                 235                 240
Thr Lys Leu Thr Val Leu Gly
                245
```

<210> SEQ ID NO 85
<211> LENGTH: 243
<212> TYPE: PRT
<213> ORGANISM: Artificial sequence
<220> FEATURE:
<223> OTHER INFORMATION: scFv protein GMBC662

<400> SEQUENCE: 85

```
Gly Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Thr Ile Ser Trp Val Arg Gln Ala Pro Gly Gln Gly Leu Glu Trp Met
        35                  40                  45
Gly Arg Ile Ile Pro Ile Leu Gly Ile Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Lys Leu Arg Asp Phe Gln His Trp Gly Gln Gly Thr Leu
            100                 105                 110
Val Thr Val Ser Ser Gly Gly Gly Gly Ser Gly Gly Gly Gly Ser Gly
        115                 120                 125
Gly Gly Gly Ser Gln Ser Val Leu Thr Gln Pro Ala Ser Val Ser Gly
    130                 135                 140
Ser Pro Gly Gln Ser Ile Thr Ile Ser Cys Thr Gly Thr Ser Ser Asp
145                 150                 155                 160
Val Gly Gly Tyr Asn Tyr Val Ser Trp Tyr Gln Gln His Pro Gly Lys
                165                 170                 175
Ala Pro Lys Leu Met Ile Tyr Glu Gly Ser Lys Arg Pro Ser Gly Ile
            180                 185                 190
Ser Asn Arg Phe Ser Gly Ser Lys Ser Gly Asn Thr Ala Ser Leu Thr
        195                 200                 205
Ile Ser Arg Leu Gln Ala Glu Asp Glu Ala Asp Tyr Tyr Cys Ser Ser
    210                 215                 220
Tyr Thr Thr Arg Ser Thr Arg Val Phe Gly Gly Gly Thr Lys Leu Thr
225                 230                 235                 240
Val Leu Gly
```

<210> SEQ ID NO 86
<211> LENGTH: 247
<212> TYPE: PRT

<213> ORGANISM: Artificial sequence
<220> FEATURE:
<223> OTHER INFORMATION: scFv protein GMBC664

<400> SEQUENCE: 86

| | | | | | | | | | | | | | | |
|---|---|---|---|---|---|---|---|---|---|---|---|---|---|---|
| Glu | Val | Gln | Leu | Val | Glu | Thr | Gly | Gly | Ala | Leu | Val | Lys | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asp | Ala |
| | | | 20 | | | | | 25 | | | | | 30 | | |
| Trp | Met | Asn | Trp | Val | Arg | Gln | Ala | Pro | Gly | Lys | Gly | Leu | Glu | Trp | Val |
| | | | 35 | | | | 40 | | | | | 45 | | | |
| Gly | Arg | Ile | Lys | Ser | Lys | Gly | Ser | Gly | Gly | Thr | Ile | Asp | Tyr | Ala | Ala |
| | 50 | | | | | 55 | | | | | 60 | | | | |
| Pro | Val | Lys | Asp | Arg | Phe | Thr | Ile | Ser | Arg | Asp | Asp | Ser | Lys | Asn | Thr |
| 65 | | | | | 70 | | | | | 75 | | | | | 80 |
| Leu | Tyr | Leu | Gln | Met | Asn | Ser | Leu | Lys | Thr | Glu | Asp | Thr | Ala | Leu | Tyr |
| | | | | 85 | | | | | 90 | | | | | 95 | |
| Tyr | Cys | Thr | Trp | Asp | Trp | Asp | Phe | Tyr | Tyr | Gly | Met | Asn | Val | Trp | Ser |
| | | | | 100 | | | | | 105 | | | | | 110 | |
| Arg | Gly | Thr | Met | Val | Thr | Val | Ser | Ser | Gly | Gly | Gly | Ser | Gly | Gly | |
| | | | 115 | | | | | 120 | | | | | 125 | | |
| Gly | Gly | Ser | Gly | Gly | Gly | Ser | Gln | Ser | Val | Leu | Thr | Gln | Pro | Ala | |
| | 130 | | | | | 135 | | | | | 140 | | | | |
| Ser | Val | Ser | Gly | Ser | Pro | Gly | Gln | Ser | Ile | Thr | Ile | Ser | Cys | Thr | Gly |
| 145 | | | | | 150 | | | | | 155 | | | | | 160 |
| Thr | Ser | Ser | Asp | Val | Gly | Gly | Tyr | Asn | Tyr | Val | Ser | Trp | Tyr | Gln | Gln |
| | | | | 165 | | | | | 170 | | | | | 175 | |
| His | Pro | Gly | Lys | Ala | Pro | Lys | Leu | Met | Ile | Tyr | Glu | Gly | Ser | Lys | Arg |
| | | | 180 | | | | | 185 | | | | | 190 | | |
| Pro | Ser | Gly | Val | Ser | Asn | Arg | Phe | Ser | Gly | Ser | Lys | Ser | Gly | Asn | Thr |
| | | | 195 | | | | | 200 | | | | | 205 | | |
| Ala | Ser | Leu | Thr | Ile | Ser | Gly | Leu | Gln | Ala | Glu | Asp | Glu | Ala | Asp | Tyr |
| | 210 | | | | | 215 | | | | | 220 | | | | |
| Tyr | Cys | Ser | Ser | Tyr | Thr | Thr | Arg | Ser | Thr | Arg | Val | Phe | Gly | Gly | Gly |
| 225 | | | | | 230 | | | | | 235 | | | | | 240 |
| Thr | Lys | Leu | Thr | Val | Leu | Gly | | | | | | | | | |
| | | | | 245 | | | | | | | | | | | |

<210> SEQ ID NO 87
<211> LENGTH: 244
<212> TYPE: PRT
<213> ORGANISM: Artificial sequence
<220> FEATURE:
<223> OTHER INFORMATION: scFv protein GMBC665

<400> SEQUENCE: 87

| | | | | | | | | | | | | | | |
|---|---|---|---|---|---|---|---|---|---|---|---|---|---|---|
| Glu | Val | Gln | Leu | Val | Glu | Thr | Gly | Gly | Gly | Leu | Val | Lys | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asp | Ala |
| | | | 20 | | | | | 25 | | | | | 30 | | |
| Trp | Met | Asn | Trp | Val | Arg | Gln | Ala | Pro | Gly | Lys | Gly | Leu | Glu | Trp | Val |
| | | | 35 | | | | 40 | | | | | 45 | | | |
| Gly | Arg | Ile | Lys | Ser | Lys | Gly | Ser | Gly | Gly | Thr | Ile | Asp | Tyr | Ala | Ala |
| | 50 | | | | | 55 | | | | | 60 | | | | |
| Pro | Val | Lys | Asp | Arg | Phe | Thr | Ile | Ser | Arg | Asp | Asp | Ser | Lys | Asn | Thr |
| 65 | | | | | 70 | | | | | 75 | | | | | 80 |

```
Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Gln Gly Thr Met Val Thr Val Ser Ser Gly Gly Gly Ser Gly Gly
        115                 120                 125

Gly Gly Ser Gly Gly Gly Gly Ser Ser Glu Leu Thr Gln Asp Pro Ala
130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Gly Asn Thr Ala Ser Leu Thr
                195                 200                 205

Ile Thr Gly Ala Gln Ala Glu Asp Glu Ala Asp Tyr Tyr Cys Asn Ser
        210                 215                 220

Arg Asp Ser Ser Gly Asn His Val Val Phe Gly Gly Gly Thr Lys Leu
225                 230                 235                 240

Thr Val Leu Gly

<210> SEQ ID NO 88
<211> LENGTH: 247
<212> TYPE: PRT
<213> ORGANISM: Artificial sequence
<220> FEATURE:
<223> OTHER INFORMATION: scFv protein GMBC666

<400> SEQUENCE: 88

Glu Val Gln Leu Val Glu Ser Gly Gly Gly Leu Ala Lys Pro Gly Glu
1               5                   10                  15

Ser Leu Arg Leu Ser Cys Glu Ala Ser Gly Phe Glu Phe Asn Tyr Ala
            20                  25                  30

Trp Met Ser Trp Val Arg Gln Ala Pro Gly Lys Gly Leu Glu Trp Val
        35                  40                  45

Gly Arg Ser Arg Ser Glu Ala Ser Gly Gly Thr Thr Asp Tyr Ala Ala
    50                  55                  60

Pro Leu Gln Asp Arg Phe Thr Ile Ser Arg Asp Asp Ser Lys Asn Thr
65                  70                  75                  80

Leu Tyr Leu Gln Val Asn Ser Leu Lys Ile Glu Asp Thr Gly Val Tyr
                85                  90                  95

Phe Cys Lys Trp Glu Lys Ser Glu Tyr Tyr Gly Met Asp Val Trp Gly
            100                 105                 110

Lys Gly Thr Met Val Thr Val Ser Ser Gly Gly Gly Gly Ser Gly Gly
        115                 120                 125

Gly Gly Ser Gly Gly Gly Gly Ser Gln Ser Val Leu Thr Gln Pro Pro
130                 135                 140

Ser Val Ser Ala Ala Pro Gly Gln Lys Val Thr Ile Ser Cys Ser Gly
145                 150                 155                 160

Ser Thr Ser Asn Ile Gly Asn Asn Tyr Val Ser Trp Tyr Gln Gln His
                165                 170                 175

Pro Gly Lys Ala Pro Lys Leu Met Ile Tyr Asp Val Ser Lys Arg Pro
            180                 185                 190

Ser Gly Val Pro Asp Arg Phe Ser Gly Ser Lys Ser Gly Asn Ser Ala
```

```
                  195                 200                 205
Ser Leu Asp Ile Ser Gly Leu Gln Ser Glu Asp Glu Ala Asp Tyr Tyr
    210                 215                 220

Cys Ala Ala Trp Asp Asp Ser Leu Ser Glu Phe Leu Phe Gly Thr Gly
225                 230                 235                 240

Thr Lys Leu Thr Val Leu Gly
                245

<210> SEQ ID NO 89
<211> LENGTH: 247
<212> TYPE: PRT
<213> ORGANISM: Artificial sequence
<220> FEATURE:
<223> OTHER INFORMATION: scFv protein GMBC667

<400> SEQUENCE: 89

Gln Val Gln Leu Gln Glu Ser Gly Gly Gly Leu Val Lys Pro Gly Gly
1               5                   10                  15

Ser Leu Arg Leu Ser Cys Ala Gly Ser Gly Phe Pro Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
    50                  55                  60

Pro Val Lys Asp Arg Phe Arg Ile Ser Arg Asp Asp Ser Lys Asn Thr
65                  70                  75                  80

Leu Tyr Leu Gln Met Asn Ser Leu Asn Ile Glu Asp Thr Ala Leu Tyr
                85                  90                  95

Tyr Cys Thr Trp Asp Trp Asp Phe Tyr Tyr Gly Met Asn Val Trp Gly
            100                 105                 110

Gln Gly Thr Thr Val Thr Val Ser Ser Gly Gly Gly Ser Gly Gly
        115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly Gly
225                 230                 235                 240

Thr Lys Leu Thr Val Leu Gly
                245

<210> SEQ ID NO 90
<211> LENGTH: 244
<212> TYPE: PRT
<213> ORGANISM: Artificial sequence
<220> FEATURE:
<223> OTHER INFORMATION: scFv protein GMBC668

<400> SEQUENCE: 90
```

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Thr Asp Tyr Ala Ala
    50                  55                  60

Pro Val Lys Gly Arg Phe Thr Ile Ser Arg Asp Asp Ser Glu Asn Thr
65                  70                  75                  80

Leu Tyr Leu Gln Met Asn Ser Leu Lys Thr Glu Asp Thr Ala Val Tyr
                85                  90                  95

Tyr Cys Thr Trp Asp His Ser Tyr Tyr Tyr Asp Met Ala Val Trp Gly
            100                 105                 110

Arg Gly Thr Leu Val Thr Val Ser Ser Gly Gly Gly Ser Gly Gly
            115                 120                 125

Gly Gly Ser Gly Gly Gly Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Gly Asn Thr Ala Ser Leu Thr
            195                 200                 205

Ile Thr Gly Ala Gln Ala Glu Asp Glu Ala Asp Tyr Tyr Cys Asn Ser
    210                 215                 220

Arg Asp Ser Ser Gly Asn His Val Val Phe Gly Gly Gly Thr Lys Leu
225                 230                 235                 240

Thr Val Leu Gly

<210> SEQ ID NO 91
<211> LENGTH: 247
<212> TYPE: PRT
<213> ORGANISM: Artificial sequence
<220> FEATURE:
<223> OTHER INFORMATION: scFv protein GMBC669

<400> SEQUENCE: 91

Gln Val Gln Leu Val Glu Ser Gly Gly Ala Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
    50                  55                  60

Pro Val Lys Asp Arg Phe Thr Ile Ser Arg Asp Ser Lys Asn Thr
65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Gln Gly Thr Leu Val Thr Val Ser Ser Gly Gly Gly Gly Ser Gly Gly
```

-continued

```
            115                 120                 125
Gly Gly Ser Gly Gly Gly Ser Gln Ser Val Leu Thr Gln Pro Pro
        130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Phe Met Ile Tyr Asp Val Ser Lys Arg
                180                 185                 190

Pro Ser Gly Val Ser Asn Arg Phe Ser Gly Ser Lys Ser Gly Asn Thr
            195                 200                 205

Ala Ser Leu Thr Ile Ser Gly Val Gln Ala Glu Asp Glu Ala Asp Tyr
        210                 215                 220

Tyr Cys Ser Ser Tyr Thr Ser Ala Ser Thr Val Ile Phe Gly Gly Gly
225                 230                 235                 240

Thr Lys Leu Thr Val Leu Gly
                245

<210> SEQ ID NO 92
<211> LENGTH: 247
<212> TYPE: PRT
<213> ORGANISM: Artificial sequence
<220> FEATURE:
<223> OTHER INFORMATION: scFv protein GMBC670

<400> SEQUENCE: 92

Glu Val Gln Leu Val Glu Thr Gly Gly Gly Leu Val Lys Pro Gly Gly
1               5                   10                  15

Ser Leu Arg Leu Ser Cys Val Ala Ser Gly Phe Thr Phe Ser Asp Ala
                20                  25                  30

Trp Met Asn Trp Val Arg Gln Ala Pro Gly Lys Gly Leu Glu Trp Val
            35                  40                  45

Gly Arg Ile Lys Ser Lys Gly Ser Gly Gly Thr Ile Asp Tyr Ala Ala
        50                  55                  60

Pro Val Lys Asp Arg Phe Ile Ile Ser Arg Asp Asp Ser Lys Asn Thr
65                  70                  75                  80

Leu Tyr Leu Gln Val Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
                100                 105                 110

Gln Gly Thr Leu Val Thr Val Ser Ser Gly Gly Gly Ser Gly Gly
            115                 120                 125

Gly Gly Ser Gly Gly Gly Ser Gln Ser Val Leu Thr Gln Pro Ala
        130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
                180                 185                 190

Pro Ser Gly Val Ser Asn Arg Phe Ser Gly Ser Lys Ser Gly Asn Thr
            195                 200                 205

Ala Ser Leu Thr Ile Ser Gly Leu Gln Ala Glu Asp Glu Ala Asp Tyr
        210                 215                 220

Tyr Cys Ser Ser Tyr Thr Thr Arg Ser Thr Arg Val Phe Gly Gly Gly
```

```
                    225                 230                 235                 240

Thr Lys Leu Thr Val Leu Gly
                245

<210> SEQ ID NO 93
<211> LENGTH: 247
<212> TYPE: PRT
<213> ORGANISM: Artificial sequence
<220> FEATURE:
<223> OTHER INFORMATION: scFv protein GMBC672

<400> SEQUENCE: 93

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Ala
                20                  25                  30

Trp Met Asn Trp Val Arg Gln Ala Pro Gly Lys Gly Leu Glu Trp Val
            35                  40                  45

Gly Arg Ile Lys Ser Lys Gly Ser Gly Thr Ile Asp Tyr Ala Ala
        50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Gln Gly Thr Leu Val Thr Val Ser Gly Gly Gly Gly Ser Gly Gly
        115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Glu Gly
225                 230                 235                 240

Thr Lys Leu Thr Val Leu Gly
                245

<210> SEQ ID NO 94
<211> LENGTH: 243
<212> TYPE: PRT
<213> ORGANISM: Artificial sequence
<220> FEATURE:
<223> OTHER INFORMATION: scFv protein GMBC673

<400> SEQUENCE: 94

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Pro Ile Gly Ser His
                20                  25                  30
```

```
Trp Met Ser Trp Val Arg Gln Ser Pro Gly Lys Gly Leu Glu Trp Val
            35                  40                  45

Ala Ser Ile Lys Gln Asp Gly Arg Glu Lys His Phe Val Asp Ser Val
 50                      55                  60

Lys Gly Arg Phe Gly Ile Ser Arg Asp Asn Ala Lys Asp Ser Leu Tyr
 65                  70                  75                  80

Leu Gln Met Asn Ser Leu Arg Ile Glu Asp Thr Ala Val Tyr Tyr Cys
                85                  90                  95

Ala Arg Glu Thr Tyr Gly Gly Tyr Tyr Tyr Phe Met Asp Val Trp
                100                 105                 110

Gly Arg Gly Thr Leu Val Thr Val Ser Ser Gly Gly Gly Ser Gly
                115                 120                 125

Gly Gly Gly Ser Gly Gly Gly Ser Glu Leu Thr Gln Asp Pro
            130                 135                 140

Ala Val Ser Val Ala Leu Gly Gln Thr Val Arg Ile Thr Cys Gln Gly
145                 150                 155                 160

Asp Ser Leu Arg Ser Tyr Tyr Ala Ser Trp Tyr Gln Gln Lys Pro Gly
                165                 170                 175

Gln Ala Pro Val Leu Val Ile Tyr Gly Lys Asn Asn Arg Pro Ser Gly
                180                 185                 190

Ile Pro Asp Arg Phe Ser Gly Ser Ser Ser Gly Asn Thr Ala Ser Leu
                195                 200                 205

Thr Ile Thr Gly Ala Gln Ala Glu Asp Glu Ala Asp Tyr Tyr Cys Gln
                210                 215                 220

Thr Trp Gly Pro Gly Ile Arg Val Phe Gly Gly Thr Lys Leu Thr
225                 230                 235                 240

Val Leu Gly

<210> SEQ ID NO 95
<211> LENGTH: 247
<212> TYPE: PRT
<213> ORGANISM: Artificial sequence
<220> FEATURE:
<223> OTHER INFORMATION: scFv protein GMBC676

<400> SEQUENCE: 95

Glu Val Gln Leu Val Gln Ser Gly Gly Gly Leu Val Gln Pro Gly Gly
 1               5                   10                  15

Ser Leu Arg Leu Ser Cys Ala Ala Ser Gly Phe Thr Phe Ser His Ala
            20                  25                  30

Trp Met Asn Trp Val Arg Gln Ala Pro Gly Lys Gly Leu Glu Trp Val
            35                  40                  45

Gly Arg Ile Lys Ser Lys Ala Ser Gly Gly Thr Ile Asp Tyr Ala Ala
 50                      55                  60

Pro Val Lys Asp Arg Phe Thr Ile Ser Arg Asp Asp Ser Lys Asn Thr
 65                  70                  75                  80

Leu Tyr Leu His Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
                100                 105                 110

Arg Gly Thr Met Val Thr Val Ser Ser Gly Gly Gly Ser Gly Gly
            115                 120                 125

Gly Gly Ser Gly Gly Gly Gly Ser Gln Ser Val Leu Thr Gln Pro Ala
            130                 135                 140

Ser Val Ser Gly Ser Pro Gly Gln Pro Ile Thr Ile Ser Cys Thr Gly
```

-continued

```
            145                 150                 155                 160
Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
            195                 200                 205

Ala Ser Leu Thr Ile Ser Gly Leu Gln Ala Glu Asp Glu Ala Asp Tyr
            210                 215                 220

Tyr Cys Ser Ser Tyr Thr Thr Arg Ser Thr Arg Val Phe Gly Gly Gly
225                 230                 235                 240

Thr Lys Leu Thr Val Leu Gly
                245

<210> SEQ ID NO 96
<211> LENGTH: 247
<212> TYPE: PRT
<213> ORGANISM: Artificial sequence
<220> FEATURE:
<223> OTHER INFORMATION: scFv protein GMBC678

<400> SEQUENCE: 96

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
    50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Gln Ser Val Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Phe Met Ile Tyr Asp Val Ser Lys Arg
            180                 185                 190

Pro Ser Gly Val Ser Asn Arg Phe Ser Gly Ser Lys Ser Gly Asn Thr
            195                 200                 205

Ala Ser Leu Thr Ile Ser Gly Val Gln Ala Glu Asp Glu Ala Asp Tyr
            210                 215                 220

Tyr Cys Ser Ser Tyr Thr Ser Ala Ser Thr Val Ile Phe Gly Gly Gly
225                 230                 235                 240

Thr Lys Leu Thr Val Leu Gly
                245
```

<210> SEQ ID NO 97
<211> LENGTH: 247
<212> TYPE: PRT
<213> ORGANISM: Artificial sequence
<220> FEATURE:
<223> OTHER INFORMATION: scFv protein GMBC679

<400> SEQUENCE: 97

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Thr Thr Asp Tyr Ala Ala
    50                  55                  60

Pro Val Lys Asp Arg Phe Thr Ile Ser Arg Asp Asp Ser Glu Asn Thr
65                  70                  75                  80

Leu Tyr Leu Gln Met Asn Ser Leu Lys Thr Glu Asp Thr Ala Val Tyr
                85                  90                  95

Tyr Cys Thr Trp Asp His Ser Tyr Tyr Tyr Asp Met Ala Val Trp Gly
            100                 105                 110

Arg Gly Thr Leu Val Thr Val Ser Ser Gly Gly Gly Ser Gly Gly
        115                 120                 125

Gly Gly Ser Gly Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Val Ile Tyr Glu Gly Ser Lys Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly
225                 230                 235                 240

Thr Lys Leu Thr Val Leu Gly
                245

<210> SEQ ID NO 98
<211> LENGTH: 240
<212> TYPE: PRT
<213> ORGANISM: Artificial sequence
<220> FEATURE:
<223> OTHER INFORMATION: scFv protein GMBC681

<400> SEQUENCE: 98

Gln Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Gly Thr Gly Tyr Phe Asp Leu Trp Gly Arg Gly Thr Leu
        100                 105                 110

Val Thr Val Ser Ser Gly Gly Gly Ser Gly Gly Gly Ser Gly
        115                 120                 125

Gly Gly Gly Ser Asp Ile Gln Met Thr Gln Ser Pro Ser Thr Leu Ser
    130                 135                 140

Ala Ser Ile Gly Asp Arg Val Thr Ile Thr Cys Arg Ala Ser Glu Gly
145                 150                 155                 160

Ile Tyr His Trp Leu Ala Trp Tyr Gln Gln Lys Pro Gly Lys Ala Pro
                165                 170                 175

Lys Leu Leu Ile Tyr Lys Ala Ser Ser Leu Ala Ser Gly Ala Pro Ser
            180                 185                 190

Arg Phe Ser Gly Ser Gly Ser Gly Thr Asp Phe Thr Leu Thr Ile Ser
        195                 200                 205

Ser Leu Gln Pro Asp Asp Phe Ala Thr Tyr Tyr Cys Gln Gln Tyr Ser
    210                 215                 220

Asn Tyr Pro Leu Thr Phe Gly Gly Gly Thr Lys Leu Glu Ile Lys Arg
225                 230                 235                 240

<210> SEQ ID NO 99
<211> LENGTH: 244
<212> TYPE: PRT
<213> ORGANISM: Artificial sequence
<220> FEATURE:
<223> OTHER INFORMATION: scFv protein GMBC682

<400> SEQUENCE: 99

Gln Val Gln Leu Val Glu Ser Gly Gly Gly Val Val Lys Pro Gly Gly
1               5                   10                  15

Ser Leu Arg Leu Ser Cys Ala Ala Ser Gly Phe Lys Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
    50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
            85                  90                  95

Tyr Cys Thr Trp Asp Trp Asp Phe Tyr Tyr Gly Met Asn Val Trp Gly
        100                 105                 110

Arg Gly Thr Leu Val Thr Val Ser Ser Gly Gly Gly Gly Ser Gly Gly
    115                 120                 125

Gly Gly Ser Gly Gly Gly Gly Ser Ser Glu Leu Thr Gln Asp Pro Ala
130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

```
Pro Asp Arg Phe Ser Gly Ser Ser Gly Asn Thr Ala Ser Leu Thr
        195                 200                 205

Ile Thr Gly Ala Gln Ala Glu Asp Glu Ala Asp Tyr Tyr Cys Asn Ser
        210                 215                 220

Arg Asp Ser Ser Gly Asn His Val Val Phe Gly Gly Gly Thr Lys Leu
225                 230                 235                 240

Thr Val Leu Gly

<210> SEQ ID NO 100
<211> LENGTH: 241
<212> TYPE: PRT
<213> ORGANISM: Artificial sequence
<220> FEATURE:
<223> OTHER INFORMATION: scFv protein GMBC683

<400> SEQUENCE: 100

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Arg Ala Ala Gly Thr Leu Asp Tyr Trp Gly Gln Gly Thr
        100                 105                 110

Thr Val Thr Val Ser Ser Gly Gly Gly Ser Gly Gly Gly Gly Ser
    115                 120                 125

Gly Gly Gly Gly Ser Ser Glu Leu Thr Gln Asp Pro Ala Val Ser Val
130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
            165                 170                 175

Leu Val Ile Tyr Gly Lys Asn Asn Arg Pro Ser Gly Ile Pro Asp Arg
        180                 185                 190

Phe Ser Gly Ser Ser Ser Gly Asn Thr Ala Ser Leu Thr Ile Thr Gly
    195                 200                 205

Ala Gln Ala Glu Asp Glu Ala Asp Tyr Tyr Cys Asn Ser Arg Asp Ser
        210                 215                 220

Ser Gly Asn His Val Val Phe Gly Gly Gly Thr Lys Leu Thr Val Leu
225                 230                 235                 240

Gly

<210> SEQ ID NO 101
<211> LENGTH: 247
<212> TYPE: PRT
<213> ORGANISM: Artificial sequence
<220> FEATURE:
<223> OTHER INFORMATION: scFv protein GMBC684

<400> SEQUENCE: 101

Gln Val Gln Leu Val Gln Ser Gly Gly Gly Leu Val Lys Pro Gly Gly
```

```
                1               5                  10                 15
Ser Leu Arg Leu Ser Cys Ala Ala Ser Gly Phe Lys Phe Ser Asp Ala
                20                 25                 30

Trp Met Asn Trp Val Arg Gln Ala Pro Gly Lys Gly Leu Glu Trp Val
            35                 40                 45

Gly Arg Ile Lys Ser Lys Gly Ser Gly Gly Thr Ile Asp Tyr Ala Ala
            50                 55                 60

Pro Val Lys Asp Arg Phe Thr Ile Ser Arg Asp Asp Ser Lys Asn Thr
65                  70                 75                 80

Leu Tyr Leu Gln Met Asn Ser Leu Lys Thr Glu Asp Thr Ala Leu Tyr
                85                 90                 95

Tyr Cys Thr Trp Asp Trp Asp Phe Tyr Tyr Gly Met Asn Val Trp Gly
            100                105                110

Gln Gly Thr Pro Val Thr Val Ser Ser Gly Gly Gly Ser Gly Gly Gly
            115                120                125

Gly Gly Ser Gly Gly Gly Ser Gln Ser Ala Leu Thr Gln Pro Ala
            130                135                140

Ser Val Ser Gly Ser Pro Gly Gln Ser Ile Thr Ile Ser Cys Thr Gly
145                 150                155                160

Thr Ser Ser Asp Val Gly Gly Tyr Asn Tyr Val Ser Trp Tyr Gln Gln
                165                170                175

His Pro Gly Lys Ala Pro Lys Leu Met Ile Tyr Glu Gly Ser Lys Arg
            180                185                190

Pro Ser Gly Val Ser Asn Arg Phe Ser Gly Ser Lys Ser Gly Asn Thr
            195                200                205

Ala Ser Leu Thr Ile Ser Gly Leu Gln Ala Glu Asp Glu Ala Asp Tyr
            210                215                220

Tyr Cys Ser Ser Tyr Thr Thr Arg Ser Thr Arg Val Phe Gly Gly
225                 230                235                240

Thr Lys Leu Thr Val Leu Gly
                245

<210> SEQ ID NO 102
<211> LENGTH: 244
<212> TYPE: PRT
<213> ORGANISM: Artificial sequence
<220> FEATURE:
<223> OTHER INFORMATION: scFv protein GMBC685

<400> SEQUENCE: 102

Gln Val Gln Leu Val Glu Ser Gly Gly Val Val Gln Pro Gly Gly
1               5                  10                 15

Ser Leu Arg Leu Ser Cys Ala Ala Ser Gly Phe Thr Phe Ser Asp Ala
                20                 25                 30

Trp Met Asn Trp Val Arg Gln Ala Pro Gly Lys Gly Leu Glu Trp Val
            35                 40                 45

Gly Arg Ile Lys Ser Lys Gly Ser Gly Gly Thr Ile Asp Tyr Ala Ala
            50                 55                 60

Pro Val Lys Asp Arg Phe Thr Ile Ser Arg Asp Asp Ser Lys Asn Thr
65                  70                 75                 80

Leu Tyr Leu Gln Met Asn Ser Leu Lys Thr Glu Asp Thr Ala Leu Tyr
                85                 90                 95

Tyr Cys Thr Trp Asp Trp Asp Phe Tyr Tyr Gly Met Asn Val Trp Gly
            100                105                110

Lys Gly Thr Met Val Thr Val Ser Ser Gly Gly Gly Gly Ser Gly Gly
```

```
              115                 120                 125
Gly Gly Ser Gly Gly Gly Ser Ser Glu Leu Thr Gln Asp Pro Ala
        130                 135                 140
Val Ser Val Ala Leu Gly Gln Thr Val Arg Ile Thr Cys Gln Gly Asp
145                 150                 155                 160
Ser Leu Arg Ser Tyr Tyr Thr Asn Trp Phe Gln Gln Lys Pro Gly Gln
                165                 170                 175
Ala Pro Leu Leu Val Val Tyr Ala Lys Asn Lys Arg Pro Ser Gly Ile
                180                 185                 190
Pro Asp Arg Phe Ser Gly Ser Ser Ser Gly Asn Thr Ala Ser Leu Thr
                195                 200                 205
Ile Thr Gly Ala Gln Ala Glu Asp Glu Ala Asp Tyr Tyr Cys His Ser
        210                 215                 220
Arg Asp Ser Ser Gly Asn His Val Leu Phe Gly Gly Gly Thr Lys Leu
225                 230                 235                 240
Thr Val Leu Gly

<210> SEQ ID NO 103
<211> LENGTH: 247
<212> TYPE: PRT
<213> ORGANISM: Artificial sequence
<220> FEATURE:
<223> OTHER INFORMATION: scFv protein GMBC686

<400> SEQUENCE: 103

Glu Val Gln Leu Val Gln Ser Gly Gly Gly Leu Val Lys Pro Gly Gly
1               5                   10                  15
Ser Leu Arg Leu Ser Cys Ala Ala Ser Gly Phe Thr Phe Ser Asp Ala
                20                  25                  30
Trp Met Asn Trp Val Arg Gln Ala Pro Gly Lys Gly Leu Glu Trp Val
            35                  40                  45
Gly Arg Ile Lys Ser Lys Gly Ser Gly Gly Thr Ile Asp Tyr Ala Ala
        50                  55                  60
Pro Val Lys Asp Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Leu Tyr
                85                  90                  95
Tyr Cys Thr Trp Asp Trp Asp Phe Tyr Tyr Gly Met Asn Val Trp Gly
                100                 105                 110
Gln Gly Thr Thr Val Thr Val Ser Ser Gly Gly Gly Ser Gly Gly
            115                 120                 125
Gly Gly Ser Gly Gly Gly Ser Gln Ser Val Leu Thr Gln Pro Ala
        130                 135                 140
Ser Val Ser Gly Ser Pro Gly Gln Ser Ile Thr Ile Ser Cys Thr Gly
145                 150                 155                 160
Thr Ser Ser Asp Val Gly Gly Tyr Asn Tyr Val Ser Trp Tyr Gln Gln
                165                 170                 175
His Pro Gly Lys Ala Pro Lys Leu Met Ile Tyr Glu Gly Ser Lys Arg
                180                 185                 190
Pro Ser Gly Val Ser Asn Arg Phe Ser Gly Ser Lys Ser Gly Asn Thr
                195                 200                 205
Ala Ser Leu Thr Ile Ser Gly Leu Gln Ala Glu Asp Glu Ala Asp Tyr
        210                 215                 220
Tyr Cys Ser Ser Tyr Thr Thr Arg Ser Thr Arg Val Phe Gly Gly Gly
225                 230                 235                 240
```

-continued

Thr Lys Leu Thr Val Leu Gly
            245

<210> SEQ ID NO 104
<211> LENGTH: 247
<212> TYPE: PRT
<213> ORGANISM: Artificial sequence
<220> FEATURE:
<223> OTHER INFORMATION: scFv protein GMBC687

<400> SEQUENCE: 104

Gln Val Gln Leu Val Gln Ser Gly Ala Glu Val Lys Lys Pro Gly Ser
1               5                   10                  15

Ser Val Lys Val Ser Cys Lys Ala Pro Gly Asp Thr Phe Ser Asn Tyr
            20                  25                  30

Ile Phe Asn Trp Val Arg Gln Ala Pro Gly Gln Gly Leu Glu Trp Met
        35                  40                  45

Gly Gly Ile Ile Pro Lys Phe Gly Thr Val Asn Asp Ala His Lys Phe
    50                  55                  60

Gln Asp Arg Val Thr Ile Ala Ala Asp Glu Ser Thr Asn Thr Ala Ser
65                  70                  75                  80

Met Glu Leu Ser Ser Leu Thr Ser Glu Asp Thr Ala Val Tyr Tyr Cys
                85                  90                  95

Ala Cys Glu Pro Ile Pro Lys Asp Tyr Gly Asp Val Asn Gly Leu Glu
            100                 105                 110

Ile Trp Gly Lys Gly Thr Met Val Thr Val Ser Ser Gly Gly Gly Gly
        115                 120                 125

Ser Gly Gly Gly Gly Ser Gly Gly Gly Gly Ser Asp Ile Gln Met Thr
    130                 135                 140

Gln Ser Pro Ser Thr Leu Ser Ala Ser Ile Gly Asp Arg Val Thr Ile
145                 150                 155                 160

Thr Cys Arg Ala Ser Glu Gly Ile Tyr His Trp Leu Ala Trp Tyr Gln
                165                 170                 175

Gln Lys Pro Gly Lys Ala Pro Lys Leu Leu Ile Tyr Lys Ala Ser Ser
            180                 185                 190

Leu Ala Ser Gly Ala Pro Ser Arg Phe Ser Gly Ser Gly Ser Gly Thr
        195                 200                 205

Asp Phe Thr Leu Thr Ile Ser Ser Leu Gln Pro Asp Asp Phe Ala Thr
    210                 215                 220

Tyr Tyr Cys Gln Gln Tyr Ser Asn Tyr Pro Leu Thr Phe Gly Gly Gly
225                 230                 235                 240

Thr Lys Leu Glu Ile Lys Arg
            245

<210> SEQ ID NO 105
<211> LENGTH: 247
<212> TYPE: PRT
<213> ORGANISM: Artificial sequence
<220> FEATURE:
<223> OTHER INFORMATION: scFv protein GMBC689

<400> SEQUENCE: 105

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val

-continued

```
                35                  40                  45
Gly Arg Ile Lys Ser Lys Gly Ser Gly Gly Thr Ile Asp Tyr Ala Ala
         50                  55                  60
Pro Val Lys Asp Arg Phe Thr Ile Ser Arg Asp Asp Ser Lys Asn Thr
 65                  70                  75                  80
Leu Tyr Leu Gln Met Asn Ser Leu Lys Thr Glu Asp Thr Ala Leu Tyr
                 85                  90                  95
Tyr Cys Thr Trp Asp Trp Asp Phe Tyr Tyr Gly Met Asn Val Trp Gly
                100                 105                 110
Gln Gly Thr Leu Val Thr Val Ser Ser Gly Gly Gly Ser Gly Gly
            115                 120                 125
Gly Gly Ser Gly Gly Gly Ser Gln Ser Val Leu Thr Gln Pro Pro
    130                 135                 140
Ser Ala Ser Gly Ser Pro Gly Gln Ser Val Thr Ile Ser Cys Thr Gly
145                 150                 155                 160
Thr Ser Ser Asp Val Gly Gly Tyr Asn Tyr Val Ser Trp Tyr Gln Gln
                165                 170                 175
His Pro Gly Lys Ala Pro Lys Phe Met Ile Tyr Asp Val Ser Lys Arg
            180                 185                 190
Pro Ser Gly Val Ser Asn Arg Phe Ser Gly Ser Lys Ser Gly Asn Thr
        195                 200                 205
Ala Ser Leu Thr Ile Ser Gly Val Gln Ala Glu Asp Glu Ala Asp Tyr
    210                 215                 220
Tyr Cys Ser Ser Tyr Thr Ser Ala Ser Thr Val Val Phe Gly Gly Gly
225                 230                 235                 240
Thr Lys Leu Thr Val Leu Gly
                245
```

<210> SEQ ID NO 106
<211> LENGTH: 247
<212> TYPE: PRT
<213> ORGANISM: Artificial sequence
<220> FEATURE:
<223> OTHER INFORMATION: scFv protein GMBC690

<400> SEQUENCE: 106

```
Glu Val Gln Leu Val Gln Ser Gly Gly Gly Val Val Gln Pro Gly Arg
  1               5                  10                  15
Ser Leu Arg Leu Ser Cys Ala Ala Ser Gly Phe Thr Phe Ser Asp Ala
             20                  25                  30
Trp Met Asn Trp Val Arg Gln Ala Pro Gly Lys Gly Leu Glu Trp Val
             35                  40                  45
Gly Arg Ile Lys Ser Lys Gly Ser Gly Gly Thr Ile Asp Tyr Ala Ala
         50                  55                  60
Pro Val Lys Asp Arg Phe Thr Ile Ser Arg Asp Asp Ser Lys Asn Thr
 65                  70                  75                  80
Leu Tyr Leu Gln Met Asn Ser Leu Lys Thr Glu Asp Thr Ala Leu Tyr
                 85                  90                  95
Tyr Cys Thr Trp Asp Trp Asp Phe Tyr Tyr Gly Met Asn Val Trp Gly
                100                 105                 110
Arg Gly Thr Leu Val Thr Val Ser Ser Gly Gly Gly Ser Gly Gly
            115                 120                 125
Gly Gly Ser Gly Gly Gly Gly Ser Gln Ser Val Leu Thr Gln Pro Ala
    130                 135                 140
Ser Val Ser Gly Ser Pro Gly Gln Ser Ile Thr Ile Ser Cys Thr Gly
```

-continued

```
                145                 150                 155                 160
Thr Ser Ser Asp Val Gly Gly Tyr Ile Tyr Val Ser Trp Tyr Gln Gln
                    165                 170                 175

His Pro Gly Arg Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
            195                 200                 205

Ala Ser Leu Thr Ile Ser Gly Leu Gln Ala Glu Asp Glu Ala Asp Tyr
        210                 215                 220

Tyr Cys Ser Ser Tyr Thr Thr Arg Ser Thr Arg Val Phe Gly Gly Gly
225                 230                 235                 240

Thr Lys Leu Thr Val Leu Gly
                245

<210> SEQ ID NO 107
<211> LENGTH: 253
<212> TYPE: PRT
<213> ORGANISM: Artificial sequence
<220> FEATURE:
<223> OTHER INFORMATION: scFv protein GMBC691

<400> SEQUENCE: 107

Glu Val Gln Leu Val Gln Ser Gly Ala Glu Val Lys Lys Pro Gly Ala
1               5                   10                  15

Ser Met Lys Val Ser Cys Lys Thr Ser Gly Asp Thr Phe Asn Gly Phe
            20                  25                  30

Tyr Val His Trp Val Arg Gln Ala Pro Gly Gln Gly Leu Glu Trp Met
        35                  40                  45

Gly Arg Ile Asn Pro Asn Gly Gly Thr Asn Tyr Ala Gln Lys Phe
    50                  55                  60

Gln Gly Arg Val Thr Met Thr Arg Asp Thr Ser Met Asn Thr Ala Tyr
65                  70                  75                  80

Met Glu Leu Arg Ser Leu Arg Ser Asp Thr Ala Val Tyr Tyr Cys
                85                  90                  95

Ala Arg Asp Leu Phe Tyr Asp Phe Trp Ser Asp Tyr Tyr Arg Asn Asp
            100                 105                 110

Gln Tyr Tyr Tyr Met Asp Val Trp Gly Arg Gly Thr Leu Val Thr Val
        115                 120                 125

Ser Ser Gly Gly Gly Gly Ser Gly Gly Gly Ser Gly Gly Gly Gly
    130                 135                 140

Ser Ser Glu Leu Thr Gln Asp Pro Ala Val Ser Val Ala Leu Gly Gln
145                 150                 155                 160

Thr Val Arg Ile Thr Cys Gln Gly Asp Ser Leu Arg Ser Tyr Tyr Ala
                165                 170                 175

Ser Trp Tyr Gln Gln Lys Pro Gly Gln Ala Pro Val Leu Val Ile Tyr
            180                 185                 190

Gly Lys Asn Asn Arg Pro Ser Gly Ile Pro Asp Arg Phe Ser Gly Ser
        195                 200                 205

Ser Ser Gly Asn Thr Ala Ser Leu Thr Ile Thr Gly Ala Gln Ala Glu
    210                 215                 220

Asp Glu Ala Asp Tyr Tyr Cys Asn Ser Arg Asp Ser Ser Gly Asn His
225                 230                 235                 240

Val Val Phe Gly Gly Gly Thr Lys Leu Thr Val Leu Gly
                245                 250
```

<210> SEQ ID NO 108
<211> LENGTH: 247
<212> TYPE: PRT
<213> ORGANISM: Artificial sequence
<220> FEATURE:
<223> OTHER INFORMATION: scFv protein GMBC692

<400> SEQUENCE: 108

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
    50                  55                  60

Pro Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
            100                 105                 110

Arg Gly Thr Leu Val Thr Val Ser Ser Gly Gly Gly Ser Gly Gly
        115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly Gly
225                 230                 235                 240

Thr Lys Leu Thr Val Leu Gly
                245
```

<210> SEQ ID NO 109
<211> LENGTH: 247
<212> TYPE: PRT
<213> ORGANISM: Artificial sequence
<220> FEATURE:
<223> OTHER INFORMATION: scFv protein GMBC693

<400> SEQUENCE: 109

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Gly Ser Gly Gly Thr Ile Asp Tyr Ala Ala
    50                  55                  60
```

Pro Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
            85                  90                  95

Tyr Cys Thr Trp Asp Trp Asp Phe Tyr Tyr Gly Met Asn Val Trp Gly
            100                 105                 110

Lys Gly Thr Leu Val Thr Val Ser Ser Gly Gly Gly Ser Gly Gly
        115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asp Thr
            195                 200                 205

Ala Ser Leu Thr Ile Ser Gly Leu Gln Ala Glu Asp Glu Ala Asp Tyr
            210                 215                 220

Tyr Cys Ser Ser Tyr Thr Thr Arg Ser Thr Arg Val Phe Gly Gly Gly
225                 230                 235                 240

Thr Lys Leu Thr Val Leu Gly
                245

<210> SEQ ID NO 110
<211> LENGTH: 241
<212> TYPE: PRT
<213> ORGANISM: Artificial sequence
<220> FEATURE:
<223> OTHER INFORMATION: scFv protein GMBC696

<400> SEQUENCE: 110

Glu Val Gln Leu Val Gln Ser Arg Ala Glu Val Lys Lys Pro Gly Ala
1               5                   10                  15

Ser Val Lys Val Ser Cys Lys Thr Ser Gly Tyr Thr Phe Asn Gly Tyr
            20                  25                  30

Tyr Ile His Trp Val Arg Gln Ala Pro Gly Gln Gly Leu Glu Trp Met
            35                  40                  45

Gly Trp Ile Asp Pro Ile Asn Ser Val Thr Asn Tyr Ala Gln Asn Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Thr Ser Asp Asp Thr Ala Val Tyr Tyr Cys
            85                  90                  95

Ala Arg Ala Arg Val Ser Thr Ile Leu Gln Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

-continued

Leu Val Ile Tyr Gly Lys Asn Asn Arg Pro Ser Gly Ile Pro Asp Arg
                180                 185                 190

Phe Ser Gly Ser Ser Gly Asn Thr Ala Ser Leu Thr Ile Thr Gly
            195                 200                 205

Ala Gln Ala Glu Asp Glu Ala Asp Tyr Tyr Cys Asn Ser Arg Asp Ser
        210                 215                 220

Ser Gly Asn His Val Val Phe Gly Gly Gly Thr Lys Leu Thr Val Leu
225                 230                 235                 240

Gly

<210> SEQ ID NO 111
<211> LENGTH: 242
<212> TYPE: PRT
<213> ORGANISM: Artificial sequence
<220> FEATURE:
<223> OTHER INFORMATION: scFv protein GMBC725

<400> SEQUENCE: 111

Glu Val Gln Leu Val Gln Thr Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Leu Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ser Ala Ser Ala Phe Asp Ile Trp Arg Gln Arg
            100                 105                 110

Thr Thr Val Thr Val Ser Ser Gly Gly Gly Ser Gly Gly Gly Gly
        115                 120                 125

Ser Gly Gly Gly Gly Ser Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
            180                 185                 190

Arg Phe Ser Gly Ser Ser Gly Asn Thr Ala Ser Leu Thr Ile Thr
        195                 200                 205

Gly Ala Gln Ala Glu Asp Glu Ala Asp Tyr Tyr Cys Asn Ser Arg Asp
    210                 215                 220

Ser Ser Gly Asn His Val Val Phe Gly Gly Gly Thr Lys Leu Thr Val
225                 230                 235                 240

Leu Gly

<210> SEQ ID NO 112
<211> LENGTH: 247
<212> TYPE: PRT
<213> ORGANISM: Artificial sequence
<220> FEATURE:
<223> OTHER INFORMATION: scFv protein GMBC727

```
<400> SEQUENCE: 112

Glu Val Gln Leu Val Glu Ser Gly Gly Asp Thr Val Lys Pro Gly Gly
1               5                   10                  15

Ser Leu Arg Leu Ser Cys Ala Gly Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Met Lys Ser Lys Gly Ser Gly Gly Thr Arg Asp Tyr Ala Ala
    50                  55                  60

Pro Val Asn Gly Arg Phe Thr Ile Ser Arg Asp Asp Ser Lys Asn Thr
65                  70                  75                  80

Leu Tyr Leu Gln Met Asn Ser Leu Asn Thr Glu Asp Thr Gly Val Tyr
                85                  90                  95

Tyr Cys Thr Trp Asp Trp Asp Phe Tyr Tyr Gly Met Asn Val Trp Gly
            100                 105                 110

Arg Gly Thr Leu Val Thr Val Ser Ser Gly Gly Gly Ser Gly Gly
            115                 120                 125

Gly Gly Ser Gly Gly Gly Ser Gln Ser Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Glu Gly Ser Lys Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Thr Arg Ser Thr Arg Val Phe Gly Gly Gly
225                 230                 235                 240

Thr Lys Leu Thr Val Leu Gly
                245

<210> SEQ ID NO 113
<211> LENGTH: 244
<212> TYPE: PRT
<213> ORGANISM: Artificial sequence
<220> FEATURE:
<223> OTHER INFORMATION: scFv protein GMBC729

<400> SEQUENCE: 113

Gln Val Gln Leu Gln Glu Ser Gly Gly Gly Leu Val Lys Pro Gly Gly
1               5                   10                  15

Ser Leu Arg Leu Ser Cys Ala Gly Ser Gly Phe Lys Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Ser Lys Ser Gly Gly Thr Ile Glu Tyr Ala Ala
    50                  55                  60

Pro Val Lys Asp Arg Phe Ile Ile Ser Arg Asp Asp Ser Lys Asp Thr
65                  70                  75                  80

Leu Tyr Leu Gln Met Asp Ser Leu Lys Thr Glu Asp Thr Ala Leu Tyr
                85                  90                  95

Tyr Cys Thr Trp Asp Trp Asp Phe Tyr Tyr Gly Met Asn Val Trp Gly
```

-continued

```
                    100                 105                 110
Gln Gly Thr Leu Val Thr Val Ser Ser Gly Gly Gly Ser Gly Gly
            115                 120                 125
Gly Gly Ser Gly Gly Gly Ser Ser Glu Leu Thr Gln Asp Pro Ala
        130                 135                 140
Val Ser Val Ala Leu Gly Gln Thr Val Arg Ile Thr Cys Gln Gly Asp
145                 150                 155                 160
Ser Leu Arg Asn Tyr Tyr Thr Asn Trp Phe Gln Lys Pro Gly Gln
                165                 170                 175
Ala Pro Leu Leu Val Val Tyr Ala Lys Asn Lys Arg Pro Ser Gly Ile
            180                 185                 190
Pro Asp Arg Phe Ser Gly Ser Ser Ser Gly Asn Thr Ala Ser Leu Thr
            195                 200                 205
Ile Thr Gly Ala Gln Ala Glu Asp Glu Ala Asp Tyr Tyr Cys His Ser
        210                 215                 220
Arg Asp Ser Ser Gly Asn His Val Leu Phe Gly Gly Gly Thr Lys Leu
225                 230                 235                 240
Thr Val Leu Gly

<210> SEQ ID NO 114
<211> LENGTH: 247
<212> TYPE: PRT
<213> ORGANISM: Artificial sequence
<220> FEATURE:
<223> OTHER INFORMATION: scFv protein GMBC730

<400> SEQUENCE: 114

Gln Val Gln Leu Val Glu Ser Gly Gly Asp Ser Val Lys Pro Gly Gly
1               5                   10                  15
Ser Leu Arg Leu Ser Cys Ala Gly Ser Gly Phe Thr Phe Ser Asp Ala
            20                  25                  30
Trp Met Asn Trp Val Arg Gln Ala Pro Gly Lys Gly Leu Glu Trp Val
        35                  40                  45
Gly Arg Met Lys Ser Lys Gly Ser Gly Gly Thr Arg Asp Tyr Ala Ala
    50                  55                  60
Pro Val Asn Gly Arg Phe Thr Ile Ser Arg Asp Asp Ser Lys Asn Thr
65                  70                  75                  80
Leu Tyr Leu Gln Met Asn Ser Leu Asn Thr Glu Asp Thr Gly Val Tyr
                85                  90                  95
Tyr Cys Thr Trp Asp Trp Asp Phe Tyr Tyr Gly Met Asp Val Trp Gly
            100                 105                 110
Lys Gly Thr Thr Val Thr Val Ser Ser Gly Gly Gly Ser Gly Gly
        115                 120                 125
Gly Gly Ser Gly Gly Gly Gly Ser Gln Ser Val Leu Thr Gln Pro Ala
    130                 135                 140
Ser Val Ser Gly Ser Pro Gly Gln Ser Ile Thr Ile Ser Cys Thr Gly
145                 150                 155                 160
Thr Ser Ser Asp Val Gly Gly Tyr Asn Tyr Val Ser Trp Tyr Gln Gln
                165                 170                 175
His Pro Gly Lys Ala Pro Lys Leu Met Ile Tyr Glu Gly Ser Lys Arg
            180                 185                 190
Pro Ser Gly Val Ser Asn Arg Phe Ser Gly Ser Lys Ser Gly Asn Thr
        195                 200                 205
Ala Ser Leu Thr Ile Ser Gly Leu Gln Ala Glu Asp Glu Ala Asp Tyr
    210                 215                 220
```

Tyr Cys Ser Ser Tyr Thr Thr Arg Ser Thr Arg Val Phe Gly Gly Gly
225                 230                 235                 240

Thr Lys Leu Thr Val Leu Gly
                245

<210> SEQ ID NO 115
<211> LENGTH: 245
<212> TYPE: PRT
<213> ORGANISM: Artificial sequence
<220> FEATURE:
<223> OTHER INFORMATION: scFv protein GMCC101

<400> SEQUENCE: 115

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Thr Tyr
            20                  25                  30

Ala Ile Thr Trp Val Arg Gln Ala Pro Gly Gln Gly Leu Glu Trp Met
        35                  40                  45

Gly Gly Ile Ile Pro Ile Ser Ala Thr Ala Asn Tyr Ala Gln Lys Phe
    50                  55                  60

Gln Gly Arg Val Thr Ile Thr Ala Asp Glu Ser Met Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Glu Pro His Tyr Phe Asp Asn Trp Gly Arg Gly Thr
            100                 105                 110

Met Val Thr Val Ser Ser Gly Gly Gly Gly Ser Gly Gly Gly Gly Ser
        115                 120                 125

Gly Gly Gly Gly Ser Ala Leu Pro Val Leu Thr Gln Pro Pro Ser Val
130                 135                 140

Ser Glu Ala Pro Arg Gln Gly Val Thr Ile Ser Cys Ser Gly Ser Ser
145                 150                 155                 160

Ser Asn Ile Gly Asn Asn Ala Val Ser Trp Tyr Gln Gln Leu Pro Gly
                165                 170                 175

Gln Ala Pro Lys Leu Leu Ile Tyr Tyr Asp Asp Leu Leu Pro Ser Gly
            180                 185                 190

Val Ser Asp Arg Phe Ser Ala Ser Lys Ser Gly Thr Ser Ala Ser Leu
        195                 200                 205

Ala Ile Ser Gly Leu Gln Ser Glu Asp Glu Ala Asp Tyr Tyr Cys Ala
    210                 215                 220

Ala Trp Asp Asp Ser Leu Asn Gly Val Ile Phe Gly Gly Gly Thr Gln
225                 230                 235                 240

Leu Thr Val Leu Ser
                245

<210> SEQ ID NO 116
<211> LENGTH: 260
<212> TYPE: PRT
<213> ORGANISM: Artificial sequence
<220> FEATURE:
<223> OTHER INFORMATION: scFv protein GMCC102

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Pro Gly Tyr Thr Phe Thr Ser Tyr

```
                    20                  25                  30
Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Arg Ser Asn Asp Ser Ser Gly Tyr Tyr Lys Ser
            100                 105                 110

Pro Leu Ser Tyr Tyr Gly Met Asp Val Trp Gly Arg Gly Thr Met
            115                 120                 125

Val Thr Val Ser Ser Gly Gly Gly Ser Gly Gly Gly Ser Gly
        130                 135                 140

Gly Gly Gly Ser Ala Gln Ser Val Leu Thr Gln Pro Pro Ser Ala Ser
145                 150                 155                 160

Gly Thr Pro Gly Gln Arg Val Thr Ile Ser Cys Ser Gly Ser Ser Ser
                165                 170                 175

Asn Ile Gly Ser Asn Thr Val Asn Trp Tyr Gln Gln Leu Pro Gly Thr
            180                 185                 190

Ala Pro Lys Leu Leu Ile Tyr Ser Asn Asn Gln Arg Pro Ser Gly Val
        195                 200                 205

Pro Asp Arg Phe Ser Gly Ser Lys Ser Gly Thr Ser Ala Ser Leu Ala
    210                 215                 220

Ile Ser Gly Leu Gln Ser Glu Asp Glu Ala Asp Tyr Tyr Cys Ala Ala
225                 230                 235                 240

Trp Asp Asp Ser Leu Asn Gly Val Val Phe Gly Gly Gly Thr Lys Val
                245                 250                 255

Thr Val Leu Gly
            260

<210> SEQ ID NO 117
<211> LENGTH: 250
<212> TYPE: PRT
<213> ORGANISM: Artificial sequence
<220> FEATURE:
<223> OTHER INFORMATION: scFv protein GMCC105

<400> SEQUENCE: 117

Gln Val Gln Leu Val Gln Ser Gly Gly Gly Val Val Gln Pro Gly Arg
1               5                   10                  15

Ser Leu Arg Leu Ser Cys Thr Ala Ser Gly Phe Asn Leu Gly Ser His
            20                  25                  30

Gly Met His Trp Val Arg Gln Ala Pro Gly Lys Gly Leu Glu Trp Val
        35                  40                  45

Ala Val Ile Gly Phe Asp Gly Thr Thr Lys Tyr Tyr Val Asp Ser Val
    50                  55                  60

Lys Gly Arg Phe Thr Ile Ser Arg Asp Asn Ser Arg Asn Thr Leu Ser
65                  70                  75                  80

Leu Gln Met Asn Ser Leu Arg Ala Glu Asp Thr Ala Val Tyr Tyr Cys
                85                  90                  95

Val Arg Glu Asp Tyr Tyr Tyr Asp Ser Ser Gly Tyr Tyr Phe Asp Tyr
            100                 105                 110

Trp Gly Arg Gly Thr Leu Val Thr Val Ser Ser Gly Gly Gly Gly Ser
```

```
            115                 120                 125
Gly Gly Gly Gly Ser Gly Gly Gly Ser Ala Leu Ser Ser Glu Leu
        130                 135                 140

Thr Gln Asp Pro Phe Val Ser Val Ala Leu Gly Gln Thr Val Arg Ile
145                 150                 155                 160

Ala Cys Arg Gly Asp Ser Leu Arg Asp Ser Tyr Ala Ser Trp Tyr Gln
                165                 170                 175

Gln Lys Pro Gly Gln Ala Pro Arg Leu Leu Val Tyr Gly Asn Asn Leu
                180                 185                 190

Arg Pro Ser Gly Ile Pro Gly Arg Phe Ser Gly Ser Ser Ser Gly Asp
                195                 200                 205

Thr Ala Ser Leu Ser Ile Thr Glu Thr Gln Ala Gly Asp Glu Ala Asp
        210                 215                 220

Tyr Tyr Cys Ser Ser Arg Gly Asn Ser Thr Ser Arg Leu Tyr Val Phe
225                 230                 235                 240

Gly Thr Gly Thr Lys Leu Thr Val Leu Gly
                245                 250

<210> SEQ ID NO 118
<211> LENGTH: 245
<212> TYPE: PRT
<213> ORGANISM: Artificial sequence
<220> FEATURE:
<223> OTHER INFORMATION: scFv protein GMCC106

<400> SEQUENCE: 118

Gln Val Gln Leu Gln Glu Ser Gly Pro Gly Leu Val Lys Pro Ser Gly
1               5                   10                  15

Thr Leu Ser Leu Thr Cys Ala Val Ser Val Gly Ser Ile Asn Glu Ser
            20                  25                  30

Asn Trp Trp Ser Trp Val Arg Gln Ser Pro Gly Lys Gly Leu Glu Trp
        35                  40                  45

Ile Gly Glu Ile Tyr Pro Thr Gly Thr Thr Asn Tyr Asn Pro Ser Leu
    50                  55                  60

Glu Ser Arg Val Thr Ile Ser Val Asp Lys Ser Arg Asn Leu Phe Ser
65                  70                  75                  80

Leu Lys Leu Lys Ser Val Thr Ala Ala Asp Ser Ala Met Tyr Phe Cys
                85                  90                  95

Ala Arg Asp Arg Trp Ala Gly Phe Asp Leu Trp Gly Arg Gly Thr
                100                 105                 110

Met Val Thr Val Ser Ser Gly Gly Gly Gly Ser Gly Gly Gly Gly Ser
            115                 120                 125

Gly Gly Gly Gly Ser Ala Gln Ser Val Leu Thr Gln Pro Pro Ser Ala
        130                 135                 140

Ser Gly Thr Pro Gly Gln Arg Val Thr Ile Ser Cys Ser Gly Ser Ser
145                 150                 155                 160

Ser Asn Ile Gly Ser Asn Ser Val Tyr Trp Tyr Gln Gln Leu Pro Gly
                165                 170                 175

Thr Ala Pro Lys Leu Leu Ile Tyr Arg Asn Asn Gln Arg Pro Ser Gly
                180                 185                 190

Val Pro Asp Arg Phe Ser Ala Ser Lys Ser Gly Thr Ser Ala Ser Leu
                195                 200                 205

Ala Ile Ser Gly Leu Arg Ser Glu Asp Glu Ala Asp Tyr Tyr Cys Ala
        210                 215                 220

Ala Trp Asp Asp Ser Leu Ser Gly Leu Val Phe Gly Gly Gly Thr Lys
```

Leu Thr Val Leu Gly
            245

<210> SEQ ID NO 119
<211> LENGTH: 250
<212> TYPE: PRT
<213> ORGANISM: Artificial sequence
<220> FEATURE:
<223> OTHER INFORMATION: scFv protein GMCC107

<400> SEQUENCE: 119

Gln Val Gln Leu Val Gln Ser Gly Ala Glu Val Lys Lys Pro Gly Ala
1               5                   10                  15

Ser Val Lys Val Ser Cys Arg Thr Ser Gly Tyr Thr Phe Thr Asp His
            20                  25                  30

Ser Met His Trp Val Arg Gln Ala Pro Gly Gln Arg Phe Glu Trp Met
        35                  40                  45

Gly Trp Ile Gly Ala Asp Ser Gly Ser Thr Gln Tyr Ser Arg Asn Phe
    50                  55                  60

Gln Gly Arg Leu Thr Ile Gly Arg Asp Thr Ser Ala Ser Thr Val Tyr
65                  70                  75                  80

Met Glu Leu Thr Ser Leu Arg Ser Glu Asp Thr Ala Val Tyr Tyr Cys
                85                  90                  95

Ala Arg Val Gly Gly Gln Gly Trp Tyr Ser Gly Met Asp Val Trp
            100                 105                 110

Gly Arg Gly Thr Leu Val Thr Val Ser Ser Gly Gly Gly Gly Ser Gly
        115                 120                 125

Gly Gly Gly Ser Gly Gly Gly Ser Ala Gln Ala Val Leu Thr Gln
    130                 135                 140

Pro Ser Ser Val Ser Gly Ala Pro Gly Gln Arg Val Thr Ile Ser Cys
145                 150                 155                 160

Thr Gly Ser Ser Ser Asn Ile Gly Ala Ser Tyr Asp Val His Trp Tyr
                165                 170                 175

Gln Gln Leu Pro Gly Thr Ala Pro Lys Leu Leu Ile Tyr Asn Asn Asn
            180                 185                 190

Asn Arg Pro Ser Gly Val Pro Asp Arg Phe Ser Gly Ser Arg Ser Gly
        195                 200                 205

Thr Ser Ala Ser Leu Ala Ile Thr Gly Leu Gln Ala Glu Asp Glu Ala
    210                 215                 220

Asp Tyr Tyr Cys His Ser Tyr Asp Ser Asn Leu Ser Gly Asp Val Phe
225                 230                 235                 240

Gly Ser Gly Thr Lys Leu Thr Val Leu Gly
                245                 250

<210> SEQ ID NO 120
<211> LENGTH: 255
<212> TYPE: PRT
<213> ORGANISM: Artificial sequence
<220> FEATURE:
<223> OTHER INFORMATION: scFv protein GMCC108

<400> SEQUENCE: 120

Glu Val Gln Leu Val Gln Ser Gly Ala Glu Val Lys Glu Pro Gly Ala
1               5                   10                  15

Ser Val Thr Val Ser Cys Lys Ala Ser Gly Tyr Thr Phe Ile Ser Tyr
            20                  25                  30

```
His Met His Trp Val Arg Gln Ala Pro Gly Gln Gly Leu Glu Trp Met
            35                  40                  45

Gly Ile Ile Asn Pro Ser Gly Gly Asp Thr Thr Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Arg Ser Leu Arg Phe Glu Asp Thr Ala Arg Tyr Tyr Cys
                85                  90                  95

Ala Arg Asp Leu Lys Phe Tyr Asp Phe Arg Ser Gly Lys Tyr Gln Asp
            100                 105                 110

Tyr Gly Met Asp Val Trp Gly Gln Gly Thr Leu Val Thr Val Ser Ser
            115                 120                 125

Gly Gly Gly Gly Ser Gly Gly Gly Ser Gly Gly Gly Gly Ser Ala
        130                 135                 140

Gln Ser Val Leu Thr Gln Pro Pro Ser Leu Ser Val Ala Pro Gly Gln
145                 150                 155                 160

Thr Ala Ser Ile Thr Cys Gly Gly Asn Asp Ile Gly Thr Lys Ser Val
            165                 170                 175

His Trp Tyr Gln Leu Lys Pro Gly Gln Ala Pro Val Leu Val Val Tyr
            180                 185                 190

Asp Asn Arg Asp Arg Pro Ser Gly Ile Pro Glu Arg Phe Ser Gly Ser
            195                 200                 205

Asn Ser Gly Asn Thr Ala Thr Leu Thr Ile Ser Arg Val Glu Gly Gly
        210                 215                 220

Asp Glu Ala Asp Tyr Tyr Cys Gln Val Trp Asp Ser Ser Ile Asp His
225                 230                 235                 240

Ser Glu Tyr Val Phe Gly Thr Gly Thr Lys Leu Thr Val Leu Gly
            245                 250                 255

<210> SEQ ID NO 121
<211> LENGTH: 244
<212> TYPE: PRT
<213> ORGANISM: Artificial sequence
<220> FEATURE:
<223> OTHER INFORMATION: scFv protein GMCC109

<400> SEQUENCE: 121

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gln Trp Ser Gly Ser Tyr Tyr Gly Ser Phe Asp Tyr Trp
            100                 105                 110

Gly Arg Gly Thr Met Val Thr Val Ser Ser Gly Gly Gly Gly Ser Gly
            115                 120                 125

Gly Gly Gly Ser Gly Gly Gly Gly Ser Ala Gln Ser Val Leu Thr Gln
        130                 135                 140
```

```
Pro Pro Ser Val Ser Val Ser Pro Gly Gln Thr Ala Thr Ile Thr Cys
145                 150                 155                 160

Ser Gly Asp Lys Leu Gly Asp Lys Tyr Val Ser Trp Tyr Gln Lys Lys
                165                 170                 175

Pro Gly Gln Ala Pro Val Leu Val Ile Tyr Gln Asp Asp Lys Arg Pro
            180                 185                 190

Ser Gly Ile Pro Glu Arg Phe Ser Gly Ser Asn Ser Gly Asn Thr Ala
        195                 200                 205

Thr Leu Thr Ile Ser Gly Thr Gln Ala Met Asp Glu Gly Asp Tyr Tyr
    210                 215                 220

Cys Gln Ala Trp Asp Arg Ser Val Ile Phe Gly Gly Gly Thr Lys Val
225                 230                 235                 240

Thr Val Leu Gly

<210> SEQ ID NO 122
<211> LENGTH: 250
<212> TYPE: PRT
<213> ORGANISM: Artificial sequence
<220> FEATURE:
<223> OTHER INFORMATION: scFv protein GMCC110

<400> SEQUENCE: 122

Gln Val Gln Leu Gln Glu Ser Gly Pro Gly Leu Val Lys Pro Ser Gln
1               5                   10                  15

Thr Leu Ser Leu Thr Cys Thr Val Ser Gly Ala Ser Ile Ser Ser Gly
            20                  25                  30

Gly Tyr Arg Trp Ile Trp Ile Arg Gln His Pro Gly Gln Gly Leu Glu
        35                  40                  45

Trp Ile Gly Asp Ile His Tyr Ser Gly Ser Thr Gln Tyr Asn Pro Ser
    50                  55                  60

Leu Lys Ser Arg Val Ala Leu Thr Leu Asp Arg Ser Lys Asn Gln Phe
65                  70                  75                  80

Ser Leu Gln Leu Ser Ser Val Thr Ala Ala Asp Thr Ala Val Tyr Tyr
                85                  90                  95

Cys Ala Arg Asp Pro Arg Gly His Thr Tyr Gly Tyr Gly Tyr Tyr Phe
            100                 105                 110

Asp Tyr Trp Gly Lys Gly Thr Leu Val Thr Val Ser Ser Gly Gly Gly
        115                 120                 125

Gly Ser Gly Gly Gly Gly Ser Gly Gly Gly Gly Ser Ala Leu Ser Ser
    130                 135                 140

Glu Leu Thr Gln Asp Pro Asp Val Ser Val Ala Leu Gly Gln Thr Val
145                 150                 155                 160

Thr Ile Thr Cys Gln Gly Asp Arg Leu Arg Tyr Tyr Ala Ser Trp
                165                 170                 175

Tyr Gln Gln Lys Pro Gly Gln Ala Pro Val Leu Val Ile Phe Arg Lys
            180                 185                 190

Asn Asn Arg Pro Ser Gly Ile Pro Asp Arg Phe Ser Gly Ser Ser Ser
        195                 200                 205

Gly Asp Thr Ala Ser Leu Thr Ile Thr Gly Ala Gln Ala Glu Asp Glu
    210                 215                 220

Ala Asp Tyr Tyr Cys Asn Ser Arg Asp Thr Ser Gly Thr Leu Ser Phe
225                 230                 235                 240

Gly Gly Gly Thr Gln Leu Thr Val Leu Ser
                245                 250
```

```
<210> SEQ ID NO 123
<211> LENGTH: 245
<212> TYPE: PRT
<213> ORGANISM: Artificial sequence
<220> FEATURE:
<223> OTHER INFORMATION: scFv protein GMCC112

<400> SEQUENCE: 123

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Ser Phe Ser Thr Tyr
            20                  25                  30

Ala Met Ser Trp Val Arg Gln Ala Pro Gly Lys Gly Leu Glu Trp Val
        35                  40                  45

Ser Gly Val Ser Asp Gly Gly Asp Thr Phe Tyr Ala Asp Ser Val Arg
    50                  55                  60

Gly Arg Phe Thr Leu Ser Arg Asp Asn Ala Lys Asn Thr Leu Phe Leu
65                  70                  75                  80

Gln Met Asn Ser Leu Thr Ala Glu Asp Thr Ala Thr Tyr Tyr Cys Ala
                85                  90                  95

Lys Glu Ile Ala Arg Ile Gly Val Pro Asn Phe Asp His Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Ala Leu Glu Thr Thr Leu Thr Gln Ser
    130                 135                 140

Pro Gly Thr Leu Ser Leu Ser Pro Gly Asp Arg Ala Thr Leu Ser Cys
145                 150                 155                 160

Arg Ala Ser Gln Ser Ile Arg Asn Asn Asp Val Ala Trp Tyr Gln Gln
                165                 170                 175

Lys Pro Gly Gln Ala Pro Arg Leu Leu Ile Tyr Ser Ala Ser Arg Arg
            180                 185                 190

Ala Thr Asp Ile Pro Asp Arg Phe Ser Gly Ser Ala Ser Gly Thr Asp
        195                 200                 205

Phe Thr Leu Thr Ile Ser Arg Leu Glu Pro Glu Asp Phe Ala Met Tyr
    210                 215                 220

Tyr Cys Gln Gln Tyr Gly Gly Ser Ala Ser Phe Gly Gln Gly Thr Arg
225                 230                 235                 240

Leu Glu Ile Lys Arg
                245

<210> SEQ ID NO 124
<211> LENGTH: 250
<212> TYPE: PRT
<213> ORGANISM: Artificial sequence
<220> FEATURE:
<223> OTHER INFORMATION: scFv protein GMCC114

<400> SEQUENCE: 124

Glu Val Gln Leu Val Glu Ser Gly Pro Glu Val Lys Lys Pro Gly Ser
1               5                   10                  15

Ser Val Lys Val Ser Cys Lys Ala Ser Gly Ala Ala Ala Phe Ser Ser
            20                  25                  30

Tyr Ala Ile Ser Trp Val Arg Gln Ala Pro Gly Arg Gly Leu Glu Trp
        35                  40                  45

Met Gly Gly Ile Ile Pro Ile Ser Asp Thr Pro Lys Tyr Ala His Lys
    50                  55                  60
```

```
Phe Gln Gly Arg Val Thr Ile Thr Ala Asp Glu Ser Thr Thr Thr Val
 65                  70                  75                  80

Phe Met Glu Val Ser Gly Leu Arg Ser Asp Thr Ala Val Tyr Tyr
                 85                  90                  95

Cys Ala Thr Thr Thr Arg Tyr Gly Ser Gly Thr Tyr Tyr Met Asp
                100                 105                 110

Val Trp Gly Gln Gly Thr Met Val Thr Val Ser Ser Gly Gly Gly
            115                 120                 125

Ser Gly Gly Gly Gly Ser Gly Gly Gly Ser Ala Leu Ser Ser Glu
        130                 135                 140

Leu Thr Gln Asp Pro Ala Val Ser Val Ala Leu Gly Gln Thr Val Arg
145                 150                 155                 160

Ile Thr Cys Gln Gly Asp Ser Leu Arg Ser Tyr Tyr Ala Ser Trp Tyr
                165                 170                 175

Gln Gln Lys Pro Gly Gln Ala Pro Val Leu Val Phe Tyr Gly Lys Asn
            180                 185                 190

Lys Arg Pro Ser Gly Ile Pro Asp Arg Phe Ser Gly Ser Thr Ser Gly
        195                 200                 205

Asn Thr Ala Ser Leu Ser Ile Thr Gly Ala Leu Ala Asp Asp Glu Ala
    210                 215                 220

Asp Tyr Tyr Cys His Ser Arg Asp Thr Ser Gly Ala Gln Ile Leu Phe
225                 230                 235                 240

Gly Gly Gly Thr Lys Leu Thr Val Leu Gly
                245                 250

<210> SEQ ID NO 125
<211> LENGTH: 251
<212> TYPE: PRT
<213> ORGANISM: Artificial sequence
<220> FEATURE:
<223> OTHER INFORMATION: scFv protein GMCC118

<400> SEQUENCE: 125

Glu Val Gln Leu Val Gln Ser Gly Gly Gly Leu Val Lys Pro Gly Gly
1               5                  10                  15

Ser Leu Arg Leu Ser Cys Thr Ala Ser Gly Phe Ser Phe Thr Asn Ala
            20                  25                  30

Trp Met Ser Trp Val Arg Gln Ala Pro Gly Lys Gly Leu Glu Trp Val
        35                  40                  45

Gly Arg Ile Lys Ser Arg Asn Asp Gly Gly Ala Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Asp Asp Thr Ala Val Tyr
                85                  90                  95

Tyr Cys Thr Thr Asp Asn Phe Pro Leu Arg Phe Leu Glu Trp Leu Ser
            100                 105                 110

His Pro Asp Tyr Trp Gly Gln Gly Thr Met Val Thr Val Ser Ser Gly
        115                 120                 125

Gly Gly Gly Ser Gly Gly Gly Gly Ser Gly Gly Gly Ser Ala Gln
    130                 135                 140

Ala Val Leu Thr Gln Pro Ser Ser Val Ser Val Ser Pro Gly Gln Thr
145                 150                 155                 160

Val Thr Ile Thr Cys Ser Gly Glu Lys Leu Asp Asn Lys Tyr Ile Ser
                165                 170                 175
```

```
Trp Tyr Gln Gln Arg Pro Gly Arg Ser Pro Ile Leu Val Ile Tyr Gln
            180                 185                 190

Asp Arg Lys Arg Pro Ser Gly Ile Pro Glu Arg Phe Ser Gly Ser Asn
        195                 200                 205

Ser Gly Asn Thr Ala Thr Leu Thr Ile Thr Gly Ser Gln Pro Leu Asp
        210                 215                 220

Glu Ala Asp Tyr Tyr Cys Gln Ala Trp Asp Ser Ser Thr Ala Trp Glu
225                 230                 235                 240

Phe Gly Gly Gly Thr Lys Leu Thr Val Leu Gly
                245                 250

<210> SEQ ID NO 126
<211> LENGTH: 252
<212> TYPE: PRT
<213> ORGANISM: Artificial sequence
<220> FEATURE:
<223> OTHER INFORMATION: scFv protein GMCC119

<400> SEQUENCE: 126

Glu Val Gln Leu Val Gln Ser Gly Pro Glu Val Lys Lys Pro Gly Ala
1               5                   10                  15

Ser Val Lys Val Ser Cys Lys Ala Ser Asn Tyr Thr Phe Thr Thr Tyr
            20                  25                  30

Asp Ile Ser Trp Val Arg Gln Ala Pro Gly Gln Gly Leu Glu Trp Met
        35                  40                  45

Gly Trp Ile Ser Thr Tyr Ser Gly Asn Thr Lys Tyr Ala Gln Lys Phe
    50                  55                  60

Gln Gly Arg Val Thr Met Thr Arg Asp Thr Ser Thr Ser Ala Ala Tyr
65                  70                  75                  80

Met Glu Leu Arg Asn Leu Arg Ser Asp Asp Thr Ala Val Tyr Phe Cys
                85                  90                  95

Ala Arg Asp Ile Arg Val Trp Arg Gly Ser Gly Ser Val His Tyr Phe
            100                 105                 110

Asp Pro Trp Gly Arg Gly Thr Thr Val Thr Val Ser Ser Gly Gly Gly
        115                 120                 125

Gly Ser Gly Gly Gly Gly Ser Gly Gly Gly Gly Ser Ala Gln Ser Ala
    130                 135                 140

Leu Thr Gln Pro Arg Ser Val Ser Gly Ser Pro Gly Gln Ser Val Thr
145                 150                 155                 160

Ile Ser Cys Thr Gly Thr Ser Asn Asp Val Gly Gly Tyr Asn Phe Val
                165                 170                 175

Ser Trp Tyr Gln Gln His Pro Gly Lys Ala Pro Lys Leu Met Val Tyr
            180                 185                 190

Asn Val Ser Lys Arg Pro Ser Gly Val Pro Asp Arg Phe Ser Gly Ser
        195                 200                 205

Lys Ser Gly Asn Thr Ala Ser Leu Thr Ile Ser Gly Leu Gln Ala Glu
    210                 215                 220

Asp Glu Ala Asp Tyr Tyr Cys Ser Ser Tyr Ala His Ser Tyr Thr Leu
225                 230                 235                 240

Val Phe Gly Gly Gly Thr Lys Val Thr Val Leu Gly
                245                 250

<210> SEQ ID NO 127
<211> LENGTH: 251
<212> TYPE: PRT
<213> ORGANISM: Artificial sequence
<220> FEATURE:
```

```
<223> OTHER INFORMATION: scFv protein GMCC124

<400> SEQUENCE: 127

Gln Val Thr Leu Lys Glu Ser Gly Ala Glu Val Lys Lys Pro Gly Ala
1               5                   10                  15

Ser Val Lys Val Ser Cys Lys Ala Ser Gly Tyr Thr Phe Thr Asp Asn
            20                  25                  30

Ala Leu His Trp Val Arg Gln Ala Pro Gly Gln Arg Pro Glu Trp Met
        35                  40                  45

Ala Trp Ile Asn Thr Ala Asn Gly Asn Thr Arg Tyr Ser Gln Lys Phe
    50                  55                  60

Gln Gly Arg Leu Thr Ile Thr Arg Asp Thr Ser Ala Ser Thr Ala Phe
65                  70                  75                  80

Met Asp Leu Ser Ser Leu Arg Ser Glu Asp Thr Ala Val Tyr Tyr Cys
                85                  90                  95

Ala Arg Gln Lys Ala Tyr Lys Asn Tyr Tyr Tyr Tyr Gly Met Asp
            100                 105                 110

Val Trp Gly Gln Gly Thr Leu Val Thr Val Ser Ser Gly Gly Gly Gly
        115                 120                 125

Ser Gly Gly Gly Gly Ser Gly Gly Gly Ser Ala Gln Ser Val Val
    130                 135                 140

Thr Gln Pro Pro Ser Val Ser Ala Ala Pro Gly Gln Lys Val Thr Ile
145                 150                 155                 160

Ser Cys Ser Gly Ser Ser Ser Asn Ile Gly Asn Asn Tyr Val Ser Trp
                165                 170                 175

Tyr Gln Gln Leu Pro Gly Thr Ala Pro Lys Leu Leu Ile Tyr Glu Asn
            180                 185                 190

Asn Lys Arg Pro Ser Gly Ile Pro Asp Arg Phe Ser Gly Ser Gln Ser
        195                 200                 205

Gly Thr Ser Ala Thr Leu Gly Ile Ser Gly Leu Gln Thr Gly Asp Glu
    210                 215                 220

Ala Asp Tyr Tyr Cys Gly Thr Trp Asp Ser Ser Leu Arg Ala Gly Val
225                 230                 235                 240

Phe Gly Gly Gly Thr Lys Leu Thr Val Leu Gly
                245                 250

<210> SEQ ID NO 128
<211> LENGTH: 247
<212> TYPE: PRT
<213> ORGANISM: Artificial sequence
<220> FEATURE:
<223> OTHER INFORMATION: scFv protein GMCC125

<400> SEQUENCE: 128

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Ser Phe Ser Asp Tyr
            20                  25                  30

Ser Met His Trp Ile Arg Gln Ala Pro Gly Lys Gly Leu Glu Trp Leu
        35                  40                  45

Ser His Ile Gly Thr Ser Thr Ser Tyr Thr Asn Tyr Ala Asp Ser Val
    50                  55                  60

Lys Gly Arg Phe Thr Ile Ser Arg Asp Asn Ala Lys Asn Ser Phe Tyr
65                  70                  75                  80

Leu Gln Met Asn Ser Leu Arg Val Asp Asp Thr Ala Val Tyr Phe Cys
                85                  90                  95
```

```
Ala Arg Gly Phe Gly Gly Leu Arg Gly Tyr Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Ala Leu Ser Ser Glu Leu Thr Gln Asp
    130                 135                 140

Pro Ala Val Ser Val Ala Leu Gly Gln Thr Val Lys Ile Thr Cys Gln
145                 150                 155                 160

Gly Asp Arg Leu Arg Arg Phe Tyr Ala Ser Trp Tyr Gln Gln Lys Pro
                165                 170                 175

Gly Gln Ala Pro Leu Leu Ile Tyr Gly Lys Asn Ser Arg Pro Ser
            180                 185                 190

Gly Ile Pro Asp Arg Phe Ser Gly Ser Thr Ser Gly Ala Thr Ala Ser
            195                 200                 205

Leu Thr Ile Thr Gly Ala Gln Ala Glu Asp Glu Ala Asp Tyr Tyr Cys
    210                 215                 220

Asn Ser Arg Asp Ser Ser Gly Ser Leu His Ser Val Phe Gly Thr Gly
225                 230                 235                 240

Thr Lys Val Thr Val Leu Gly
                245

<210> SEQ ID NO 129
<211> LENGTH: 246
<212> TYPE: PRT
<213> ORGANISM: Artificial sequence
<220> FEATURE:
<223> OTHER INFORMATION: scFv protein GMCC126

<400> SEQUENCE: 129

Gln Val Gln Leu Gln Glu Ser Gly Pro Gly Leu Val Lys Pro Ser Gln
1               5                   10                  15

Thr Leu Ser Leu Ser Cys Ala Val Ser Gly Phe Ser Val Thr Ser Gly
            20                  25                  30

His Tyr Trp Gly Trp Ile Arg Gln Ser Pro Gly Lys Gly Leu Glu Trp
        35                  40                  45

Ile Gly Asn Ile Tyr His Thr Gly Ser Thr Arg Tyr Asn Pro Ser Leu
    50                  55                  60

Glu Ser Arg Val Ser Met Ser Val Asp Thr Ser Lys Asn Gln Phe Ser
65                  70                  75                  80

Leu Arg Leu Thr Ser Val Thr Ala Ala Asp Thr Ala Ile Tyr Tyr Cys
                85                  90                  95

Ala Arg Val Gly Arg Gly Gln His Leu Val Arg Gly Asp Phe Asp Tyr
            100                 105                 110

Trp Gly Arg Gly Thr Leu Val Thr Val Ser Ser Gly Gly Gly Gly Ser
        115                 120                 125

Gly Gly Gly Gly Ser Gly Gly Gly Ser Ala Gln Ser Val Leu Thr
    130                 135                 140

Gln Pro Pro Ser Ile Ser Val Ser Pro Gly Gln Thr Ala Ser Ile Thr
145                 150                 155                 160

Cys Ser Gly Asp Glu Leu Gly His Lys Tyr Ala Ser Trp Tyr Gln Gln
                165                 170                 175

Lys Pro Gly Gln Ser Pro Val Val Val Tyr Gln Asp Asn Lys Arg
            180                 185                 190

Pro Ser Gly Ile Pro Glu Arg Phe Ser Gly Ser Ser Ser Gly Asn Thr
            195                 200                 205
```

```
Ala Thr Leu Thr Ile Ser Gly Thr Gln Ala Val Asp Glu Ala Asp Tyr
    210                 215                 220

Phe Cys Gln Ala Trp Asp Ser Ser Ala Val Val Phe Gly Gly Gly Thr
225                 230                 235                 240

Lys Leu Thr Val Leu Gly
                245

<210> SEQ ID NO 130
<211> LENGTH: 242
<212> TYPE: PRT
<213> ORGANISM: Artificial sequence
<220> FEATURE:
<223> OTHER INFORMATION: scFv protein GMCC127

<400> SEQUENCE: 130

Gln Val Gln Leu Val Gln Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Arg Tyr Ala Leu Asp Tyr Trp Gly Arg Gly Thr Leu Val
            100                 105                 110

Thr Val Ser Ser Gly Gly Gly Ser Gly Gly Gly Ser Gly Gly
        115                 120                 125

Gly Gly Ser Ala Leu Ser Ser Glu Leu Thr Gln Asp Pro Ala Val Ser
    130                 135                 140

Val Ala Leu Gly Gln Ala Val Arg Ile Thr Cys Gln Gly Asp Ser Leu
145                 150                 155                 160

Arg Thr Asn Tyr Ala Ser Trp Tyr Gln Gln Arg Pro Gly Gln Ala Pro
                165                 170                 175

Val Leu Val Ile Arg Gly Asn Asn Asn Arg Pro Ser Gly Ile Pro Asp
            180                 185                 190

Arg Phe Ser Gly Ser Asn Ser Gly Asp Thr Val Ser Leu Thr Ile Thr
        195                 200                 205

Gly Ala Gln Ala Glu Asp Glu Ala Asp Tyr Tyr Cys Asn Ser Arg Asp
    210                 215                 220

Thr Ser Gly Tyr His Tyr Val Phe Gly Thr Gly Thr Lys Leu Thr Val
225                 230                 235                 240

Leu Gly

<210> SEQ ID NO 131
<211> LENGTH: 246
<212> TYPE: PRT
<213> ORGANISM: Artificial sequence
<220> FEATURE:
<223> OTHER INFORMATION: scFv protein GMCC129

<400> SEQUENCE: 131

Glu Val Gln Leu Val Glu Thr Gly Gly Gly Leu Ala Gln Pro Gly Gly
1               5                   10                  15
```

```
Ser Leu Arg Leu Ser Cys Glu Ala Ser Gly Phe Thr Phe Asn Asn Tyr
            20                  25                  30

Ala Met Ser Trp Val Arg Gln Ala Pro Gly Lys Gly Leu Glu Trp Val
        35                  40                  45

Ser Gly Ile Ser Ile Ser Gly Tyr Ser Thr Phe Tyr Thr Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Gly Val Asp Thr Ala Val Tyr Tyr Cys
                85                  90                  95

Ala Lys Arg Arg Gly Glu Gly Gly Asp Phe Asp Tyr Trp Gly Arg Gly
            100                 105                 110

Thr Met Val Thr Val Ser Ser Gly Gly Gly Ser Gly Gly Gly Gly
            115                 120                 125

Ser Gly Gly Gly Gly Ser Ala Leu Ser Ser Glu Leu Thr Gln Asp Pro
    130                 135                 140

Ala Val Ser Val Ala Leu Gly Gln Thr Val Arg Ile Thr Cys Gln Gly
145                 150                 155                 160

Asp Ser Leu Arg Gly Tyr Tyr Ala Ser Trp Tyr Gln Gln Lys Ala Gly
                165                 170                 175

Gln Ala Pro Val Leu Val Ile Tyr Gly Lys Asn Asn Arg Pro Ser Gly
            180                 185                 190

Ile Pro Asp Arg Phe Ser Gly Ser Ser Ser Gly Asn Thr Ala Ser Leu
            195                 200                 205

Thr Ile Thr Gly Ala Gln Ala Glu Asp Glu Ala Asp Tyr Tyr Cys Tyr
    210                 215                 220

Ser Arg Asp Arg Ser Gly Asn His Leu Gly Met Phe Gly Gly Gly Thr
225                 230                 235                 240

Lys Val Thr Val Leu Gly
                245

<210> SEQ ID NO 132
<211> LENGTH: 248
<212> TYPE: PRT
<213> ORGANISM: Artificial sequence
<220> FEATURE:
<223> OTHER INFORMATION: scFv protein GMCC131

<400> SEQUENCE: 132

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Arg Ser His
            20                  25                  30

Tyr Trp Ser Trp Met Arg Gln Pro Pro Gly Lys Gly Leu Glu Trp Ile
        35                  40                  45

Gly Tyr Val Tyr Tyr Thr Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Asn Leu Ser Ser Val Thr Ala Ala Asp Thr Ala Ile Tyr Tyr Cys Ala
                85                  90                  95

Arg Phe Pro Tyr Ser Gly Ser Asn Pro Leu Asp Tyr Trp Gly Arg
            100                 105                 110

Gly Thr Leu Val Thr Val Ser Ser Gly Gly Gly Ser Gly Gly Gly
            115                 120                 125
```

```
Gly Ser Gly Gly Gly Ser Ala Gln Ser Val Leu Thr Gln Pro Pro
        130                 135                 140
Ser Val Ser Ala Ala Pro Gly Gln Arg Val Thr Ile Ser Cys Thr Gly
145                 150                 155                 160
Ser Ser Ser Asn Ile Gly Ala Arg Tyr Asp Val His Trp Tyr Gln His
                165                 170                 175
Leu Pro Gly Thr Ala Pro Lys Leu Leu Ile Tyr Gly Asp Ser Asn Arg
            180                 185                 190
Pro Ser Gly Val Pro Asp Arg Phe Ser Gly Ser Lys Ser Gly Thr Ser
        195                 200                 205
Ala Ser Leu Ala Ile Thr Gly Leu Gln Pro Glu Asp Glu Ala Asp Tyr
    210                 215                 220
Tyr Cys Gln Ser Tyr Asp Ser Ser Leu Ser Gly Val Val Phe Gly Gly
225                 230                 235                 240
Gly Thr Lys Val Thr Val Leu Gly
                245
```

<210> SEQ ID NO 133
<211> LENGTH: 245
<212> TYPE: PRT
<213> ORGANISM: Artificial sequence
<220> FEATURE:
<223> OTHER INFORMATION: scFv protein GMCC136

<400> SEQUENCE: 133

```
Glu Val Gln Leu Val Gln Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Ser Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Cys Trp Arg Ser Gly Thr Ser Cys Pro Asp Gly Trp Gly Lys
            100                 105                 110
Gly Thr Met Val Thr Val Ser Ser Gly Gly Gly Ser Gly Gly Gly Gly
        115                 120                 125
Gly Ser Gly Gly Gly Gly Ser Ala Leu Glu Ile Val Leu Thr Gln Ser
    130                 135                 140
Pro Ala Thr Leu Ser Val Ser Pro Gly Glu Arg Ala Thr Leu Ser Cys
145                 150                 155                 160
Arg Thr Ser Gln Ser Val Gly Ser Lys Leu Ala Trp Tyr Gln Gln Lys
                165                 170                 175
Pro Gly Gln Ala Pro Arg Leu Leu Ile Tyr Asp Ala Ser Thr Gly Ala
            180                 185                 190
Thr Gly Asp Pro Ala Arg Phe Ser Gly Ser Gly Ser Gly Thr Glu Phe
        195                 200                 205
Thr Leu Thr Ile Ser Asn Leu Gln Ser Glu Asp Leu Ala Ile Tyr Tyr
    210                 215                 220
Cys Gln Gln Tyr His Lys Trp Pro Ile Thr Phe Gly Gln Gly Thr Arg
225                 230                 235                 240
```

Leu Glu Ile Lys Arg
            245

<210> SEQ ID NO 134
<211> LENGTH: 248
<212> TYPE: PRT
<213> ORGANISM: Artificial sequence
<220> FEATURE:
<223> OTHER INFORMATION: scFv protein GMCC138

<400> SEQUENCE: 134

Glu Val Gln Leu Val Glu Thr Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Val Pro Gly Lys Gly Leu Glu
        35                  40                  45

Trp Ile Gly Tyr Asn Phe Tyr Asn Gly Ser Thr Tyr Phe Asn Pro Ser
    50                  55                  60

Leu Lys Ser Arg Ala Thr Ile Ser Ile Asp Thr Thr Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Asn Gly Tyr Arg Tyr Gly Arg Trp Phe Asp Pro Trp
            100                 105                 110

Gly Arg Gly Thr Leu Val Thr Val Ser Ser Gly Gly Gly Gly Ser Gly
        115                 120                 125

Gly Gly Gly Ser Gly Gly Gly Ser Ala Leu Ser Tyr Glu Leu Thr
    130                 135                 140

Gln Pro Pro Ser Val Ser Val Ser Pro Gly Gln Thr Ala Arg Ile Thr
145                 150                 155                 160

Cys Ser Gly Asp Ala Leu Pro Lys Gln Tyr Ala Tyr Trp Tyr Gln Gln
                165                 170                 175

Lys Pro Gly Gln Ala Pro Val Leu Val Ile Ser Lys Asp Ser Glu Arg
            180                 185                 190

Pro Ser Gly Ile Pro Glu Arg Phe Ser Gly Ser Ser Gly Thr Thr
        195                 200                 205

Val Thr Leu Thr Ile Ser Gly Val Gln Ala Glu Asp Glu Ala Asp Tyr
    210                 215                 220

Tyr Cys Gln Ser Ala Asp Ser Ser Gly Thr Tyr Trp Val Phe Gly Gly
225                 230                 235                 240

Gly Thr Lys Val Thr Val Leu Gly
            245

<210> SEQ ID NO 135
<211> LENGTH: 246
<212> TYPE: PRT
<213> ORGANISM: Artificial sequence
<220> FEATURE:
<223> OTHER INFORMATION: scFv protein GMCC142

<400> SEQUENCE: 135

Glu Val Gln Leu Val Gln Ser Gly Ala Glu Val Lys Lys Pro Gly Ala
1               5                   10                  15

Ser Val Thr Ile Ser Cys Lys Ala Ser Gly Tyr Thr Phe Thr Ala Tyr
            20                  25                  30

Tyr Ile Tyr Trp Val Arg Gln Ala Pro Gly Gln Gly Leu Glu Trp Met

-continued

```
                35                  40                  45
Gly Met Ser Asn Pro Asn Gly Gly Tyr Thr Val Tyr Pro Pro Asn Phe
 50                  55                  60

Leu Gly Arg Val Thr Thr Thr Pro Asp Thr Ser Thr Asn Thr Ile Tyr
 65                  70                  75                  80

Met Glu Leu Arg Ser Leu Arg Ser Glu Asp Thr Ala Val Tyr Tyr Cys
                 85                  90                  95

Ala Arg Gly Arg Gly Arg Ala Pro Ser Asn Ala Phe Asp Phe Trp Gly
                100                 105                 110

Arg Gly Thr Leu Val Thr Val Ser Ser Gly Gly Gly Ser Gly Gly
            115                 120                 125

Gly Gly Ser Gly Gly Gly Ser Ala Leu Ser Ser Glu Leu Thr Gln
            130                 135                 140

Asp Pro Ala Val Ser Val Ala Leu Gly Gln Thr Val Arg Ile Thr Cys
145                 150                 155                 160

Gln Gly Asp Ser Leu Lys Phe Tyr Tyr Ala Ser Trp Tyr Gln Gln Lys
                165                 170                 175

Pro Gly Gln Ala Pro Val Leu Val Leu His Gly Lys Asn Asn Arg Pro
                180                 185                 190

Ser Gly Ile Pro Asp Arg Phe Ser Gly Ser Thr Ser Arg Asp Thr Ala
                195                 200                 205

Ser Leu Thr Ile Thr Gly Thr Gln Ala Glu Asp Glu Ala Asp Tyr Tyr
                210                 215                 220

Cys Asn Ser Arg Asp Asn Ser Asp Asn Ile Val Phe Gly Thr Gly Thr
225                 230                 235                 240

Lys Leu Thr Val Leu Gly
                245
```

<210> SEQ ID NO 136
<211> LENGTH: 250
<212> TYPE: PRT
<213> ORGANISM: Artificial sequence
<220> FEATURE:
<223> OTHER INFORMATION: scFv protein GMCC151
<220> FEATURE:
<221> NAME/KEY: Site
<222> LOCATION: (201)
<223> OTHER INFORMATION: Xaa equals any of the naturally occurring
      L-amino acids

<400> SEQUENCE: 136

```
Gln Val Gln Leu Val Gln Ser Gly Gly Gly Val Gln Pro Gly Arg
 1               5                  10                  15

Ser Leu Arg Leu Ser Cys Thr Ala Ser Gly Phe Asn Leu Gly Ser His
                 20                  25                  30

Gly Met His Trp Val Arg Gln Ala Pro Gly Lys Gly Leu Glu Trp Val
             35                  40                  45

Ala Val Ile Gly Phe Asp Gly Thr Thr Lys Tyr Tyr Val Asp Ser Val
 50                  55                  60

Lys Gly Arg Phe Thr Ile Ser Arg Asp Asn Ser Arg Asn Thr Leu Ser
 65                  70                  75                  80

Leu Gln Met Asn Ser Leu Arg Ala Glu Asp Thr Ala Val Tyr Tyr Cys
                 85                  90                  95

Val Arg Glu Asp Tyr Tyr Tyr Asp Ser Ser Gly Tyr Tyr Phe Asp Tyr
                100                 105                 110

Trp Gly Arg Gly Thr Leu Val Thr Val Ser Ser Gly Gly Gly Gly Ser
            115                 120                 125
```

```
Gly Gly Gly Gly Ser Gly Gly Gly Ser Ala Leu Ser Ser Glu Leu
        130                 135                 140

Thr Gln Asp Pro Phe Val Ser Val Ala Leu Gly Gln Thr Val Arg Ile
145                 150                 155                 160

Ala Cys Arg Gly Asp Ser Leu Arg Asp Ser Tyr Ala Ser Trp Tyr Gln
            165                 170                 175

Gln Lys Pro Gly Gln Ala Pro Arg Leu Leu Val Tyr Gly Asn Asn Leu
        180                 185                 190

Arg Pro Ser Gly Ile Pro Gly Arg Xaa Ser Gly Phe Ser Ser Gly Asp
        195                 200                 205

Thr Ser Ser Leu Ala Ile Thr Glu Thr Gln Ala Gly Asp Glu Ala Asp
    210                 215                 220

Tyr Tyr Cys Ser Ser Arg Gly Asn Ser Thr Ser Arg Leu Tyr Val Phe
225                 230                 235                 240

Gly Thr Gly Thr Lys Leu Thr Val Leu Gly
                245                 250

<210> SEQ ID NO 137
<211> LENGTH: 747
<212> TYPE: DNA
<213> ORGANISM: Artificial sequence
<220> FEATURE:
<221> NAME/KEY: CDS
<222> LOCATION: (1)..(747)
<223> OTHER INFORMATION: Polynucleotide encoding GMBC603 scFv protein

<400> SEQUENCE: 137 cag gtc cag ctg gta cag tct ggg gga ggt gtg gta cgg cct ggg ggg      48
Gln Val Gln Leu Val Gln Ser Gly Gly Gly Val Val Arg Pro Gly Gly
1               5                   10                  15 tcc ctg aga ctc tcc tgt gca gcc tct gga ttc aca ttt gat gat tat      96
Ser Leu Arg Leu Ser Cys Ala Ala Ser Gly Phe Thr Phe Asp Asp Tyr
            20                  25                  30 ggc atg agc tgg gtc cgc caa gct cca ggg aag ggg ctg gag tgg gtc     144
Gly Met Ser Trp Val Arg Gln Ala Pro Gly Lys Gly Leu Glu Trp Val
        35                  40                  45 tct ggt att aat tgg aat ggt ggt agc aca ggt tat gca gac tct gtg     192
Ser Gly Ile Asn Trp Asn Gly Gly Ser Thr Gly Tyr Ala Asp Ser Val
    50                  55                  60 aag ggc cga ttc acc atc tcc aga gac aac gcc aag aac tcc ctc tat     240
Lys Gly Arg Phe Thr Ile Ser Arg Asp Asn Ala Lys Asn Ser Leu Tyr
65                  70                  75                  80 ctc caa atg aac agt ctg aga gct gag gac acc gcc ttg tat tac tgt     288
Leu Gln Met Asn Ser Leu Arg Ala Glu Asp Thr Ala Leu Tyr Tyr Cys
                85                  90                  95 gca aaa gat ctg aat tac gat ttt tgg agt ggt tcc ggt atg gac gtc     336
Ala Lys Asp Leu Asn Tyr Asp Phe Trp Ser Gly Ser Gly Met Asp Val
            100                 105                 110 tgg ggc cga gga acc ctg gtc acc gtc tcc tca ggt gga ggc ggt tca     384
Trp Gly Arg Gly Thr Leu Val Thr Val Ser Ser Gly Gly Gly Gly Ser
        115                 120                 125 ggc gga ggt ggc agc ggc ggt ggc gga tcg cag tct gtg ctg act cag     432
Gly Gly Gly Gly Ser Gly Gly Gly Gly Ser Gln Ser Val Leu Thr Gln
    130                 135                 140 cct gcc tcc gtg tct ggg tct cct gga cag tcg atc acc atc tcc tgc     480
Pro Ala Ser Val Ser Gly Ser Pro Gly Gln Ser Ile Thr Ile Ser Cys
145                 150                 155                 160 act gga acc agc agt gac gtt ggt ggt tat aac tat gtc tcc tgg tac     528
Thr Gly Thr Ser Ser Asp Val Gly Gly Tyr Asn Tyr Val Ser Trp Tyr
```

```
                      165                 170                 175
caa caa cac cca ggc aaa gcc ccc aaa ctc atg att tat gag ggc agt          576
Gln Gln His Pro Gly Lys Ala Pro Lys Leu Met Ile Tyr Glu Gly Ser
                180                 185                 190 aag cgg ccc tca ggg gtt tct aat cgc ttc tct ggc tcc aag tct ggc          624
Lys Arg Pro Ser Gly Val Ser Asn Arg Phe Ser Gly Ser Lys Ser Gly
            195                 200                 205 aac acg gcc tcc ctg aca atc tct ggg ctc cag gct gag gac gag gct          672
Asn Thr Ala Ser Leu Thr Ile Ser Gly Leu Gln Ala Glu Asp Glu Ala
        210                 215                 220 gat tat tac tgc agc tca tat aca acc agg agc act cga gtt ttc ggc          720
Asp Tyr Tyr Cys Ser Ser Tyr Thr Thr Arg Ser Thr Arg Val Phe Gly
225                 230                 235                 240 gga ggg acc aag ctg acc gtc cta ggt                                      747
Gly Gly Thr Lys Leu Thr Val Leu Gly
                245

<210> SEQ ID NO 138
<211> LENGTH: 729
<212> TYPE: DNA
<213> ORGANISM: Artificial sequence
<220> FEATURE:
<221> NAME/KEY: CDS
<222> LOCATION: (1)..(729)
<223> OTHER INFORMATION: Polynucleotide encoding GMBC604 scFv protein

<400> SEQUENCE: 138 gaa gtg cag ctg gtg cag tct ggg gca gag gtg aaa aag ccc ggg gag           48
Glu Val Gln Leu Val Gln Ser Gly Ala Glu Val Lys Lys Pro Gly Glu
1               5                   10                  15 tcc ctg agg atc tca tgt aag ggt tct gga tac acc ttt acc aac tac           96
Ser Leu Arg Ile Ser Cys Lys Gly Ser Gly Tyr Thr Phe Thr Asn Tyr
            20                  25                  30 tgg atc aac tgg gtg cgc cag gtg ccc gga aaa ggc ctg gag tgg atg          144
Trp Ile Asn Trp Val Arg Gln Val Pro Gly Lys Gly Leu Glu Trp Met
        35                  40                  45 ggg atg att gat cct act gac tct tat gcc aaa tac agc ccg tcc ttc          192
Gly Met Ile Asp Pro Thr Asp Ser Tyr Ala Lys Tyr Ser Pro Ser Phe
    50                  55                  60 caa ggc cac gtc acc atc tca act gac aag tcc gtc agc act gcc tac          240
Gln Gly His Val Thr Ile Ser Thr Asp Lys Ser Val Ser Thr Ala Tyr
65                  70                  75                  80 ctg cag tgg aga agc ctg cag gcc tcg gac agc gcc ata tat tat tgt          288
Leu Gln Trp Arg Ser Leu Gln Ala Ser Asp Ser Ala Ile Tyr Tyr Cys
                85                  90                  95 gtg agg gga tac agt tat gac ctt gac tac tgg ggc aag gga acc ctg          336
Val Arg Gly Tyr Ser Tyr Asp Leu Asp Tyr Trp Gly Lys Gly Thr Leu
            100                 105                 110 gtc acc gtc tcg agt ggt gga ggc ggt tca ggc gga ggt ggc agc ggc          384
Val Thr Val Ser Ser Gly Gly Gly Gly Ser Gly Gly Gly Gly Ser Gly
        115                 120                 125 ggt ggc gga tcg cag tct gtg ctg act cag cct gcc tcc gtg tct ggg          432
Gly Gly Gly Ser Gln Ser Val Leu Thr Gln Pro Ala Ser Val Ser Gly
    130                 135                 140 tct cct gga cag tcg atc acc atc tcc tgc act gga acc agc agt gac          480
Ser Pro Gly Gln Ser Ile Thr Ile Ser Cys Thr Gly Thr Ser Ser Asp
145                 150                 155                 160 gtt ggt ggt tat aac tat gtc tcc tgg tat caa caa cac cca ggc aaa          528
Val Gly Gly Tyr Asn Tyr Val Ser Trp Tyr Gln Gln His Pro Gly Lys
                165                 170                 175 gcc ccc aaa ctc atg att tat gag ggc agt aag cgg ccc tcg ggg gtt          576
```

```
Ala Pro Lys Leu Met Ile Tyr Glu Gly Ser Lys Arg Pro Ser Gly Val
            180                 185                 190 tct aat cgc ttc tct ggc tcc aag tct ggc aac acg gcc tcc ctg aca       624
Ser Asn Arg Phe Ser Gly Ser Lys Ser Gly Asn Thr Ala Ser Leu Thr
        195                 200                 205 atc tct ggg ctc cag gct gag gac gag gct gat tat tac tgc agc tca       672
Ile Ser Gly Leu Gln Ala Glu Asp Glu Ala Asp Tyr Tyr Cys Ser Ser
    210                 215                 220 tat aca acc agg agc act cga gtt ttc ggc gga ggg acc aag ctg acc       720
Tyr Thr Thr Arg Ser Thr Arg Val Phe Gly Gly Gly Thr Lys Leu Thr
225                 230                 235                 240 gtc cta ggt                                                            729
Val Leu Gly <210> SEQ ID NO 139
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC605 scFv protein

<400> SEQUENCE: 139 cag gtg cag ctg gtg cag tct ggg gga ggc ttg gta aag ccg ggg ggg        48
Gln Val Gln Leu Val Gln Ser Gly Gly Gly Leu Val Lys Pro Gly Gly
1               5                   10                  15 tcc ctt aga ctc tcc tgt gaa acc tct ggt ttc aaa ttc agt gac gcc        96
Ser Leu Arg Leu Ser Cys Glu Thr Ser Gly Phe Lys Phe Ser Asp Ala
            20                  25                  30 tgg atg aac tgg gtc cgc cag gct cca ggg aag ggg ctg gag tgg gtc       144
Trp Met Asn Trp Val Arg Gln Ala Pro Gly Lys Gly Leu Glu Trp Val
        35                  40                  45 ggc cgt att aaa agc aaa ggt agt ggt ggg aca ata gac tac gct gca       192
Gly Arg Ile Lys Ser Lys Gly Ser Gly Gly Thr Ile Asp Tyr Ala Ala
    50                  55                  60 ccc gtg aaa gac aga ttc acc atc tca cga gat gat tca aaa aac acg       240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc ctg tat       288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc       336
Tyr Cys Thr Trp Asp Trp Asp Phe Tyr Tyr Gly Met Asn Val Trp Gly
            100                 105                 110 aga ggc acc ctg gtc acc gtc tcc tca ggt gga ggc ggt tca ggc gga       384
Arg Gly Thr Leu Val Thr Val Ser Ser Gly Gly Gly Gly Ser Gly Gly
        115                 120                 125 ggt ggc agc ggc ggt ggc gga tcg cag tct gtg ctg act cag cct gcc       432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga       480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa       528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg       576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg       624
```

```
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat          672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg          720
Tyr Cys Ser Ser Tyr Thr Thr Arg Ser Thr Arg Val Phe Gly Gly Gly
225                 230                 235                 240 acc aag ctg acc gtc cta ggt                                              741
Thr Lys Leu Thr Val Leu Gly
                245

<210> SEQ ID NO 140
<211> LENGTH: 726
<212> TYPE: DNA
<213> ORGANISM: Artificial sequence
<220> FEATURE:
<221> NAME/KEY: CDS
<222> LOCATION: (1)..(726)
<223> OTHER INFORMATION: Polynucleotide encoding GMBC606 scFv protein

<400> SEQUENCE: 140 gag gtc cag ctg gtg cag tct ggg gga ggc gtg gtc cag cct ggg ggg           48
Glu Val Gln Leu Val Gln Ser Gly Gly Gly Val Val Gln Pro Gly Gly
1               5                   10                  15 tcc ctg aga ctc tcc tgt gca gcg tct gga ttc acc ttc agt agc tat           96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg          144
Gly Met His Trp Val Arg Gln Ala Pro Gly Lys Gly Leu Glu Trp Val
        35                  40                  45 gca ttt ata cgg tat gat gga agt aat aaa tac tat gca gac tcc gtg          192
Ala Phe Ile Arg Tyr Asp Gly Ser Asn Lys Tyr Tyr Ala Asp Ser Val
    50                  55                  60 aag ggc cga ttc acc atc tcc aga gac aat tcc aag aac acg ctg tat          240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt          288
Leu Gln Met Asn Ser Leu Arg Ala Glu Asp Thr Ala Val Tyr Tyr Cys
                85                  90                  95 gcg aaa tcc tcg tcc ttt gcc aat gct ttt gat atc tgg ggc caa gga          336
Ala Lys Ser Ser Ser Phe Ala Asn Ala Phe Asp Ile Trp Gly Gln Gly
            100                 105                 110 acc acg gtc acc gtc tcc tca ggt gga ggc ggt tca ggc gga ggt ggc          384
Thr Thr Val Thr Val Ser Ser Gly Gly Gly Gly Ser Gly Gly Gly Gly
        115                 120                 125 agc ggc ggt ggc gga tcg tct gag ctg act cag gac cct gct gtg tct          432
Ser Gly Gly Gly Gly Ser Ser Glu Leu Thr Gln Asp Pro Ala Val Ser
    130                 135                 140 gtg gcc ttg gga cag aca gtc agg atc aca tgc caa gga gac agc ctc          480
Val Ala Leu Gly Gln Thr Val Arg Ile Thr Cys Gln Gly Asp Ser Leu
145                 150                 155                 160 aga agc tat tat gcg agc tgg tac cag cag aag cca gga cag gcc cct          528
Arg Ser Tyr Tyr Ala Ser Trp Tyr Gln Gln Lys Pro Gly Gln Ala Pro
                165                 170                 175 gta ctt gtc atc tat ggt aaa aac aac cgg ccc tca ggg atc cca gac          576
Val Leu Val Ile Tyr Gly Lys Asn Asn Arg Pro Ser Gly Ile Pro Asp
            180                 185                 190 cga ttc tct ggc tcc agc tca gga aac aca gct tcc ttg acc atc act          624
Arg Phe Ser Gly Ser Ser Ser Gly Asn Thr Ala Ser Leu Thr Ile Thr
        195                 200                 205
```

```
ggg gct cag gcg gaa gat gag gct gac tat tac tgt aac tcc cgg gac        672
Gly Ala Gln Ala Glu Asp Glu Ala Asp Tyr Tyr Cys Asn Ser Arg Asp
    210                 215                 220 agc agt ggt aac cat gtg gta ttc ggc gga ggg acc aag ctg acc gtc        720
Ser Ser Gly Asn His Val Val Phe Gly Gly Gly Thr Lys Leu Thr Val
225                 230                 235                 240 cta ggt                                                                726
Leu Gly <210> SEQ ID NO 141
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC607 scFv protein

<400> SEQUENCE: 141 gag gtg cag ctg gtg cag tct ggg gga ggc ttg gta aag ccg ggg ggg         48
Glu Val Gln Leu Val Gln Ser Gly Gly Gly Leu Val Lys Pro Gly Gly
1               5                   10                  15 tcc ctt aga ctc tcc tgt gca gcc tct ggt ttc act ttc agt gac gcc         96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc        144
Trp Met Asn Trp Val Arg Gln Ala Pro Gly Lys Gly Leu Glu Trp Val
        35                  40                  45 ggc cgt att aaa agc aaa ggt agt ggg aca ata gac tac gct gca            192
Gly Arg Ile Lys Ser Lys Gly Ser Gly Thr Ile Asp Tyr Ala Ala
    50                  55                  60 ccc gtg aaa gac aga ttc acc atc tca cga gat gat tca aaa aac atg        240
Pro Val Lys Asp Arg Phe Thr Ile Ser Arg Asp Asp Ser Lys Asn Met
65                  70                  75                  80 ctg tat ctg gaa atg aac agt ctg aaa acc gag gac aca gcc ctg tat        288
Leu Tyr Leu Glu Met Asn Ser Leu Lys Thr Glu Asp Thr Ala Leu Tyr
                85                  90                  95 tac tgt acg tgg gac tgg gat ttc tat tac ggt atg aac gtc tgg ggc        336
Tyr Cys Thr Trp Asp Trp Asp Phe Tyr Tyr Gly Met Asn Val Trp Gly
            100                 105                 110 caa ggg aca atg gtc acc gtc tct tca ggt gga ggc ggt tca ggc gga        384
Gln Gly Thr Met Val Thr Val Ser Ser Gly Gly Gly Gly Ser Gly Gly
        115                 120                 125 ggt ggc agc ggc ggt ggc gga tcg cag tct gtg ctg act cag cct gcc        432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga        480
Ser Val Ser Gly Ser Pro Gly Gln Ser Ile Thr Ile Ser Cys Thr Gly
145                 150                 155                 160 acc agc agt gac gtt ggt gat tat aac tat gtc tcc tgg tac caa caa        528
Thr Ser Ser Asp Val Gly Asp Tyr Asn Tyr Val Ser Trp Tyr Gln Gln
                165                 170                 175 cac cca ggc aaa gcc ccc aaa ctc atg att tat gag ggc agt aag cgg        576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg        624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat        672
Ala Ser Leu Thr Ile Ser Gly Leu Gln Ala Glu Asp Glu Ala Asp Tyr
    210                 215                 220
```

```
tac tgc agc tca tat aca acc agg agc act cga gtt ttc ggc gga ggg        720
Tyr Cys Ser Ser Tyr Thr Thr Arg Ser Thr Arg Val Phe Gly Gly Gly
225                 230                 235                 240 acc aag ctg acc gtc cta ggt                                             741
Thr Lys Leu Thr Val Leu Gly
                245

<210> SEQ ID NO 142
<211> LENGTH: 738
<212> TYPE: DNA
<213> ORGANISM: Artificial sequence
<220> FEATURE:
<221> NAME/KEY: CDS
<222> LOCATION: (1)..(738)
<223> OTHER INFORMATION: Polynucleotide encoding GMBC608 scFv protein

<400> SEQUENCE: 142 gaa gtg cag ctg gtg cag tct ggg gga ggc ttg gta cag cct ggc agg         48
Glu Val Gln Leu Val Gln Ser Gly Gly Gly Leu Val Gln Pro Gly Arg
1               5                   10                  15 tcc ctg aga ctc tcc tgt gca gcc tct gga ttc acc ttt agt gac tcc         96
Ser Leu Arg Leu Ser Cys Ala Ala Ser Gly Phe Thr Phe Ser Asp Ser
                20                  25                  30 tac atg acc tgg atc cgc cag gct cca ggg gag ggg ctg gag ttt gtt        144
Tyr Met Thr Trp Ile Arg Gln Ala Pro Gly Glu Gly Leu Glu Phe Val
            35                  40                  45 tca tat att agt agt ggt agt agt acc act tac tat aca gac tct gtg        192
Ser Tyr Ile Ser Ser Gly Ser Ser Thr Thr Tyr Tyr Thr Asp Ser Val
        50                  55                  60 aag ggc cga ttc acc atc tcc agg gac aat tcc aaa aac act ctg tat        240
Lys Gly Arg Phe Thr Ile Ser Arg Asp Asn Ser Lys Asn Thr Leu Tyr
65                  70                  75                  80 cta caa atg aac agc ctg aga cct gag gac acg gct gtg tat tac tgt        288
Leu Gln Met Asn Ser Leu Arg Pro Glu Asp Thr Ala Val Tyr Tyr Cys
                85                  90                  95 gcg agg aga agc atc tcg tcc gac tac tac tcc tac tac ttg gac gtc        336
Ala Arg Arg Ser Ile Ser Ser Asp Tyr Tyr Ser Tyr Tyr Leu Asp Val
            100                 105                 110 tgg ggc aag gga acc ctg gtc acc gtc tcc tca ggt gga ggc ggt tca        384
Trp Gly Lys Gly Thr Leu Val Thr Val Ser Ser Gly Gly Gly Gly Ser
        115                 120                 125 ggc gga ggt ggc agc ggc ggt ggc gga tcg tct gag ctg act cag gac        432
Gly Gly Gly Gly Ser Gly Gly Gly Ser Ser Glu Leu Thr Gln Asp
    130                 135                 140 cct gct gtg tct gtg gcc ttg gga cag aca gtc agg atc aca tgc caa        480
Pro Ala Val Ser Val Ala Leu Gly Gln Thr Val Arg Ile Thr Cys Gln
145                 150                 155                 160 gga gac agc ctc aga agc tat tat gca agc tgg tac cag cag aag cca        528
Gly Asp Ser Leu Arg Ser Tyr Tyr Ala Ser Trp Tyr Gln Gln Lys Pro
                165                 170                 175 gga cag gcc cct gta ctt gtc atc tat ggt aaa aac aac cgg ccc tca        576
Gly Gln Ala Pro Val Leu Val Ile Tyr Gly Lys Asn Asn Arg Pro Ser
            180                 185                 190 ggg atc cca gac cga ttc tct ggc tcc agc tca gga aac aca gct tcc        624
Gly Ile Pro Asp Arg Phe Ser Gly Ser Ser Ser Gly Asn Thr Ala Ser
        195                 200                 205 ttg acc atc act ggg gct cag gcg gaa gat gag gct gac tat tac tgt        672
Leu Thr Ile Thr Gly Ala Gln Ala Glu Asp Glu Ala Asp Tyr Tyr Cys
    210                 215                 220 aac tcc cgg gac agc agt ggt aac cat gtg gta ttc ggc gga ggg acc        720
Asn Ser Arg Asp Ser Ser Gly Asn His Val Val Phe Gly Gly Gly Thr
225                 230                 235                 240
```

```
aag ctg acc gtc cta ggt                                                     738
Lys Leu Thr Val Leu Gly
                245

<210> SEQ ID NO 143
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC609 scFv protein

<400> SEQUENCE: 143 cag gtg cag ctg gtg gag tct ggg gga ggc ttg gta aag cct ggg gag             48
Gln Val Gln Leu Val Glu Ser Gly Gly Gly Leu Val Lys Pro Gly Glu
1               5                   10                  15 tca ctg aga ctc tcc tgt gaa gcc tct gga ttc gaa ttt aat tat gcc             96
Ser Leu Arg Leu Ser Cys Glu Ala Ser Gly Phe Glu Phe Asn Tyr Ala
            20                  25                  30 tgg atg agt tgg gtc cgc cag gct cca ggg aag ggg ctg gag tgg gtt            144
Trp Met Ser Trp Val Arg Gln Ala Pro Gly Lys Gly Leu Glu Trp Val
        35                  40                  45 ggc cgt agt aga agc gaa gct agt ggt ggg aca aca gac tac gct gca            192
Gly Arg Ser Arg Ser Glu Ala Ser Gly Gly Thr Thr Asp Tyr Ala Ala
    50                  55                  60 ccc ctg caa gac aga ttc acc atc tca aga gat gat tca aaa aac aca            240
Pro Leu Gln Asp Arg Phe Thr Ile Ser Arg Asp Asp Ser Lys Asn Thr
65                  70                  75                  80 ctg tat cta caa gtc aac agc ctg aaa atc gag gac aca ggc gtg tat            288
Leu Tyr Leu Gln Val Asn Ser Leu Lys Ile Glu Asp Thr Gly Val Tyr
                85                  90                  95 ttc tgt aag tgg gag aaa tca gag tac tac ggt atg gac gtc tgg ggc            336
Phe Cys Lys Trp Glu Lys Ser Glu Tyr Tyr Gly Met Asp Val Trp Gly
            100                 105                 110 cgg gga acc ccg gtc acc gtc tcc tca ggt gga ggc ggt tca ggc gga            384
Arg Gly Thr Pro Val Thr Val Ser Ser Gly Gly Gly Gly Ser Gly Gly
        115                 120                 125 ggt ggc agc ggc ggt ggc gga tcg cag tct gtg ttg acg cag ccg ccc            432
Gly Gly Ser Gly Gly Gly Gly Ser Gln Ser Val Leu Thr Gln Pro Pro
    130                 135                 140 tca gtg tct gcg gcc cca gga cag aag gtc acc att tcc tgc tct gga            480
Ser Val Ser Ala Ala Pro Gly Gln Lys Val Thr Ile Ser Cys Ser Gly
145                 150                 155                 160 agc acc tcc aac att ggg aat aat tat gtc tcc tgg tac caa cag cac            528
Ser Thr Ser Asn Ile Gly Asn Asn Tyr Val Ser Trp Tyr Gln Gln His
                165                 170                 175 cca ggc aaa gcc ccc aaa ctc atg att tat gat gtc agt aag cgg ccc            576
Pro Gly Lys Ala Pro Lys Leu Met Ile Tyr Asp Val Ser Lys Arg Pro
            180                 185                 190 tca ggg gtc cct gac cga ttc tct ggc tcc aag tct ggc aac tca gcc            624
Ser Gly Val Pro Asp Arg Phe Ser Gly Ser Lys Ser Gly Asn Ser Ala
        195                 200                 205 tcc ctg gac atc agt ggg ctc cag tct gag gat gag gct gat tat tac            672
Ser Leu Asp Ile Ser Gly Leu Gln Ser Glu Asp Glu Ala Asp Tyr Tyr
    210                 215                 220 tgt gca gca tgg gat gac agc ctg agt gaa ttt ctc ttc gga act ggg            720
Cys Ala Ala Trp Asp Asp Ser Leu Ser Glu Phe Leu Phe Gly Thr Gly
225                 230                 235                 240 acc aag ctg acc gtc cta ggt                                                741
Thr Lys Leu Thr Val Leu Gly
                245
```

<210> SEQ ID NO 144
<211> LENGTH: 723
<212> TYPE: DNA
<213> ORGANISM: Artificial sequence
<220> FEATURE:
<221> NAME/KEY: CDS
<222> LOCATION: (1)..(723)
<223> OTHER INFORMATION: Polynucleotide encoding GMBC610 scFv protein

<400> SEQUENCE: 144

```
cag gtc acc ttg aag gag tct ggg gct gaa gtg aag aag cct ggg gcc        48
Gln Val Thr Leu Lys Glu Ser Gly Ala Glu Val Lys Lys Pro Gly Ala
1               5                   10                  15 tca gtg aaa gtt tcc tgt aag act tct gga ttc aca ttc ggc gcc tac        96
Ser Val Lys Val Ser Cys Lys Thr Ser Gly Phe Thr Phe Gly Ala Tyr
            20                  25                  30 tac atc cac tgg gtg cga cag gtc cct gga caa ggg ctt gag tgg atg       144
Tyr Ile His Trp Val Arg Gln Val Pro Gly Gln Gly Leu Glu Trp Met
        35                  40                  45 gga tgg atc gac cct aac aat ggt ggc aca aac tat gca cag aaa ttt       192
Gly Trp Ile Asp Pro Asn Asn Gly Gly Thr Asn Tyr Ala Gln Lys Phe
    50                  55                  60 cag ggc agg gtc acc atg acc agg gac atg tcc acc acc aca acc tac       240
Gln Gly Arg Val Thr Met Thr Arg Asp Met Ser Thr Thr Thr Thr Tyr
65                  70                  75                  80 atg gag gtc agt ggg cta cat tct gac gac acg gcc gtg tat tac tgt       288
Met Glu Val Ser Gly Leu His Ser Asp Asp Thr Ala Val Tyr Tyr Cys
                85                  90                  95 gcg agg gcc aga gtg gcg aca atc ctt gaa tat tgg ggc agg ggc acc       336
Ala Arg Ala Arg Val Ala Thr Ile Leu Glu Tyr Trp Gly Arg Gly Thr
            100                 105                 110 ctg gtc acc gtc tcc tca ggt gga ggc ggt tca ggc gga ggt ggc agc       384
Leu Val Thr Val Ser Ser Gly Gly Gly Gly Ser Gly Gly Gly Gly Ser
        115                 120                 125 ggc ggt ggc gga tcg cct gag ctg act cag gac cct gct gtg tct gtg       432
Gly Gly Gly Gly Ser Pro Glu Leu Thr Gln Asp Pro Ala Val Ser Val
    130                 135                 140 gcc ttg gga cag aca gtc agg atc aca tgc caa gga gac agc ctc aga       480
Ala Leu Gly Gln Thr Val Arg Ile Thr Cys Gln Gly Asp Ser Leu Arg
145                 150                 155                 160 agc tat tat gca agc tgg tac cag cag aag cca gga cag gcc cct gta       528
Ser Tyr Tyr Ala Ser Trp Tyr Gln Gln Lys Pro Gly Gln Ala Pro Val
                165                 170                 175 ctt gtc atc tat ggt aaa aac aac cgg ccc tca ggg atc cca gac cga       576
Leu Val Ile Tyr Gly Lys Asn Asn Arg Pro Ser Gly Ile Pro Asp Arg
            180                 185                 190 ttc tct ggc tcc agc tca gga aac aca gct tcc ttg acc atc act ggg       624
Phe Ser Gly Ser Ser Ser Gly Asn Thr Ala Ser Leu Thr Ile Thr Gly
        195                 200                 205 gct cag gcg gaa gat gag gct gac tat tac tgt aac tcc cgg gac agc       672
Ala Gln Ala Glu Asp Glu Ala Asp Tyr Tyr Cys Asn Ser Arg Asp Ser
    210                 215                 220 agt ggt aac cat gtg gta ttc ggc gga ggg acc aag ctg acc gtc cta       720
Ser Gly Asn His Val Val Phe Gly Gly Gly Thr Lys Leu Thr Val Leu
225                 230                 235                 240 ggt                                                                    723
Gly
```

<210> SEQ ID NO 145

<211> LENGTH: 717
<212> TYPE: DNA
<213> ORGANISM: Artificial sequence
<220> FEATURE:
<221> NAME/KEY: CDS
<222> LOCATION: (1)..(717)
<223> OTHER INFORMATION: Polynucleotide encoding GMBC612 scFv protein

<400> SEQUENCE: 145

```
gag gtg cag ctg gtg gag tct ggg gga ggc gtg gtc cag cct ggg ggg        48
Glu Val Gln Leu Val Glu Ser Gly Gly Gly Val Val Gln Pro Gly Gly
1               5                   10                  15 tcc ctg aga ctc tcc tgt gca gcg tct gga ttc agc ttc agt agt tat        96
Ser Leu Arg Leu Ser Cys Ala Ala Ser Gly Phe Ser Phe Ser Ser Tyr
            20                  25                  30 ggc atg caa tgg gtc cgc cag gct cca ggc aag ggg ctg gag tgg gtg       144
Gly Met Gln Trp Val Arg Gln Ala Pro Gly Lys Gly Leu Glu Trp Val
        35                  40                  45 gca ttt ata cgg tat gat gga agt att aaa tac tat gca gac tcc gtg       192
Ala Phe Ile Arg Tyr Asp Gly Ser Ile Lys Tyr Tyr Ala Asp Ser Val
    50                  55                  60 aag ggc cga ttc acc gtc tcc aga gac aac tcc aag aac acg ctg tat       240
Lys Gly Arg Phe Thr Val Ser Arg Asp Asn Ser Lys Asn Thr Leu Tyr
65                  70                  75                  80 ctg caa atg aac agc ctg aga gcc gag gac acg gct gtc tat tac tgt       288
Leu Gln Met Asn Ser Leu Arg Ala Glu Asp Thr Ala Val Tyr Tyr Cys
                85                  90                  95 gcg aga ggt tat cga atc gtt gac tac tgg ggc caa gga acc ctg gtc       336
Ala Arg Gly Tyr Arg Ile Val Asp Tyr Trp Gly Gln Gly Thr Leu Val
            100                 105                 110 acc gtc tcc tca ggt gga ggc ggt tca ggc gga ggt ggc agc ggc ggt       384
Thr Val Ser Ser Gly Gly Gly Gly Ser Gly Gly Gly Gly Ser Gly Gly
        115                 120                 125 ggc gga tcg gac atc cag atg acc cag tct cct tcc acc ctg tcc cca       432
Gly Gly Ser Asp Ile Gln Met Thr Gln Ser Pro Ser Thr Leu Ser Pro
    130                 135                 140 tct att gga gac aga gtc acc atc acc tgc cgg gcc agt gag ggt att       480
Ser Ile Gly Asp Arg Val Thr Ile Thr Cys Arg Ala Ser Glu Gly Ile
145                 150                 155                 160 tat cac tgg ttg gcc tgg tat cag cag aag cca ggg aaa gcc cct aaa       528
Tyr His Trp Leu Ala Trp Tyr Gln Gln Lys Pro Gly Lys Ala Pro Lys
                165                 170                 175 ctc ctg atc tat aag gcc tct agt tta gcc agt ggg gcc cca tca agg       576
Leu Leu Ile Tyr Lys Ala Ser Ser Leu Ala Ser Gly Ala Pro Ser Arg
            180                 185                 190 ttc agc ggc agt gga tct ggg aca gat ttc act ctc acc atc agc agc       624
Phe Ser Gly Ser Gly Ser Gly Thr Asp Phe Thr Leu Thr Ile Ser Ser
        195                 200                 205 ctg cag cct gat gat ttt gca act tat tac tgc caa caa tat agt aat       672
Leu Gln Pro Asp Asp Phe Ala Thr Tyr Tyr Cys Gln Gln Tyr Ser Asn
    210                 215                 220 tat ccg ctc act ttc ggc gga ggg acc aag ctg gag atc aaa cgt           717
Tyr Pro Leu Thr Phe Gly Gly Gly Thr Lys Leu Glu Ile Lys Arg
225                 230                 235
```

<210> SEQ ID NO 146
<211> LENGTH: 735
<212> TYPE: DNA
<213> ORGANISM: Artificial sequence
<220> FEATURE:
<221> NAME/KEY: CDS
<222> LOCATION: (1)..(735)
<223> OTHER INFORMATION: Polynucleotide encoding GMBC613 scFv protein

<400> SEQUENCE: 146

```
aag gtg cag ctg gtg gag tct ggg gga ggc ttg gtc cag cct ggg ggg      48
Lys Val Gln Leu Val Glu Ser Gly Gly Gly Leu Val Gln Pro Gly Gly
1               5                   10                  15 tcc ctg aga ctc tct tgt gca gcc tct gga ttc acc att agt agc cat      96
Ser Leu Arg Leu Ser Cys Ala Ala Ser Gly Phe Thr Ile Ser Ser His
            20                  25                  30 tgg atg agc tgg gtc cgc cag gct ccg ggg aag ggg ctg gag tgg gtg     144
Trp Met Ser Trp Val Arg Gln Ala Pro Gly Lys Gly Leu Glu Trp Val
        35                  40                  45 gcc agt ata aag caa gat gga cgt gag aaa cac ttt gtg gat tct gtg     192
Ala Ser Ile Lys Gln Asp Gly Arg Glu Lys His Phe Val Asp Ser Val
    50                  55                  60 aag ggc cga ttc agc atc tcc aga gac aac gcc aag aac tca ctg tat     240
Lys Gly Arg Phe Ser Ile Ser Arg Asp Asn Ala Lys Asn Ser Leu Tyr
65                  70                  75                  80 ctg caa atg aac agc ctg aga acc gag gac acg gct gtc tac tac tgt     288
Leu Gln Met Asn Ser Leu Arg Thr Glu Asp Thr Ala Val Tyr Tyr Cys
                85                  90                  95 gcg aga gag acg tac ggg gga tac tac tat tac ttc atg gac gtc tgg     336
Ala Arg Glu Thr Tyr Gly Gly Tyr Tyr Tyr Tyr Phe Met Asp Val Trp
            100                 105                 110 ggc aaa gga acc ctg gtc acc gtc tcc tca ggt gga ggc ggt tca ggc     384
Gly Lys Gly Thr Leu Val Thr Val Ser Ser Gly Gly Gly Gly Ser Gly
        115                 120                 125 gga ggt ggc agc ggc ggt ggc gga tcg tct gag ctg act cag gac cct     432
Gly Gly Gly Ser Gly Gly Gly Gly Ser Ser Glu Leu Thr Gln Asp Pro
    130                 135                 140 gct gtg tct gtg gcc ttg gga cag aca gtc agg atc aca tgc caa gga     480
Ala Val Ser Val Ala Leu Gly Gln Thr Val Arg Ile Thr Cys Gln Gly
145                 150                 155                 160 gac agc ctc aga agc tat tat gca agc tgg tac cag cag aag cca gga     528
Asp Ser Leu Arg Ser Tyr Tyr Ala Ser Trp Tyr Gln Gln Lys Pro Gly
                165                 170                 175 cag gcc cct gta ctt gtc atc tat ggt aaa aac aac cgg ccc tca ggg     576
Gln Ala Pro Val Leu Val Ile Tyr Gly Lys Asn Asn Arg Pro Ser Gly
            180                 185                 190 atc cca gac cga ttc tct ggc tcc agc tca gga aac aca gct tcc ttg     624
Ile Pro Asp Arg Phe Ser Gly Ser Ser Ser Gly Asn Thr Ala Ser Leu
        195                 200                 205 acc atc act ggg gct cag gcg gaa gat gag gct gac tat tac tgt aac     672
Thr Ile Thr Gly Ala Gln Ala Glu Asp Glu Ala Asp Tyr Tyr Cys Asn
    210                 215                 220 tcc cgg gac agc agt ggt aac cat gtg gta ttc ggc gga ggg acc aag     720
Ser Arg Asp Ser Ser Gly Asn His Val Val Phe Gly Gly Gly Thr Lys
225                 230                 235                 240 ctg acc gtc cta ggt                                                 735
Leu Thr Val Leu Gly
                245
```

<210> SEQ ID NO 147
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC614 scFv protein

<400> SEQUENCE: 147

| | | |
|---|---|---|
| gag gtg cag ctg gtg cag tct ggg gga ggc ttg gta aag ccg ggg ggg<br>Glu Val Gln Leu Val Gln Ser Gly Gly Gly Leu Val Lys Pro Gly Gly<br>1                   5                      10               15 | | 48 |
| tcc ctt aga ctc tcc tgt gca gcc tct ggt ttc act ttc agt gac gcc<br>Ser Leu Arg Leu Ser Cys Ala Ala Ser Gly Phe Thr Phe Ser Asp Ala<br>                   20                     25                     30 | | 96 |
| tgg atg aac tgg gtc cgc cag gct cca ggg aag ggg ctg gag tgg gtc<br>Trp Met Asn Trp Val Arg Gln Ala Pro Gly Lys Gly Leu Glu Trp Val<br>        35                     40                     45 | | 144 |
| ggc cgt att aaa agc aaa ggt agt ggt ggg aca ata gac tac gcc gca<br>Gly Arg Ile Lys Ser Lys Gly Ser Gly Gly Thr Ile Asp Tyr Ala Ala<br>50                     55                     60 | | 192 |
| ccc gtg aaa gac aga ttc acc atc tca cga gat gat tca aaa aac acg<br>Pro Val Lys Asp Arg Phe Thr Ile Ser Arg Asp Asp Ser Lys Asn Thr<br>65                     70                     75                     80 | | 240 |
| ctg tat ctg caa atg aac agt ctg aaa acc gag gac aca gcc ctg tat<br>Leu Tyr Leu Gln Met Asn Ser Leu Lys Thr Glu Asp Thr Ala Leu Tyr<br>                   85                     90                     95 | | 288 |
| tac tgt acg tgg gac tgg gat ttc tac tac ggt atg aac gtc tgg ggc<br>Tyr Cys Thr Trp Asp Trp Asp Phe Tyr Tyr Gly Met Asn Val Trp Gly<br>                 100                    105                 110 | | 336 |
| cga ggg aca atg gtc acc gtc tcg agt ggt gga ggc ggt tca ggc gga<br>Arg Gly Thr Met Val Thr Val Ser Ser Gly Gly Gly Gly Ser Gly Gly<br>               115                    120                 125 | | 384 |
| ggt ggc agc ggc ggt ggc gga tcg cag tct gtg ctg act cag cct gcc<br>Gly Gly Ser Gly Gly Gly Gly Ser Gln Ser Val Leu Thr Gln Pro Ala<br>130                    135                    140 | | 432 |
| tcc gtg tct ggg tct cct gga cag tcg atc acc atc tcc tgc act gga<br>Ser Val Ser Gly Ser Pro Gly Gln Ser Ile Thr Ile Ser Cys Thr Gly<br>145                    150                    155                  160 | | 480 |
| acc agc agt gac gtt ggt ggt tat aac tat gtc tcc tgg tac caa caa<br>Thr Ser Ser Asp Val Gly Gly Tyr Asn Tyr Val Ser Trp Tyr Gln Gln<br>                   165                    170                 175 | | 528 |
| cac cca ggc aaa gcc ccc aaa ctc atg att tat gag ggc agt aag cgg<br>His Pro Gly Lys Ala Pro Lys Leu Met Ile Tyr Glu Gly Ser Lys Arg<br>               180                    185                 190 | | 576 |
| ccc tca ggg gtt tct aat cgc ttc tct ggc tcc aag tct ggc aac acg<br>Pro Ser Gly Val Ser Asn Arg Phe Ser Gly Ser Lys Ser Gly Asn Thr<br>195                    200                    205 | | 624 |
| gcc tcc ctg aca atc tct ggg ctc cag gct gag gac gag gct gat tat<br>Ala Ser Leu Thr Ile Ser Gly Leu Gln Ala Glu Asp Glu Ala Asp Tyr<br>210                    215                    220 | | 672 |
| tac tgc agc tca tat aca acc agg agc act cga gtt ttc ggc gga ggg<br>Tyr Cys Ser Ser Tyr Thr Thr Arg Ser Thr Arg Val Phe Gly Gly Gly<br>225                    230                    235                  240 | | 720 |
| acc aag ctg acc gtc cta ggt<br>Thr Lys Leu Thr Val Leu Gly<br>                   245 | | 741 |

<210> SEQ ID NO 148
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC615 scFv protein

<400> SEQUENCE: 148

| | | |
|---|---|---|
| gag gtg cag ctg gtg gag tct ggg gga ggc ttg gta aag ccg ggg ggg<br>Glu Val Gln Leu Val Glu Ser Gly Gly Gly Leu Val Lys Pro Gly Gly<br>1                   5                      10               15 | | 48 |

-continued

```
tcc ctt aga ctc tcc tgt gca gcc tct ggt ttc aaa ttc agt gac gcc      96
Ser Leu Arg Leu Ser Cys Ala Ala Ser Gly Phe Lys Phe Ser Asp Ala
         20                  25                  30 tgg atg aac tgg gtc cgc cag gct cca ggg aag ggg ctg gag tgg gtc     144
Trp Met Asn Trp Val Arg Gln Ala Pro Gly Lys Gly Leu Glu Trp Val
             35                  40                  45 ggc cgt att aaa agc aaa ggt agt ggt ggg aca ata gac tac gct gca     192
Gly Arg Ile Lys Ser Lys Gly Ser Gly Gly Thr Ile Asp Tyr Ala Ala
     50                  55                  60 ccc gtg aaa gac aga ttc acc atc tca cga gat gat tca aaa aac acg     240
Pro Val Lys Asp Arg Phe Thr Ile Ser Arg Asp Asp Ser Lys Asn Thr
 65                  70                  75                  80 ctg tat ctg caa atg aac agt ctg aaa acc gag gac aca gcc ctg tat     288
Leu Tyr Leu Gln Met Asn Ser Leu Lys Thr Glu Asp Thr Ala Leu Tyr
                 85                  90                  95 tac tgt acg tgg gac tgg gat ttc tac tac ggt atg aac gtc tgg ggc     336
Tyr Cys Thr Trp Asp Trp Asp Phe Tyr Tyr Gly Met Asn Val Trp Gly
            100                 105                 110 aaa ggc acc ctg gtc gcc gtc tcc tca ggt gga ggc ggt tca ggc gga     384
Lys Gly Thr Leu Val Ala Val Ser Ser Gly Gly Gly Gly Ser Gly Gly
        115                 120                 125 ggt ggc agc ggc ggt ggc gga tcg cag tct gtg ctg act cag cct gcc     432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga     480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa     528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg     576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg     624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat     672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg     720
Tyr Cys Ser Ser Tyr Thr Thr Arg Ser Thr Arg Val Phe Gly Gly Gly
225                 230                 235                 240 acc aag ctg acc gtc cta ggt                                         741
Thr Lys Leu Thr Val Leu Gly
                245
```

<210> SEQ ID NO 149
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC616 scFv protein

<400> SEQUENCE: 149

```
gag gtg cag ctg gtg gag tct ggg gga ggc ttg gta aag cct ggg ggg      48
Glu Val Gln Leu Val Glu Ser Gly Gly Gly Leu Val Lys Pro Gly Gly
 1               5                  10                  15 tcc ctt aga ctc tcc tgt gca gcc tct ggt ttc act ttc agt gac gcc      96
Ser Leu Arg Leu Ser Cys Ala Ala Ser Gly Phe Thr Phe Ser Asp Ala
```

-continued

```
                    20                  25                  30
tgg atg aac tgg gtc cgc cag gct cca ggg aag ggg ctg gag tgg gtc      144
Trp Met Asn Trp Val Arg Gln Ala Pro Gly Lys Gly Leu Glu Trp Val
        35                  40                  45 ggc cgt att aaa agt aaa ggt agt ggg aca aca gac tac gct gca          192
Gly Arg Ile Lys Ser Lys Gly Ser Gly Thr Thr Asp Tyr Ala Ala
 50                  55                  60 ccc gtg aaa gac aga ttc acc atc tca aga gat gat tca gaa aac acg     240
Pro Val Lys Asp Arg Phe Thr Ile Ser Arg Asp Asp Ser Glu Asn Thr
 65                  70                  75                  80 ctg tat cta caa atg aac agc ctg aaa acc gag gac aca gcc gta tat     288
Leu Tyr Leu Gln Met Asn Ser Leu Lys Thr Glu Asp Thr Ala Val Tyr
                 85                  90                  95 tac tgt acg tgg gac cat agt tat tat tat gat atg gcc gtc tgg ggc     336
Tyr Cys Thr Trp Asp His Ser Tyr Tyr Tyr Asp Met Ala Val Trp Gly
            100                 105                 110 cgg gga acc ctg gtc acc gtc tcc tca ggt gga ggc ggt tca ggc gga     384
Arg Gly Thr Leu Val Thr Val Ser Ser Gly Gly Gly Gly Ser Gly Gly
        115                 120                 125 ggt ggc agc ggc ggt ggc gga tcg cag tct gtg ctg act cag cct ccc     432
Gly Gly Ser Gly Gly Gly Gly Ser Gln Ser Val Leu Thr Gln Pro Pro
130                 135                 140 ttc gtg tct ggg tct cct gga cag tcg atc acc atc tcc tgc act gga     480
Phe Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa     528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg     576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg     624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat     672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg     720
Tyr Cys Ser Ser Tyr Thr Thr Arg Ser Thr Arg Val Phe Gly Gly Gly
225                 230                 235                 240 acc aag ctg acc gtc cta ggt                                         741
Thr Lys Leu Thr Val Leu Gly
                245
```

<210> SEQ ID NO 150
<211> LENGTH: 729
<212> TYPE: DNA
<213> ORGANISM: Artificial sequence
<220> FEATURE:
<221> NAME/KEY: CDS
<222> LOCATION: (1)..(729)
<223> OTHER INFORMATION: Polynucleotide encoding GMBC617 scFv protein

<400> SEQUENCE: 150

```
gag gtg cag ctg gtg gag act gga gga ggc ttg gtc cag cct ggg ggg      48
Glu Val Gln Leu Val Glu Thr Gly Gly Gly Leu Val Gln Pro Gly Gly
 1               5                  10                  15 tcc ctg aga ctc tcc tgt gca gcc tct ggg ttc acc gtc agt agc aac     96
Ser Leu Arg Leu Ser Cys Ala Ala Ser Gly Phe Thr Val Ser Ser Asn
            20                  25                  30 tac atg agc tgg gtc cgc cag gct cca ggg aag ggg ctg gag tgg gtc    144
```

| | | |
|---|---|---|
| Tyr Met Ser Trp Val Arg Gln Ala Pro Gly Lys Gly Leu Glu Trp Val<br>             35                   40                   45 | |

```
tca gtt att tat agc ggt ggt agc aca tac tac gca gac tcc gtg aag       192
Ser Val Ile Tyr Ser Gly Gly Ser Thr Tyr Tyr Ala Asp Ser Val Lys
 50                  55                  60 ggc cga ttc acc atc tcc aga cac aat tcc aag aac acg ctg tat ctt       240
Gly Arg Phe Thr Ile Ser Arg His Asn Ser Lys Asn Thr Leu Tyr Leu
 65                  70                  75                  80 caa atg aac agc ctg aga gct gag gac acg gcc gtg tat tac tgt gcg       288
Gln Met Asn Ser Leu Arg Ala Glu Asp Thr Ala Val Tyr Tyr Cys Ala
                 85                  90                  95 aga ggt cta tgg ttc ggg gag tta ttg tac tgg ggc cag ggc acc ctg       336
Arg Gly Leu Trp Phe Gly Glu Leu Leu Tyr Trp Gly Gln Gly Thr Leu
            100                 105                 110 gtc acc gtc tcc tca ggt gga ggc ggt tca ggc gga ggt ggc agc ggc       384
Val Thr Val Ser Ser Gly Gly Gly Gly Ser Gly Gly Gly Gly Ser Gly
        115                 120                 125 ggt ggc gga tcg cag tct gcc ctg act cag cct gcc tcc gtg tct gga       432
Gly Gly Gly Ser Gln Ser Ala Leu Thr Gln Pro Ala Ser Val Ser Gly
    130                 135                 140 tct cgt gga cag tcg atc acc atc tcc tgc act gga acc act ggt gac       480
Ser Arg Gly Gln Ser Ile Thr Ile Ser Cys Thr Gly Thr Thr Gly Asp
145                 150                 155                 160 gtt ggt ggt tat gac tat gtc tcc tgg tac caa cag cac cca ggc aaa       528
Val Gly Gly Tyr Asp Tyr Val Ser Trp Tyr Gln Gln His Pro Gly Lys
                165                 170                 175 gcc ccc aaa ctc ctc atc tat ggt aac agc aat cgg ccc tca ggg gtc       576
Ala Pro Lys Leu Leu Ile Tyr Gly Asn Ser Asn Arg Pro Ser Gly Val
            180                 185                 190 cct gat cgc ttc tct gcc tcc aag tcc ggc aat acg gcc tcc ctg acc       624
Pro Asp Arg Phe Ser Ala Ser Lys Ser Gly Asn Thr Ala Ser Leu Thr
        195                 200                 205 atc tct gga ctc cag gct gag gat gag gct gat tat ttc tgc agc aca       672
Ile Ser Gly Leu Gln Ala Glu Asp Glu Ala Asp Tyr Phe Cys Ser Thr
    210                 215                 220 tat gca ccc ccc ggt att att atg ttc ggc gga ggg acc aag ctg acc       720
Tyr Ala Pro Pro Gly Ile Ile Met Phe Gly Gly Gly Thr Lys Leu Thr
225                 230                 235                 240 gtc cta ggt                                                           729
Val Leu Gly <210> SEQ ID NO 151
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC618 scFv protein

<400> SEQUENCE: 151 gaa gtg cag ctg gtg cag tct ggg gga ggc ttg gta aag ccg ggg ggg        48
Glu Val Gln Leu Val Gln Ser Gly Gly Gly Leu Val Lys Pro Gly Gly
  1               5                  10                  15 tcc ctt aga ctc tcc tgt gca gcc tct ggt ttc aaa ttc gat gac gcc        96
Ser Leu Arg Leu Ser Cys Ala Ala Ser Gly Phe Lys Phe Asp Asp Ala
             20                  25                  30 tgg atg aac tgg gtc cgc cag gct cca ggg aag ggg ctg gag tgg gtc       144
Trp Met Asn Trp Val Arg Gln Ala Pro Gly Lys Gly Leu Glu Trp Val
         35                  40                  45 ggc cgt att aaa agc aaa cgt agt ggt ggg aca ata gac tac gct gca       192
```

```
Gly Arg Ile Lys Ser Lys Arg Ser Gly Gly Thr Ile Asp Tyr Ala Ala
         50                  55                  60 ccc gtg aaa gac aga ttc acc atc tca cga gat gat tca aaa aac acg      240
Pro Val Lys Asp Arg Phe Thr Ile Ser Arg Asp Asp Ser Lys Asn Thr
 65              70                  75                  80 ctg tat ctg caa atg aat agt ctg aga acc gag gac aca gcc ttg tat      288
Leu Tyr Leu Gln Met Asn Ser Leu Arg Thr Glu Asp Thr Ala Leu Tyr
                 85                  90                  95 tac tgt acg tgg gac tgg gat ttc tac tac ggt atg aac gtc tgg ggc      336
Tyr Cys Thr Trp Asp Trp Asp Phe Tyr Tyr Gly Met Asn Val Trp Gly
            100                 105                 110 aga ggc acc ctg gtc acc gtc tcc tca ggc gga ggt tca ggc gga          384
Arg Gly Thr Leu Val Thr Val Ser Ser Gly Gly Gly Ser Gly Gly
        115                 120                 125 ggt ggc agc ggc ggt ggc gga tcg cag tct gtg ctg act cag cca ccc      432
Gly Gly Ser Gly Gly Gly Gly Ser Gln Ser Val Leu Thr Gln Pro Pro
130                 135                 140 tca gcg tct ggg acc ccc ggg cag agg gtc acc atc tct tgt tct gga      480
Ser Ala Ser Gly Thr Pro Gly Gln Arg Val Thr Ile Ser Cys Ser Gly
145                 150                 155                 160 agc agc tcc aac atc ggg agt aac act gta aac tgg tac cag cga ctc      528
Ser Ser Ser Asn Ile Gly Ser Asn Thr Val Asn Trp Tyr Gln Arg Leu
                165                 170                 175 cca gga gcg gcc ccc caa ctc ctc atc tac aat aat gac cag cgg ccc      576
Pro Gly Ala Ala Pro Gln Leu Leu Ile Tyr Asn Asn Asp Gln Arg Pro
            180                 185                 190 tca ggg atc cct gac cga ttc tct ggc tcc aag tct ggc acc tca ggc      624
Ser Gly Ile Pro Asp Arg Phe Ser Gly Ser Lys Ser Gly Thr Ser Gly
        195                 200                 205 tcc ctg gtc atc agt ggg ctc cag tct gaa gat gag gct gat tac tac      672
Ser Leu Val Ile Ser Gly Leu Gln Ser Glu Asp Glu Ala Asp Tyr Tyr
210                 215                 220 tgt gcg tca tgg gat gac agt ctg aat ggt cgg gtg ttc ggc gga ggg      720
Cys Ala Ser Trp Asp Asp Ser Leu Asn Gly Arg Val Phe Gly Gly Gly
225                 230                 235                 240 acc aag ctg acc gtc cta ggt                                          741
Thr Lys Leu Thr Val Leu Gly
                245

<210> SEQ ID NO 152
<211> LENGTH: 732
<212> TYPE: DNA
<213> ORGANISM: Artificial sequence
<220> FEATURE:
<221> NAME/KEY: CDS
<222> LOCATION: (1)..(732)
<223> OTHER INFORMATION: Polynucleotide encoding GMBC619 scFv protein

<400> SEQUENCE: 152 gag gtc cag ctg gtg gag tct ggg gga ggc gtg gtc cag cct ggg agg       48
Glu Val Gln Leu Val Glu Ser Gly Gly Gly Val Val Gln Pro Gly Arg
 1               5                  10                  15 tcc ctg aga ctc tcc tgt gca gcc tct gga ttc acc ttc agg agc tat       96
Ser Leu Arg Leu Ser Cys Ala Ala Ser Gly Phe Thr Phe Arg Ser Tyr
             20                  25                  30 ggc atg cac tgg gtc cgc cag gct cca ggc aag ggg ctg gag tgg gtg      144
Gly Met His Trp Val Arg Gln Ala Pro Gly Lys Gly Leu Glu Trp Val
         35                  40                  45 gca gtt ata aca tat gat gga agt aat aaa tac tat gca gac tcc gtg      192
Ala Val Ile Thr Tyr Asp Gly Ser Asn Lys Tyr Tyr Ala Asp Ser Val
     50                  55                  60
```

```
aag ggc cga ttc acc atc tcc aga gac aat tcc aag aac acg ctg tat    240
Lys Gly Arg Phe Thr Ile Ser Arg Asp Asn Ser Lys Asn Thr Leu Tyr
 65                  70                  75                  80 ctg caa atg aac agc ctg aga gct gac gac acg gct gtg tat tac tgt    288
Leu Gln Met Asn Ser Leu Arg Ala Asp Asp Thr Ala Val Tyr Tyr Cys
                 85                  90                  95 gcg aga gat ggg ggt ggc tgg tac cac ccg agg ctt gac tac tgg ggc    336
Ala Arg Asp Gly Gly Gly Trp Tyr His Pro Arg Leu Asp Tyr Trp Gly
            100                 105                 110 caa ggc aca atg gtc acc gtc tcg agt ggt gga ggc ggt tca ggc gga    384
Gln Gly Thr Met Val Thr Val Ser Ser Gly Gly Gly Gly Ser Gly Gly
        115                 120                 125 ggt ggc agc ggc ggt ggc gga tcg tct gag ctg act cag gac cct gct    432
Gly Gly Ser Gly Gly Gly Gly Ser Ser Glu Leu Thr Gln Asp Pro Ala
    130                 135                 140 gtg tct gtg gcc ttg gga cag aca gtc agg atc aca tgc caa gga gac    480
Val Ser Val Ala Leu Gly Gln Thr Val Arg Ile Thr Cys Gln Gly Asp
145                 150                 155                 160 agc ctc aga agc tat tat gca agc tgg tac cag cag aag cca gga cag    528
Ser Leu Arg Ser Tyr Tyr Ala Ser Trp Tyr Gln Gln Lys Pro Gly Gln
                165                 170                 175 gcc cct gta ctt gtc atc tat ggt aaa aac aac cgg ccc tca ggg atc    576
Ala Pro Val Leu Val Ile Tyr Gly Lys Asn Asn Arg Pro Ser Gly Ile
            180                 185                 190 cca gac cga ttc tct ggc tcc agc tca gga aac aca gct tcc ttg acc    624
Pro Asp Arg Phe Ser Gly Ser Ser Ser Gly Asn Thr Ala Ser Leu Thr
        195                 200                 205 atc act ggg gct cag gcg gaa gat gag gct gac tat tac tgt aac tcc    672
Ile Thr Gly Ala Gln Ala Glu Asp Glu Ala Asp Tyr Tyr Cys Asn Ser
    210                 215                 220 cgg gac agc agt ggt aac cat gtg gta ttc ggc gga ggg acc aag ctg    720
Arg Asp Ser Ser Gly Asn His Val Val Phe Gly Gly Gly Thr Lys Leu
225                 230                 235                 240 acc gtc cta ggt                                                    732
Thr Val Leu Gly <210> SEQ ID NO 153
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC620 scFv protein

<400> SEQUENCE: 153 gag gtg cag ctg gtg gag tcc ggg gga ggc ttg gta aag ccg ggg ggg     48
Glu Val Gln Leu Val Glu Ser Gly Gly Gly Leu Val Lys Pro Gly Gly
  1               5                  10                  15 tcc ctt aga ctc tcc tgt gca gcc tct ggt ttc act ttc agt gac gcc     96
Ser Leu Arg Leu Ser Cys Ala Ala Ser Gly Phe Thr Phe Ser Asp Ala
             20                  25                  30 tgg atg aac tgg gtc cgc cag gct cca ggg aag ggg ctg gag tgg gtc    144
Trp Met Asn Trp Val Arg Gln Ala Pro Gly Lys Gly Leu Glu Trp Val
         35                  40                  45 ggc cgt att aaa agc aaa ggt agt ggt ggg aca ata gac tac gcc gcg    192
Gly Arg Ile Lys Ser Lys Gly Ser Gly Gly Thr Ile Asp Tyr Ala Ala
     50                  55                  60 ccc gtg aaa gac aga ttc acc atc tca cga gat gat tca aaa aac acg    240
Pro Val Lys Asp Arg Phe Thr Ile Ser Arg Asp Asp Ser Lys Asn Thr
 65                  70                  75                  80
```

```
ctg tat ctg caa atg aac agt ctg aaa acc gag gac aca gcc ctg tat        288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc        336
Tyr Cys Thr Trp Asp Trp Asp Phe Tyr Tyr Gly Met Asn Val Trp Gly
            100                 105                 110 cgg ggc aca atg gtc acc gtc tcg agt ggt gga ggc ggt tca ggc gga        384
Arg Gly Thr Met Val Thr Val Ser Ser Gly Gly Gly Gly Ser Gly Gly
        115                 120                 125 ggt ggc agc ggc ggt ggc gga tcg cag tct gtg ctg act cag cct gcc        432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga        480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa        528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg        576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg        624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat        672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg        720
Tyr Cys Ser Ser Tyr Thr Thr Arg Ser Thr Arg Val Phe Gly Gly Gly
225                 230                 235                 240 acc aag ctg acc gtc cta ggg                                            741
Thr Lys Leu Thr Val Leu Gly
                245

<210> SEQ ID NO 154
<211> LENGTH: 723
<212> TYPE: DNA
<213> ORGANISM: Artificial sequence
<220> FEATURE:
<221> NAME/KEY: CDS
<222> LOCATION: (1)..(723)
<223> OTHER INFORMATION: Polynucleotide encoding GMBC621 scFv protein

<400> SEQUENCE: 154 gaa gtg cag ctg gtg cag tct ggg gga ggc gtg gtc cag cct ggg agg         48
Glu Val Gln Leu Val Gln Ser Gly Gly Gly Val Val Gln Pro Gly Arg
1               5                   10                  15 tcc ctg aga ctc tcc tgt gca gcc tct gga ttc acc ttc agt agc tat         96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg        144
Gly Met His Trp Val Arg Gln Ala Pro Gly Lys Gly Leu Glu Trp Val
        35                  40                  45 gca gtt ata tca tat gat gga agt aat aaa tac tat gca gac tcc gtg        192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aat acg ctg tat        240
Lys Gly Arg Phe Thr Ile Ser Arg Asp Asn Ser Lys Asn Thr Leu Tyr
65                  70                  75                  80 ctg caa atg gac agc ctg aga gcc gag gac acg gcc gta tat ttc tgt        288
Leu Gln Met Asp Ser Leu Arg Ala Glu Asp Thr Ala Val Tyr Phe Cys
                85                  90                  95
```

```
gcg aaa aga ggt cta tgg acg cca att gac tac tgg ggc aaa gga acc        336
Ala Lys Arg Gly Leu Trp Thr Pro Ile Asp Tyr Trp Gly Lys Gly Thr
            100                 105                 110 ctg gtc acc gtc tcc tca ggt gga ggc ggt tca ggc gga ggt ggc agc        384
Leu Val Thr Val Ser Ser Gly Gly Gly Gly Ser Gly Gly Gly Gly Ser
        115                 120                 125 ggc ggt ggc gga tcg tct gag ctg act cag gac cct gct gtg tct gtg        432
Gly Gly Gly Gly Ser Ser Glu Leu Thr Gln Asp Pro Ala Val Ser Val
130                 135                 140 gcc ttg gga cag aca gtc agg atc aca tgc caa gga gac agc ctc aga        480
Ala Leu Gly Gln Thr Val Arg Ile Thr Cys Gln Gly Asp Ser Leu Arg
145                 150                 155                 160 agc tat tat gca agc tgg tac cag cag aag cca gga cag gcc cct gta        528
Ser Tyr Tyr Ala Ser Trp Tyr Gln Gln Lys Pro Gly Gln Ala Pro Val
                165                 170                 175 ctt gtc atc tat ggt aaa aac aac cgg ccc tca ggg atc cca gac cga        576
Leu Val Ile Tyr Gly Lys Asn Asn Arg Pro Ser Gly Ile Pro Asp Arg
            180                 185                 190 ttc tct ggc tcc aac tca gga aac aca gct tcc ttg acc atc act ggg        624
Phe Ser Gly Ser Asn Ser Gly Asn Thr Ala Ser Leu Thr Ile Thr Gly
        195                 200                 205 gct cag gcg gaa gat gag gct gac tat tac tgt aac tcc cgg gac agc        672
Ala Gln Ala Glu Asp Glu Ala Asp Tyr Tyr Cys Asn Ser Arg Asp Ser
    210                 215                 220 agt ggt aac cat gtg gta ttc ggc gga ggg acc aag ctg acc gtc cta        720
Ser Gly Asn His Val Val Phe Gly Gly Gly Thr Lys Leu Thr Val Leu
225                 230                 235                 240 ggt                                                                    723
Gly

<210> SEQ ID NO 155
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC625 scFv protein

<400> SEQUENCE: 155 gaa gtg cag ctg gtg cag tct ggg gga ggc ttg gta aag ccg ggg ggg         48
Glu Val Gln Leu Val Gln Ser Gly Gly Gly Leu Val Lys Pro Gly Gly
1               5                   10                  15 tcc ctt aga ctc tcc tgt gca gcc tct ggt ttc act ttc agt gac gcc         96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc        144
Trp Met Asn Trp Val Arg Gln Ala Pro Gly Lys Gly Leu Glu Trp Val
        35                  40                  45 ggc cgt att aaa agt aaa cgt agt ggt ggg aca ata gac tac gcc gca        192
Gly Arg Ile Lys Ser Lys Arg Ser Gly Gly Thr Ile Asp Tyr Ala Ala
50                  55                  60 ccc gtg aaa gac aga ttc acc atc tca cga gat gat tca aaa gac acg        240
Pro Val Lys Asp Arg Phe Thr Ile Ser Arg Asp Asp Ser Lys Asp Thr
65                  70                  75                  80 atg tat ctg caa atg aac agt ctg aaa acc gag gac aca gcc ctg tat        288
Met Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc        336
Tyr Cys Thr Trp Asp Trp Asp Phe Tyr Tyr Gly Met Asn Val Trp Gly
            100                 105                 110
```

| caa ggg aca atg gtc acc gtc tcg agt ggt gga ggc ggt tca ggc gga | 384 |
|---|---|
| Gln Gly Thr Met Val Thr Val Ser Ser Gly Gly Gly Gly Ser Gly Gly | |
|     115                 120                 125 | |

| ggt ggc agc ggc ggt ggc gga tcg cag tct gtg ctg act cag cct gcc | 432 |
|---|---|
| Gly Gly Ser Gly Gly Gly Gly Ser Gln Ser Val Leu Thr Gln Pro Ala | |
| 130                 135                 140 | |

| tcc gtg tct ggg tct cct gga cag tcg atc acc atc tcc tgc act gga | 480 |
|---|---|
| Ser Val Ser Gly Ser Pro Gly Gln Ser Ile Thr Ile Ser Cys Thr Gly | |
| 145                 150                 155                 160 | |

| acc agc agt gac gtt ggt ggt tat aac tat gtc tcc tgg tac caa caa | 528 |
|---|---|
| Thr Ser Ser Asp Val Gly Gly Tyr Asn Tyr Val Ser Trp Tyr Gln Gln | |
|     165                 170                 175 | |

| cac cca ggc aaa gcc ccc aaa ctc atg att tat gag ggc agt aag cgg | 576 |
|---|---|
| His Pro Gly Lys Ala Pro Lys Leu Met Ile Tyr Glu Gly Ser Lys Arg | |
| 180                 185                 190 | |

| ccc tca ggg gtt tct aat cgc ttc ttt ggc tcc aag tct ggc aac acg | 624 |
|---|---|
| Pro Ser Gly Val Ser Asn Arg Phe Phe Gly Ser Lys Ser Gly Asn Thr | |
|     195                 200                 205 | |

| gcc tcc ctg aca atc tct ggg ctc cag gct gag gac gag gct gat tat | 672 |
|---|---|
| Ala Ser Leu Thr Ile Ser Gly Leu Gln Ala Glu Asp Glu Ala Asp Tyr | |
| 210                 215                 220 | |

| tac tgc agc tca tat aca acc agg agc act cga gtt ttc ggc gga ggg | 720 |
|---|---|
| Tyr Cys Ser Ser Tyr Thr Thr Arg Ser Thr Arg Val Phe Gly Gly Gly | |
| 225                 230                 235                 240 | |

| acc aag ctg acc gtc cta ggt | 741 |
|---|---|
| Thr Lys Leu Thr Val Leu Gly | |
|     245 | |

<210> SEQ ID NO 156
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC626 scFv protein

<400> SEQUENCE: 156

| gaa gtg cag ctg gtg cag tct ggg gga ggc ttg gta aag cct ggg gag | 48 |
|---|---|
| Glu Val Gln Leu Val Gln Ser Gly Gly Gly Leu Val Lys Pro Gly Glu | |
| 1               5                   10                  15 | |

| tca ctg aga ctc tcc tgt gaa gcc tct gga ttc gaa ttt aat tat gcc | 96 |
|---|---|
| Ser Leu Arg Leu Ser Cys Glu Ala Ser Gly Phe Glu Phe Asn Tyr Ala | |
|     20                  25                  30 | |

| tgg atg agt tgg gtc cgc cag gct cca ggg aag ggg ctg gag tgg gtt | 144 |
|---|---|
| Trp Met Ser Trp Val Arg Gln Ala Pro Gly Lys Gly Leu Glu Trp Val | |
|             35                  40                  45 | |

| ggc cgt agt aga agc gaa gct agt ggt ggg aca aca gac tac gct gca | 192 |
|---|---|
| Gly Arg Ser Arg Ser Glu Ala Ser Gly Gly Thr Thr Asp Tyr Ala Ala | |
|     50                  55                  60 | |

| ccc ctg caa gac aga ttc acc atc tca aga gat gat tca aaa aac aca | 240 |
|---|---|
| Pro Leu Gln Asp Arg Phe Thr Ile Ser Arg Asp Asp Ser Lys Asn Thr | |
| 65                  70                  75                  80 | |

| ctg tat cta caa gtc aac agc ctg aaa atc gag gac aca ggc gtg tat | 288 |
|---|---|
| Leu Tyr Leu Gln Val Asn Ser Leu Lys Ile Glu Asp Thr Gly Val Tyr | |
|                 85                  90                  95 | |

| ttc tgt aag tgg gag aaa tca gag tac tac ggt atg gac gtc tgg ggc | 336 |
|---|---|
| Phe Cys Lys Trp Glu Lys Ser Glu Tyr Tyr Gly Met Asp Val Trp Gly | |
|             100                 105                 110 | |

| cgg gga acc ccg gtc acc gtc tcc tca ggt gga ggc ggt tca ggc gga | 384 |
|---|---|
| Arg Gly Thr Pro Val Thr Val Ser Ser Gly Gly Gly Gly Ser Gly Gly | |

```
                   115                 120                 125
ggt ggc agc ggt ggt ggc gga tcg cag tct gtg ctg act cag cct gcc       432
Gly Gly Ser Gly Gly Gly Gly Ser Gln Ser Val Leu Thr Gln Pro Ala
        130                 135                 140 tcc gtg tct ggg tct cct gga cag tcg atc acc atc tcc tgc act gga       480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa       528
Thr Ser Ser Asp Val Gly Gly Tyr Asn Tyr Val Ser Trp Tyr Gln Gln
                165                 170                 175 cac cca ggc aag gcc ccc aaa ctc atg att tat gag ggc agt aag cgg       576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg       624
Pro Ser Gly Val Ser Asn Arg Phe Ser Gly Ser Lys Ser Gly Asn Thr
        195                 200                 205 gcc tcc ctg aca atc tct ggg ctc cgg gct gag gac gag gct gat tat       672
Ala Ser Leu Thr Ile Ser Gly Leu Arg Ala Glu Asp Glu Ala Asp Tyr
    210                 215                 220 tac tgc agc tca tat aca acc aag agc act caa gtt ttc ggc gga ggg       720
Tyr Cys Ser Ser Tyr Thr Thr Lys Ser Thr Gln Val Phe Gly Gly Gly
225                 230                 235                 240 acc aag ctg acc gtc cta ggt                                           741
Thr Lys Leu Thr Val Leu Gly
                245

<210> SEQ ID NO 157
<211> LENGTH: 732
<212> TYPE: DNA
<213> ORGANISM: Artificial sequence
<220> FEATURE:
<221> NAME/KEY: CDS
<222> LOCATION: (1)..(732)
<223> OTHER INFORMATION: Polynucleotide encoding GMBC627 scFv protein

<400> SEQUENCE: 157 ggg gtc cag ctg gta cag tct gga ggt gag gtg aag aag cct ggg gcc        48
Gly Val Gln Leu Val Gln Ser Gly Gly Glu Val Lys Lys Pro Gly Ala
1               5                   10                  15 tca gtg agg gtc tcc tgc aag gct tcc cgt tac atc ttt agt aac tat        96
Ser Val Arg Val Ser Cys Lys Ala Ser Arg Tyr Ile Phe Ser Asn Tyr
            20                  25                  30 ggt ttc agc tgg gtg cga cag gcc ccc gga caa ggg ctt gag tgg atg       144
Gly Phe Ser Trp Val Arg Gln Ala Pro Gly Gln Gly Leu Glu Trp Met
        35                  40                  45 ggg tcg atc agg aat gac aaa ggt agc aca aat tat gca cag ggg ttc       192
Gly Ser Ile Arg Asn Asp Lys Gly Ser Thr Asn Tyr Ala Gln Gly Phe
    50                  55                  60 cag gac aga ctc acc atg acc aca gac aca tcc acg aac aca gtc ttc       240
Gln Asp Arg Leu Thr Met Thr Thr Asp Thr Ser Thr Asn Thr Val Phe
65                  70                  75                  80 atg gag ctg agg agc ctg agt tct gac gac acg gcc gtg tat tac tgt       288
Met Glu Leu Arg Ser Leu Ser Ser Asp Asp Thr Ala Val Tyr Tyr Cys
                85                  90                  95 gcg agt gcc ccc tac tat tac ggt atg ggc atc tgg ggc aag gga acc       336
Ala Ser Ala Pro Tyr Tyr Tyr Gly Met Gly Ile Trp Gly Lys Gly Thr
            100                 105                 110 ctg gtc acc gtc tcg agt ggt gga ggc ggt tca ggc gga ggt ggc agc       384
Leu Val Thr Val Ser Ser Gly Gly Gly Gly Ser Gly Gly Gly Gly Ser
        115                 120                 125 ggc ggt ggc gga tcg cag tct gtg ctg act cag cct gcc tcc gtg tct       432
```

```

Gly Gly Gly Gly Ser Gln Ser Val Leu Thr Gln Pro Ala Ser Val Ser
        130                 135                 140 ggg tct tct gga cag tcg atc acc atc tcc tgc act gga acc agc agt    480
Gly Ser Ser Gly Gln Ser Ile Thr Ile Ser Cys Thr Gly Thr Ser Ser
145                 150                 155                 160 gac gtt ggt ggt tat aac tat gtc tcc tgg tac caa caa cac cca ggc    528
Asp Val Gly Gly Tyr Asn Tyr Val Ser Trp Tyr Gln Gln His Pro Gly
                165                 170                 175 aaa gcc ccc aaa ctc atg att tat gag gtc ggt aat cgg ccc tca ggg    576
Lys Ala Pro Lys Leu Met Ile Tyr Glu Val Gly Asn Arg Pro Ser Gly
            180                 185                 190 gtt tct aat cgc ttc tct ggc tcc aag tct ggc aac acg gcc tcc ctg    624
Val Ser Asn Arg Phe Ser Gly Ser Lys Ser Gly Asn Thr Ala Ser Leu
        195                 200                 205 aca atc tct ggg ctc cag gct gag gac gag gct gat tat tac tgc agc    672
Thr Ile Ser Gly Leu Gln Ala Glu Asp Glu Ala Asp Tyr Tyr Cys Ser
    210                 215                 220 tca tat aca acc agg agc act cga gtt ttc ggc gga ggg acc aag ctg    720
Ser Tyr Thr Thr Arg Ser Thr Arg Val Phe Gly Gly Gly Thr Lys Leu
225                 230                 235                 240 acc gtc cta ggt                                                    732
Thr Val Leu Gly <210> SEQ ID NO 158
<211> LENGTH: 747
<212> TYPE: DNA
<213> ORGANISM: Artificial sequence
<220> FEATURE:
<221> NAME/KEY: CDS
<222> LOCATION: (1)..(747)
<223> OTHER INFORMATION: Polynucleotide encoding GMBC628 scFv protein

<400> SEQUENCE: 158 cag gta cag ctg cag cag tca ggg gct gag gtg aag aag cct ggg gcc     48
Gln Val Gln Leu Gln Gln Ser Gly Ala Glu Val Lys Lys Pro Gly Ala
1               5                   10                  15 tca gtg agg gtc tcc tgc aag gct tct ggt tac acc ttt acc agc tat     96
Ser Val Arg Val Ser Cys Lys Ala Ser Gly Tyr Thr Phe Thr Ser Tyr
            20                  25                  30 ggt ttc agc tgg gtg cga cag gcc cct ggg caa agg ctt gag tgg atg    144
Gly Phe Ser Trp Val Arg Gln Ala Pro Gly Gln Arg Leu Glu Trp Met
        35                  40                  45 gga tgg atc agc gct tac aaa gga aac gcg aac tat gca gag aag ttc    192
Gly Trp Ile Ser Ala Tyr Lys Gly Asn Ala Asn Tyr Ala Glu Lys Phe
    50                  55                  60 cag ggc aga gtc acc atg acc aca gac aca tcc acg aac aca gcc tac    240
Gln Gly Arg Val Thr Met Thr Thr Asp Thr Ser Thr Asn Thr Ala Tyr
65                  70                  75                  80 atg gaa ctg agg agc ctg aga tct gac gac acg gcc gtg tat tac tgt    288
Met Glu Leu Arg Ser Leu Arg Ser Asp Asp Thr Ala Val Tyr Tyr Cys
                85                  90                  95 gcg aga act cgg ata tca gtg gct ggc cta gac tac tac tac ggt        336
Ala Arg Thr Arg Ile Ser Val Ala Gly Leu Asp Tyr Tyr Tyr Gly
            100                 105                 110 ttg gac gtc tgg ggg agg gga acc ctg gtc acc gtc tcc tca ggt gga    384
Leu Asp Val Trp Gly Arg Gly Thr Leu Val Thr Val Ser Ser Gly Gly
        115                 120                 125 ggc ggt tca ggc gga ggt ggc agc ggc ggt ggc gga tcg tct gag ctg    432
Gly Gly Ser Gly Gly Gly Gly Ser Gly Gly Gly Gly Ser Ser Glu Leu
    130                 135                 140 act cag gac cct gct gtg tct gtg gcc ttg gga cag aca gtc agg atc    480
```

```
Thr Gln Asp Pro Ala Val Ser Val Ala Leu Gly Gln Thr Val Arg Ile
145                 150                 155                 160 act tgc caa gga gac agt ctc aga agc tat tac aca aac tgg ttc cag       528
Thr Cys Gln Gly Asp Ser Leu Arg Ser Tyr Tyr Thr Asn Trp Phe Gln
                165                 170                 175 cag aag cca gga cag gcc cct cta ctt gtc gtc tat gct aaa aac aac       576
Gln Lys Pro Gly Gln Ala Pro Leu Leu Val Val Tyr Ala Lys Asn Asn
            180                 185                 190 cgg ccc tca ggg atc cca gac cga ttc tct ggc tcc agc tca gga aac       624
Arg Pro Ser Gly Ile Pro Asp Arg Phe Ser Gly Ser Ser Ser Gly Asn
        195                 200                 205 aca gct tcc ttg acc atc act ggg gct caa gcg gaa gat gag gct gac       672
Thr Ala Ser Leu Thr Ile Thr Gly Ala Gln Ala Glu Asp Glu Ala Asp
    210                 215                 220 tat tac tgt aac tcc cgg gac agc agt ggt aac cat gtg gta ttc ggc       720
Tyr Tyr Cys Asn Ser Arg Asp Ser Ser Gly Asn His Val Val Phe Gly
225                 230                 235                 240 gga ggg acc aag ctg acc gtc cta ggt                                   747
Gly Gly Thr Lys Leu Thr Val Leu Gly
                245
```

<210> SEQ ID NO 159
<211> LENGTH: 732
<212> TYPE: DNA
<213> ORGANISM: Artificial sequence
<220> FEATURE:
<221> NAME/KEY: CDS
<222> LOCATION: (1)..(732)
<223> OTHER INFORMATION: Polynucleotide encoding GMBC629 scFv protein

<400> SEQUENCE: 159

```
cag gtg cag ctg gtg gag tct ggg gga ggc ttg gta aag ccg ggg ggg        48
Gln Val Gln Leu Val Glu Ser Gly Gly Gly Leu Val Lys Pro Gly Gly
1               5                   10                  15 tcc ctt aga ctc tcc tgt gca ggc tct ggt ttc aaa ttc agt gac gcc        96
Ser Leu Arg Leu Ser Cys Ala Gly Ser Gly Phe Lys Phe Ser Asp Ala
            20                  25                  30 tgg atg aat tgg gtc cgc cag gct cca ggg aag ggg ctg gag tgg gtc       144
Trp Met Asn Trp Val Arg Gln Ala Pro Gly Lys Gly Leu Glu Trp Val
        35                  40                  45 ggc cgt att aaa agc aaa ggt agt ggt ggg aca ata gag tac gct gta       192
Gly Arg Ile Lys Ser Lys Gly Ser Gly Gly Thr Ile Glu Tyr Ala Val
    50                  55                  60 ccc gtg aaa gac aga ttc atc atc tca cga gat gat tca aaa gac acg       240
Pro Val Lys Asp Arg Phe Ile Ile Ser Arg Asp Asp Ser Lys Asp Thr
65                  70                  75                  80 ttg tat ctg caa atg aac agt ctg aaa acc gag gac aca gcc ctg tat       288
Leu Tyr Leu Gln Met Asn Ser Leu Lys Thr Glu Asp Thr Ala Leu Tyr
                85                  90                  95 tat tgt acg tgg gac tgg gat ttc tac tac ggt atg aac gtc tgg ggc       336
Tyr Cys Thr Trp Asp Trp Asp Phe Tyr Tyr Gly Met Asn Val Trp Gly
            100                 105                 110 cag gga acc ctg gtc acc gtc tcg agt ggt gga ggc ggt tca ggc gga       384
Gln Gly Thr Leu Val Thr Val Ser Ser Gly Gly Gly Gly Ser Gly Gly
        115                 120                 125 ggt ggc agc ggc ggt ggc gga tcg tct gag ctg act cag gac cct gct       432
Gly Gly Ser Gly Gly Gly Gly Ser Ser Glu Leu Thr Gln Asp Pro Ala
    130                 135                 140 gtg tct gtg gcc ttg gga cag aca gtc agg atc act tgc caa gga gac       480
Val Ser Val Ala Leu Gly Gln Thr Val Arg Ile Thr Cys Gln Gly Asp
145                 150                 155                 160
```

-continued

```
agt ctc aga agc tat tac aca aac tgg ttc cag cag aag cca gga cag    528
Ser Leu Arg Ser Tyr Tyr Thr Asn Trp Phe Gln Gln Lys Pro Gly Gln
            165                 170                 175 gcc cct cta ctt gtc gtc tat gct aaa aat aag cgg ccc tca ggg atc    576
Ala Pro Leu Leu Val Val Tyr Ala Lys Asn Lys Arg Pro Ser Gly Ile
        180                 185                 190 cca gac cga ttc tct ggc tcc agc tca gga aac aca gct tcc ttg acc    624
Pro Asp Arg Phe Ser Gly Ser Ser Ser Gly Asn Thr Ala Ser Leu Thr
            195                 200                 205 atc act ggg gct cag gcg gaa gat gag gct gac tat tac tgt cat tcc    672
Ile Thr Gly Ala Gln Ala Glu Asp Glu Ala Asp Tyr Tyr Cys His Ser
        210                 215                 220 cgg gac agc agt ggt aac cat gtg ctt ttc ggc gga ggg acc aaa ctg    720
Arg Asp Ser Ser Gly Asn His Val Leu Phe Gly Gly Gly Thr Lys Leu
225                 230                 235                 240 acc gtc cta ggt                                                    732
Thr Val Leu Gly
```

```
<210> SEQ ID NO 160
<211> LENGTH: 726
<212> TYPE: DNA
<213> ORGANISM: Artificial sequence
<220> FEATURE:
<221> NAME/KEY: CDS
<222> LOCATION: (1)..(726)
<223> OTHER INFORMATION: Polynucleotide encoding GMBC630 scFv protein

<400> SEQUENCE: 160
```

```
cag gtg cag ctg gtg gag tct ggg gga ggc ttg gtc cag cct ggg agg     48
Gln Val Gln Leu Val Glu Ser Gly Gly Gly Leu Val Gln Pro Gly Arg
1               5                   10                  15 tcc ctg aga ctc ccc tgt gca gcc tct gga ttc act ttc agt agc tat    96
Ser Leu Arg Leu Pro Cys Ala Ala Ser Gly Phe Thr Phe Ser Ser Tyr
            20                  25                  30 ggc atg cac tgg gtc cgc cag gct cca ggc aag ggg ctg gag tgg gtg   144
Gly Met His Trp Val Arg Gln Ala Pro Gly Lys Gly Leu Glu Trp Val
        35                  40                  45 gca gtt ata tca tat gat gga agt aat aaa tac tat gca gac tcc gtg   192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aac acg ctg tat   240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt   288
Leu Gln Met Asn Ser Leu Arg Ala Glu Asp Thr Ala Val Tyr Tyr Cys
                85                  90                  95 gcg aag gct act tct ttg cta aat gct ttt gat atc tgg ggc cgg gga   336
Ala Lys Ala Thr Ser Leu Leu Asn Ala Phe Asp Ile Trp Gly Arg Gly
            100                 105                 110 acc atg gtc acc gtc tct tca ggt gga ggc ggt tca ggc gga ggt ggc   384
Thr Met Val Thr Val Ser Ser Gly Gly Gly Gly Ser Gly Gly Gly Gly
        115                 120                 125 agc ggc ggt ggc gga tcg tct gag ctg act cag gac cct gct gtg tct   432
Ser Gly Gly Gly Gly Ser Ser Glu Leu Thr Gln Asp Pro Ala Val Ser
    130                 135                 140 gtg gcc ttg gga cag aca gtc agg atc aca tgc caa gga gac agc ctc   480
Val Ala Leu Gly Gln Thr Val Arg Ile Thr Cys Gln Gly Asp Ser Leu
145                 150                 155                 160 aga agc tat tat gca agc tgg tac cag cag aag cca gga cag gcc cct   528
Arg Ser Tyr Tyr Ala Ser Trp Tyr Gln Gln Lys Pro Gly Gln Ala Pro
                165                 170                 175
```

```
gta ctt gtc atc tat ggt aaa aac aac cgg ccc tca ggg atc cca gac      576
Val Leu Val Ile Tyr Gly Lys Asn Asn Arg Pro Ser Gly Ile Pro Asp
        180                 185                 190 cga ttc tct ggc tcc agc tca gga aac aca gct tcc ttg acc atc act      624
Arg Phe Ser Gly Ser Ser Ser Gly Asn Thr Ala Ser Leu Thr Ile Thr
    195                 200                 205 ggg gct cag gcg gaa gat gag gct gac tat tac tgt aac tcc cgg gac      672
Gly Ala Gln Ala Glu Asp Glu Ala Asp Tyr Tyr Cys Asn Ser Arg Asp
210                 215                 220 agc agt ggt aac cat gtg gta ttc ggc gga ggg acc aag ctg acc gtc      720
Ser Ser Gly Asn His Val Val Phe Gly Gly Gly Thr Lys Leu Thr Val
225                 230                 235                 240 cta ggt                                                              726
Leu Gly <210> SEQ ID NO 161
<211> LENGTH: 732
<212> TYPE: DNA
<213> ORGANISM: Artificial sequence
<220> FEATURE:
<221> NAME/KEY: CDS
<222> LOCATION: (1)..(732)
<223> OTHER INFORMATION: Polynucleotide encoding GMBC632 scFv protein

<400> SEQUENCE: 161 cag gtc cag ctg gtg cag tct ggg gga ggc ttg gta aag ccg ggg ggg       48
Gln Val Gln Leu Val Gln Ser Gly Gly Gly Leu Val Lys Pro Gly Gly
1               5                   10                  15 tcc ctt aga ctc tcc tgt gca ggc tct ggt ttc aaa ttc agt gac gcc       96
Ser Leu Arg Leu Ser Cys Ala Gly Ser Gly Phe Lys Phe Ser Asp Ala
            20                  25                  30 tgg atg aat tgg gtc cgc cag gct cca ggg aag ggg ctg gag tgg gtc      144
Trp Met Asn Trp Val Arg Gln Ala Pro Gly Lys Gly Leu Glu Trp Val
        35                  40                  45 ggc cgt att aaa agc aaa ggt agt ggg gga aca ata gag tac gct gca      192
Gly Arg Ile Lys Ser Lys Gly Ser Gly Gly Thr Ile Glu Tyr Ala Ala
    50                  55                  60 ccc gtg aaa gac aga ttc atc atc tca cga gat gat tca aaa gac acg      240
Pro Val Lys Asp Arg Phe Ile Ile Ser Arg Asp Asp Ser Lys Asp Thr
65                  70                  75                  80 ctg tat ctg caa atg aac agt ctg aaa acc gag gac aca gcc ctg tat      288
Leu Tyr Leu Gln Met Asn Ser Leu Lys Thr Glu Asp Thr Ala Leu Tyr
                85                  90                  95 tat tgt acg tgg gac tgg gat ttc tac tac gat atg aac gtc tgg ggc      336
Tyr Cys Thr Trp Asp Trp Asp Phe Tyr Tyr Asp Met Asn Val Trp Gly
            100                 105                 110 cag ggg aca atg gtc acc gtc tcc tca ggt gga ggc ggt tca ggc gga      384
Gln Gly Thr Met Val Thr Val Ser Ser Gly Gly Gly Gly Ser Gly Gly
        115                 120                 125 ggt ggc agc ggc ggt ggc gga tcg tct gag ctg act cag gac cct gct      432
Gly Gly Ser Gly Gly Gly Gly Ser Ser Glu Leu Thr Gln Asp Pro Ala
    130                 135                 140 gtg tct gtg gcc ttg gga cag aca gtc agg atc aca tgc caa gga gac      480
Val Ser Val Ala Leu Gly Gln Thr Val Arg Ile Thr Cys Gln Gly Asp
145                 150                 155                 160 agc ctc aga agc tat tat gca agc tgg tac cag cag aag cca gga cag      528
Ser Leu Arg Ser Tyr Tyr Ala Ser Trp Tyr Gln Gln Lys Pro Gly Gln
                165                 170                 175 gcc cct gta ctt gtc atc tat ggt aaa aac aac cgg ccc tca ggg atc      576
Ala Pro Val Leu Val Ile Tyr Gly Lys Asn Asn Arg Pro Ser Gly Ile
            180                 185                 190
```

```
cca gac cga ttc ttt ggc tcc agc tca gga aac aca gct tcc ttg acc      624
Pro Asp Arg Phe Phe Gly Ser Ser Ser Gly Asn Thr Ala Ser Leu Thr
        195                 200                 205 atc act ggg gct cag gcg gaa gat gag gct gac tat tac tgt aac tcc      672
Ile Thr Gly Ala Gln Ala Glu Asp Glu Ala Asp Tyr Tyr Cys Asn Ser
    210                 215                 220 cgg gac agc agt ggt aac cat gtg gta ttc ggc gga ggg acc aag ctg      720
Arg Asp Ser Ser Gly Asn His Val Val Phe Gly Gly Gly Thr Lys Leu
225                 230                 235                 240 acc gtc cta ggt                                                      732
Thr Val Leu Gly <210> SEQ ID NO 162
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC634 scFv protein

<400> SEQUENCE: 162 cag gtg cag ctg gtg cag tct ggg gga ggc ttg gta aag ccg ggg ggg       48
Gln Val Gln Leu Val Gln Ser Gly Gly Gly Leu Val Lys Pro Gly Gly
1               5                   10                  15 tcc ctt aga ctc tcc tgt gca gcc tct ggt ttc act ttc agt gac gcc      96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc     144
Trp Met Asn Trp Val Arg Gln Ala Pro Gly Lys Gly Leu Glu Trp Val
        35                  40                  45 ggc cgt att aaa agc aaa ggt agt ggg aca ata gac tac gct gca         192
Gly Arg Ile Lys Ser Lys Gly Ser Gly Gly Thr Ile Asp Tyr Ala Ala
    50                  55                  60 ccc gtg aaa gac aga ttc acc atc tca cga gat gat tca aaa aac acg     240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc ctg tat     288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc     336
Tyr Cys Thr Trp Asp Trp Asp Phe Tyr Tyr Gly Met Asn Val Trp Gly
            100                 105                 110 caa ggc acc ctg gtc acc gtc tcg agt ggt gga ggc ggt tca ggc gga     384
Gln Gly Thr Leu Val Thr Val Ser Ser Gly Gly Gly Gly Ser Gly Gly
        115                 120                 125 ggt ggc agc ggc ggt ggc gga tcg cag tct gtg ctg act cag cct gcc     432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga     480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa     528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg     576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg     624
Pro Ser Gly Val Ser Asn Arg Phe Ser Gly Ser Lys Ser Gly Asn Thr
        195                 200                 205
```

| | | |
|---|---|---|
| gcc tcc ctg aca atc tct ggg ctc cag gct gag gac gag gct gat tat<br>Ala Ser Leu Thr Ile Ser Gly Leu Gln Ala Glu Asp Glu Ala Asp Tyr<br>210 215 220 | | 672 |
| tac tgc agc tca tat aca acc agg agc act cga gtt ttc ggc gga ggg<br>Tyr Cys Ser Ser Tyr Thr Thr Arg Ser Thr Arg Val Phe Gly Gly Gly<br>225 230 235 240 | | 720 |
| acc aag ctg acc gtc cta ggt<br>Thr Lys Leu Thr Val Leu Gly<br>245 | | 741 |

<210> SEQ ID NO 163
<211> LENGTH: 732
<212> TYPE: DNA
<213> ORGANISM: Artificial sequence
<220> FEATURE:
<221> NAME/KEY: CDS
<222> LOCATION: (1)..(732)
<223> OTHER INFORMATION: Polynucleotide encoding GMBC635 scFv protein

<400> SEQUENCE: 163

| | | |
|---|---|---|
| gag gtg cag ctg gtg gag tct ggg gga ggc ttg gta aag ccg ggg ggg<br>Glu Val Gln Leu Val Glu Ser Gly Gly Gly Leu Val Lys Pro Gly Gly<br>1 5 10 15 | | 48 |
| tcc ctt aga ctc tcc tgt gca gcc tct ggt ttc act ttc agt gac gcc<br>Ser Leu Arg Leu Ser Cys Ala Ala Ser Gly Phe Thr Phe Ser Asp Ala<br>20 25 30 | | 96 |
| tgg atg aac tgg gtc cgc cag gct cca ggg aag ggg ctg gag tgg gtc<br>Trp Met Asn Trp Val Arg Gln Ala Pro Gly Lys Gly Leu Glu Trp Val<br>35 40 45 | | 144 |
| ggc cgt att aaa agc aaa ggt agt ggt ggg aca ata gac tac gcc gca<br>Gly Arg Ile Lys Ser Lys Gly Ser Gly Gly Thr Ile Asp Tyr Ala Ala<br>50 55 60 | | 192 |
| ccc gtg aaa gac aga tac acc atc tca cga gat gat tca aaa aac acg<br>Pro Val Lys Asp Arg Tyr Thr Ile Ser Arg Asp Asp Ser Lys Asn Thr<br>65 70 75 80 | | 240 |
| ctg tat ctg caa atg aac agt ctg aaa acc gag gac aca gcc ctg tat<br>Leu Tyr Leu Gln Met Asn Ser Leu Lys Thr Glu Asp Thr Ala Leu Tyr<br>85 90 95 | | 288 |
| tac tgt acg tgg gac tgg gat ttc tac tac ggt atg aac gtc tgg ggc<br>Tyr Cys Thr Trp Asp Trp Asp Phe Tyr Tyr Gly Met Asn Val Trp Gly<br>100 105 110 | | 336 |
| aag ggg aca atg gtc acc gtc tcg agt ggt gga ggc ggt tca ggc gga<br>Lys Gly Thr Met Val Thr Val Ser Ser Gly Gly Gly Gly Ser Gly Gly<br>115 120 125 | | 384 |
| ggt ggc agc ggc ggt ggc gga tcg tct gag ctg act cag gac cct gct<br>Gly Gly Ser Gly Gly Gly Gly Ser Ser Glu Leu Thr Gln Asp Pro Ala<br>130 135 140 | | 432 |
| gtg tct gtg gcc ttg gga cag aca gtc agg atc aca tgc caa gga gac<br>Val Ser Val Ala Leu Gly Gln Thr Val Arg Ile Thr Cys Gln Gly Asp<br>145 150 155 160 | | 480 |
| agc ctc aga agc tat tat gca agc tgg tac cag cag aag cca gga cag<br>Ser Leu Arg Ser Tyr Tyr Ala Ser Trp Tyr Gln Gln Lys Pro Gly Gln<br>165 170 175 | | 528 |
| gcc cct gta ctt gtc atc tat ggt aaa aac aac cgg ccc tca ggg atc<br>Ala Pro Val Leu Val Ile Tyr Gly Lys Asn Asn Arg Pro Ser Gly Ile<br>180 185 190 | | 576 |
| cca gac cga ttc tct ggc tcc agc tca gga aac aca gct tcc ttg acc<br>Pro Asp Arg Phe Ser Gly Ser Ser Ser Gly Asn Thr Ala Ser Leu Thr<br>195 200 205 | | 624 |
| atc act ggg gct cag gcg gaa gat gag gct gac tat tac tgt aac tcc<br>Ile Thr Gly Ala Gln Ala Glu Asp Glu Ala Asp Tyr Tyr Cys Asn Ser<br>210 215 220 | | 672 |

```
cgg gac agc agt ggt aac cat gtg gta ttc ggc gga ggg acc aag ctg      720
Arg Asp Ser Ser Gly Asn His Val Val Phe Gly Gly Gly Thr Lys Leu
225                 230                 235                 240 acc gtc cta ggt                                                       732
Thr Val Leu Gly <210> SEQ ID NO 164
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC638 scFv protein

<400> SEQUENCE: 164 cag gtg cag ctg gtg caa tct ggg gga ggc ttg gta aag cct ggg gag       48
Gln Val Gln Leu Val Gln Ser Gly Gly Gly Leu Val Lys Pro Gly Glu
1               5                   10                  15 tca ctg aga ctc tcc tgt gaa gcc tct gga ttc gaa ttt aat tat gcc       96
Ser Leu Arg Leu Ser Cys Glu Ala Ser Gly Phe Glu Phe Asn Tyr Ala
            20                  25                  30 tgg atg agt tgg gtc cgc cag gct cca ggg aag ggg ctg gag tgg gtt      144
Trp Met Ser Trp Val Arg Gln Ala Pro Gly Lys Gly Leu Glu Trp Val
        35                  40                  45 ggc cgt agt aga agc gta gct agt ggt ggg aca aca gac tac gct gcg      192
Gly Arg Ser Arg Ser Val Ala Ser Gly Gly Thr Thr Asp Tyr Ala Ala
    50                  55                  60 ccc ctg caa gac aga ttc acc atc tca aga gat gat tca aaa aac aca      240
Pro Leu Gln Asp Arg Phe Thr Ile Ser Arg Asp Asp Ser Lys Asn Thr
65                  70                  75                  80 ctg tat cta caa gtc aac agc ctg aaa atc gag gac aca ggc gtg tat      288
Leu Tyr Leu Gln Val Asn Ser Leu Lys Ile Glu Asp Thr Gly Val Tyr
                85                  90                  95 ttc tgt aag tgg gag aaa tca gag tac tac ggt atg gac gtc tgg ggc      336
Phe Cys Lys Trp Glu Lys Ser Glu Tyr Tyr Gly Met Asp Val Trp Gly
            100                 105                 110 cga ggg aca atg gtc acc gtc tcg agt ggt gga ggc ggt tca ggc gga      384
Arg Gly Thr Met Val Thr Val Ser Ser Gly Gly Gly Gly Ser Gly Gly
        115                 120                 125 ggt ggc agc ggc ggt ggc gga tcg cag tct gtg ctg act cag cct gcc      432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga      480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa      528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg      576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg      624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat      672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg      720
Tyr Cys Ser Ser Tyr Thr Thr Arg Ser Thr Arg Val Phe Gly Gly Gly
225                 230                 235                 240
```

```
acc aag ctg acc gtc cta ggt                                              741
Thr Lys Leu Thr Val Leu Gly
            245

<210> SEQ ID NO 165
<211> LENGTH: 759
<212> TYPE: DNA
<213> ORGANISM: Artificial sequence
<220> FEATURE:
<221> NAME/KEY: CDS
<222> LOCATION: (1)..(759)
<223> OTHER INFORMATION: Polynucleotide encoding GMBC639 scFv protein

<400> SEQUENCE: 165 gga gtg cag ctg gtg cag tct ggg gct gag gtg aag acg cct ggg gcc           48
Gly Val Gln Leu Val Gln Ser Gly Ala Glu Val Lys Thr Pro Gly Ala
1               5                   10                  15 tca gtg aag gtt tcc tgc aag gca tct gga tac act ttc acc aac cac           96
Ser Val Lys Val Ser Cys Lys Ala Ser Gly Tyr Thr Phe Thr Asn His
            20                  25                  30 tat atg cac tgg gtg cga cag gcc cct gga caa gga att gag tgg gtg          144
Tyr Met His Trp Val Arg Gln Ala Pro Gly Gln Gly Ile Glu Trp Val
        35                  40                  45 gga gta atc aat cct agt ggt gat ggt tca agc tac gca cag acg ttc          192
Gly Val Ile Asn Pro Ser Gly Asp Gly Ser Ser Tyr Ala Gln Thr Phe
    50                  55                  60 cag ggc aga gtc acc atg acc agg gac acg tcc acg agc aca gtt tac          240
Gln Gly Arg Val Thr Met Thr Arg Asp Thr Ser Thr Ser Thr Val Tyr
65                  70                  75                  80 atg gag ttg agg agc ctg aga tct gac gac acg gcc gtc tac tac tgt          288
Met Glu Leu Arg Ser Leu Arg Ser Asp Asp Thr Ala Val Tyr Tyr Cys
                85                  90                  95 gcg aga gat ctg ttt tac gat ttt tgg agt gat tat tat cga aat gat          336
Ala Arg Asp Leu Phe Tyr Asp Phe Trp Ser Asp Tyr Tyr Arg Asn Asp
            100                 105                 110 cag tac tac tac atg gac gtc tgg ggc aag ggc acc ctg gtc acc gtc          384
Gln Tyr Tyr Tyr Met Asp Val Trp Gly Lys Gly Thr Leu Val Thr Val
        115                 120                 125 tct tca ggt gga ggc ggt tca ggc gga ggt ggc agc ggc ggt ggc gga          432
Ser Ser Gly Gly Gly Gly Ser Gly Gly Gly Gly Ser Gly Gly Gly Gly
    130                 135                 140 tcg tct gag ctg act cag gac cct gct gtg tct gtg gcc ttg gga cag          480
Ser Ser Glu Leu Thr Gln Asp Pro Ala Val Ser Val Ala Leu Gly Gln
145                 150                 155                 160 gca gtc agg atc aca tgc caa gga gac agc ctc aga agc tat tat gca          528
Ala Val Arg Ile Thr Cys Gln Gly Asp Ser Leu Arg Ser Tyr Tyr Ala
                165                 170                 175 agc tgg tac cag cag aag cca gga cag gcc cct gta ctt gtc atc tat          576
Ser Trp Tyr Gln Gln Lys Pro Gly Gln Ala Pro Val Leu Val Ile Tyr
            180                 185                 190 ggt aaa aac aac cgg ccc tca ggg atc cca gac cga ttc tct ggc tcc          624
Gly Lys Asn Asn Arg Pro Ser Gly Ile Pro Asp Arg Phe Ser Gly Ser
        195                 200                 205 agc tca gga aac aca gct tcc ttg acc atc act ggg gct cag gcg gaa          672
Ser Ser Gly Asn Thr Ala Ser Leu Thr Ile Thr Gly Ala Gln Ala Glu
    210                 215                 220 gat gag gct gac tat tac tgt aac tcc cgg gac agc agt ggt aac cat          720
Asp Glu Ala Asp Tyr Tyr Cys Asn Ser Arg Asp Ser Ser Gly Asn His
225                 230                 235                 240 gtg gta ttc ggc gga ggg acc aag ctg acc gtc cta ggt                      759
Val Val Phe Gly Gly Gly Thr Lys Leu Thr Val Leu Gly
                245                 250
```

<210> SEQ ID NO 166
<211> LENGTH: 729
<212> TYPE: DNA
<213> ORGANISM: Artificial sequence
<220> FEATURE:
<221> NAME/KEY: CDS
<222> LOCATION: (1)..(729)
<223> OTHER INFORMATION: Polynucleotide encoding GMBC641 scFv protein

<400> SEQUENCE: 166

```
gag gtg cag ctg gtg gag tct ggg gga ggc gtg gtc cgg cct ggg agg      48
Glu Val Gln Leu Val Glu Ser Gly Gly Gly Val Val Arg Pro Gly Arg
1               5                   10                  15 tcc ctg aga ctc tcc tgt gca gcc tct gga ttc agc ttc agt agc tat      96
Ser Leu Arg Leu Ser Cys Ala Ala Ser Gly Phe Ser Phe Ser Ser Tyr
            20                  25                  30 ggc atg cac tgg gtc cgc cag gct cca ggg aag ggg ctg gag tgg gtc     144
Gly Met His Trp Val Arg Gln Ala Pro Gly Lys Gly Leu Glu Trp Val
        35                  40                  45 tca gct att agt ggt agt ggt ggt agc aca tac tac gca gac tcc gtg     192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agt ctg aga gcc gag gac acg gct gtg tat ttc tgt     288
Leu Gln Met Asn Ser Leu Arg Ala Glu Asp Thr Ala Val Tyr Phe Cys
                85                  90                  95 gca aag ggt gga gac cgg agc ttc cgt gct ttt gat ttc tgg ggc cag     336
Ala Lys Gly Gly Asp Arg Ser Phe Arg Ala Phe Asp Phe Trp Gly Gln
            100                 105                 110 ggg aca atg gtc acc gtc tcc tca ggt gga ggc ggt tca ggc gga ggt     384
Gly Thr Met Val Thr Val Ser Ser Gly Gly Gly Gly Ser Gly Gly Gly
        115                 120                 125 ggc agc ggc ggt ggc gga tcg tct gag ctg act cag gac cct gct gtg     432
Gly Ser Gly Gly Gly Gly Ser Ser Glu Leu Thr Gln Asp Pro Ala Val
    130                 135                 140 tct gtg gcc ttg gga cag aca gtc agg atc aca tgc caa gga gac agc     480
Ser Val Ala Leu Gly Gln Thr Val Arg Ile Thr Cys Gln Gly Asp Ser
145                 150                 155                 160 ctc aga agc tat tat gca agc tgg tac cag cag aag cca gga cag gcc     528
Leu Arg Ser Tyr Tyr Ala Ser Trp Tyr Gln Gln Lys Pro Gly Gln Ala
                165                 170                 175 cct gta ctt gtc atc tat ggt aaa aac aac cgg ccc tca ggg atc cca     576
Pro Val Leu Val Ile Tyr Gly Lys Asn Asn Arg Pro Ser Gly Ile Pro
            180                 185                 190 gac cga ttc tct ggc tcc agc tca gga aac aca gct tcc ttg acc atc     624
Asp Arg Phe Ser Gly Ser Ser Ser Gly Asn Thr Ala Ser Leu Thr Ile
        195                 200                 205 act ggg gct cag gcg gaa gat gag gct gac tat tac tgt aac tcc cgg     672
Thr Gly Ala Gln Ala Glu Asp Glu Ala Asp Tyr Tyr Cys Asn Ser Arg
    210                 215                 220 gac agc agt ggt aac cat gtg gta ttc ggc gga ggg acc aag ctg acc     720
Asp Ser Ser Gly Asn His Val Val Phe Gly Gly Gly Thr Lys Leu Thr
225                 230                 235                 240 gtc cta ggt                                                          729
Val Leu Gly
```

<210> SEQ ID NO 167

<211> LENGTH: 729
<212> TYPE: DNA
<213> ORGANISM: Artificial sequence
<220> FEATURE:
<221> NAME/KEY: CDS
<222> LOCATION: (1)..(729)
<223> OTHER INFORMATION: Polynucleotide encoding GMBC642 scFv protein

<400> SEQUENCE: 167

| | | | | | | | | | | | | | | | | |
|---|---|---|---|---|---|---|---|---|---|---|---|---|---|---|---|---|
| cag | gta | cag | ctg | cag | cag | tca | ggg | gct | gag | gtg | aag | aag | cct | ggg | gcc | 48 |
| Gln | Val | Gln | Leu | Gln | Gln | Ser | Gly | Ala | Glu | Val | Lys | Lys | Pro | Gly | Ala | |
| 1 | | | | 5 | | | | | 10 | | | | | 15 | | |
| tca | gtg | aag | gtt | tcc | tgc | aag | gca | tct | gga | tac | acc | ttc | acc | atc | cac | 96 |
| Ser | Val | Lys | Val | Ser | Cys | Lys | Ala | Ser | Gly | Tyr | Thr | Phe | Thr | Ile | His | |
| | | | 20 | | | | | 25 | | | | | 30 | | | |
| tat | atg | cat | tgg | gtg | cga | cag | gcc | cct | gga | caa | gga | ctt | gag | tgg | atg | 144 |
| Tyr | Met | His | Trp | Val | Arg | Gln | Ala | Pro | Gly | Gln | Gly | Leu | Glu | Trp | Met | |
| | | 35 | | | | | 40 | | | | | 45 | | | | |
| gga | ata | atc | aac | cct | ggt | gat | ggt | agc | act | agt | tac | gca | cag | aac | ttc | 192 |
| Gly | Ile | Ile | Asn | Pro | Gly | Asp | Gly | Ser | Thr | Ser | Tyr | Ala | Gln | Asn | Phe | |
| | 50 | | | | | 55 | | | | | 60 | | | | | |
| cag | ggc | aga | gtc | acc | atg | acc | agg | gac | acg | tcc | acg | agc | aca | gtc | tat | 240 |
| Gln | Gly | Arg | Val | Thr | Met | Thr | Arg | Asp | Thr | Ser | Thr | Ser | Thr | Val | Tyr | |
| 65 | | | | | 70 | | | | | 75 | | | | | 80 | |
| atg | gag | ctg | agc | agc | ctg | aga | tct | gag | gac | acg | gcc | gtg | tat | tac | tgt | 288 |
| Met | Glu | Leu | Ser | Ser | Leu | Arg | Ser | Glu | Asp | Thr | Ala | Val | Tyr | Tyr | Cys | |
| | | | | 85 | | | | | 90 | | | | | 95 | | |
| gcg | aga | gca | ggg | cga | act | gtg | act | tct | cac | ttt | gac | tac | tgg | ggc | cga | 336 |
| Ala | Arg | Ala | Gly | Arg | Thr | Val | Thr | Ser | His | Phe | Asp | Tyr | Trp | Gly | Arg | |
| | | | 100 | | | | | 105 | | | | | 110 | | | |
| ggc | acc | ctg | gcc | acc | gtc | tcc | tca | ggt | gga | ggc | ggt | tca | ggc | gga | ggt | 384 |
| Gly | Thr | Leu | Ala | Thr | Val | Ser | Ser | Gly | Gly | Gly | Gly | Ser | Gly | Gly | Gly | |
| | | 115 | | | | | 120 | | | | | 125 | | | | |
| ggc | agc | ggc | ggt | ggc | gga | tcg | tct | gag | ctg | act | cag | gac | cct | gct | gtg | 432 |
| Gly | Ser | Gly | Gly | Gly | Gly | Ser | Ser | Glu | Leu | Thr | Gln | Asp | Pro | Ala | Val | |
| | 130 | | | | | 135 | | | | | 140 | | | | | |
| tct | gtg | gcc | ttg | gga | cag | aca | gtc | agg | atc | aca | tgc | caa | gga | gac | agc | 480 |
| Ser | Val | Ala | Leu | Gly | Gln | Thr | Val | Arg | Ile | Thr | Cys | Gln | Gly | Asp | Ser | |
| 145 | | | | | 150 | | | | | 155 | | | | | 160 | |
| ctc | aga | agc | tat | tat | gca | agc | tgg | tac | cag | cag | aag | cca | gga | cag | gcc | 528 |
| Leu | Arg | Ser | Tyr | Tyr | Ala | Ser | Trp | Tyr | Gln | Gln | Lys | Pro | Gly | Gln | Ala | |
| | | | | 165 | | | | | 170 | | | | | 175 | | |
| cct | gta | ctt | gtc | atc | tat | ggt | aaa | aac | aac | cgg | ccc | tca | ggg | atc | cca | 576 |
| Pro | Val | Leu | Val | Ile | Tyr | Gly | Lys | Asn | Asn | Arg | Pro | Ser | Gly | Ile | Pro | |
| | | | 180 | | | | | 185 | | | | | 190 | | | |
| gac | cga | ttc | tct | ggc | tcc | agc | tca | gga | aac | aca | gct | tcc | ttg | acc | atc | 624 |
| Asp | Arg | Phe | Ser | Gly | Ser | Ser | Ser | Gly | Asn | Thr | Ala | Ser | Leu | Thr | Ile | |
| | | 195 | | | | | 200 | | | | | 205 | | | | |
| act | ggg | gct | cag | gcg | gaa | gat | gag | gct | gac | tat | tac | tgt | aac | tcc | cgg | 672 |
| Thr | Gly | Ala | Gln | Ala | Glu | Asp | Glu | Ala | Asp | Tyr | Tyr | Cys | Asn | Ser | Arg | |
| | 210 | | | | | 215 | | | | | 220 | | | | | |
| gac | agc | agt | ggt | aac | cat | gtg | gta | ttc | ggc | gga | ggg | acc | aag | ctg | acc | 720 |
| Asp | Ser | Ser | Gly | Asn | His | Val | Val | Phe | Gly | Gly | Gly | Thr | Lys | Leu | Thr | |
| 225 | | | | | 230 | | | | | 235 | | | | | 240 | |
| gtc | cta | ggt | | | | | | | | | | | | | | 729 |
| Val | Leu | Gly | | | | | | | | | | | | | | |

<210> SEQ ID NO 168
<211> LENGTH: 741
<212> TYPE: DNA
<213> ORGANISM: Artificial sequence
<220> FEATURE:

```
<221> NAME/KEY: CDS
<222> LOCATION: (1)..(741)
<223> OTHER INFORMATION: Polynucleotide encoding GMBC645 scFv protein

<400> SEQUENCE: 168 gag gtg cag ctg gtg gag tcc ggg gga ggc ttg gta aag ccg ggg ggg       48
Glu Val Gln Leu Val Glu Ser Gly Gly Gly Leu Val Lys Pro Gly Gly
1               5                   10                  15 tcc ctt aga ctc tcc tgt gca ggc tct ggt ttc aaa ttc agt gac gcc       96
Ser Leu Arg Leu Ser Cys Ala Gly Ser Gly Phe Lys Phe Ser Asp Ala
            20                  25                  30 tgg atg aat tgg gtc cgc cag gct cca ggg aag ggg ctg gag tgg gtc      144
Trp Met Asn Trp Val Arg Gln Ala Pro Gly Lys Gly Leu Glu Trp Val
        35                  40                  45 ggc cgt att aaa agc aaa ggt agt ggg gga aca ata gag tac gct gca      192
Gly Arg Ile Lys Ser Lys Gly Ser Gly Gly Thr Ile Glu Tyr Ala Ala
    50                  55                  60 ccc gtg aaa gac aga ttc atc atc tca cga gat gat tca aaa gac acg      240
Pro Val Lys Asp Arg Phe Ile Ile Ser Arg Asp Asp Ser Lys Asp Thr
65                  70                  75                  80 ctg tat ctg caa atg aac agt ctg aaa acc gag gac aca gcc ctg tat      288
Leu Tyr Leu Gln Met Asn Ser Leu Lys Thr Glu Asp Thr Ala Leu Tyr
                85                  90                  95 tat tgt acg tgg gac tgg gat ttc tac tac ggt atg aac gtc tgg ggc      336
Tyr Cys Thr Trp Asp Trp Asp Phe Tyr Tyr Gly Met Asn Val Trp Gly
            100                 105                 110 agg gga acc ctg gtc acc gtc tcg agt ggt gga ggc ggt tca ggc gga      384
Arg Gly Thr Leu Val Thr Val Ser Ser Gly Gly Gly Gly Ser Gly Gly
        115                 120                 125 ggt ggc agc ggc ggt ggc gga tcg cag tct gtg ctg act cag cct gcc      432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga      480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa      528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg      576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg      624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat      672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg      720
Tyr Cys Ser Ser Tyr Thr Thr Arg Ser Thr Arg Val Phe Gly Gly Gly
225                 230                 235                 240 acc gag ctg acc gtc cta ggt                                          741
Thr Glu Leu Thr Val Leu Gly
                245

<210> SEQ ID NO 169
<211> LENGTH: 723
<212> TYPE: DNA
<213> ORGANISM: Artificial sequence
<220> FEATURE:
<221> NAME/KEY: CDS
<222> LOCATION: (1)..(723)
<223> OTHER INFORMATION: Polynucleotide encoding GMBC646 scFv protein
```

-continued

<400> SEQUENCE: 169

```
ggg gtc cag ctg gtg cag tct ggg gct gag gtg aag aag cct ggg gcc      48
Gly Val Gln Leu Val Gln Ser Gly Ala Glu Val Lys Lys Pro Gly Ala
 1               5                  10                  15 tca gtg aag gtt tcc tgc aag gca tct gga tac acc ttc acc agc tac      96
Ser Val Lys Val Ser Cys Lys Ala Ser Gly Tyr Thr Phe Thr Ser Tyr
             20                  25                  30 tat atc cac tgg gtg cga cag gcc cct gga caa ggg ctt gag tgg atg     144
Tyr Ile His Trp Val Arg Gln Ala Pro Gly Gln Gly Leu Glu Trp Met
         35                  40                  45 gga ata atc aac cct agt ggt ggt acc aca agc tac gca cag aag ttc     192
Gly Ile Ile Asn Pro Ser Gly Gly Thr Thr Ser Tyr Ala Gln Lys Phe
     50                  55                  60 cag ggc aga gtc acc atg acc agg gac acg tcc acg agc aca gtc tac     240
Gln Gly Arg Val Thr Met Thr Arg Asp Thr Ser Thr Ser Thr Val Tyr
 65                  70                  75                  80 atg gag ctg agc agc ctg aga tct gag gac acg gcc atg tat tac tgt     288
Met Glu Leu Ser Ser Leu Arg Ser Glu Asp Thr Ala Met Tyr Tyr Cys
                 85                  90                  95 gcg aga gag cgc ttc ctg cgc ggt atg gac gtc tgg ggc cga ggg aca     336
Ala Arg Glu Arg Phe Leu Arg Gly Met Asp Val Trp Gly Arg Gly Thr
            100                 105                 110 atg gtc acc gtc tcg agt ggt gga ggc ggt tca ggc gga ggt ggc agc     384
Met Val Thr Val Ser Ser Gly Gly Gly Gly Ser Gly Gly Gly Gly Ser
        115                 120                 125 ggc ggt ggc gga tcg gac atc gtg atg acc cag tct cct tcc acc ctg     432
Gly Gly Gly Gly Ser Asp Ile Val Met Thr Gln Ser Pro Ser Thr Leu
    130                 135                 140 tct gca tct gta gga gac aga gtc acc atc act tgc cgg gcc agt cag     480
Ser Ala Ser Val Gly Asp Arg Val Thr Ile Thr Cys Arg Ala Ser Gln
145                 150                 155                 160 ggc att agt agc tgg ttg gcc tgg tat cag cag aaa cca ggg aga gcc     528
Gly Ile Ser Ser Trp Leu Ala Trp Tyr Gln Gln Lys Pro Gly Arg Ala
                165                 170                 175 cct aag gtc ttg atc tat aag gca tct act tta gaa agt ggg gtc cca     576
Pro Lys Val Leu Ile Tyr Lys Ala Ser Thr Leu Glu Ser Gly Val Pro
            180                 185                 190 tca agg ttc agc ggc agt gga tct ggg aca gat ttc act ctc acc atc     624
Ser Arg Phe Ser Gly Ser Gly Ser Gly Thr Asp Phe Thr Leu Thr Ile
        195                 200                 205 agc agt ctg caa cct gaa gat ttt gca act tac tac tgt caa cag agt     672
Ser Ser Leu Gln Pro Glu Asp Phe Ala Thr Tyr Tyr Cys Gln Gln Ser
    210                 215                 220 tac agt acc ccg tgg acg ttc ggc caa ggg acc aag ctg gag atc aaa     720
Tyr Ser Thr Pro Trp Thr Phe Gly Gln Gly Thr Lys Leu Glu Ile Lys
225                 230                 235                 240 cgt                                                                  723
Arg
```

<210> SEQ ID NO 170
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC647 scFv protein

<400> SEQUENCE: 170

```
gag gtg cag ctg gtg gag tct ggg gga ggc ttg gta aag ccg ggg ggg      48
```

|   |   |   |   |   |   |   |   |   |   |   |   |   |   |   |   |   |
|---|---|---|---|---|---|---|---|---|---|---|---|---|---|---|---|---|
| Glu | Val | Gln | Leu | Val | Glu | Ser | Gly | Gly | Gly | Leu | Val | Lys | Pro | Gly | Gly | |
| 1 | | | | 5 | | | | | 10 | | | | | 15 | | |

| tcc | ctt | aga | ctc | tcc | tgt | gca | gcc | tct | ggt | ttc | act | ttc | agt | gac | gcc | 96 |
|---|---|---|---|---|---|---|---|---|---|---|---|---|---|---|---|---|
| Ser | Leu | Arg | Leu | Ser | Cys | Ala | Ala | Ser | Gly | Phe | Thr | Phe | Ser | Asp | Ala | |
| | | | 20 | | | | | 25 | | | | | 30 | | | |

| tgg | atg | aac | tgg | gtc | cgc | cag | gct | cca | ggg | aag | ggg | ctg | gag | tgg | gtc | 144 |
|---|---|---|---|---|---|---|---|---|---|---|---|---|---|---|---|---|
| Trp | Met | Asn | Trp | Val | Arg | Gln | Ala | Pro | Gly | Lys | Gly | Leu | Glu | Trp | Val | |
| | | 35 | | | | | 40 | | | | | 45 | | | | |

| ggc | cgt | att | aaa | agc | aaa | ggt | agt | ggt | ggg | aca | ata | gac | tac | gcc | gca | 192 |
|---|---|---|---|---|---|---|---|---|---|---|---|---|---|---|---|---|
| Gly | Arg | Ile | Lys | Ser | Lys | Gly | Ser | Gly | Gly | Thr | Ile | Asp | Tyr | Ala | Ala | |
| 50 | | | | | 55 | | | | | 60 | | | | | | |

| ccc | gtg | aaa | gac | aga | ttc | acc | atc | tca | cga | gat | gat | tca | aaa | aac | acg | 240 |
|---|---|---|---|---|---|---|---|---|---|---|---|---|---|---|---|---|
| Pro | Val | Lys | Asp | Arg | Phe | Thr | Ile | Ser | Arg | Asp | Asp | Ser | Lys | Asn | Thr | |
| 65 | | | | | 70 | | | | | 75 | | | | | 80 | |

| ctg | tat | ctg | caa | atg | aac | agt | ctg | aaa | acc | gag | gac | aca | gcc | ctg | tat | 288 |
|---|---|---|---|---|---|---|---|---|---|---|---|---|---|---|---|---|
| Leu | Tyr | Leu | Gln | Met | Asn | Ser | Leu | Lys | Thr | Glu | Asp | Thr | Ala | Leu | Tyr | |
| | | | | 85 | | | | | 90 | | | | | 95 | | |

| tac | tgt | acg | tgg | gac | tgg | gat | ttc | tac | tac | ggt | atg | aac | gtc | tgg | ggg | 336 |
|---|---|---|---|---|---|---|---|---|---|---|---|---|---|---|---|---|
| Tyr | Cys | Thr | Trp | Asp | Trp | Asp | Phe | Tyr | Tyr | Gly | Met | Asn | Val | Trp | Gly | |
| | | | 100 | | | | | 105 | | | | | 110 | | | |

| caa | ggg | acc | acg | gtc | acc | gtc | tcg | agt | ggt | gga | ggc | ggt | tca | ggc | gga | 384 |
|---|---|---|---|---|---|---|---|---|---|---|---|---|---|---|---|---|
| Gln | Gly | Thr | Thr | Val | Thr | Val | Ser | Ser | Gly | Gly | Gly | Gly | Ser | Gly | Gly | |
| | | | 115 | | | | | 120 | | | | | 125 | | | |

| ggt | ggc | agc | ggc | ggt | ggc | gga | tcg | cag | tct | gtg | ctg | act | cag | cct | gcc | 432 |
|---|---|---|---|---|---|---|---|---|---|---|---|---|---|---|---|---|
| Gly | Gly | Ser | Gly | Gly | Gly | Gly | Ser | Gln | Ser | Val | Leu | Thr | Gln | Pro | Ala | |
| | 130 | | | | | 135 | | | | | 140 | | | | | |

| tcc | gtg | tct | ggg | tct | cct | gga | cag | tcg | atc | acc | atc | tcc | tgc | act | gga | 480 |
|---|---|---|---|---|---|---|---|---|---|---|---|---|---|---|---|---|
| Ser | Val | Ser | Gly | Ser | Pro | Gly | Gln | Ser | Ile | Thr | Ile | Ser | Cys | Thr | Gly | |
| 145 | | | | | 150 | | | | | 155 | | | | | 160 | |

| acc | agc | agt | gac | gtt | ggt | ggt | tat | aac | tat | gtc | tcc | tgg | tac | caa | caa | 528 |
|---|---|---|---|---|---|---|---|---|---|---|---|---|---|---|---|---|
| Thr | Ser | Ser | Asp | Val | Gly | Gly | Tyr | Asn | Tyr | Val | Ser | Trp | Tyr | Gln | Gln | |
| | | | | 165 | | | | | 170 | | | | | 175 | | |

| cac | cca | ggc | aaa | gcc | ccc | aaa | ctc | atg | att | tat | gag | ggc | agt | aag | cgg | 576 |
|---|---|---|---|---|---|---|---|---|---|---|---|---|---|---|---|---|
| His | Pro | Gly | Lys | Ala | Pro | Lys | Leu | Met | Ile | Tyr | Glu | Gly | Ser | Lys | Arg | |
| | | | 180 | | | | | 185 | | | | | 190 | | | |

| ccc | tca | ggg | gtt | tct | aat | cgc | ttc | tct | ggc | tcc | aag | tct | ggc | aac | acg | 624 |
|---|---|---|---|---|---|---|---|---|---|---|---|---|---|---|---|---|
| Pro | Ser | Gly | Val | Ser | Asn | Arg | Phe | Ser | Gly | Ser | Lys | Ser | Gly | Asn | Thr | |
| | | 195 | | | | | 200 | | | | | 205 | | | | |

| gcc | tcc | ctg | aca | atc | tct | ggg | ctc | cag | gct | gag | gac | gag | gct | gat | tat | 672 |
|---|---|---|---|---|---|---|---|---|---|---|---|---|---|---|---|---|
| Ala | Ser | Leu | Thr | Ile | Ser | Gly | Leu | Gln | Ala | Glu | Asp | Glu | Ala | Asp | Tyr | |
| | 210 | | | | | 215 | | | | | 220 | | | | | |

| tac | tgc | agc | tca | tat | aca | acc | agg | agc | act | cga | gtt | ttc | ggc | gga | ggg | 720 |
|---|---|---|---|---|---|---|---|---|---|---|---|---|---|---|---|---|
| Tyr | Cys | Ser | Ser | Tyr | Thr | Thr | Arg | Ser | Thr | Arg | Val | Phe | Gly | Gly | Gly | |
| 225 | | | | 230 | | | | | 235 | | | | | 240 | | |

| acc | aag | ctg | acc | gtc | cta | ggt | | | | | | | | | | 741 |
|---|---|---|---|---|---|---|---|---|---|---|---|---|---|---|---|---|
| Thr | Lys | Leu | Thr | Val | Leu | Gly | | | | | | | | | | |
| | | | 245 | | | | | | | | | | | | | |

```
<210> SEQ ID NO 171
<211> LENGTH: 732
<212> TYPE: DNA
<213> ORGANISM: Artificial sequence
<220> FEATURE:
<221> NAME/KEY: CDS
<222> LOCATION: (1)..(732)
<223> OTHER INFORMATION: Polynucleotide encoding GMBC648 scFv protein

<400> SEQUENCE: 171
```

| cag | gtg | cag | ctg | gtg | gag | tct | ggg | gga | ggc | ttg | gta | aag | ccg | ggg | ggg | 48 |
|---|---|---|---|---|---|---|---|---|---|---|---|---|---|---|---|---|
| Gln | Val | Gln | Leu | Val | Glu | Ser | Gly | Gly | Gly | Leu | Val | Lys | Pro | Gly | Gly | |
| 1 | | | | 5 | | | | | 10 | | | | | 15 | | |

```
tcc ctt aga ctc tcc tgt gca gcc tct ggt ttc act ttc agt gac gcc      96
Ser Leu Arg Leu Ser Cys Ala Ala Ser Gly Phe Thr Phe Ser Asp Ala
         20                  25                  30 tgg atg aac tgg gtc cgc cag gct cca ggg aag ggg ctg gag tgg gtc     144
Trp Met Asn Trp Val Arg Gln Ala Pro Gly Lys Gly Leu Glu Trp Val
         35                  40                  45 ggc cgt att aaa agc aaa cgt agt ggt ggg aca ata gac tac gcc gca     192
Gly Arg Ile Lys Ser Lys Arg Ser Gly Gly Thr Ile Asp Tyr Ala Ala
 50                  55                  60 ccc gtg aaa gac aga ttc acc atc tca cga gat gat tca aaa aac acg     240
Pro Val Lys Asp Arg Phe Thr Ile Ser Arg Asp Asp Ser Lys Asn Thr
 65                  70                  75                  80 ttg tat ctg caa atg aac agt ctg aaa acc gag gac aca gcc ctg tat     288
Leu Tyr Leu Gln Met Asn Ser Leu Lys Thr Glu Asp Thr Ala Leu Tyr
                 85                  90                  95 tac tgt acg tgg gac tgg gat ttc tac tac ggt atg aac gtc tgg ggc     336
Tyr Cys Thr Trp Asp Trp Asp Phe Tyr Tyr Gly Met Asn Val Trp Gly
                100                 105                 110 caa ggg aca atg gtc acc gtc tct tct ggt gga ggc ggt tca ggc gga     384
Gln Gly Thr Met Val Thr Val Ser Ser Gly Gly Gly Gly Ser Gly Gly
            115                 120                 125 ggt ggc agc ggc ggt ggc gga tcg tct gag ctg act cag gac cct act     432
Gly Gly Ser Gly Gly Gly Gly Ser Ser Glu Leu Thr Gln Asp Pro Thr
130                 135                 140 gtg tct gtg gcc ttg gga cag aca gtc agg atc aca tgc caa gga gac     480
Val Ser Val Ala Leu Gly Gln Thr Val Arg Ile Thr Cys Gln Gly Asp
145                 150                 155                 160 agc ctc aga agc tat tat gca agc tgg tac cag cag aag cca gga cag     528
Ser Leu Arg Ser Tyr Tyr Ala Ser Trp Tyr Gln Gln Lys Pro Gly Gln
                165                 170                 175 gcc cct gta ctt gtc atc tat ggt aaa aac aac cgg ccc tca ggg atc     576
Ala Pro Val Leu Val Ile Tyr Gly Lys Asn Asn Arg Pro Ser Gly Ile
            180                 185                 190 cca gac cga ttc tct ggc tcc agc tca gga aac aca gct tcc ttg acc     624
Pro Asp Arg Phe Ser Gly Ser Ser Ser Gly Asn Thr Ala Ser Leu Thr
        195                 200                 205 atc act ggg gct cag gcg gaa gat gag gct gac tat tac tgt aac tcc     672
Ile Thr Gly Ala Gln Ala Glu Asp Glu Ala Asp Tyr Tyr Cys Asn Ser
210                 215                 220 cgg gac agc agt ggt aac cat gtg gta ttc ggc gga ggg acc aag ctg     720
Arg Asp Ser Ser Gly Asn His Val Val Phe Gly Gly Gly Thr Lys Leu
225                 230                 235                 240 acc gtc cta ggt                                                     732
Thr Val Leu Gly
```

<210> SEQ ID NO 172
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC649 scFv protein

<400> SEQUENCE: 172

```
cag gtc cag ctg gtg cag tct ggg gga ggc ttg gta aag ccg ggg ggg      48
Gln Val Gln Leu Val Gln Ser Gly Gly Gly Leu Val Lys Pro Gly Gly
 1               5                  10                  15 tcc ctt aga ctc tcc tgt gca gcc tct ggt ttc act ttc agt gac gcc      96
Ser Leu Arg Leu Ser Cys Ala Ala Ser Gly Phe Thr Phe Ser Asp Ala
             20                  25                  30
```

| | | |
|---|---|---|
| tgg atg aac tgg gtc cgc cag gct cca ggg aag ggg ctg gag tgg gtc<br>Trp Met Asn Trp Val Arg Gln Ala Pro Gly Lys Gly Leu Glu Trp Val<br>35 40 45 | | 144 |
| ggc cgt att aaa agc aaa ggt agt ggt ggg aca ata gac tac gcc gca<br>Gly Arg Ile Lys Ser Lys Gly Ser Gly Gly Thr Ile Asp Tyr Ala Ala<br>50 55 60 | | 192 |
| ccc gtg aaa gac aga ttc acc atc tca cga gat gat tca aaa aac acg<br>Pro Val Lys Asp Arg Phe Thr Ile Ser Arg Asp Asp Ser Lys Asn Thr<br>65 70 75 80 | | 240 |
| ctg tat ctg caa atg aac agt ctg aaa acc gag gac aca gcc ctg tat<br>Leu Tyr Leu Gln Met Asn Ser Leu Lys Thr Glu Asp Thr Ala Leu Tyr<br>85 90 95 | | 288 |
| tac tgt acg tgg gac tgg gat ttc tac tac ggt atg aac gtc tgg ggc<br>Tyr Cys Thr Trp Asp Trp Asp Phe Tyr Tyr Gly Met Asn Val Trp Gly<br>100 105 110 | | 336 |
| cga gga acc ctg gtc acc gtc tcg agt ggt gga ggc ggt tca ggc gga<br>Arg Gly Thr Leu Val Thr Val Ser Ser Gly Gly Gly Gly Ser Gly Gly<br>115 120 125 | | 384 |
| ggt ggc agc ggc ggt ggc gga tca cag tct gtg ctg act cag cct gcc<br>Gly Gly Ser Gly Gly Gly Gly Ser Gln Ser Val Leu Thr Gln Pro Ala<br>130 135 140 | | 432 |
| tcc gtg tct ggg tct cct gga cag tcg atc acc atc tcc tgc act gga<br>Ser Val Ser Gly Ser Pro Gly Gln Ser Ile Thr Ile Ser Cys Thr Gly<br>145 150 155 160 | | 480 |
| acc agc agt gac gtt ggt ggc tat aac tat gtc tcc tgg tac caa caa<br>Thr Ser Ser Asp Val Gly Gly Tyr Asn Tyr Val Ser Trp Tyr Gln Gln<br>165 170 175 | | 528 |
| cac cca ggc aaa gcc ccc aaa ctc atg att tat gag ggc agt aag cgg<br>His Pro Gly Lys Ala Pro Lys Leu Met Ile Tyr Glu Gly Ser Lys Arg<br>180 185 190 | | 576 |
| ccc tca ggg gtt tct aat cgc ttc tct ggc tcc aag tct ggc aac acg<br>Pro Ser Gly Val Ser Asn Arg Phe Ser Gly Ser Lys Ser Gly Asn Thr<br>195 200 205 | | 624 |
| gcc tcc ctg aca atc tct ggg ctc cag gct gag gac gag gct gat tat<br>Ala Ser Leu Thr Ile Ser Gly Leu Gln Ala Glu Asp Glu Ala Asp Tyr<br>210 215 220 | | 672 |
| tac tgc agc tca tat aca acc agg agc act cga gtt ttc ggc gga ggg<br>Tyr Cys Ser Ser Tyr Thr Thr Arg Ser Thr Arg Val Phe Gly Gly Gly<br>225 230 235 240 | | 720 |
| acc aag ctg acc gtc cta ggt<br>Thr Lys Leu Thr Val Leu Gly<br>245 | | 741 |

<210> SEQ ID NO 173
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC651 scFv protein

<400> SEQUENCE: 173

| | | |
|---|---|---|
| gag gtg cag ctg gtg gag tct ggg gga ggc ttg gta cag cct ggg ggg<br>Glu Val Gln Leu Val Glu Ser Gly Gly Gly Leu Val Gln Pro Gly Gly<br>1 5 10 15 | | 48 |
| tcc ctg aga ctc tcc tgt gca gcc tct ggt ttc act ttc agt gac gcc<br>Ser Leu Arg Leu Ser Cys Ala Ala Ser Gly Phe Thr Phe Ser Asp Ala<br>20 25 30 | | 96 |
| tgg atg aac tgg gtc cgc cag gct cca ggg aag ggg ctg gag tgg gtc<br>Trp Met Asn Trp Val Arg Gln Ala Pro Gly Lys Gly Leu Glu Trp Val<br>35 40 45 | | 144 |

```
ggc cgt att aaa agt aaa ggt agt ggt ggg aca ata gac tac gcc gca      192
Gly Arg Ile Lys Ser Lys Gly Ser Gly Gly Thr Ile Asp Tyr Ala Ala
     50                  55                  60 ccc gtg aaa gac aga ttc acc atc tca cga gat gat tca aaa aac acg      240
Pro Val Lys Asp Arg Phe Thr Ile Ser Arg Asp Asp Ser Lys Asn Thr
 65                  70                  75                  80 ctg tat ctg caa atg aac agt ctg aaa acc gag gac aca gcc ctg tat      288
Leu Tyr Leu Gln Met Asn Ser Leu Lys Thr Glu Asp Thr Ala Leu Tyr
                 85                  90                  95 tac tgt acg tgg gac tgg gat ttc tac tac ggt atg aac gtc tgg ggc      336
Tyr Cys Thr Trp Asp Trp Asp Phe Tyr Tyr Gly Met Asn Val Trp Gly
            100                 105                 110 cgg ggg aca atg gtc acc gtc tct tca ggt gga ggc ggt tca ggc gga      384
Arg Gly Thr Met Val Thr Val Ser Ser Gly Gly Gly Gly Ser Gly Gly
        115                 120                 125 ggt ggc agc ggc ggt ggc gga tcg cag tct gtg ctg act cag cct gcc      432
Gly Gly Ser Gly Gly Gly Gly Ser Gln Ser Val Leu Thr Gln Pro Ala
130                 135                 140 tcc gtg tct ggg tct cct gga cag tcg atc acc atc tcc tgc act gga      480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa      528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg      576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg      624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat      672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg      720
Tyr Cys Ser Ser Tyr Thr Thr Arg Ser Thr Arg Val Phe Gly Gly Gly
225                 230                 235                 240 acc aag ctg acc gtc cta ggt                                          741
Thr Lys Leu Thr Val Leu Gly
                245

<210> SEQ ID NO 174
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC652 scFv protein

<400> SEQUENCE: 174 ggg gtg cag ctg gtg cag tct ggg gga gtc gtg gta aag cct ggg ggg       48
Gly Val Gln Leu Val Gln Ser Gly Gly Val Val Val Lys Pro Gly Gly
 1               5                  10                  15 tcc ctt aga ctc tcc tgt gca gcc tct ggt ttc act ttc agt gac gcc       96
Ser Leu Arg Leu Ser Cys Ala Ala Ser Gly Phe Thr Phe Ser Asp Ala
            20                  25                  30 tgg atg aac tgg gtc cga cag gct cca ggg aag ggg ctg gag tgg gtc      144
Trp Met Asn Trp Val Arg Gln Ala Pro Gly Lys Gly Leu Glu Trp Val
        35                  40                  45 ggc cgt att aaa agt aaa ggt agt ggt ggg aca aca gac tac gct gca      192
Gly Arg Ile Lys Ser Lys Gly Ser Gly Gly Thr Thr Asp Tyr Ala Ala
```

```
                    50                      55                      60
ccc gtg aaa ggc aga ttc acc atc tca aga gat gat tca gaa aac acg      240
Pro Val Lys Gly Arg Phe Thr Ile Ser Arg Asp Asp Ser Glu Asn Thr
 65                  70                  75                  80 ctg tat ctg caa atg aac agc ctg aaa acc gag gac aca gcc gta tat      288
Leu Tyr Leu Gln Met Asn Ser Leu Lys Thr Glu Asp Thr Ala Val Tyr
                 85                  90                  95 tac tgt acg tgg gac cac agt tac tac tac gat atg gcc gtc tgg ggc      336
Tyr Cys Thr Trp Asp His Ser Tyr Tyr Tyr Asp Met Ala Val Trp Gly
            100                 105                 110 cga ggg acg atg gtc acc gcc tcc tca ggt gga ggc ggt tca ggc gga      384
Arg Gly Thr Met Val Thr Ala Ser Ser Gly Gly Gly Gly Ser Gly Gly
        115                 120                 125 ggt ggc agc ggc ggt ggc gga tcg cag tct gtg ctg act cag cct gcc      432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga      480
Ser Val Ser Gly Ser Pro Gly Gln Ser Ile Thr Ile Ser Cys Thr Gly
145                 150                 155                 160 acc agc agt gat gtt ggt ggt tat aac tat gtc tcc tgg tac caa cag      528
Thr Ser Ser Asp Val Gly Gly Tyr Asn Tyr Val Ser Trp Tyr Gln Gln
                165                 170                 175 cac cca ggc aaa gcc ccc aaa ttc atg att tat gat gtc agt aag cgg      576
His Pro Gly Lys Ala Pro Lys Phe Met Ile Tyr Asp Val Ser Lys Arg
            180                 185                 190 ccc tca ggg gtt tct aat cgc ttc tct ggc tcc aag tct ggc aac acg      624
Pro Ser Gly Val Ser Asn Arg Phe Ser Gly Ser Lys Ser Gly Asn Thr
        195                 200                 205 gcg tcc ctg acc atc tct ggg gtc cag gcc gag gac gag gct gat tat      672
Ala Ser Leu Thr Ile Ser Gly Val Gln Ala Glu Asp Glu Ala Asp Tyr
    210                 215                 220 tac tgc agc tca tat aca agc gcc agc act gtg ata ttc ggc gga ggg      720
Tyr Cys Ser Ser Tyr Thr Ser Ala Ser Thr Val Ile Phe Gly Gly Gly
225                 230                 235                 240 acc aag ctg acc gtc cta ggt                                          741
Thr Lys Leu Thr Val Leu Gly
                245

<210> SEQ ID NO 175
<211> LENGTH: 738
<212> TYPE: DNA
<213> ORGANISM: Artificial sequence
<220> FEATURE:
<221> NAME/KEY: CDS
<222> LOCATION: (1)..(738)
<223> OTHER INFORMATION: Polynucleotide encoding GMBC653 scFv protein

<400> SEQUENCE: 175 cag gtg cag ctg gtg caa tct ggg gct gag gtg aag aag cct ggg gcc       48
Gln Val Gln Leu Val Gln Ser Gly Ala Glu Val Lys Lys Pro Gly Ala
  1               5                  10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
             20                  25                  30 tat atg cac tgg gtg cga cag gcc cct gga caa ggg ctt gag tgg atg      144
Tyr Met His Trp Val Arg Gln Ala Pro Gly Gln Gly Leu Glu Trp Met
         35                  40                  45 gga tgg atc aac cct aac agt ggt ggc aca aac tat gca cag aag ttt      192
Gly Trp Ile Asn Pro Asn Ser Gly Gly Thr Asn Tyr Ala Gln Lys Phe
     50                  55                  60 cag ggc agg gtc acc atg acc agg gac acg tcc atc agc aca gcc tac      240
```

| | | |
|---|---|---|
| Gln Gly Arg Val Thr Met Thr Arg Asp Thr Ser Ile Ser Thr Ala Tyr<br>65                              70                     75                   80 | | |
| atg gag ctg agc agg ctg aga tct gac gac acg gcc gtg tat tac tgt<br>Met Glu Leu Ser Arg Leu Arg Ser Asp Asp Thr Ala Val Tyr Tyr Cys<br>                    85                     90                    95 | 288 |
| gcg aga ggt ggt agc cgc tac tac ggt atg gac gtc tgg agc cga gga<br>Ala Arg Gly Gly Ser Arg Tyr Tyr Gly Met Asp Val Trp Ser Arg Gly<br>                 100                   105                  110 | 336 |
| acc ctg gtc acc gtc tct tca ggt gga ggc ggt tca ggc gga ggt ggc<br>Thr Leu Val Thr Val Ser Ser Gly Gly Gly Gly Ser Gly Gly Gly Gly<br>          115                   120                   125 | 384 |
| agc ggc ggt ggc gga tcg tcc tat gtg ctg act cag ccc ccc tca gtg<br>Ser Gly Gly Gly Gly Ser Ser Tyr Val Leu Thr Gln Pro Pro Ser Val<br>130                              135                    140 | 432 |
| tct ggg acc ccc ggg cag aga gtc acc atc tct tgt tct gga ggc aga<br>Ser Gly Thr Pro Gly Gln Arg Val Thr Ile Ser Cys Ser Gly Gly Arg<br>145                            150                 155               160 | 480 |
| tcc aac atc ggc agt aat act gta aag tgg tat cag cag ctc cca gga<br>Ser Asn Ile Gly Ser Asn Thr Val Lys Trp Tyr Gln Gln Leu Pro Gly<br>                 165                   170                  175 | 528 |
| gcg gcc ccc aaa ctc ctc atc tat ggc aat gat cag cgg ccc tca ggg<br>Ala Ala Pro Lys Leu Leu Ile Tyr Gly Asn Asp Gln Arg Pro Ser Gly<br>            180                   185                  190 | 576 |
| gtc cct gac cga ttc tct ggc tcc aag tct ggc acc tca gcc tcc ctg<br>Val Pro Asp Arg Phe Ser Gly Ser Lys Ser Gly Thr Ser Ala Ser Leu<br>      195                   200                   205 | 624 |
| gcc atc act ggg gtc cag gct gaa gac gag gct gac tat tac tgc cag<br>Ala Ile Thr Gly Val Gln Ala Glu Asp Glu Ala Asp Tyr Tyr Cys Gln<br>210                              215                    220 | 672 |
| tca tat gac agc agc ctg agg ggt tcg agg gtc ttc gga act ggg acc<br>Ser Tyr Asp Ser Ser Leu Arg Gly Ser Arg Val Phe Gly Thr Gly Thr<br>225                            230                    235               240 | 720 |
| aag gtc acc gtc cta ggt<br>Lys Val Thr Val Leu Gly<br>            245 | 738 |

```
<210> SEQ ID NO 176
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC654 scFv protein

<400> SEQUENCE: 176
```

| | | |
|---|---|---|
| gag gtg cag ctg gtg gag acc ggg gga ggc ttg gta gag ccg ggg ggg<br>Glu Val Gln Leu Val Glu Thr Gly Gly Gly Leu Val Glu Pro Gly Gly<br>1                   5                     10                   15 | 48 |
| tcc ctt aga ctc tcc tgt gca gcc tct ggt ttc act ttc agt gac gcc<br>Ser Leu Arg Leu Ser Cys Ala Ala Ser Gly Phe Thr Phe Ser Asp Ala<br>               20                     25                  30 | 96 |
| tgg atg aac tgg gtc cgc cag gct cca ggg aag ggg ctg gag tgg gtc<br>Trp Met Asn Trp Val Arg Gln Ala Pro Gly Lys Gly Leu Glu Trp Val<br>          35                   40                   45 | 144 |
| ggc cgt att aaa agc aaa cgt agt ggt ggg aca ata gac tac gcc gca<br>Gly Arg Ile Lys Ser Lys Arg Ser Gly Gly Thr Ile Asp Tyr Ala Ala<br>50                              55                    60 | 192 |
| ccc gtg aaa gac aga ttc acc atc tca cga gat gat tca aaa aat acg<br>Pro Val Lys Asp Arg Phe Thr Ile Ser Arg Asp Asp Ser Lys Asn Thr<br>65                              70                    75                   80 | 240 |

```
ctg tat ctg caa atg aac agt ctg aaa att gag gac aca gcc ctg tat      288
Leu Tyr Leu Gln Met Asn Ser Leu Lys Ile Glu Asp Thr Ala Leu Tyr
                85                  90                  95 tac tgt acg tgg gac tgg gat ttc tac tac ggt atg aac gtc tgg ggc      336
Tyr Cys Thr Trp Asp Trp Asp Phe Tyr Tyr Gly Met Asn Val Trp Gly
            100                 105                 110 aaa ggg acc acg gtc acc gtc tcc tca ggt gga ggc ggt tca ggc gga      384
Lys Gly Thr Thr Val Thr Val Ser Ser Gly Gly Gly Gly Ser Gly Gly
        115                 120                 125 ggt ggc agc ggc ggt ggc gga tcg cag tct gtg ctg act cag cct gcc      432
Gly Gly Ser Gly Gly Gly Gly Ser Gln Ser Val Leu Thr Gln Pro Ala
    130                 135                 140 tcc gtg tct gga tct cct gga cag tcg atc acc atc tcc tgc act gga      480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa      528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg      576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg      624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat      672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg      720
Tyr Cys Ser Ser Tyr Thr Thr Arg Ser Thr Arg Val Phe Gly Gly Gly
225                 230                 235                 240 acc aag ctg acc gtc cta ggt                                          741
Thr Lys Leu Thr Val Leu Gly
                245

<210> SEQ ID NO 177
<211> LENGTH: 717
<212> TYPE: DNA
<213> ORGANISM: Artificial sequence
<220> FEATURE:
<221> NAME/KEY: CDS
<222> LOCATION: (1)..(717)
<223> OTHER INFORMATION: Polynucleotide encoding GMBC655 scFv protein

<400> SEQUENCE: 177 gag gtg cag ctg gtg gag tct ggg gga ggc ctg gtc aag cct ggg ggg      48
Glu Val Gln Leu Val Glu Ser Gly Gly Gly Leu Val Lys Pro Gly Gly
1               5                   10                  15 tcc ctg aga ctc tct tgt gca gcg tct gga ttc acc ttc agt agc tat      96
Ser Leu Arg Leu Ser Cys Ala Ala Ser Gly Phe Thr Phe Ser Ser Tyr
            20                  25                  30 ggc atg agc tgg atc cgc cag gct cca ggg aag ggg cag gag tgg gtc      144
Gly Met Ser Trp Ile Arg Gln Ala Pro Gly Lys Gly Gln Glu Trp Val
        35                  40                  45 tca gct att agt ggt agt ggt ggt agc gca tac tac gca gac tcc gtg      192
Ser Ala Ile Ser Gly Ser Gly Gly Ser Ala Tyr Tyr Ala Asp Ser Val
    50                  55                  60 aag gcc cgg ttc acc att tcc aga gac aat tcc aag aac acg ctg tat      240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt      288
Leu Gln Met Asn Ser Leu Arg Ala Glu Asp Thr Ala Val Tyr Tyr Cys
                85                  90                  95
```

```
gcg aaa gcc tat agc agt gaa gac tac tgg ggc agg ggg aca atg gtc      336
Ala Lys Ala Tyr Ser Ser Glu Asp Tyr Trp Gly Arg Gly Thr Met Val
        100                 105                 110 acc gtc tct tca ggt gga ggc ggt tca ggc gga ggt ggc agc ggc ggt      384
Thr Val Ser Ser Gly Gly Gly Gly Ser Gly Gly Gly Gly Ser Gly Gly
        115                 120                 125 ggc gga tcg aac atc cag atg acc cag tct cca tcc ttc ctg tct gca      432
Gly Gly Ser Asn Ile Gln Met Thr Gln Ser Pro Ser Phe Leu Ser Ala
        130                 135                 140 tct gta gga gac aga gtc acc atc act tgc cgg gcc agt cag ggc att      480
Ser Val Gly Asp Arg Val Thr Ile Thr Cys Arg Ala Ser Gln Gly Ile
145                 150                 155                 160 aac aat tat tta gcc tgg tat cag caa aaa cca ggg aga gcc cct aag      528
Asn Asn Tyr Leu Ala Trp Tyr Gln Gln Lys Pro Gly Arg Ala Pro Lys
                165                 170                 175 ctc ctg atc tac gct gca tcc agt tta caa agt ggg gtc cca tca agg      576
Leu Leu Ile Tyr Ala Ala Ser Ser Leu Gln Ser Gly Val Pro Ser Arg
                180                 185                 190 ttc agc ggc agt gga tct ggc aca gat ttc act ctc acc atc agc agc      624
Phe Ser Gly Ser Gly Ser Gly Thr Asp Phe Thr Leu Thr Ile Ser Ser
                195                 200                 205 ctg cag cct gat gat ttt gca act tat tac tgc caa caa tat agt aat      672
Leu Gln Pro Asp Asp Phe Ala Thr Tyr Tyr Cys Gln Gln Tyr Ser Asn
210                 215                 220 tat ccg ctc act ttc ggc gga ggg acc aag ctg gag atc aaa cgt         717
Tyr Pro Leu Thr Phe Gly Gly Gly Thr Lys Leu Glu Ile Lys Arg
225                 230                 235

<210> SEQ ID NO 178
<211> LENGTH: 732
<212> TYPE: DNA
<213> ORGANISM: Artificial sequence
<220> FEATURE:
<221> NAME/KEY: CDS
<222> LOCATION: (1)..(732)
<223> OTHER INFORMATION: Polynucleotide encoding GMBC657 scFv protein

<400> SEQUENCE: 178 cag atg cag ctg atg cag tct ggg gga ggc ttg gta aag ccg ggg ggg      48
Gln Met Gln Leu Met Gln Ser Gly Gly Gly Leu Val Lys Pro Gly Gly
1               5                   10                  15 tcc ctt aga ctc tcc tgt gca ggc tct ggt ttc aaa ttc agt gac gcc      96
Ser Leu Arg Leu Ser Cys Ala Gly Ser Gly Phe Lys Phe Ser Asp Ala
                20                  25                  30 tgg atg aat tgg gtc cgc cag gct cca ggg aag ggg ctg gag tgg gtc     144
Trp Met Asn Trp Val Arg Gln Ala Pro Gly Lys Gly Leu Glu Trp Val
            35                  40                  45 ggc cgt att aaa agc aaa ggt agt ggt ggg aca ata gag tac gct gca     192
Gly Arg Ile Lys Ser Lys Gly Ser Gly Gly Thr Ile Glu Tyr Ala Ala
    50                  55                  60 ccc gtg aaa gac aga ttc atc atc tca cga gat gat tca aaa gac acg     240
Pro Val Lys Asp Arg Phe Ile Ile Ser Arg Asp Asp Ser Lys Asp Thr
65                  70                  75                  80 ctg tat ctg caa atg aac agt ctg aaa acc gag gac aca gcc ctg tat     288
Leu Tyr Leu Gln Met Asn Ser Leu Lys Thr Glu Asp Thr Ala Leu Tyr
                85                  90                  95 tat tgt acg tgg gac tgg gat ttc tac tac ggt atg aac gtc tgg ggc     336
Tyr Cys Thr Trp Asp Trp Asp Phe Tyr Tyr Gly Met Asn Val Trp Gly
            100                 105                 110 cag gga acc ctg gtc acc gtc tcc tca ggt gga ggc ggt tca ggc gga     384
Gln Gly Thr Leu Val Thr Val Ser Ser Gly Gly Gly Gly Ser Gly Gly
```

```
ggt ggc agc ggc ggt ggc gga tcg tct gag ctg act cag gac cct gct    432
Gly Gly Ser Gly Gly Gly Gly Ser Ser Glu Leu Thr Gln Asp Pro Ala
        130                 135                 140 gtg tct gtg gcc ttg gga cag aca gtc agg atc aca tgc caa gga gac    480
Val Ser Val Ala Leu Gly Gln Thr Val Arg Ile Thr Cys Gln Gly Asp
145                 150                 155                 160 agc ctc aga agc tat tat gca agc tgg tac cag cag aag cca gga cag    528
Ser Leu Arg Ser Tyr Tyr Ala Ser Trp Tyr Gln Gln Lys Pro Gly Gln
                165                 170                 175 gcc cct gta ctt gtc atc tat ggt aaa aac aac cgg ccc tca ggg atc    576
Ala Pro Val Leu Val Ile Tyr Gly Lys Asn Asn Arg Pro Ser Gly Ile
            180                 185                 190 cca gac cga ttc tct ggc tcc agc tca gga aac aca gct tcc ttg acc    624
Pro Asp Arg Phe Ser Gly Ser Ser Ser Gly Asn Thr Ala Ser Leu Thr
        195                 200                 205 atc act ggg gct cag gcg gaa gat gag gct gac tat tac tgt aac tcc    672
Ile Thr Gly Ala Gln Ala Glu Asp Glu Ala Asp Tyr Tyr Cys Asn Ser
    210                 215                 220 cgg gac agc agt ggt aac cat gtg gta ttc ggc gga ggg acc aag ctg    720
Arg Asp Ser Ser Gly Asn His Val Val Phe Gly Gly Gly Thr Lys Leu
225                 230                 235                 240 acc gtc cta ggt                                                    732
Thr Val Leu Gly <210> SEQ ID NO 179
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC658 scFv protein

<400> SEQUENCE: 179 gag gtc cag ctg gtg cag tct ggg gga ggc ttg gta aag ccg ggg ggg     48
Glu Val Gln Leu Val Gln Ser Gly Gly Gly Leu Val Lys Pro Gly Gly
1               5                   10                  15 tcc ctt aga ctt tcc tgt gca gcc tct ggt ttc act ttc agt gac gcc     96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc    144
Trp Met Asn Trp Val Arg Gln Ala Pro Gly Lys Gly Leu Glu Trp Val
        35                  40                  45 ggc cgt att aaa agc aaa ggt agt ggt ggg aca ata gac tac gct gca    192
Gly Arg Ile Lys Ser Lys Gly Ser Gly Gly Thr Ile Asp Tyr Ala Ala
    50                  55                  60 ccc gtg aaa gac aga ttc acc atc tca cga gat gat tca aaa aac acg    240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc ctg tat    288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc    336
Tyr Cys Thr Trp Asp Trp Asp Phe Tyr Tyr Gly Met Asn Val Trp Gly
            100                 105                 110 cgg ggg acc acg gtc acc gtc tcc tca ggt gga ggc ggt tca ggc gga    384
Arg Gly Thr Thr Val Thr Val Ser Ser Gly Gly Gly Gly Ser Gly Gly
        115                 120                 125 ggt ggc agc ggc ggt ggc gga tcg cag tct gtg ctg act cag cct gcc    432
Gly Gly Ser Gly Gly Gly Gly Ser Gln Ser Val Leu Thr Gln Pro Ala
```

```
                 130                 135                 140
tcc gtg tct ggg tct cct gga cag tcg atc acc atc tcc tgc act gga      480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa      528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg      576
His Pro Gly Lys Ala Pro Lys Leu Met Ile Tyr Glu Gly Ser Lys Arg
            180                 185                 190 ccc tca ggg gtt tct aat cgc ttc tct ggt tcc aag tct ggc aac acg      624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat      672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg      720
Tyr Cys Ser Ser Tyr Thr Thr Arg Ser Thr Arg Val Phe Gly Gly Gly
225                 230                 235                 240 acc aag ctg acc gtc cta ggt                                          741
Thr Lys Leu Thr Val Leu Gly
                245

<210> SEQ ID NO 180
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC659 scFv protein

<400> SEQUENCE: 180 cag gtg cag ctg gtg gag tct ggg gga ggc ttg gta aag cct ggg gag       48
Gln Val Gln Leu Val Glu Ser Gly Gly Gly Leu Val Lys Pro Gly Glu
1               5                   10                  15 tca ctg aga ctc tcc tgt gaa gcc tct gga ttc gaa ttt aat tat gcc       96
Ser Leu Arg Leu Ser Cys Glu Ala Ser Gly Phe Glu Phe Asn Tyr Ala
            20                  25                  30 tgg atg agt tgg gtc cgc cag gct cca ggg aag ggg ctg gag tgg gtt      144
Trp Met Ser Trp Val Arg Gln Ala Pro Gly Lys Gly Leu Glu Trp Val
        35                  40                  45 ggc cgt agt aga agc gaa gct agt ggt ggg aca aca gac tac gct gca      192
Gly Arg Ser Arg Ser Glu Ala Ser Gly Gly Thr Thr Asp Tyr Ala Ala
    50                  55                  60 ccc ctg caa gac aga ttc acc atc tca aga gat gat tca aaa aac aca      240
Pro Leu Gln Asp Arg Phe Thr Ile Ser Arg Asp Asp Ser Lys Asn Thr
65                  70                  75                  80 ctg tat cta caa gtc aac agc ctg aaa atc gag gac aca ggc gtg tat      288
Leu Tyr Leu Gln Val Asn Ser Leu Lys Ile Glu Asp Thr Gly Val Tyr
                85                  90                  95 ttc tgt aag tgg gag aaa tca gag tac tac ggt atg gac gtc tgg ggc      336
Phe Cys Lys Trp Glu Lys Ser Glu Tyr Tyr Gly Met Asp Val Trp Gly
            100                 105                 110 aga ggc acc ctg gtc acc gtc tcg agt ggt gga ggc ggt tca ggc gga      384
Arg Gly Thr Leu Val Thr Val Ser Ser Gly Gly Gly Gly Ser Gly Gly
        115                 120                 125 ggt ggc agc ggc ggt ggc gga tcg cag tct gtg ctg act cag cct gcc      432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga      480
```

```
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa      528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg      576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg      624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat      672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg      720
Tyr Cys Ser Ser Tyr Thr Thr Arg Ser Thr Arg Val Phe Gly Gly Gly
225                 230                 235                 240 acc aag ctg acc gtc cta ggt                                          741
Thr Lys Leu Thr Val Leu Gly
                245

<210> SEQ ID NO 181
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC660 scFv protein

<400> SEQUENCE: 181 gag gtg cag ctg gtg cag tct ggg gga ggc ttg gta aag ccg ggg ggg       48
Glu Val Gln Leu Val Gln Ser Gly Gly Gly Leu Val Lys Pro Gly Gly
1               5                   10                  15 tcc ctt aga ctc tcc tgt gca gcc tct ggt ttc att ttc agt gac gcc       96
Ser Leu Arg Leu Ser Cys Ala Ala Ser Gly Phe Ile Phe Ser Asp Ala
            20                  25                  30 tgg atg aac tgg gtc cgc cag gct cca ggg aag ggg ctg gag tgg gtc      144
Trp Met Asn Trp Val Arg Gln Ala Pro Gly Lys Gly Leu Glu Trp Val
        35                  40                  45 ggc cgt att aaa agc aaa ggt agt ggt ggg aca ata gac tac gcc gca      192
Gly Arg Ile Lys Ser Lys Gly Ser Gly Gly Thr Ile Asp Tyr Ala Ala
    50                  55                  60 ccc gtg aaa gac aga ttc acc atc tca cga gat gat tca aaa aac acg      240
Pro Val Lys Asp Arg Phe Thr Ile Ser Arg Asp Asp Ser Lys Asn Thr
65                  70                  75                  80 ctg tat ctg caa atg aac agt cta aaa acc gag gac aca gcc ctg tat      288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc      336
Tyr Cys Thr Trp Asp Trp Asp Phe Tyr Tyr Gly Met Asn Val Trp Gly
            100                 105                 110 cag ggc acc ccg gtc acc gtc tcc tca ggt gga ggc ggt tca ggc gga      384
Gln Gly Thr Pro Val Thr Val Ser Ser Gly Gly Gly Gly Ser Gly Gly
        115                 120                 125 ggt ggc agc ggc ggt ggc gga tcg cag tct gtg ctg act cag cct gcc      432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga      480
Ser Val Ser Gly Ser Pro Gly Gln Ser Ile Thr Ile Ser Cys Thr Gly
145                 150                 155                 160
```

-continued

```
acc agc agt gac gtt ggt ggt tat aac tat gtc tcc tgg tac caa caa      528
Thr Ser Ser Asp Val Gly Gly Tyr Asn Tyr Val Ser Trp Tyr Gln Gln
            165                 170                 175 cac cca ggc aaa gcc ccc aaa ctc atg att tat gag ggc agt aag cgg      576
His Pro Gly Lys Ala Pro Lys Leu Met Ile Tyr Glu Gly Ser Lys Arg
        180                 185                 190 ccc tca ggg gtt tct aat cgc ttc tct ggc tcc aag tct ggc aac acg      624
Pro Ser Gly Val Ser Asn Arg Phe Ser Gly Ser Lys Ser Gly Asn Thr
    195                 200                 205 gcc tcc ctg aca atc tct ggg ctc cag gct gag gac gag gct gat tat      672
Ala Ser Leu Thr Ile Ser Gly Leu Gln Ala Glu Asp Glu Ala Asp Tyr
210                 215                 220 tac tgc agc tca tat aca acc agg agc act cga gtc ttc ggc gga ggg      720
Tyr Cys Ser Ser Tyr Thr Thr Arg Ser Thr Arg Val Phe Gly Gly Gly
225                 230                 235                 240 acc aag ctg acc gtc cta ggt                                          741
Thr Lys Leu Thr Val Leu Gly
                245
```

<210> SEQ ID NO 182
<211> LENGTH: 729
<212> TYPE: DNA
<213> ORGANISM: Artificial sequence
<220> FEATURE:
<221> NAME/KEY: CDS
<222> LOCATION: (1)..(729)
<223> OTHER INFORMATION: Polynucleotide encoding GMBC662 scFv protein

<400> SEQUENCE: 182

```
ggg gtc cag ctg gtg cag tct ggg gct gag gtg aag aag cct ggg tcc       48
Gly Val Gln Leu Val Gln Ser Gly Ala Glu Val Lys Lys Pro Gly Ser
1               5                   10                  15 tcg gtg aag gtc tcc tgc aag gct tct gga ggc acc ttc agc agc tat       96
Ser Val Lys Val Ser Cys Lys Ala Ser Gly Gly Thr Phe Ser Ser Tyr
            20                  25                  30 act atc agc tgg gtg cga cag gcc cct gga caa ggg ctt gag tgg atg      144
Thr Ile Ser Trp Val Arg Gln Ala Pro Gly Gln Gly Leu Glu Trp Met
        35                  40                  45 gga agg atc atc cct atc ctt ggt ata gca aac tac gca cag aag ttc      192
Gly Arg Ile Ile Pro Ile Leu Gly Ile Ala Asn Tyr Ala Gln Lys Phe
    50                  55                  60 cag ggc aga gtc acg att acc gcg gac aaa tcc acg agc aca gcc tac      240
Gln Gly Arg Val Thr Ile Thr Ala Asp Lys Ser Thr Ser Thr Ala Tyr
65                  70                  75                  80 atg gag ctg agc agc ctg aga tct gag gac acg gcc gtg tat tac tgt      288
Met Glu Leu Ser Ser Leu Arg Ser Glu Asp Thr Ala Val Tyr Tyr Cys
                85                  90                  95 gcg aga gaa aag ttg agg gac ttc cag cac tgg ggc caa gga acc ctg      336
Ala Arg Glu Lys Leu Arg Asp Phe Gln His Trp Gly Gln Gly Thr Leu
            100                 105                 110 gtc acc gtc tct tca ggt gga ggc ggt tca ggc gga ggt ggc agc ggc      384
Val Thr Val Ser Ser Gly Gly Gly Gly Ser Gly Gly Gly Gly Ser Gly
        115                 120                 125 ggt ggc gga tcg cag tct gtg ctg act cag cct gcc tcc gtg tct ggg      432
Gly Gly Gly Ser Gln Ser Val Leu Thr Gln Pro Ala Ser Val Ser Gly
    130                 135                 140 tct cct gga cag tcg atc acc atc tcc tgc act gga acc agc agt gac      480
Ser Pro Gly Gln Ser Ile Thr Ile Ser Cys Thr Gly Thr Ser Ser Asp
145                 150                 155                 160 gtt ggt ggt tat aac tat gtc tcc tgg tac caa caa cac cca ggc aaa      528
Val Gly Gly Tyr Asn Tyr Val Ser Trp Tyr Gln Gln His Pro Gly Lys
                165                 170                 175
```

```
gcc ccc aaa ctc atg att tat gag ggc agt aag cgg ccc tca ggg att      576
Ala Pro Lys Leu Met Ile Tyr Glu Gly Ser Lys Arg Pro Ser Gly Ile
        180                 185                 190 tct aat cgc ttc tct ggc tcc aag tct ggc aac acg gcc tcc ctg aca      624
Ser Asn Arg Phe Ser Gly Ser Lys Ser Gly Asn Thr Ala Ser Leu Thr
    195                 200                 205 atc tct agg ctc cag gct gag gac gag gct gat tat tac tgc agc tca      672
Ile Ser Arg Leu Gln Ala Glu Asp Glu Ala Asp Tyr Tyr Cys Ser Ser
210                 215                 220 tat aca acc agg agc act cga gtt ttc ggc gga ggg acc aag ctg acc      720
Tyr Thr Thr Arg Ser Thr Arg Val Phe Gly Gly Gly Thr Lys Leu Thr
225                 230                 235                 240 gtc cta ggt                                                           729
Val Leu Gly <210> SEQ ID NO 183
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC664 scFv protein

<400> SEQUENCE: 183 gag gtg cag ctg gtg gag acc ggg gga gcc ttg gta aag ccg ggg ggg       48
Glu Val Gln Leu Val Glu Thr Gly Gly Ala Leu Val Lys Pro Gly Gly
1               5                   10                  15 tcc ctt aga ctc tcc tgt gca gcc tct ggt ttc act ttc agt gac gcc       96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc      144
Trp Met Asn Trp Val Arg Gln Ala Pro Gly Lys Gly Leu Glu Trp Val
        35                  40                  45 ggc cgt att aaa agc aaa ggt agt ggt ggg aca ata gac tac gct gca      192
Gly Arg Ile Lys Ser Lys Gly Ser Gly Gly Thr Ile Asp Tyr Ala Ala
    50                  55                  60 ccc gtg aaa gac aga ttc acc atc tca cga gat gat tca aaa aac acg      240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc ctg tat      288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg agc      336
Tyr Cys Thr Trp Asp Trp Asp Phe Tyr Tyr Gly Met Asn Val Trp Ser
            100                 105                 110 cgg ggg aca atg gtc acc gtc tcg agt ggt gga ggc ggt tca ggc gga      384
Arg Gly Thr Met Val Thr Val Ser Ser Gly Gly Gly Gly Ser Gly Gly
        115                 120                 125 ggt ggc agc ggc ggt ggc gga tcg cag tct gtg ctg act cag cct gcc      432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga      480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa      528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg      576
His Pro Gly Lys Ala Pro Lys Leu Met Ile Tyr Glu Gly Ser Lys Arg
            180                 185                 190
```

```
ccc tca ggg gtt tct aat cgc ttc tct ggc tcc aag tct ggc aac acg      624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat      672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg      720
Tyr Cys Ser Ser Tyr Thr Thr Arg Ser Thr Arg Val Phe Gly Gly Gly
225                 230                 235                 240 acc aag ctg acc gtc cta ggt                                          741
Thr Lys Leu Thr Val Leu Gly
                245

<210> SEQ ID NO 184
<211> LENGTH: 732
<212> TYPE: DNA
<213> ORGANISM: Artificial sequence
<220> FEATURE:
<221> NAME/KEY: CDS
<222> LOCATION: (1)..(732)
<223> OTHER INFORMATION: Polynucleotide encoding GMBC665 scFv protein

<400> SEQUENCE: 184 gag gtg cag ctg gtg gag act ggg gga ggc ttg gta aag ccg ggg ggg       48
Glu Val Gln Leu Val Glu Thr Gly Gly Gly Leu Val Lys Pro Gly Gly
1               5                   10                  15 tcc ctt aga ctc tcc tgt gca gcc tct ggt ttc act ttc agt gac gcc       96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc      144
Trp Met Asn Trp Val Arg Gln Ala Pro Gly Lys Gly Leu Glu Trp Val
        35                  40                  45 ggc cgt att aaa agt aaa ggt agt ggt ggg aca ata gac tac gcc gca      192
Gly Arg Ile Lys Ser Lys Gly Ser Gly Gly Thr Ile Asp Tyr Ala Ala
    50                  55                  60 ccc gtg aaa gac aga ttc acc atc tca cga gat gat tca aaa aac acg      240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc ctg tat      288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc      336
Tyr Cys Thr Trp Asp Trp Asp Phe Tyr Tyr Gly Met Asn Val Trp Gly
            100                 105                 110 caa ggg aca atg gtc acc gtc tct tca ggt gga ggc ggt tca ggc gga      384
Gln Gly Thr Met Val Thr Val Ser Ser Gly Gly Gly Gly Ser Gly Gly
        115                 120                 125 ggt ggc agc ggc ggt ggc gga tcg tct gag ctg act cag gac cct gct      432
Gly Gly Ser Gly Gly Gly Gly Ser Ser Glu Leu Thr Gln Asp Pro Ala
    130                 135                 140 gtg tct gtg gcc ttg gga cag aca gtc agg atc aca tgc caa gga gac      480
Val Ser Val Ala Leu Gly Gln Thr Val Arg Ile Thr Cys Gln Gly Asp
145                 150                 155                 160 agc ctc aga agc tat tat gca agc tgg tac cag cag aag cca gga cag      528
Ser Leu Arg Ser Tyr Tyr Ala Ser Trp Tyr Gln Gln Lys Pro Gly Gln
                165                 170                 175 gcc cct gta ctt gtc atc tat ggt aaa aac aac cgg ccc tca ggg atc      576
Ala Pro Val Leu Val Ile Tyr Gly Lys Asn Asn Arg Pro Ser Gly Ile
            180                 185                 190 cca gac cga ttc tct ggc tcc agc tca gga aac aca gct tcc ttg acc      624
Pro Asp Arg Phe Ser Gly Ser Ser Ser Gly Asn Thr Ala Ser Leu Thr
```

| | | |
|---|---|---|
| atc act ggg gct cag gcg gaa gat gag gct gac tat tac tgt aac tcc<br>Ile Thr Gly Ala Gln Ala Glu Asp Glu Ala Asp Tyr Tyr Cys Asn Ser<br>210                       215                      220 | | 672 |
| cgg gac agc agt ggt aac cat gtg gta ttc ggc gga ggg acc aag ctg<br>Arg Asp Ser Ser Gly Asn His Val Val Phe Gly Gly Gly Thr Lys Leu<br>225                       230                      235                      240 | | 720 |
| acc gtc cta ggt<br>Thr Val Leu Gly | | 732 |

```
<210> SEQ ID NO 185
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC666 scFv protein

<400> SEQUENCE: 185
```

| | |
|---|---|
| gag gtg cag ctg gtg gag tct ggg gga ggc ttg gca aag cct ggg gag<br>Glu Val Gln Leu Val Glu Ser Gly Gly Gly Leu Ala Lys Pro Gly Glu<br>1              5                    10                     15 | 48 |
| tca ctg aga ctc tcc tgt gaa gcc tct gga ttc gaa ttt aat tat gcc<br>Ser Leu Arg Leu Ser Cys Glu Ala Ser Gly Phe Glu Phe Asn Tyr Ala<br>20                      25                    30 | 96 |
| tgg atg agt tgg gtc cgc cag gct cca ggg aag ggg ctg gag tgg gtt<br>Trp Met Ser Trp Val Arg Gln Ala Pro Gly Lys Gly Leu Glu Trp Val<br>35                    40                    45 | 144 |
| ggc cgt agt aga agc gaa gct agt ggt ggg aca aca gac tac gct gca<br>Gly Arg Ser Arg Ser Glu Ala Ser Gly Gly Thr Thr Asp Tyr Ala Ala<br>50                    55                    60 | 192 |
| ccc ctg caa gac aga ttc acc atc tca aga gat gat tca aaa aac aca<br>Pro Leu Gln Asp Arg Phe Thr Ile Ser Arg Asp Asp Ser Lys Asn Thr<br>65                      70                    75                    80 | 240 |
| ctg tat cta caa gtc aac agc ctg aaa atc gag gac aca ggc gtg tat<br>Leu Tyr Leu Gln Val Asn Ser Leu Lys Ile Glu Asp Thr Gly Val Tyr<br>                    85                    90                    95 | 288 |
| ttc tgt aag tgg gag aaa tca gag tac tac ggt atg gac gtc tgg ggc<br>Phe Cys Lys Trp Glu Lys Ser Glu Tyr Tyr Gly Met Asp Val Trp Gly<br>                    100                 105              110 | 336 |
| aaa ggg aca atg gtc acc gtc tcg agt ggt gga ggc ggt tca ggc gga<br>Lys Gly Thr Met Val Thr Val Ser Ser Gly Gly Gly Gly Ser Gly Gly<br>115                   120                 125 | 384 |
| ggt ggc agc ggc ggt ggc gga tcg cag tct gtg ttg acg cag ccg ccc<br>Gly Gly Ser Gly Gly Gly Gly Ser Gln Ser Val Leu Thr Gln Pro Pro<br>130                   135                 140 | 432 |
| tca gtg tct gcg gcc cca gga cag aag gtc acc att tcc tgc tct gga<br>Ser Val Ser Ala Ala Pro Gly Gln Lys Val Thr Ile Ser Cys Ser Gly<br>145                   150                 155                160 | 480 |
| agc acc tcc aac att ggg aat aat tat gtc tcc tgg tac caa cag cac<br>Ser Thr Ser Asn Ile Gly Asn Asn Tyr Val Ser Trp Tyr Gln Gln His<br>                    165                 170              175 | 528 |
| cca ggc aaa gcc ccc aaa ctc atg att tat gat gtc agt aag cgg ccc<br>Pro Gly Lys Ala Pro Lys Leu Met Ile Tyr Asp Val Ser Lys Arg Pro<br>                180                 185              190 | 576 |
| tca ggg gtc cct gac cga ttc tct ggc tcc aag tct ggc aac tca gcc<br>Ser Gly Val Pro Asp Arg Phe Ser Gly Ser Lys Ser Gly Asn Ser Ala<br>195                   200                 205 | 624 |
| tcc ctg gac atc agt ggg ctc cag tct gag gat gag gct gat tat tac<br>Ser Leu Asp Ile Ser Gly Leu Gln Ser Glu Asp Glu Ala Asp Tyr Tyr | 672 |

```
              210                 215                 220
tgt gca gca tgg gat gac agc ctg agt gaa ttt ctc ttc gga act ggg        720
Cys Ala Ala Trp Asp Asp Ser Leu Ser Glu Phe Leu Phe Gly Thr Gly
225                 230                 235                 240 acc aag ctg acc gtc cta ggt                                            741
Thr Lys Leu Thr Val Leu Gly
                245

<210> SEQ ID NO 186
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC667 scFv protein

<400> SEQUENCE: 186 cag gtg cag ctg cag gag tcc ggg gga ggc ctg gta aag ccg ggg ggg         48
Gln Val Gln Leu Gln Glu Ser Gly Gly Gly Leu Val Lys Pro Gly Gly
1               5                   10                  15 tcc ctt aga ctg tcc tgt gca ggc tct ggt ttc cct ttc agt gac gcc         96
Ser Leu Arg Leu Ser Cys Ala Gly Ser Gly Phe Pro Phe Ser Asp Ala
                20                  25                  30 tgg atg aac tgg gtc cgc cag gct cca ggg aag ggg ctg gag tgg gtc        144
Trp Met Asn Trp Val Arg Gln Ala Pro Gly Lys Gly Leu Glu Trp Val
            35                  40                  45 ggc cgt att aaa agt aaa ggt agt ggt ggg aca ata gac tac gct gca        192
Gly Arg Ile Lys Ser Lys Gly Ser Gly Gly Thr Ile Asp Tyr Ala Ala
        50                  55                  60 ccc gtg aaa gac aga ttc agg atc tca cga gat gat tca aaa aac acg        240
Pro Val Lys Asp Arg Phe Arg Ile Ser Arg Asp Asp Ser Lys Asn Thr
65                  70                  75                  80 ctg tat ctg caa atg aac agt ctg aac atc gag gac aca gcc ctc tat        288
Leu Tyr Leu Gln Met Asn Ser Leu Asn Ile Glu Asp Thr Ala Leu Tyr
                85                  90                  95 tac tgt acg tgg gac tgg gat ttc tac tac ggt atg aac gtc tgg ggg        336
Tyr Cys Thr Trp Asp Trp Asp Phe Tyr Tyr Gly Met Asn Val Trp Gly
            100                 105                 110 cag ggg acc acg gtc acc gtc tct tca ggt gga ggc ggt tca ggc gga        384
Gln Gly Thr Thr Val Thr Val Ser Ser Gly Gly Gly Gly Ser Gly Gly
        115                 120                 125 ggt ggc agc ggc ggt ggc gga tcg cag tct gtg ctg act cag cct gcc        432
Gly Gly Ser Gly Gly Gly Gly Ser Gln Ser Val Leu Thr Gln Pro Ala
130                 135                 140 tcc gtg tct ggg tct cct gga cag tcg atc acc atc tcc tgc act gga        480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa        528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg        576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg        624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat        672
Ala Ser Leu Thr Ile Ser Gly Leu Gln Ala Glu Asp Glu Ala Asp Tyr
210                 215                 220 tac tgc agc tca tat aca acc agg agc act cga gtt ttc ggc gga ggg        720
Tyr Cys Ser Ser Tyr Thr Thr Arg Ser Thr Arg Val Phe Gly Gly Gly
```

```
Tyr Cys Ser Ser Tyr Thr Thr Arg Ser Thr Arg Val Phe Gly Gly Gly
225                 230                 235                 240 acc aag ctg acc gtc cta ggt                                              741
Thr Lys Leu Thr Val Leu Gly
                245
```

<210> SEQ ID NO 187
<211> LENGTH: 732
<212> TYPE: DNA
<213> ORGANISM: Artificial sequence
<220> FEATURE:
<221> NAME/KEY: CDS
<222> LOCATION: (1)..(732)
<223> OTHER INFORMATION: Polynucleotide encoding GMBC668 scFv protein

<400> SEQUENCE: 187

```
gag gtg cag ctg gtg gag tct ggg gga ggc ttg gta aag cct ggg ggg          48
Glu Val Gln Leu Val Glu Ser Gly Gly Gly Leu Val Lys Pro Gly Gly
1               5                   10                  15 tcc ctt aga ctc tcc tgt gca gcc tct ggt ttc act ttc agt gac gcc         96
Ser Leu Arg Leu Ser Cys Ala Ala Ser Gly Phe Thr Phe Ser Asp Ala
            20                  25                  30 tgg atg aac tgg gtc cgg cag gct cca ggg aag ggg ctg gag tgg gtc        144
Trp Met Asn Trp Val Arg Gln Ala Pro Gly Lys Gly Leu Glu Trp Val
        35                  40                  45 ggc cgt att aaa agt aaa ggt agt ggg aca aca gac tac gct gca             192
Gly Arg Ile Lys Ser Lys Gly Ser Gly Thr Thr Asp Tyr Ala Ala
    50                  55                  60 ccc gtg aaa ggc aga ttc acc atc tca aga gat gat tca gaa aac acg        240
Pro Val Lys Gly Arg Phe Thr Ile Ser Arg Asp Asp Ser Glu Asn Thr
65                  70                  75                  80 ctg tat ctg caa atg aac agc ctg aaa acc gag gac aca gcc gta tat        288
Leu Tyr Leu Gln Met Asn Ser Leu Lys Thr Glu Asp Thr Ala Val Tyr
                85                  90                  95 tac tgt acg tgg gac cac agt tac tac tac gat atg gcc gtc tgg ggc        336
Tyr Cys Thr Trp Asp His Ser Tyr Tyr Tyr Asp Met Ala Val Trp Gly
            100                 105                 110 cga ggc acc ctg gtc acc gtc tcg agt ggt gga ggc ggt tca ggc gga        384
Arg Gly Thr Leu Val Thr Val Ser Ser Gly Gly Gly Gly Ser Gly Gly
        115                 120                 125 ggt ggc agc ggc ggt ggc gga tcg tct gag ctg act cag gac cct gct        432
Gly Gly Ser Gly Gly Gly Gly Ser Ser Glu Leu Thr Gln Asp Pro Ala
    130                 135                 140 gtg tct gtg gcc ttg gga cag aca gtc agg atc aca tgc caa gga gac        480
Val Ser Val Ala Leu Gly Gln Thr Val Arg Ile Thr Cys Gln Gly Asp
145                 150                 155                 160 agc ctc aga agc tat tat gca agc tgg tac cag cag aag cca gga cag        528
Ser Leu Arg Ser Tyr Tyr Ala Ser Trp Tyr Gln Gln Lys Pro Gly Gln
                165                 170                 175 gcc cct gta ctt gtc atc tat ggt aaa aac aac cgg ccc tca ggg atc        576
Ala Pro Val Leu Val Ile Tyr Gly Lys Asn Asn Arg Pro Ser Gly Ile
            180                 185                 190 cca gac cga ttc tct ggc tcc agc tca gga aac aca gct tcc ttg acc        624
Pro Asp Arg Phe Ser Gly Ser Ser Ser Gly Asn Thr Ala Ser Leu Thr
        195                 200                 205 atc act ggg gct cag gcg gaa gat gag gct gac tat tac tgt aac tcc        672
Ile Thr Gly Ala Gln Ala Glu Asp Glu Ala Asp Tyr Tyr Cys Asn Ser
    210                 215                 220 cgg gac agc agt ggt aac cat gtg gta ttc ggc gga ggg acc aag ctg        720
Arg Asp Ser Ser Gly Asn His Val Val Phe Gly Gly Gly Thr Lys Leu
225                 230                 235                 240
```

```
acc gtc cta ggt                                                    732
Thr Val Leu Gly <210> SEQ ID NO 188
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC669 scFv protein

<400> SEQUENCE: 188 cag gtg cag ctg gtg gag tct ggg gga ggc ttg gta aag ccg ggg ggg    48
Gln Val Gln Leu Val Glu Ser Gly Gly Ala Leu Val Lys Pro Gly Gly
1               5                   10                  15 tcc ctt aga ctc tcc tgt gca gcc tct ggt ttc act ttc agt gac gcc    96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc   144
Trp Met Asn Trp Val Arg Gln Ala Pro Gly Lys Gly Leu Glu Trp Val
        35                  40                  45 ggc cgt att aaa agc aaa ggt agt ggg gga aca ata gac tac gct gca   192
Gly Arg Ile Lys Ser Lys Gly Ser Gly Gly Thr Ile Asp Tyr Ala Ala
    50                  55                  60 ccc gtg aaa gac aga ttc acc atc tca cga gat gat tca aaa aac acg   240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc ctg tat   288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc   336
Tyr Cys Thr Trp Asp Trp Asp Phe Tyr Tyr Gly Met Asn Val Trp Gly
            100                 105                 110 caa ggc acc ctg gtc acc gtc tcg agt ggt gga ggc ggt tca ggc gga   384
Gln Gly Thr Leu Val Thr Val Ser Ser Gly Gly Gly Gly Ser Gly Gly
        115                 120                 125 ggt ggc agc ggc ggt ggc gga tcg cag tct gtg ctg act cag cct ccc   432
Gly Gly Ser Gly Gly Gly Gly Ser Gln Ser Val Leu Thr Gln Pro Pro
    130                 135                 140 tcc gcg tcc ggg tct cct gga cag tca gtc acc atc tcc tgc act gga   480
Ser Ala Ser Gly Ser Pro Gly Gln Ser Val Thr Ile Ser Cys Thr Gly
145                 150                 155                 160 acc agc agt gat gtt ggt ggt tat aac tat gtc tcc tgg tac caa cag   528
Thr Ser Ser Asp Val Gly Gly Tyr Asn Tyr Val Ser Trp Tyr Gln Gln
                165                 170                 175 cac cca ggc aaa gcc ccc aaa ttc atg att tat gat gtc agt aag cgg   576
His Pro Gly Lys Ala Pro Lys Phe Met Ile Tyr Asp Val Ser Lys Arg
            180                 185                 190 ccc tca ggg gtt tct aat cgc ttc tct ggc tcc aag tct ggc aac acg   624
Pro Ser Gly Val Ser Asn Arg Phe Ser Gly Ser Lys Ser Gly Asn Thr
        195                 200                 205 gcg tcc ctg acc atc tct ggg gtc cag gct gag gac gag gct gat tat   672
Ala Ser Leu Thr Ile Ser Gly Val Gln Ala Glu Asp Glu Ala Asp Tyr
    210                 215                 220 tac tgc agc tca tat aca agc gcc agc act gtg ata ttc ggc gga ggg   720
Tyr Cys Ser Ser Tyr Thr Ser Ala Ser Thr Val Ile Phe Gly Gly Gly
225                 230                 235                 240 acc aag ctg acc gtc cta ggt                                       741
Thr Lys Leu Thr Val Leu Gly
                245
```

<210> SEQ ID NO 189
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC670 scFv protein

<400> SEQUENCE: 189

```
gag gtg cag ctg gtg gag act ggg gga ggc ttg gta aag ccg ggg ggg      48
Glu Val Gln Leu Val Glu Thr Gly Gly Gly Leu Val Lys Pro Gly Gly
1               5                   10                  15 tcc ctt aga ctc tcc tgt gta gcc tct ggt ttc act ttc agt gac gcc      96
Ser Leu Arg Leu Ser Cys Val Ala Ser Gly Phe Thr Phe Ser Asp Ala
            20                  25                  30 tgg atg aac tgg gtc cgc cag gct cca ggg aag ggg ctg gag tgg gtc     144
Trp Met Asn Trp Val Arg Gln Ala Pro Gly Lys Gly Leu Glu Trp Val
        35                  40                  45 ggc cgt att aaa agt aaa ggt agt ggt ggg aca ata gac tac gct gca     192
Gly Arg Ile Lys Ser Lys Gly Ser Gly Gly Thr Ile Asp Tyr Ala Ala
    50                  55                  60 ccc gtg aaa gac aga ttc att atc tca cga gat gat tca aaa aac acg     240
Pro Val Lys Asp Arg Phe Ile Ile Ser Arg Asp Asp Ser Lys Asn Thr
65                  70                  75                  80 ctg tat ctg caa gtg aac agt ctg aaa acc gag gac aca gcc cta tat     288
Leu Tyr Leu Gln Val Asn Ser Leu Lys Thr Glu Asp Thr Ala Leu Tyr
                85                  90                  95 tat tgt acg tgg gac tgg gat ttc tac tac ggt atg aac gtc tgg ggc     336
Tyr Cys Thr Trp Asp Trp Asp Phe Tyr Tyr Gly Met Asn Val Trp Gly
            100                 105                 110 caa ggc acc ctg gtc acc gtc tcc tct ggt gga ggc ggt tca ggc gga     384
Gln Gly Thr Leu Val Thr Val Ser Ser Gly Gly Gly Gly Ser Gly Gly
        115                 120                 125 ggt ggc agc ggc ggt ggc gga tcg cag tct gtg ctg act cag cct gcc     432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga     480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa     528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg     576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg     624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat     672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg     720
Tyr Cys Ser Ser Tyr Thr Thr Arg Ser Thr Arg Val Phe Gly Gly Gly
225                 230                 235                 240 acc aag ctg acc gtc cta ggt                                         741
Thr Lys Leu Thr Val Leu Gly
                245
```

<210> SEQ ID NO 190
<211> LENGTH: 741

```
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC672 scFv protein

<400> SEQUENCE: 190 cag gtc cag ctg gta cag tct ggg gga ggc ttg gta aag ccg ggg ggg        48
Gln Val Gln Leu Val Gln Ser Gly Gly Gly Leu Val Lys Pro Gly Gly
1               5                   10                  15 tcc ctt aga ctc tcc tgt gca gcc tct ggt ttc act ttc agt gac gcc        96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc       144
Trp Met Asn Trp Val Arg Gln Ala Pro Gly Lys Gly Leu Glu Trp Val
        35                  40                  45 ggc cgt att aaa agc aaa ggt agt ggt ggg aca ata gac tac gct gca       192
Gly Arg Ile Lys Ser Lys Gly Ser Gly Gly Thr Ile Asp Tyr Ala Ala
    50                  55                  60 ccc gtg aaa gac aga ttc acc atc tca cga gat gat tca aaa aac acg       240
Pro Val Lys Asp Arg Phe Thr Ile Ser Arg Asp Asp Ser Lys Asn Thr
65                  70                  75                  80 ctg tat ctg caa atg aat agt ctg aaa acc gag gac aca gcc ctg tat       288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc       336
Tyr Cys Thr Trp Asp Trp Asp Phe Tyr Tyr Gly Met Asn Val Trp Gly
            100                 105                 110 cag gga acc ctg gtc acc gtc tcg agt ggt gga ggc ggt tca ggc gga       384
Gln Gly Thr Leu Val Thr Val Ser Ser Gly Gly Gly Gly Ser Gly Gly
        115                 120                 125 ggt ggc agc ggc ggt ggc gga tcg cag tct gtg ctg act cag cct gcc       432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga       480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa       528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg       576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg       624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat       672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gaa ggg       720
Tyr Cys Ser Ser Tyr Thr Thr Arg Ser Thr Arg Val Phe Gly Glu Gly
225                 230                 235                 240 acc aag ctg acc gtc cta ggt                                           741
Thr Lys Leu Thr Val Leu Gly
                245

<210> SEQ ID NO 191
<211> LENGTH: 729
<212> TYPE: DNA
<213> ORGANISM: Artificial sequence
<220> FEATURE:
```

```
<221> NAME/KEY: CDS
<222> LOCATION: (1)..(729)
<223> OTHER INFORMATION: Polynucleotide encoding GMBC673 scFv protein

<400> SEQUENCE: 191 gag gtg cag ctg gtg gag tct ggg gga ggc ttg gta cag act ggg ggg         48
Glu Val Gln Leu Val Glu Ser Gly Gly Gly Leu Val Gln Thr Gly Gly
1               5                  10                  15 tcc ctg aga ctc tcc tgt gca gcc tct gga ttt ccc att ggc agt cac         96
Ser Leu Arg Leu Ser Cys Ala Ala Ser Gly Phe Pro Ile Gly Ser His
            20                  25                  30 tgg atg agc tgg gtc cgc cag tct ccg ggg aag ggg ctg gag tgg gtg        144
Trp Met Ser Trp Val Arg Gln Ser Pro Gly Lys Gly Leu Glu Trp Val
        35                  40                  45 gcc agc atc aag caa gat gga cgt gag aag cac ttt gtg gac tct gtg        192
Ala Ser Ile Lys Gln Asp Gly Arg Glu Lys His Phe Val Asp Ser Val
    50                  55                  60 aag ggc cga ttc ggc atc tcc aga gac aac gcc aag gac tca ctg tat        240
Lys Gly Arg Phe Gly Ile Ser Arg Asp Asn Ala Lys Asp Ser Leu Tyr
65                  70                  75                  80 ctc caa atg aac agc ctg aga atc gag gac acg gct gtc tac tac tgt        288
Leu Gln Met Asn Ser Leu Arg Ile Glu Asp Thr Ala Val Tyr Tyr Cys
                85                  90                  95 gcg aga gag acg tac ggg gga tac tac tat tac ttc atg gac gtc tgg        336
Ala Arg Glu Thr Tyr Gly Gly Tyr Tyr Tyr Tyr Phe Met Asp Val Trp
            100                 105                 110 ggc cga ggc acc ctg gtc acc gtc tcg agt ggt gga ggc ggt tca ggc        384
Gly Arg Gly Thr Leu Val Thr Val Ser Ser Gly Gly Gly Gly Ser Gly
        115                 120                 125 gga ggt ggc agc ggc ggt ggc gga tcg tct gag ctg act cag gac cct        432
Gly Gly Gly Ser Gly Gly Gly Ser Ser Glu Leu Thr Gln Asp Pro
130                 135                 140 gct gtg tct gtg gcc ttg gga cag aca gtc agg atc aca tgc caa gga        480
Ala Val Ser Val Ala Leu Gly Gln Thr Val Arg Ile Thr Cys Gln Gly
145                 150                 155                 160 gac agc ctc aga agc tat tat gca agc tgg tac cag cag aag cca gga        528
Asp Ser Leu Arg Ser Tyr Tyr Ala Ser Trp Tyr Gln Gln Lys Pro Gly
                165                 170                 175 cag gcc cct gta ctt gtc atc tat ggt aaa aac aac cgg ccc tca ggg        576
Gln Ala Pro Val Leu Val Ile Tyr Gly Lys Asn Asn Arg Pro Ser Gly
            180                 185                 190 atc cca gac cga ttc tct ggc tcc agc tca gga aac aca gct tcc ttg        624
Ile Pro Asp Arg Phe Ser Gly Ser Ser Ser Gly Asn Thr Ala Ser Leu
        195                 200                 205 acc atc act ggg gct cag gcg gaa gat gag gct gac tat tac tgt cag        672
Thr Ile Thr Gly Ala Gln Ala Glu Asp Glu Ala Asp Tyr Tyr Cys Gln
    210                 215                 220 acc tgg ggc cct ggc att cga gtg ttc ggc gga ggg acc aag ctg acc        720
Thr Trp Gly Pro Gly Ile Arg Val Phe Gly Gly Gly Thr Lys Leu Thr
225                 230                 235                 240 gtc cta ggt                                                            729
Val Leu Gly <210> SEQ ID NO 192
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC676 scFv protein
```

```
<400> SEQUENCE: 192 gag gtg cag ctg gtg cag tct ggg gga ggc ttg gta cag cct ggg ggg    48
Glu Val Gln Leu Val Gln Ser Gly Gly Gly Leu Val Gln Pro Gly Gly
1               5                   10                  15 tcc ctg aga ctc tcc tgt gca gcc tct ggt ttc act ttc agt cac gcc    96
Ser Leu Arg Leu Ser Cys Ala Ala Ser Gly Phe Thr Phe Ser His Ala
            20                  25                  30 tgg atg aac tgg gtc cgc cag gct cca ggg aag ggg ctg gag tgg gtc   144
Trp Met Asn Trp Val Arg Gln Ala Pro Gly Lys Gly Leu Glu Trp Val
        35                  40                  45 ggc cgt att aaa agc aaa gct agt ggg gga aca ata gac tac gcc gca   192
Gly Arg Ile Lys Ser Lys Ala Ser Gly Gly Thr Ile Asp Tyr Ala Ala
    50                  55                  60 ccc gtg aaa gac aga ttc acc atc tca cga gat gat tca aaa aac acg   240
Pro Val Lys Asp Arg Phe Thr Ile Ser Arg Asp Asp Ser Lys Asn Thr
65                  70                  75                  80 ctg tat ctg cac atg aac agt ctg aaa acc gag gac aca gcc ctg tat   288
Leu Tyr Leu His Met Asn Ser Leu Lys Thr Glu Asp Thr Ala Leu Tyr
                85                  90                  95 tac tgt acg tgg gac tgg gat ttc tac tac ggt atg aac gtc tgg ggg   336
Tyr Cys Thr Trp Asp Trp Asp Phe Tyr Tyr Gly Met Asn Val Trp Gly
            100                 105                 110 cgg ggg aca atg gtc acc gtc tct tca ggt gga ggc ggt tca ggc gga   384
Arg Gly Thr Met Val Thr Val Ser Ser Gly Gly Gly Gly Ser Gly Gly
        115                 120                 125 ggt ggc agc ggc ggt ggc gga tcg cag tct gtg ctg act cag cct gcc   432
Gly Gly Ser Gly Gly Gly Gly Ser Gln Ser Val Leu Thr Gln Pro Ala
    130                 135                 140 tcc gtg tct ggg tct cct gga cag ccg atc acc atc tcc tgc act gga   480
Ser Val Ser Gly Ser Pro Gly Gln Pro Ile Thr Ile Ser Cys Thr Gly
145                 150                 155                 160 acc agc agt gac gtt ggt ggt tat aac tat gtc tcc tgg tac caa caa   528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg   576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg   624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat   672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg   720
Tyr Cys Ser Ser Tyr Thr Thr Arg Ser Thr Arg Val Phe Gly Gly Gly
225                 230                 235                 240 acc aag ctg acc gtc cta ggt                                        741
Thr Lys Leu Thr Val Leu Gly
                245

<210> SEQ ID NO 193
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC678 scFv protein

<400> SEQUENCE: 193 gag gtg cag ctg gtg gag tct ggg gga ggc ttg gta aag ccg ggg ggg    48
```

|  |  |  |  |  |  |  |  |  |  |  |  |  |  |  |  |
|---|---|---|---|---|---|---|---|---|---|---|---|---|---|---|---|
|  | Glu | Val | Gln | Leu | Val | Glu | Ser | Gly | Gly | Gly | Leu | Val | Lys | Pro | Gly | Gly |
|  | 1 |  |  |  | 5 |  |  |  |  | 10 |  |  |  |  | 15 |  | tcc ctt aga ctc tcc tgt gca gcc tct ggt ttc act ttc agt gac gcc    96
Ser Leu Arg Leu Ser Cys Ala Ala Ser Gly Phe Thr Phe Ser Asp Ala
           20                  25                  30 tgg atg aac tgg gtc cgc cag gct cca ggg aag ggg ctg gag tgg gtc   144
Trp Met Asn Trp Val Arg Gln Ala Pro Gly Lys Gly Leu Glu Trp Val
        35                  40                  45 ggc cgt att aaa agt aaa ggt agt ggt ggg aca ata gac tac gcc gca   192
Gly Arg Ile Lys Ser Lys Gly Ser Gly Gly Thr Ile Asp Tyr Ala Ala
50                  55                  60 ccc gtg aaa gac aga ttc acc atc tca cga gat gat tca aaa aac acg   240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc ctg tat   288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc   336
Tyr Cys Thr Trp Asp Trp Asp Phe Tyr Tyr Gly Met Asn Val Trp Gly
            100                 105                 110 cag gga acc ctg gtc acc gtc tcc tca ggt ggg ggc ggt tca ggc gga   384
Gln Gly Thr Leu Val Thr Val Ser Ser Gly Gly Gly Gly Ser Gly Gly
        115                 120                 125 ggt ggc agc ggc ggt ggc gga tcg cag tct gtg ctg act cag cct ccc   432
Gly Gly Ser Gly Gly Gly Gly Ser Gln Ser Val Leu Thr Gln Pro Pro
    130                 135                 140 tcc gcg tcc ggg tct cct gga cag tca gtc acc atc tcc tgc act gga   480
Ser Ala Ser Gly Ser Pro Gly Gln Ser Val Thr Ile Ser Cys Thr Gly
145                 150                 155                 160 acc agc agt gat gtt ggt ggt tat aac tat gtc tcc tgg tac caa cag   528
Thr Ser Ser Asp Val Gly Gly Tyr Asn Tyr Val Ser Trp Tyr Gln Gln
                165                 170                 175 cac cca ggc aaa gcc ccc aaa ttc atg att tat gat gtc agt aag cgg   576
His Pro Gly Lys Ala Pro Lys Phe Met Ile Tyr Asp Val Ser Lys Arg
            180                 185                 190 ccc tca ggg gtt tct aat cgc ttc tct ggc tcc aag tct ggc aac acg   624
Pro Ser Gly Val Ser Asn Arg Phe Ser Gly Ser Lys Ser Gly Asn Thr
        195                 200                 205 gcg tcc ctg acc atc tct ggg gtc cag gct gag gac gag gct gat tat   672
Ala Ser Leu Thr Ile Ser Gly Val Gln Ala Glu Asp Glu Ala Asp Tyr
    210                 215                 220 tac tgc agc tca tat aca agc gcc agc act gtg ata ttc ggc gga ggg   720
Tyr Cys Ser Ser Tyr Thr Ser Ala Ser Thr Val Ile Phe Gly Gly Gly
225                 230                 235                 240 acc aag ctg acc gtc cta ggt                                        741
Thr Lys Leu Thr Val Leu Gly
                245

<210> SEQ ID NO 194
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC679 scFv protein

<400> SEQUENCE: 194 cag gtg cag ctg gtg gag tct ggg gga ggc ttg gta aag cct ggg ggg    48
Gln Val Gln Leu Val Glu Ser Gly Gly Gly Leu Val Lys Pro Gly Gly
1               5                   10                  15

| | | |
|---|---|---|
| tcc ctt aga ctc tcc tgt gca gcc tct ggt ttc act ttc agt gac gcc<br>Ser Leu Arg Leu Ser Cys Ala Ala Ser Gly Phe Thr Phe Ser Asp Ala<br>        20                     25                  30 | | 96 |
| tgg atg aac tgg gtc cgc cag gct cca ggg aag ggg ctg gag tgg gtc<br>Trp Met Asn Trp Val Arg Gln Ala Pro Gly Lys Gly Leu Glu Trp Val<br>        35                     40                  45 | | 144 |
| ggc cgt att aaa agt aaa ggt agt ggt ggg aca aca gac tac gct gca<br>Gly Arg Ile Lys Ser Lys Gly Ser Gly Gly Thr Thr Asp Tyr Ala Ala<br>     50                   55                  60 | | 192 |
| ccc gtg aaa gac aga ttc acc atc tca aga gat gat tca gaa aac acg<br>Pro Val Lys Asp Arg Phe Thr Ile Ser Arg Asp Asp Ser Glu Asn Thr<br>65                   70                  75                  80 | | 240 |
| ctg tat cta caa atg aac agc ctg aaa acc gag gac aca gcc gta tat<br>Leu Tyr Leu Gln Met Asn Ser Leu Lys Thr Glu Asp Thr Ala Val Tyr<br>                    85                  90                  95 | | 288 |
| tac tgt acg tgg gac cat agt tat tat tat gat atg gcc gtc tgg ggc<br>Tyr Cys Thr Trp Asp His Ser Tyr Tyr Tyr Asp Met Ala Val Trp Gly<br>            100                   105               110 | | 336 |
| cga ggc acc ctg gtc acc gtc tcc tca ggt gga ggc ggt tca ggc gga<br>Arg Gly Thr Leu Val Thr Val Ser Ser Gly Gly Gly Gly Ser Gly Gly<br>        115                   120               125 | | 384 |
| ggt ggc agc ggc ggt ggc gga tcg cag tct gtg ctg act cag cct gcc<br>Gly Gly Ser Gly Gly Gly Gly Ser Gln Ser Val Leu Thr Gln Pro Ala<br>130                    135               140 | | 432 |
| tcc gtg tct ggg tct cct gga cag tcg atc acc atc tcc tgc act gga<br>Ser Val Ser Gly Ser Pro Gly Gln Ser Ile Thr Ile Ser Cys Thr Gly<br>145                    150               155               160 | | 480 |
| acc agc agt gac gtt ggt ggt tat aac tat gtc tcc tgg tac caa caa<br>Thr Ser Ser Asp Val Gly Gly Tyr Asn Tyr Val Ser Trp Tyr Gln Gln<br>                  165               170               175 | | 528 |
| cac cca ggc aaa gcc ccc aaa ctc gtg att tat gag ggc agt aag cgg<br>His Pro Gly Lys Ala Pro Lys Leu Val Ile Tyr Glu Gly Ser Lys Arg<br>            180                   185               190 | | 576 |
| ccc tca ggg gtt tct aat cgc ttc tct ggc tcc aag tct ggc aac acg<br>Pro Ser Gly Val Ser Asn Arg Phe Ser Gly Ser Lys Ser Gly Asn Thr<br>        195                   200               205 | | 624 |
| gcc tcc ctg aca atc tct ggg ctc cag gct gag gac gag gct gat tat<br>Ala Ser Leu Thr Ile Ser Gly Leu Gln Ala Glu Asp Glu Ala Asp Tyr<br>210                    215               220 | | 672 |
| tac tgc agc tca tat aca acc agg agc act cga gtt ttc ggc gga ggg<br>Tyr Cys Ser Ser Tyr Thr Thr Arg Ser Thr Arg Val Phe Gly Gly Gly<br>225                    230               235               240 | | 720 |
| acc aag ctg acc gtc cta ggt<br>Thr Lys Leu Thr Val Leu Gly<br>        245 | | 741 |

<210> SEQ ID NO 195
<211> LENGTH: 720
<212> TYPE: DNA
<213> ORGANISM: Artificial sequence
<220> FEATURE:
<221> NAME/KEY: CDS
<222> LOCATION: (1)..(720)
<223> OTHER INFORMATION: Polynucleotide encoding GMBC681 scFv protein

<400> SEQUENCE: 195

| | | |
|---|---|---|
| cag gtg cag ctg gtg cag tct ggg gga ggc gtg gtc cag cct ggg ggg<br>Gln Val Gln Leu Val Gln Ser Gly Gly Gly Val Val Gln Pro Gly Gly<br>1                 5                  10                  15 | | 48 |
| tcc ctg aga ctc tcc tgt gca gcg tct gga ttc acc ttc agt agc tat<br>Ser Leu Arg Leu Ser Cys Ala Ala Ser Gly Phe Thr Phe Ser Ser Tyr<br>        20                     25                  30 | | 96 |

-continued

```
ggc atg cac tgg gtc cgc cag gct cca ggc aag ggg ctg gag tgg gtg      144
Gly Met His Trp Val Arg Gln Ala Pro Gly Lys Gly Leu Glu Trp Val
        35                  40                  45 gca ttt ata cgg tat gat gga agt aat aaa tac tat gca gac tcc gtg      192
Ala Phe Ile Arg Tyr Asp Gly Ser Asn Lys Tyr Tyr Ala Asp Ser Val
 50                  55                  60 aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
 65                  70                  75                  80 ctg caa atg aac agc ctg aga gct gag gac acg gct gtg tat tac tgt      288
Leu Gln Met Asn Ser Leu Arg Ala Glu Asp Thr Ala Val Tyr Tyr Cys
                 85                  90                  95 gcg aaa gga gga act ggc tac ttc gat ctc tgg ggc cga gga acc ctg      336
Ala Lys Gly Gly Thr Gly Tyr Phe Asp Leu Trp Gly Arg Gly Thr Leu
            100                 105                 110 gtc acc gtc tcc tca ggt gga ggc ggt tca ggc gga ggt ggc agc ggc      384
Val Thr Val Ser Ser Gly Gly Gly Gly Ser Gly Gly Gly Gly Ser Gly
        115                 120                 125 ggt ggc gga tcg gac atc cag atg acc cag tct cct tcc acc ctg tct      432
Gly Gly Gly Ser Asp Ile Gln Met Thr Gln Ser Pro Ser Thr Leu Ser
130                 135                 140 gca tct att gga gac aga gtc acc atc acc tgc cgg gcc agt gag ggt      480
Ala Ser Ile Gly Asp Arg Val Thr Ile Thr Cys Arg Ala Ser Glu Gly
145                 150                 155                 160 att tat cac tgg ttg gcc tgg tat cag cag aag cca ggg aaa gcc cct      528
Ile Tyr His Trp Leu Ala Trp Tyr Gln Gln Lys Pro Gly Lys Ala Pro
                165                 170                 175 aaa ctc ctg atc tat aag gcc tct agt tta gcc agt ggg gcc cca tca      576
Lys Leu Leu Ile Tyr Lys Ala Ser Ser Leu Ala Ser Gly Ala Pro Ser
            180                 185                 190 agg ttc agc ggc agt gga tct ggg aca gat ttc act ctc acc atc agc      624
Arg Phe Ser Gly Ser Gly Ser Gly Thr Asp Phe Thr Leu Thr Ile Ser
        195                 200                 205 agc ctg cag cct gat gat ttt gca act tat tac tgc caa caa tat agt      672
Ser Leu Gln Pro Asp Asp Phe Ala Thr Tyr Tyr Cys Gln Gln Tyr Ser
    210                 215                 220 aat tat ccg ctc act ttc ggc gga ggg acc aag ctg gag atc aaa cgt      720
Asn Tyr Pro Leu Thr Phe Gly Gly Gly Thr Lys Leu Glu Ile Lys Arg
225                 230                 235                 240

<210> SEQ ID NO 196
<211> LENGTH: 732
<212> TYPE: DNA
<213> ORGANISM: Artificial sequence
<220> FEATURE:
<221> NAME/KEY: CDS
<222> LOCATION: (1)..(732)
<223> OTHER INFORMATION: Polynucleotide encoding GMBC682 scFv protein

<400> SEQUENCE: 196 cag gtg cag ctg gtg gag tct ggg gga ggc gtg gta aag ccg ggg ggg       48
Gln Val Gln Leu Val Glu Ser Gly Gly Gly Val Val Lys Pro Gly Gly
 1               5                  10                  15 tcc ctt aga ctc tcc tgt gca gcc tct ggt ttc aaa ttc agt gac gcc       96
Ser Leu Arg Leu Ser Cys Ala Ala Ser Gly Phe Lys Phe Ser Asp Ala
             20                  25                  30 tgg atg aac tgg gtc cgc cag gct cca ggg aag ggg ctg gag tgg gtc      144
Trp Met Asn Trp Val Arg Gln Ala Pro Gly Lys Gly Leu Glu Trp Val
         35                  40                  45 ggc cgt att aaa agc aaa ggt agt ggt ggg aca ata gac tac gct gca      192
Gly Arg Ile Lys Ser Lys Gly Ser Gly Gly Thr Ile Asp Tyr Ala Ala
 50                  55                  60
```

```
                    50                  55                  60
ccc gtg aaa gac aga ttc acc atc tca cga gat gat tca aaa aac acg    240
Pro Val Lys Asp Arg Phe Thr Ile Ser Arg Asp Asp Ser Lys Asn Thr
 65                  70                  75                  80 ctg tat ctg caa atg aac agt ctg aaa acc gag gac aca gcc ctg tat    288
Leu Tyr Leu Gln Met Asn Ser Leu Lys Thr Glu Asp Thr Ala Leu Tyr
                 85                  90                  95 tac tgt acg tgg gac tgg gat ttc tac tac ggt atg aac gtc tgg ggc    336
Tyr Cys Thr Trp Asp Trp Asp Phe Tyr Tyr Gly Met Asn Val Trp Gly
            100                 105                 110 cgg gga acc ctg gtc acc gtc tcc tca ggt gga ggc ggt tca ggc gga    384
Arg Gly Thr Leu Val Thr Val Ser Ser Gly Gly Gly Gly Ser Gly Gly
        115                 120                 125 ggt ggc agc ggc ggt ggc gga tcg tct gag ctg act cag gac cct gct    432
Gly Gly Ser Gly Gly Gly Gly Ser Ser Glu Leu Thr Gln Asp Pro Ala
    130                 135                 140 gtg tct gtg gcc ttg gga cag aca gtc agg atc aca tgc caa gga gac    480
Val Ser Val Ala Leu Gly Gln Thr Val Arg Ile Thr Cys Gln Gly Asp
145                 150                 155                 160 agc ctc aga agc tat tat gca agc tgg tac cag cag aag cca gga cag    528
Ser Leu Arg Ser Tyr Tyr Ala Ser Trp Tyr Gln Gln Lys Pro Gly Gln
                165                 170                 175 gcc cct gta ctt gtc atc tat ggt aaa aac aac cgg ccc tca ggg atc    576
Ala Pro Val Leu Val Ile Tyr Gly Lys Asn Asn Arg Pro Ser Gly Ile
            180                 185                 190 cca gac cga ttc tct ggc tcc agc tca gga aac aca gct tcc ttg acc    624
Pro Asp Arg Phe Ser Gly Ser Ser Ser Gly Asn Thr Ala Ser Leu Thr
        195                 200                 205 atc act ggg gct cag gcg gaa gat gag gct gac tat tac tgt aac tcc    672
Ile Thr Gly Ala Gln Ala Glu Asp Glu Ala Asp Tyr Tyr Cys Asn Ser
    210                 215                 220 cgg gac agc agt ggt aac cat gtg gta ttc ggc gga ggg acc aag ctg    720
Arg Asp Ser Ser Gly Asn His Val Val Phe Gly Gly Gly Thr Lys Leu
225                 230                 235                 240 acc gtc cta ggt                                                    732
Thr Val Leu Gly <210> SEQ ID NO 197
<211> LENGTH: 723
<212> TYPE: DNA
<213> ORGANISM: Artificial sequence
<220> FEATURE:
<221> NAME/KEY: CDS
<222> LOCATION: (1)..(723)
<223> OTHER INFORMATION: Polynucleotide encoding GMBC683 scFv protein

<400> SEQUENCE: 197 gag gtg cag ctg gtg gag tcc ggg gga ggc ttg gtc cag cct ggg agg    48
Glu Val Gln Leu Val Glu Ser Gly Gly Gly Leu Val Gln Pro Gly Arg
  1               5                  10                  15 tcc ctg aga ctc tcc tgt gca gcg tct gga ttc acc ttc agt agc tat    96
Ser Leu Arg Leu Ser Cys Ala Ala Ser Gly Phe Thr Phe Ser Ser Tyr
             20                  25                  30 ggc atg cac tgg gtc cgc cag gct cca ggc aag ggg ctg gag tgg gtg    144
Gly Met His Trp Val Arg Gln Ala Pro Gly Lys Gly Leu Glu Trp Val
         35                  40                  45 gca gtt ata tca tat gat gga agt aat aaa tac tat gca gac tcc gtg    192
Ala Val Ile Ser Tyr Asp Gly Ser Asn Lys Tyr Tyr Ala Asp Ser Val
     50                  55                  60 aag ggc cga ttc acc atc tcc aga gac aat tcc aag aac acg ctg tat    240
Lys Gly Arg Phe Thr Ile Ser Arg Asp Asn Ser Lys Asn Thr Leu Tyr
 65                  70                  75                  80
```

-continued

```
                65                  70                  75                  80
ctg caa atg aac agc ctg aga gct gag gac acg gct gtg tat tac tgt        288
Leu Gln Met Asn Ser Leu Arg Ala Glu Asp Thr Ala Val Tyr Tyr Cys
                    85                  90                  95 gcg aaa cgg gca gca gct ggt acc ctt gac tac tgg ggg cag ggg acc        336
Ala Lys Arg Ala Ala Ala Gly Thr Leu Asp Tyr Trp Gly Gln Gly Thr
            100                 105                 110 acg gtc acc gtc tcg agt ggt gga ggc ggt tca ggc gga ggt ggc agc        384
Thr Val Thr Val Ser Ser Gly Gly Gly Gly Ser Gly Gly Gly Gly Ser
        115                 120                 125 ggc ggt ggc gga tcg tct gag ctg act cag gac cct gct gtg tct gtg        432
Gly Gly Gly Gly Ser Ser Glu Leu Thr Gln Asp Pro Ala Val Ser Val
    130                 135                 140 gcc ttg gga cag aca gtc agg atc aca tgc caa gga gac agt ctc aga        480
Ala Leu Gly Gln Thr Val Arg Ile Thr Cys Gln Gly Asp Ser Leu Arg
145                 150                 155                 160 agc tat tat gca agc tgg tac cag cag aag cca gga cag gcc cct gta        528
Ser Tyr Tyr Ala Ser Trp Tyr Gln Gln Lys Pro Gly Gln Ala Pro Val
                165                 170                 175 ctt gtc atc tat ggt aaa aac aac cgg ccc tca ggg atc cca gac cga        576
Leu Val Ile Tyr Gly Lys Asn Asn Arg Pro Ser Gly Ile Pro Asp Arg
            180                 185                 190 ttc tct ggc tcc agc tca gga aac aca gct tcc ttg acc atc act ggg        624
Phe Ser Gly Ser Ser Ser Gly Asn Thr Ala Ser Leu Thr Ile Thr Gly
        195                 200                 205 gct cag gcg gaa gat gag gct gac tat tac tgt aac tcc cgg gac agc        672
Ala Gln Ala Glu Asp Glu Ala Asp Tyr Tyr Cys Asn Ser Arg Asp Ser
    210                 215                 220 agt ggt aac cat gtg gta ttc ggc gga ggg acc aag ctg acc gtc cta        720
Ser Gly Asn His Val Val Phe Gly Gly Gly Thr Lys Leu Thr Val Leu
225                 230                 235                 240 ggt                                                                    723
Gly

<210> SEQ ID NO 198
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC684 scFv protein

<400> SEQUENCE: 198 cag gtg cag ctg gtg caa tct ggg gga ggc ttg gta aag ccg ggg ggg         48
Gln Val Gln Leu Val Gln Ser Gly Gly Gly Leu Val Lys Pro Gly Gly
1               5                   10                  15 tcc ctt aga ctc tcc tgt gca gcc tct ggt ttc aaa ttc agt gac gcc         96
Ser Leu Arg Leu Ser Cys Ala Ala Ser Gly Phe Lys Phe Ser Asp Ala
                20                  25                  30 tgg atg aac tgg gtc cgc cag gct cca ggg aag ggg ctg gag tgg gtc        144
Trp Met Asn Trp Val Arg Gln Ala Pro Gly Lys Gly Leu Glu Trp Val
            35                  40                  45 ggc cgt att aaa agc aaa ggt agt ggc ggg aca ata gac tac gct gca        192
Gly Arg Ile Lys Ser Lys Gly Ser Gly Gly Thr Ile Asp Tyr Ala Ala
        50                  55                  60 ccc gtg aaa gac aga ttc acc atc tca cga gat gat tca aaa aac acg        240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc cta tat        288
Leu Tyr Leu Gln Met Asn Ser Leu Lys Thr Glu Asp Thr Ala Leu Tyr
```

```
                85                  90                  95
tac tgt acg tgg gac tgg gat ttc tac tac ggt atg aac gtc tgg ggc       336
Tyr Cys Thr Trp Asp Trp Asp Phe Tyr Tyr Gly Met Asn Val Trp Gly
            100                 105                 110 caa gga acc ccg gtc acc gtc tcg agt ggt gga ggc ggt tca ggc gga       384
Gln Gly Thr Pro Val Thr Val Ser Ser Gly Gly Gly Gly Ser Gly Gly
        115                 120                 125 ggt ggc agc ggc ggt ggc gga tcg cag tct gcg ctg act cag cct gcc       432
Gly Gly Ser Gly Gly Gly Gly Ser Gln Ser Ala Leu Thr Gln Pro Ala
    130                 135                 140 tcc gtg tct ggg tct cct gga cag tcg atc acc atc tcc tgc act gga       480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa       528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg       576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg       624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat       672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg       720
Tyr Cys Ser Ser Tyr Thr Thr Arg Ser Thr Arg Val Phe Gly Gly Gly
225                 230                 235                 240 acc aag ctg acc gtc cta ggt                                           741
Thr Lys Leu Thr Val Leu Gly
                245

<210> SEQ ID NO 199
<211> LENGTH: 732
<212> TYPE: DNA
<213> ORGANISM: Artificial sequence
<220> FEATURE:
<221> NAME/KEY: CDS
<222> LOCATION: (1)..(732)
<223> OTHER INFORMATION: Polynucleotide encoding GMBC685 scFv protein

<400> SEQUENCE: 199 cag gtg cag ctg gtg gag tct ggg gga gtc gtg gta cag cct ggg ggg       48
Gln Val Gln Leu Val Glu Ser Gly Gly Val Val Val Gln Pro Gly Gly
1               5                   10                  15 tcc ctt aga ctc tcc tgt gca gcc tct ggt ttc act ttc agt gac gcc       96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc       144
Trp Met Asn Trp Val Arg Gln Ala Pro Gly Lys Gly Leu Glu Trp Val
        35                  40                  45 ggc cgt att aaa agc aaa ggt agt ggt ggg aca ata gac tac gcc gca       192
Gly Arg Ile Lys Ser Lys Gly Ser Gly Gly Thr Ile Asp Tyr Ala Ala
    50                  55                  60 ccc gtg aaa gac aga ttc acc atc tca cga gat gat tca aaa aac acg       240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc ctg tat       288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc       336
```

-continued

| | | |
|---|---|---|
| Tyr Cys Thr Trp Asp Trp Asp Phe Tyr Tyr Gly Met Asn Val Trp Gly<br>100               105               110 | | |

```
aag ggg aca atg gtc acc gtc tcg agt ggt gga ggc ggt tca ggc gga      384
Lys Gly Thr Met Val Thr Val Ser Ser Gly Gly Gly Gly Ser Gly Gly
        115                 120                 125 ggt ggc agc ggc ggt ggc gga tcg tct gag ctg act cag gac cct gct      432
Gly Gly Ser Gly Gly Gly Gly Ser Ser Glu Leu Thr Gln Asp Pro Ala
130                 135                 140 gtg tct gtg gcc ttg gga cag aca gtc agg atc act tgc caa gga gac      480
Val Ser Val Ala Leu Gly Gln Thr Val Arg Ile Thr Cys Gln Gly Asp
145                 150                 155                 160 agt ctc aga agc tat tac aca aac tgg ttc cag cag aag cca gga cag      528
Ser Leu Arg Ser Tyr Tyr Thr Asn Trp Phe Gln Gln Lys Pro Gly Gln
                165                 170                 175 gcc cct cta ctt gtc gtc tat gct aaa aat aag cgg ccc tca ggg atc      576
Ala Pro Leu Leu Val Val Tyr Ala Lys Asn Lys Arg Pro Ser Gly Ile
            180                 185                 190 cca gac cga ttc tct ggc tcc agc tca gga aac aca gct tcc ttg acc      624
Pro Asp Arg Phe Ser Gly Ser Ser Ser Gly Asn Thr Ala Ser Leu Thr
        195                 200                 205 atc act ggg gct cag gcg gaa gat gag gct gac tat tac tgt cat tcc      672
Ile Thr Gly Ala Gln Ala Glu Asp Glu Ala Asp Tyr Tyr Cys His Ser
210                 215                 220 cgg gac agc agt ggt aac cat gtg ctt ttc ggc gga ggg acc aag ctg      720
Arg Asp Ser Ser Gly Asn His Val Leu Phe Gly Gly Gly Thr Lys Leu
225                 230                 235                 240 acc gtc cta ggt                                                      732
Thr Val Leu Gly <210> SEQ ID NO 200
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC686 scFv protein

<400> SEQUENCE: 200 gag gtg cag ctg gtg cag tct ggg gga ggc ttg gta aag ccg ggg ggg       48
Glu Val Gln Leu Val Gln Ser Gly Gly Gly Leu Val Lys Pro Gly Gly
1               5                  10                  15 tcc ctt aga ctc tcc tgt gca gcc tct ggt ttc act ttc agt gac gcc       96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc      144
Trp Met Asn Trp Val Arg Gln Ala Pro Gly Lys Gly Leu Glu Trp Val
        35                  40                  45 ggc cgt att aaa agc aaa ggt agt ggt ggg aca ata gac tac gcc gca      192
Gly Arg Ile Lys Ser Lys Gly Ser Gly Gly Thr Ile Asp Tyr Ala Ala
    50                  55                  60 ccc gtg aaa gac aga ttc acc atc tca cga gat gat tca aaa aac acg      240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc ctg tat      288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc      336
Tyr Cys Thr Trp Asp Trp Asp Phe Tyr Tyr Gly Met Asn Val Trp Gly
            100                 105                 110 cag ggg acc acg gtc acc gtc tcc tca ggt gga ggc ggt tca ggc gga      384
```

-continued

```
                    Gln Gly Thr Thr Val Thr Val Ser Ser Gly Gly Gly Ser Gly Gly
                            115                 120                 125 ggt ggc agc ggc ggt ggc gga tcg cag tct gtg ctg act cag cct gcc                  432
Gly Gly Ser Gly Gly Gly Gly Ser Gln Ser Val Leu Thr Gln Pro Ala
130                 135                 140 tcc gtg tct ggg tct cct gga cag tcg atc acc atc tcc tgc act gga                  480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa                  528
Thr Ser Ser Asp Val Gly Gly Tyr Asn Tyr Val Ser Trp Tyr Gln Gln
                    165                 170                 175 cac cca ggc aaa gcc ccc aaa ctc atg att tat gag ggc agt aag cgg                  576
His Pro Gly Lys Ala Pro Lys Leu Met Ile Tyr Glu Gly Ser Lys Arg
                180                 185                 190 ccc tca ggg gtt tct aat cgc ttc tct ggc tcc aag tct ggc aac acg                  624
Pro Ser Gly Val Ser Asn Arg Phe Ser Gly Ser Lys Ser Gly Asn Thr
            195                 200                 205 gcc tcc ctg aca atc tct ggg ctc cag gct gag gac gag gct gat tat                  672
Ala Ser Leu Thr Ile Ser Gly Leu Gln Ala Glu Asp Glu Ala Asp Tyr
        210                 215                 220 tac tgc agc tca tat aca acc agg agc act cga gtt ttc ggc gga ggg                  720
Tyr Cys Ser Ser Tyr Thr Thr Arg Ser Thr Arg Val Phe Gly Gly Gly
225                 230                 235                 240 acc aag ctg acc gtc cta ggt                                                      741
Thr Lys Leu Thr Val Leu Gly
                245

<210> SEQ ID NO 201
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC687 scFv protein

<400> SEQUENCE: 201 cag gtg cag ctg gtg cag tct ggg gca gag gtg aag aag cct ggg tcc                   48
Gln Val Gln Leu Val Gln Ser Gly Ala Glu Val Lys Lys Pro Gly Ser
1               5                   10                  15 tcg gtg aaa gtc tcc tgc aag gct cct gga gac acc ttc agc aac tat                   96
Ser Val Lys Val Ser Cys Lys Ala Pro Gly Asp Thr Phe Ser Asn Tyr
            20                  25                  30 att ttc aac tgg gtg cga cag gcc cct gga caa gga ctt gag tgg atg                  144
Ile Phe Asn Trp Val Arg Gln Ala Pro Gly Gln Gly Leu Glu Trp Met
        35                  40                  45 gga ggg atc atc cca aag ttt ggt aca gta aat gat gca cac aag ttc                  192
Gly Gly Ile Ile Pro Lys Phe Gly Thr Val Asn Asp Ala His Lys Phe
    50                  55                  60 caa gac aga gtc acc att gcc gct gac gaa tcc acg aac acg gcc tcc                  240
Gln Asp Arg Val Thr Ile Ala Ala Asp Glu Ser Thr Asn Thr Ala Ser
65                  70                  75                  80 atg gag ctg agc agc ctg aca tct gag gac acg gcc gtt tat tac tgt                  288
Met Glu Leu Ser Ser Leu Thr Ser Glu Asp Thr Ala Val Tyr Tyr Cys
                85                  90                  95 gcg tgc gaa ccc att ccc aag gac tac ggt gac gtt aat ggt ctt gaa                  336
Ala Cys Glu Pro Ile Pro Lys Asp Tyr Gly Asp Val Asn Gly Leu Glu
            100                 105                 110 atc tgg ggc aaa ggg aca atg gtc acc gtc tct tca ggt gga ggc ggt                  384
Ile Trp Gly Lys Gly Thr Met Val Thr Val Ser Ser Gly Gly Gly Gly
        115                 120                 125
```

```
tca ggc gga ggt ggc agc ggt ggt ggc gga tcg gac atc cag atg acc      432
Ser Gly Gly Gly Gly Ser Gly Gly Gly Gly Ser Asp Ile Gln Met Thr
    130                 135                 140 cag tct cct tcc acc ctg tct gca tct att gga gac aga gtc acc atc      480
Gln Ser Pro Ser Thr Leu Ser Ala Ser Ile Gly Asp Arg Val Thr Ile
145                 150                 155                 160 acc tgc cgg gcc agt gag ggt att tat cac tgg ttg gcc tgg tat cag      528
Thr Cys Arg Ala Ser Glu Gly Ile Tyr His Trp Leu Ala Trp Tyr Gln
                165                 170                 175 cag aag cca ggg aaa gcc cct aaa ctc ctg atc tat aag gcc tct agt      576
Gln Lys Pro Gly Lys Ala Pro Lys Leu Leu Ile Tyr Lys Ala Ser Ser
            180                 185                 190 tta gcc agt ggg gcc cca tca agg ttc agc ggc agt gga tct ggg aca      624
Leu Ala Ser Gly Ala Pro Ser Arg Phe Ser Gly Ser Gly Ser Gly Thr
        195                 200                 205 gat ttc act ctc acc atc agc agc ctg cag cct gat gat ttt gca act      672
Asp Phe Thr Leu Thr Ile Ser Ser Leu Gln Pro Asp Asp Phe Ala Thr
    210                 215                 220 tat tac tgc caa caa tat agt aat tat ccg ctc act ttc ggc gga ggg      720
Tyr Tyr Cys Gln Gln Tyr Ser Asn Tyr Pro Leu Thr Phe Gly Gly Gly
225                 230                 235                 240 acc aag ctg gag atc aaa cgt                                          741
Thr Lys Leu Glu Ile Lys Arg
                245

<210> SEQ ID NO 202
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC689 scFv protein

<400> SEQUENCE: 202 cag gtg cag ctg gtg gag tct ggg gga ggc ttg gta aag ccg ggg ggg      48
Gln Val Gln Leu Val Glu Ser Gly Gly Gly Leu Val Lys Pro Gly Gly
1               5                   10                  15 tcc ctt aga ctc tcc tgt gca gcc tct ggt ttc act ttc agt gac gcc      96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc      144
Trp Met Asn Trp Val Arg Gln Ala Pro Gly Lys Gly Leu Glu Trp Val
        35                  40                  45 ggc cgt att aaa agc aaa ggt agt ggt ggg aca ata gac tac gcc gca      192
Gly Arg Ile Lys Ser Lys Gly Ser Gly Gly Thr Ile Asp Tyr Ala Ala
    50                  55                  60 ccc gtg aaa gac aga ttc acc atc tca cga gat gat tca aaa aac acg      240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc ctg tat      288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc      336
Tyr Cys Thr Trp Asp Trp Asp Phe Tyr Tyr Gly Met Asn Val Trp Gly
            100                 105                 110 cag gga acc ctg gtc acc gtc tcg agt ggt gga ggc ggt tca ggc gga      384
Gln Gly Thr Leu Val Thr Val Ser Ser Gly Gly Gly Gly Ser Gly Gly
        115                 120                 125 ggt ggc agc ggc ggt ggc gga tcg cag tct gtg ctg act cag cct ccc      432
Gly Gly Ser Gly Gly Gly Gly Ser Gln Ser Val Leu Thr Gln Pro Pro
    130                 135                 140
```

```
tcc gcg tcc ggg tct ccc gga cag tca gtc acc atc tcc tgc act gga      480
Ser Ala Ser Gly Ser Pro Gly Gln Ser Val Thr Ile Ser Cys Thr Gly
145                 150                 155                 160 acc agc agt gat gtt ggt ggt tat aac tat gtc tcc tgg tac caa cag      528
Thr Ser Ser Asp Val Gly Gly Tyr Asn Tyr Val Ser Trp Tyr Gln Gln
                165                 170                 175 cac cca ggc aaa gcc ccc aaa ttc atg att tat gat gtc agt aag cgg      576
His Pro Gly Lys Ala Pro Lys Phe Met Ile Tyr Asp Val Ser Lys Arg
            180                 185                 190 ccc tca ggg gtt tct aat cgc ttc tct ggc tcc aag tct ggc aac acg      624
Pro Ser Gly Val Ser Asn Arg Phe Ser Gly Ser Lys Ser Gly Asn Thr
        195                 200                 205 gcg tcc ctg acc atc tct ggg gtc cag gct gag gac gag gct gat tat      672
Ala Ser Leu Thr Ile Ser Gly Val Gln Ala Glu Asp Glu Ala Asp Tyr
    210                 215                 220 tac tgc agc tca tat aca agc gcc agc act gtg gta ttc ggc gga ggg      720
Tyr Cys Ser Ser Tyr Thr Ser Ala Ser Thr Val Val Phe Gly Gly Gly
225                 230                 235                 240 acc aag ctg acc gtc cta ggt                                          741
Thr Lys Leu Thr Val Leu Gly
                245

<210> SEQ ID NO 203
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC690 scFv protein

<400> SEQUENCE: 203 gaa gtg cag ctg gtg cag tct ggg gga ggc gtg gtc cag cct ggg agg       48
Glu Val Gln Leu Val Gln Ser Gly Gly Gly Val Val Gln Pro Gly Arg
1               5                   10                  15 tcc ctg aga ctc tcc tgt gca gcc tct ggt ttc act ttc agt gac gcc       96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc      144
Trp Met Asn Trp Val Arg Gln Ala Pro Gly Lys Gly Leu Glu Trp Val
        35                  40                  45 ggc cgt att aaa agc aaa ggt agt ggt ggg aca ata gac tac gcc gca      192
Gly Arg Ile Lys Ser Lys Gly Ser Gly Gly Thr Ile Asp Tyr Ala Ala
    50                  55                  60 ccc gtg aaa gac aga ttc acc atc tca cga gat gat tca aaa aac acg      240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc ctg tat      288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc      336
Tyr Cys Thr Trp Asp Trp Asp Phe Tyr Tyr Gly Met Asn Val Trp Gly
            100                 105                 110 aga ggc acc ctg gtc act gtc tct tca ggc gga ggt gga tca ggc gga      384
Arg Gly Thr Leu Val Thr Val Ser Ser Gly Gly Gly Gly Ser Gly Gly
        115                 120                 125 ggt ggc agc ggc ggt ggc gga tcg cag tct gtg ctg act cag cct gcc      432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga      480
Ser Val Ser Gly Ser Pro Gly Gln Ser Ile Thr Ile Ser Cys Thr Gly
145                 150                 155                 160
```

```
                                                -continued
     145                 150                 155                 160
acc agc agt gac gtt ggt ggt tat atc tat gtc tcc tgg tac caa caa         528
Thr Ser Ser Asp Val Gly Gly Tyr Ile Tyr Val Ser Trp Tyr Gln Gln
                165                 170                 175 cac cca ggc aga gcc ccc aaa ctc atg att tat gag ggc agt aag cgg         576
His Pro Gly Arg Ala Pro Lys Leu Met Ile Tyr Glu Gly Ser Lys Arg
            180                 185                 190 ccc tca ggg gtt tct aat cgc ttc tct ggc tcc aag tct ggc aac acg         624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat         672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg         720
Tyr Cys Ser Ser Tyr Thr Thr Arg Ser Thr Arg Val Phe Gly Gly Gly
225                 230                 235                 240 acc aag ctg acc gtc cta ggt                                             741
Thr Lys Leu Thr Val Leu Gly
                245

<210> SEQ ID NO 204
<211> LENGTH: 759
<212> TYPE: DNA
<213> ORGANISM: Artificial sequence
<220> FEATURE:
<221> NAME/KEY: CDS
<222> LOCATION: (1)..(759)
<223> OTHER INFORMATION: Polynucleotide encoding GMBC691 scFv protein

<400> SEQUENCE: 204 gaa gtg cag ctg gtg cag tct ggg gct gag gtg aag aag cct ggg gcc         48
Glu Val Gln Leu Val Gln Ser Gly Ala Glu Val Lys Lys Pro Gly Ala
1               5                   10                  15 tca atg aaa gtc tcc tgc aag act tct gga gac acc ttc aac ggc ttt         96
Ser Met Lys Val Ser Cys Lys Thr Ser Gly Asp Thr Phe Asn Gly Phe
            20                  25                  30 tat gta cac tgg gtg cga cag gcc cct ggc caa ggg ctt gag tgg atg         144
Tyr Val His Trp Val Arg Gln Ala Pro Gly Gln Gly Leu Glu Trp Met
        35                  40                  45 gga cgg atc aac cct aat ggt ggt ggc aca aac tat gca cag aaa ttt         192
Gly Arg Ile Asn Pro Asn Gly Gly Gly Thr Asn Tyr Ala Gln Lys Phe
    50                  55                  60 cag ggc agg gtc acc atg acc agg gac acg tcc atg aac aca gcc tac         240
Gln Gly Arg Val Thr Met Thr Arg Asp Thr Ser Met Asn Thr Ala Tyr
65                  70                  75                  80 atg gag ttg agg agc ctg aga tct gac gac acg gcc gtc tac tac tgt         288
Met Glu Leu Arg Ser Leu Arg Ser Asp Asp Thr Ala Val Tyr Tyr Cys
                85                  90                  95 gcg aga gat ctg ttt tac gat ttt tgg agt gat tat tat cga aat gat         336
Ala Arg Asp Leu Phe Tyr Asp Phe Trp Ser Asp Tyr Tyr Arg Asn Asp
            100                 105                 110 cag tac tac tac atg gac gtc tgg ggc cgg ggc acc ctg gtc acc gtc         384
Gln Tyr Tyr Tyr Met Asp Val Trp Gly Arg Gly Thr Leu Val Thr Val
        115                 120                 125 tcg agt ggt gga ggc ggt tca ggc gga ggt ggc agc ggc ggt ggc gga         432
Ser Ser Gly Gly Gly Gly Ser Gly Gly Gly Gly Ser Gly Gly Gly Gly
    130                 135                 140 tcg tct gag ctg act cag gac cct gct gtg tct gtg gcc ttg gga cag         480
Ser Ser Glu Leu Thr Gln Asp Pro Ala Val Ser Val Ala Leu Gly Gln
145                 150                 155                 160 aca gtc agg atc aca tgc caa gga gac agc ctc aga agc tat tat gca         528
```

```
Thr Val Arg Ile Thr Cys Gln Gly Asp Ser Leu Arg Ser Tyr Tyr Ala
            165                 170                 175 agc tgg tac cag cag aag cca gga cag gcc cct gta ctt gtc atc tat      576
Ser Trp Tyr Gln Gln Lys Pro Gly Gln Ala Pro Val Leu Val Ile Tyr
            180                 185                 190 ggt aaa aac aac cgg ccc tca ggg atc cca gac cga ttc tct ggc tcc      624
Gly Lys Asn Asn Arg Pro Ser Gly Ile Pro Asp Arg Phe Ser Gly Ser
        195                 200                 205 agc tca gga aac aca gct tcc ttg acc atc act ggg gct cag gcg gaa      672
Ser Ser Gly Asn Thr Ala Ser Leu Thr Ile Thr Gly Ala Gln Ala Glu
    210                 215                 220 gat gag gct gac tat tac tgt aac tcc cgg gac agc agt ggt aac cat      720
Asp Glu Ala Asp Tyr Tyr Cys Asn Ser Arg Asp Ser Ser Gly Asn His
225                 230                 235                 240 gtg gta ttc ggc gga ggg acc aag ctg acc gtc cta ggt                  759
Val Val Phe Gly Gly Gly Thr Lys Leu Thr Val Leu Gly
                245                 250

<210> SEQ ID NO 205
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC692 scFv protein

<400> SEQUENCE: 205 gag gtg cag ctg gtg cag tct ggg gga ggc ttg gta aag ccg ggg ggg       48
Glu Val Gln Leu Val Gln Ser Gly Gly Gly Leu Val Lys Pro Gly Gly
1               5                   10                  15 tcc ctt aga ctc tcc tgt gca gcc tct ggt ttc act ttc agt gac gcc       96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc      144
Trp Met Asn Trp Val Arg Gln Ala Pro Gly Lys Gly Leu Glu Trp Val
        35                  40                  45 ggc cgt att aaa agc aaa ggt agt ggt ggg aca ata gac tac gcc gca      192
Gly Arg Ile Lys Ser Lys Gly Ser Gly Gly Thr Ile Asp Tyr Ala Ala
    50                  55                  60 ccc gtg aaa gac aga ttc acc atc tca cga gac gat tca aaa aac acg      240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc ctg tat      288
Leu Tyr Leu Gln Met Asn Ser Leu Lys Thr Glu Asp Thr Ala Leu Tyr
                85                  90                  95 tac tgt acg tgg gac tgg gat ttc tac tac ggt atg aac gtc tgg ggc      336
Tyr Cys Thr Trp Asp Trp Asp Phe Tyr Tyr Gly Met Asn Val Trp Gly
            100                 105                 110 agg gga acc ctg gtc acc gtc tcg agt ggt gga ggc ggt tca ggc gga      384
Arg Gly Thr Leu Val Thr Val Ser Ser Gly Gly Gly Gly Ser Gly Gly
        115                 120                 125 ggt ggc agc ggc ggt ggc gga tcg cag tct gtg ctg act cag cct gcc      432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga      480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa      528
Thr Ser Ser Asp Val Gly Gly Tyr Asn Tyr Val Ser Trp Tyr Gln Gln
                165                 170                 175
```

```
cac cca ggc aaa gcc ccc aaa ctc atg att tat gag ggc agt aag cgg      576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg      624
Pro Ser Gly Val Ser Asn Arg Phe Ser Gly Ser Lys Ser Gly Asn Thr
        195                 200                 205 gcc tcc cta aca atc tct ggg ctc cag gct gag gac gag gct gat tat      672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg      720
Tyr Cys Ser Ser Tyr Thr Thr Arg Ser Thr Arg Val Phe Gly Gly Gly
225                 230                 235                 240 acc aag ctg acc gtc cta ggt                                          741
Thr Lys Leu Thr Val Leu Gly
                245

<210> SEQ ID NO 206
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC693 scFv protein

<400> SEQUENCE: 206 cag gtg cag ctg gtg gag tct ggg gga ggc ttg gta aag ccg ggg ggg       48
Gln Val Gln Leu Val Glu Ser Gly Gly Gly Leu Val Lys Pro Gly Gly
1               5                   10                  15 tcc ctt aga ctc tcc tgt gca gcc tct ggt ttc act ttc agt gac gcc       96
Ser Leu Arg Leu Ser Cys Ala Ala Ser Gly Phe Thr Phe Ser Asp Ala
            20                  25                  30 tgg atg aac tgg gtc cgc cag gct cca ggg aag ggg ctg gag tgg gtc      144
Trp Met Asn Trp Val Arg Gln Ala Pro Gly Lys Gly Leu Glu Trp Val
        35                  40                  45 ggc cgt att aaa agc aaa ggt agt ggt ggg aca ata gac tac gcc gca      192
Gly Arg Ile Lys Ser Lys Gly Ser Gly Gly Thr Ile Asp Tyr Ala Ala
    50                  55                  60 ccc gtg aaa gac aga ttc acc atc tca cga gat gat tca aaa aac acg      240
Pro Val Lys Asp Arg Phe Thr Ile Ser Arg Asp Asp Ser Lys Asn Thr
65                  70                  75                  80 ctg tat ctg caa atg aac agt ctg aaa acc gag gac aca gcc ctg tat      288
Leu Tyr Leu Gln Met Asn Ser Leu Lys Thr Glu Asp Thr Ala Leu Tyr
            85                  90                  95 tac tgt acg tgg gac tgg gat ttc tac tac ggt atg aac gtc tgg ggc      336
Tyr Cys Thr Trp Asp Trp Asp Phe Tyr Tyr Gly Met Asn Val Trp Gly
        100                 105                 110 aaa ggc acc ctg gtc acc gtc tcc tca ggt gga ggc ggt tca ggc gga      384
Lys Gly Thr Leu Val Thr Val Ser Ser Gly Gly Gly Gly Ser Gly Gly
    115                 120                 125 ggt ggc agc ggc ggt ggc gga tcg cag tct gtg ctg act cag cct gcc      432
Gly Gly Ser Gly Gly Gly Gly Ser Gln Ser Val Leu Thr Gln Pro Ala
130                 135                 140 tcc gtg tct ggg tct cct gga cag tcg atc acc atc tcc tgc act gga      480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa      528
Thr Ser Ser Asp Val Gly Gly Tyr Asn Tyr Val Ser Trp Tyr Gln Gln
            165                 170                 175 cac cca ggc aaa gcc ccc aaa ctc atg att tat gag ggc agt aag cgg      576
His Pro Gly Lys Ala Pro Lys Leu Met Ile Tyr Glu Gly Ser Lys Arg
        180                 185                 190
```

```
ccc tca ggg gtt tct aat cgc ttc tct ggc tcc aag tct ggc gac acg      624
Pro Ser Gly Val Ser Asn Arg Phe Ser Gly Ser Lys Ser Gly Asp Thr
            195                 200                 205 gcc tcc ctg aca atc tct ggg ctc cag gct gag gac gag gct gat tat      672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg      720
Tyr Cys Ser Ser Tyr Thr Thr Arg Ser Thr Arg Val Phe Gly Gly Gly
225                 230                 235                 240 acc aag ctg acc gtc cta ggt                                          741
Thr Lys Leu Thr Val Leu Gly
                245

<210> SEQ ID NO 207
<211> LENGTH: 723
<212> TYPE: DNA
<213> ORGANISM: Artificial sequence
<220> FEATURE:
<221> NAME/KEY: CDS
<222> LOCATION: (1)..(723)
<223> OTHER INFORMATION: Polynucleotide encoding GMBC696 scFv protein

<400> SEQUENCE: 207 gaa gtg cag ctg gtg cag tct agg gct gag gtg aag aag cct ggg gcc       48
Glu Val Gln Leu Val Gln Ser Arg Ala Glu Val Lys Lys Pro Gly Ala
1               5                   10                  15 tca gtg aag gtc tcc tgc aaa acc tct gga tac acc ttc aac ggc tac       96
Ser Val Lys Val Ser Cys Lys Thr Ser Gly Tyr Thr Phe Asn Gly Tyr
            20                  25                  30 tat ata cac tgg gtg cga cag gcc cct gga cag ggg ctt gag tgg atg      144
Tyr Ile His Trp Val Arg Gln Ala Pro Gly Gln Gly Leu Glu Trp Met
        35                  40                  45 gga tgg atc gac cct atc aat agt gtc acg aac tat gca cag aac ttt      192
Gly Trp Ile Asp Pro Ile Asn Ser Val Thr Asn Tyr Ala Gln Asn Phe
    50                  55                  60 cag ggc agg gtc acc atg act agg gac acg tcc atc aac acg gcc tac      240
Gln Gly Arg Val Thr Met Thr Arg Asp Thr Ser Ile Asn Thr Ala Tyr
65                  70                  75                  80 atg gag ctg agc cgg ctg aca tct gac gac acg gcc gtc tat tac tgt      288
Met Glu Leu Ser Arg Leu Thr Ser Asp Asp Thr Ala Val Tyr Tyr Cys
                85                  90                  95 gcg agg gcc aga gtg tct acg att ctt caa tac tgg ggc cag ggc acc      336
Ala Arg Ala Arg Val Ser Thr Ile Leu Gln Tyr Trp Gly Gln Gly Thr
            100                 105                 110 ctg gtc acc gtc tcc tca ggt gga ggc ggt tca ggc gga ggt ggc agc      384
Leu Val Thr Val Ser Ser Gly Gly Gly Gly Ser Gly Gly Gly Gly Ser
        115                 120                 125 ggc ggt ggc gga tcg tct gag ctg act cag gac cct gct gtg tct gtg      432
Gly Gly Gly Gly Ser Ser Glu Leu Thr Gln Asp Pro Ala Val Ser Val
    130                 135                 140 gcc ttg gga cag aca gtc agg atc aca tgc caa gga gac agc ctc aga      480
Ala Leu Gly Gln Thr Val Arg Ile Thr Cys Gln Gly Asp Ser Leu Arg
145                 150                 155                 160 agc tat tat gca agc tgg tac cag cag aag cca gga cag gcc cct gta      528
Ser Tyr Tyr Ala Ser Trp Tyr Gln Gln Lys Pro Gly Gln Ala Pro Val
                165                 170                 175 ctt gtc atc tat ggt aaa aac aac cgg ccc tca ggg atc cca gac cga      576
Leu Val Ile Tyr Gly Lys Asn Asn Arg Pro Ser Gly Ile Pro Asp Arg
            180                 185                 190 ttc tct ggc tcc agc tca gga aac aca gct tcc ttg acc atc act ggg      624
Phe Ser Gly Ser Ser Ser Gly Asn Thr Ala Ser Leu Thr Ile Thr Gly
```

```
                195                 200                 205
gct cag gcg gaa gat gag gct gac tat tac tgt aac tcc cgg gac agc       672
Ala Gln Ala Glu Asp Glu Ala Asp Tyr Tyr Cys Asn Ser Arg Asp Ser
    210                 215                 220 agt ggt aac cat gtg gta ttc ggc gga ggg acc aag ctg acc gtc cta       720
Ser Gly Asn His Val Val Phe Gly Gly Gly Thr Lys Leu Thr Val Leu
225                 230                 235                 240 ggt                                                                   723
Gly

<210> SEQ ID NO 208
<211> LENGTH: 726
<212> TYPE: DNA
<213> ORGANISM: Artificial sequence
<220> FEATURE:
<221> NAME/KEY: CDS
<222> LOCATION: (1)..(726)
<223> OTHER INFORMATION: Polynucleotide encoding GMBC725 scFv protein

<400> SEQUENCE: 208 gag gtg cag ctg gtg cag acc ggg gga ggc gtg gtt cag cct ggg ggg        48
Glu Val Gln Leu Val Gln Thr Gly Gly Gly Val Val Gln Pro Gly Gly
1               5                   10                  15 tcc ctg aga ctc tcc tgt gca gcg tct gga ttc acc ttc agt agc tat        96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg       144
Gly Met His Trp Val Arg Gln Ala Pro Gly Lys Gly Leu Glu Trp Val
        35                  40                  45 gca ttt ata cta tat gat gga agt aat aaa tac tat gca gac tcc gtg       192
Ala Phe Ile Leu Tyr Asp Gly Ser Asn Lys Tyr Tyr Ala Asp Ser Val
    50                  55                  60 aag ggc cga ttc acc atc tcc aga gac aat tcc aag aac acg ctg tat       240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt       288
Leu Gln Met Asn Ser Leu Arg Ala Glu Asp Thr Ala Val Tyr Tyr Cys
                85                  90                  95 gcg aaa tcc tcg tca tca gcc agt gct ttt gat atc tgg agg caa aga       336
Ala Lys Ser Ser Ser Ser Ala Ser Ala Phe Asp Ile Trp Arg Gln Arg
            100                 105                 110 acc acg gtc act gtc tcc tca ggt gga ggc ggt tca ggc gga ggt ggc       384
Thr Thr Val Thr Val Ser Ser Gly Gly Gly Gly Ser Gly Gly Gly Gly
        115                 120                 125 agc ggc ggt ggc gga tcg tct gag ctg act cag gac cct gct gtg tct       432
Ser Gly Gly Gly Gly Ser Ser Glu Leu Thr Gln Asp Pro Ala Val Ser
    130                 135                 140 gtg gcc ttg gga cag aca gtc agg atc aca tgc caa gga gac agc ctc       480
Val Ala Leu Gly Gln Thr Val Arg Ile Thr Cys Gln Gly Asp Ser Leu
145                 150                 155                 160 aga agc tat tat gcg agc tgg tac cag cag aag cca gga cag gcc cca       528
Arg Ser Tyr Tyr Ala Ser Trp Tyr Gln Gln Lys Pro Gly Gln Ala Pro
                165                 170                 175 gta ctt gtc atc tat ggt aaa aac aac cgg ccc tca ggg atc cca gac       576
Val Leu Val Ile Tyr Gly Lys Asn Asn Arg Pro Ser Gly Ile Pro Asp
            180                 185                 190 cga ttc tct ggc tcc agc tca gga aac aca gct tcc ttg acc atc act       624
Arg Phe Ser Gly Ser Ser Ser Gly Asn Thr Ala Ser Leu Thr Ile Thr
        195                 200                 205 ggg gct cag gcg gaa gat gag gct gac tat tac tgt aac tcc cgg gac       672
Gly Ala Gln Ala Glu Asp Glu Ala Asp Tyr Tyr Cys Asn Ser Arg Asp
```

```
                210                 215                 220
agc agt ggt aac cat gtg gta ttc ggc gga ggg acc aag ctg acc gtc      720
Ser Ser Gly Asn His Val Val Phe Gly Gly Gly Thr Lys Leu Thr Val
225                 230                 235                 240 cta ggt                                                              726
Leu Gly <210> SEQ ID NO 209
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC727 scFv protein

<400> SEQUENCE: 209 gag gtg cag ctg gtg gag tct ggg gga gac acg gta aag cct ggg gga      48
Glu Val Gln Leu Val Glu Ser Gly Gly Asp Thr Val Lys Pro Gly Gly
1               5                   10                  15 tcc ctt aga ctc tcc tgt gca ggc tct ggt ttc act ttc agt gac gcc      96
Ser Leu Arg Leu Ser Cys Ala Gly Ser Gly Phe Thr Phe Ser Asp Ala
                20                  25                  30 tgg atg aac tgg gtc cgc cag gct cca ggg aag gga ctg gag tgg gtc     144
Trp Met Asn Trp Val Arg Gln Ala Pro Gly Lys Gly Leu Glu Trp Val
            35                  40                  45 ggc cgc atg aaa agc aag ggt agt ggt ggg aca aga gac tac gcc gca     192
Gly Arg Met Lys Ser Lys Gly Ser Gly Gly Thr Arg Asp Tyr Ala Ala
        50                  55                  60 ccc gtg aat ggc aga ttc acc atc tca aga gat gat tca aaa aat acg     240
Pro Val Asn Gly Arg Phe Thr Ile Ser Arg Asp Asp Ser Lys Asn Thr
65                  70                  75                  80 ctt tat ctg caa atg aac agc ctg aat acc gag gac aca ggc gta tat     288
Leu Tyr Leu Gln Met Asn Ser Leu Asn Thr Glu Asp Thr Gly Val Tyr
                85                  90                  95 tat tgt acc tgg gac tgg gat ttc tac tac ggt atg aac gtc tgg ggc     336
Tyr Cys Thr Trp Asp Trp Asp Phe Tyr Tyr Gly Met Asn Val Trp Gly
            100                 105                 110 agg ggc acc ctg gtc acc gtc tcg agt gga gga ggc ggt tca ggc gga     384
Arg Gly Thr Leu Val Thr Val Ser Ser Gly Gly Gly Gly Ser Gly Gly
        115                 120                 125 ggt ggc agc ggc ggt ggc gga tcg cag tct gtg ctg act cag cct gcc     432
Gly Gly Ser Gly Gly Gly Gly Ser Gln Ser Val Leu Thr Gln Pro Ala
130                 135                 140 tcc gtg tct ggg tct cct gga cag tcg atc acc atc tcc tgc act gga     480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa     528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg     576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg     624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat     672
Ala Ser Leu Thr Ile Ser Gly Leu Gln Ala Glu Asp Glu Ala Asp Tyr
210                 215                 220 tac tgc agc tca tat aca acc agg agc act cga gtt ttc ggc gga ggg     720
Tyr Cys Ser Ser Tyr Thr Thr Arg Ser Thr Arg Val Phe Gly Gly Gly
```

```
                    225                 230                 235                 240
acc aag ctg acc gtc cta ggt                                                           741
Thr Lys Leu Thr Val Leu Gly
                245

<210> SEQ ID NO 210
<211> LENGTH: 732
<212> TYPE: DNA
<213> ORGANISM: Artificial sequence
<220> FEATURE:
<221> NAME/KEY: CDS
<222> LOCATION: (1)..(732)
<223> OTHER INFORMATION: Polynucleotide encoding GMBC729 scFv protein

<400> SEQUENCE: 210 cag gtg cag ctg cag gag tcg ggg gga ggc ttg gta aag ccg ggg ggg    48
Gln Val Gln Leu Gln Glu Ser Gly Gly Gly Leu Val Lys Pro Gly Gly
1               5                   10                  15 tcc ctt aga ctc tcc tgt gca ggc tct ggt ttc aaa ttc agt gac gcc    96
Ser Leu Arg Leu Ser Cys Ala Gly Ser Gly Phe Lys Phe Ser Asp Ala
            20                  25                  30 tgg atg aat tgg gtc cgc cag gct cca ggg aag ggg ctg gag tgg gtc   144
Trp Met Asn Trp Val Arg Gln Ala Pro Gly Lys Gly Leu Glu Trp Val
        35                  40                  45 ggc cgt att aaa agc aaa ggt agt ggt ggg aca ata gag tac gct gca   192
Gly Arg Ile Lys Ser Lys Gly Ser Gly Gly Thr Ile Glu Tyr Ala Ala
    50                  55                  60 ccc gtg aaa gac aga ttc atc atc tca cga gat gat tca aaa gac acg   240
Pro Val Lys Asp Arg Phe Ile Ile Ser Arg Asp Asp Ser Lys Asp Thr
65                  70                  75                  80 ctg tat ctg caa atg gac agt ctg aaa acc gag gac aca gcc ctg tat   288
Leu Tyr Leu Gln Met Asp Ser Leu Lys Thr Glu Asp Thr Ala Leu Tyr
                85                  90                  95 tat tgt acg tgg gac tgg gat ttc tac tac ggt atg aac gtc tgg ggc   336
Tyr Cys Thr Trp Asp Trp Asp Phe Tyr Tyr Gly Met Asn Val Trp Gly
            100                 105                 110 cag gga acc ctg gtc acc gtc tcg agt ggt gga ggc ggt tca ggc gga   384
Gln Gly Thr Leu Val Thr Val Ser Ser Gly Gly Gly Gly Ser Gly Gly
        115                 120                 125 ggt ggc agc ggc ggt ggc gga tcg tct gag ctg act cag gac cct gct   432
Gly Gly Ser Gly Gly Gly Gly Ser Ser Glu Leu Thr Gln Asp Pro Ala
    130                 135                 140 gtg tct gtg gcc ttg gga cag aca gtc agg atc act tgc caa gga gac   480
Val Ser Val Ala Leu Gly Gln Thr Val Arg Ile Thr Cys Gln Gly Asp
145                 150                 155                 160 agt ctc aga aac tat tac aca aac tgg ttc cag cag aag cca gga cag   528
Ser Leu Arg Asn Tyr Tyr Thr Asn Trp Phe Gln Gln Lys Pro Gly Gln
                165                 170                 175 gcc cct cta ctt gtc gtc tat gct aaa aat aag cgg ccc tca ggg atc   576
Ala Pro Leu Leu Val Val Tyr Ala Lys Asn Lys Arg Pro Ser Gly Ile
            180                 185                 190 cca gac cga ttc tct ggc tcc agc tca gga aac aca gct tcc ttg acc   624
Pro Asp Arg Phe Ser Gly Ser Ser Ser Gly Asn Thr Ala Ser Leu Thr
        195                 200                 205 atc act ggg gct cag gcg gaa gat gag gct gac tat tac tgt cat tcc   672
Ile Thr Gly Ala Gln Ala Glu Asp Glu Ala Asp Tyr Tyr Cys His Ser
    210                 215                 220 cgg gac agc agt ggt aac cat gtg ctt ttc ggc gga ggg acc aag ctg   720
Arg Asp Ser Ser Gly Asn His Val Leu Phe Gly Gly Gly Thr Lys Leu
225                 230                 235                 240 acc gtc cta ggt                                                    732
```

<210> SEQ ID NO 211
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMBC730 scFv protein

<400> SEQUENCE: 211

| | | | | | | | | | | | | | | | |
|---|---|---|---|---|---|---|---|---|---|---|---|---|---|---|---|
| cag | gtg | cag | ctg | gtg | gag | tct | ggg | gga | gac | tcg | gta | aag | cct | ggg | gga | 48 |
| Gln | Val | Gln | Leu | Val | Glu | Ser | Gly | Gly | Asp | Ser | Val | Lys | Pro | Gly | Gly |
| 1 | | | | 5 | | | | | 10 | | | | | 15 | | tcc ctt aga ctc tcc tgt gca ggc tct ggt ttc act ttc agt gac gcc    96
Ser Leu Arg Leu Ser Cys Ala Gly Ser Gly Phe Thr Phe Ser Asp Ala
            20                  25                  30 tgg atg aac tgg gtc cgc cag gct cca ggg aag ggg ctg gag tgg gtc    144
Trp Met Asn Trp Val Arg Gln Ala Pro Gly Lys Gly Leu Glu Trp Val
        35                  40                  45 ggc cgt atg aaa agc aag ggt agt ggg gga aca aga gac tac gct gca    192
Gly Arg Met Lys Ser Lys Gly Ser Gly Gly Thr Arg Asp Tyr Ala Ala
    50                  55                  60 ccc gtg aat ggc aga ttc acc atc tca aga gat gat tca aaa aac acg    240
Pro Val Asn Gly Arg Phe Thr Ile Ser Arg Asp Asp Ser Lys Asn Thr
65                  70                  75                  80 ctg tat ctg caa atg aac agc ctg aat acc gag gac aca ggt gta tat    288
Leu Tyr Leu Gln Met Asn Ser Leu Asn Thr Glu Asp Thr Gly Val Tyr
                85                  90                  95 tat tgt acg tgg gac tgg gat ttc tac tac ggt atg gac gtc tgg ggg    336
Tyr Cys Thr Trp Asp Trp Asp Phe Tyr Tyr Gly Met Asp Val Trp Gly
            100                 105                 110 aag ggg acc acg gtc acc gtc tcg agt ggt gga ggc ggt tca ggc gga    384
Lys Gly Thr Thr Val Thr Val Ser Ser Gly Gly Gly Gly Ser Gly Gly
        115                 120                 125 ggt ggc agc ggc ggt ggc gga tcg cag tct gtg ctg act cag cct gcc    432
Gly Gly Ser Gly Gly Gly Gly Ser Gln Ser Val Leu Thr Gln Pro Ala
    130                 135                 140 tcc gtg tct ggg tct cct gga cag tcg atc acc atc tcc tgc act gga    480
Ser Val Ser Gly Ser Pro Gly Gln Ser Ile Thr Ile Ser Cys Thr Gly
145                 150                 155                 160 acc agc agt gac gtt ggt ggt tat aac tat gtc tcc tgg tac caa caa    528
Thr Ser Ser Asp Val Gly Gly Tyr Asn Tyr Val Ser Trp Tyr Gln Gln
                165                 170                 175 cac cca ggc aaa gcc ccc aaa ctc atg att tat gag ggc agt aag cgg    576
His Pro Gly Lys Ala Pro Lys Leu Met Ile Tyr Glu Gly Ser Lys Arg
            180                 185                 190 ccc tca ggg gtt tct aat cgc ttc tct ggc tcc aag tct ggc aac acg    624
Pro Ser Gly Val Ser Asn Arg Phe Ser Gly Ser Lys Ser Gly Asn Thr
        195                 200                 205 gcc tcc ctg aca atc tct ggg ctc cag gct gag gac gag gct gat tat    672
Ala Ser Leu Thr Ile Ser Gly Leu Gln Ala Glu Asp Glu Ala Asp Tyr
    210                 215                 220 tac tgc agc tca tat aca acc agg agc act cga gtt ttc ggc gga ggg    720
Tyr Cys Ser Ser Tyr Thr Thr Arg Ser Thr Arg Val Phe Gly Gly Gly
225                 230                 235                 240 acc aag ctg acc gtc cta ggt                                         741
Thr Lys Leu Thr Val Leu Gly
                245

```
<210> SEQ ID NO 212
<211> LENGTH: 735
<212> TYPE: DNA
<213> ORGANISM: Artificial sequence
<220> FEATURE:
<221> NAME/KEY: CDS
<222> LOCATION: (1)..(735)
<223> OTHER INFORMATION: Polynucleotide encoding GMCC101 scFv protein

<400> SEQUENCE: 212 gaa gtg cag ctg gtg cag tct ggg gct gag gtg aag aag cct ggg tcc        48
Glu Val Gln Leu Val Gln Ser Gly Ala Glu Val Lys Lys Pro Gly Ser
1               5                   10                  15 tcg gtg aag gtc tcc tgc aag gct tct gga ggc acc ttc agg acc tat        96
Ser Val Lys Val Ser Cys Lys Ala Ser Gly Gly Thr Phe Arg Thr Tyr
            20                  25                  30 gct atc acc tgg gtg cga cag gcc cct gga caa ggg ctt gag tgg atg       144
Ala Ile Thr Trp Val Arg Gln Ala Pro Gly Gln Gly Leu Glu Trp Met
        35                  40                  45 gga ggg atc atc cct atc tct gcc aca gca aac tac gca cag aag ttc       192
Gly Gly Ile Ile Pro Ile Ser Ala Thr Ala Asn Tyr Ala Gln Lys Phe
    50                  55                  60 cag ggc aga gtc acg att acc gcg gac gag tca atg agc aca gcc tac       240
Gln Gly Arg Val Thr Ile Thr Ala Asp Glu Ser Met Ser Thr Ala Tyr
65                  70                  75                  80 atg gaa ctg agc agc ctg aga tct gaa gac acg gcc gtg tat tac tgt       288
Met Glu Leu Ser Ser Leu Arg Ser Glu Asp Thr Ala Val Tyr Tyr Cys
                85                  90                  95 gcg aga gat cgg gag ccc cac tac ttt gac aac tgg ggc cgg ggg aca       336
Ala Arg Asp Arg Glu Pro His Tyr Phe Asp Asn Trp Gly Arg Gly Thr
            100                 105                 110 atg gtc acc gtc tcg agt gga ggc ggc ggt tca ggc gga ggt ggc tct       384
Met Val Thr Val Ser Ser Gly Gly Gly Gly Ser Gly Gly Gly Gly Ser
        115                 120                 125 ggc ggt ggc gga agt gca ctg cct gtg ctg act cag cca ccc tcg gtg       432
Gly Gly Gly Gly Ser Ala Leu Pro Val Leu Thr Gln Pro Pro Ser Val
    130                 135                 140 tct gaa gcc ccc agg cag ggg gtc acc atc tcc tgt tct gga agc agc       480
Ser Glu Ala Pro Arg Gln Gly Val Thr Ile Ser Cys Ser Gly Ser Ser
145                 150                 155                 160 tcc aac atc gga aat aat gct gta agc tgg tac cag cag ctc cca gga       528
Ser Asn Ile Gly Asn Asn Ala Val Ser Trp Tyr Gln Gln Leu Pro Gly
                165                 170                 175 cag gct ccc aaa ctc ctc atc tat tat gat gat ctg ctg ccc tca ggg       576
Gln Ala Pro Lys Leu Leu Ile Tyr Tyr Asp Asp Leu Leu Pro Ser Gly
            180                 185                 190 gtc tct gac cga ttc tct gcc tcc aag tct ggc acc tca gcc tcc ctg       624
Val Ser Asp Arg Phe Ser Ala Ser Lys Ser Gly Thr Ser Ala Ser Leu
        195                 200                 205 gcc atc agt ggg ctc cag tct gag gat gag gct gat tat tac tgt gca       672
Ala Ile Ser Gly Leu Gln Ser Glu Asp Glu Ala Asp Tyr Tyr Cys Ala
    210                 215                 220 gca tgg gat gac agt ctg aat ggt gtg ata ttc ggc gga ggg acc cag       720
Ala Trp Asp Asp Ser Leu Asn Gly Val Ile Phe Gly Gly Gly Thr Gln
225                 230                 235                 240 ctc acc gtt tta agt                                                   735
Leu Thr Val Leu Ser
                245

<210> SEQ ID NO 213
<211> LENGTH: 780
<212> TYPE: DNA
```

<213> ORGANISM: Artificial sequence
<220> FEATURE:
<221> NAME/KEY: CDS
<222> LOCATION: (1)..(780)
<223> OTHER INFORMATION: Polynucleotide encoding GMCC102 scFv protein

<400> SEQUENCE: 213

| | | | | | | | | | | | | | | | | |
|---|---|---|---|---|---|---|---|---|---|---|---|---|---|---|---|---|
| cag | gtc | cag | ctg | gtg | cag | tct | ggg | gct | gag | gtg | aag | aag | cct | ggg | gcc | 48 |
| Gln | Val | Gln | Leu | Val | Gln | Ser | Gly | Ala | Glu | Val | Lys | Lys | Pro | Gly | Ala | |
| 1 | | | | 5 | | | | | 10 | | | | | 15 | | |
| tca | gtg | aag | gtt | tcc | tgc | aag | gca | cct | gga | tac | acc | ttc | acc | agc | tac | 96 |
| Ser | Val | Lys | Val | Ser | Cys | Lys | Ala | Pro | Gly | Tyr | Thr | Phe | Thr | Ser | Tyr | |
| | | 20 | | | | | 25 | | | | | 30 | | | | |
| tat | atg | cac | tgg | gtg | cga | cag | gcc | cct | gga | caa | ggg | ctt | gag | tgg | atg | 144 |
| Tyr | Met | His | Trp | Val | Arg | Gln | Ala | Pro | Gly | Gln | Gly | Leu | Glu | Trp | Met | |
| | | 35 | | | | | 40 | | | | | 45 | | | | |
| gga | ata | atc | aac | cct | agt | ggt | ggt | agc | aca | agc | tac | gca | cag | aag | ttc | 192 |
| Gly | Ile | Ile | Asn | Pro | Ser | Gly | Gly | Ser | Thr | Ser | Tyr | Ala | Gln | Lys | Phe | |
| | 50 | | | | | 55 | | | | | 60 | | | | | |
| cag | ggc | aga | gtc | acc | atg | acc | agg | gac | acg | tcc | acg | agc | aca | gtc | tac | 240 |
| Gln | Gly | Arg | Val | Thr | Met | Thr | Arg | Asp | Thr | Ser | Thr | Ser | Thr | Val | Tyr | |
| 65 | | | | | 70 | | | | | 75 | | | | | 80 | |
| atg | gag | ctg | agc | agc | ctg | aga | tct | gag | gac | acg | gcc | gtg | tat | tac | tgt | 288 |
| Met | Glu | Leu | Ser | Ser | Leu | Arg | Ser | Glu | Asp | Thr | Ala | Val | Tyr | Tyr | Cys | |
| | | | | 85 | | | | | 90 | | | | | 95 | | |
| gcg | aga | ggt | ggg | gcc | aga | agc | aat | gat | agt | agt | ggt | tat | tac | aaa | tca | 336 |
| Ala | Arg | Gly | Gly | Ala | Arg | Ser | Asn | Asp | Ser | Ser | Gly | Tyr | Tyr | Lys | Ser | |
| | | | 100 | | | | | 105 | | | | | 110 | | | |
| ccc | ctc | tcc | tac | tac | tac | ggt | atg | gac | gtc | tgg | ggc | cgg | ggg | aca | atg | 384 |
| Pro | Leu | Ser | Tyr | Tyr | Tyr | Gly | Met | Asp | Val | Trp | Gly | Arg | Gly | Thr | Met | |
| | | 115 | | | | | 120 | | | | | 125 | | | | |
| gtc | acc | gtc | tcg | agt | gga | ggc | ggc | ggt | tca | ggc | gga | ggt | ggc | tct | ggc | 432 |
| Val | Thr | Val | Ser | Ser | Gly | Gly | Gly | Gly | Ser | Gly | Gly | Gly | Gly | Ser | Gly | |
| | 130 | | | | | 135 | | | | | 140 | | | | | |
| ggt | ggc | gga | agt | gca | cag | tct | gtg | ctg | act | cag | cca | ccc | tca | gcg | tct | 480 |
| Gly | Gly | Gly | Ser | Ala | Gln | Ser | Val | Leu | Thr | Gln | Pro | Pro | Ser | Ala | Ser | |
| 145 | | | | | 150 | | | | | 155 | | | | | 160 | |
| ggg | acc | ccc | ggg | cag | agg | gtc | acc | atc | tct | tgt | tct | gga | agc | agc | tcc | 528 |
| Gly | Thr | Pro | Gly | Gln | Arg | Val | Thr | Ile | Ser | Cys | Ser | Gly | Ser | Ser | Ser | |
| | | | | 165 | | | | | 170 | | | | | 175 | | |
| aac | atc | ggg | agt | aat | act | gta | aac | tgg | tac | cag | cag | ctc | cca | gga | acg | 576 |
| Asn | Ile | Gly | Ser | Asn | Thr | Val | Asn | Trp | Tyr | Gln | Gln | Leu | Pro | Gly | Thr | |
| | | | 180 | | | | | 185 | | | | | 190 | | | |
| gcc | ccc | aaa | ctc | ctc | atc | tat | agt | aat | aat | cag | cgg | ccc | tca | ggg | gtc | 624 |
| Ala | Pro | Lys | Leu | Leu | Ile | Tyr | Ser | Asn | Asn | Gln | Arg | Pro | Ser | Gly | Val | |
| | | 195 | | | | | 200 | | | | | 205 | | | | |
| cct | gac | cga | ttc | tct | ggc | tcc | aag | tct | ggc | acc | tca | gcc | tcc | ctg | gcc | 672 |
| Pro | Asp | Arg | Phe | Ser | Gly | Ser | Lys | Ser | Gly | Thr | Ser | Ala | Ser | Leu | Ala | |
| 210 | | | | | 215 | | | | | 220 | | | | | | |
| atc | agt | ggg | ctc | cag | tct | gag | gat | gag | gct | gat | tat | tac | tgt | gca | gca | 720 |
| Ile | Ser | Gly | Leu | Gln | Ser | Glu | Asp | Glu | Ala | Asp | Tyr | Tyr | Cys | Ala | Ala | |
| 225 | | | | | 230 | | | | | 235 | | | | | 240 | |
| tgg | gat | gac | agc | ctg | aat | ggt | gtg | gta | ttc | ggc | gga | ggg | acc | aag | gtc | 768 |
| Trp | Asp | Asp | Ser | Leu | Asn | Gly | Val | Val | Phe | Gly | Gly | Gly | Thr | Lys | Val | |
| | | | | 245 | | | | | 250 | | | | | 255 | | |
| acc | gtc | cta | ggt | | | | | | | | | | | | | 780 |
| Thr | Val | Leu | Gly | | | | | | | | | | | | | |
| | | | 260 | | | | | | | | | | | | | |

<210> SEQ ID NO 214
<211> LENGTH: 750

```
<212> TYPE: DNA
<213> ORGANISM: Artificial sequence
<220> FEATURE:
<221> NAME/KEY: CDS
<222> LOCATION: (1)..(750)
<223> OTHER INFORMATION: Polynucleotide encoding GMCC105 scFv protein

<400> SEQUENCE: 214 cag gtc cag ctg gtg cag tct ggg gga gga gtg gtc cag cct ggg agg        48
Gln Val Gln Leu Val Gln Ser Gly Gly Gly Val Val Gln Pro Gly Arg
1               5                   10                  15 tcc ctg aga ctc tcc tgc aca gcc tct gga ttc aac ctc ggt tcc cat        96
Ser Leu Arg Leu Ser Cys Thr Ala Ser Gly Phe Asn Leu Gly Ser His
            20                  25                  30 ggc atg cac tgg gtc cgc cag gct ccc ggc aag ggg ctg gag tgg gtg       144
Gly Met His Trp Val Arg Gln Ala Pro Gly Lys Gly Leu Glu Trp Val
        35                  40                  45 gca gtt ata gga ttt gat gga acg act aaa tat tat gtg gac tcc gtg       192
Ala Val Ile Gly Phe Asp Gly Thr Thr Lys Tyr Tyr Val Asp Ser Val
    50                  55                  60 aag ggc cga ttc acc atc tcc agg gac aac tcc agg aac acc cta tct       240
Lys Gly Arg Phe Thr Ile Ser Arg Asp Asn Ser Arg Asn Thr Leu Ser
65                  70                  75                  80 ctg caa atg aac agc ctg aga gct gag gac acg gct gtc tat tac tgt       288
Leu Gln Met Asn Ser Leu Arg Ala Glu Asp Thr Ala Val Tyr Tyr Cys
                85                  90                  95 gtg aga gaa gat tac tac tat gat agt agt ggt tat tac ttt gac tac       336
Val Arg Glu Asp Tyr Tyr Tyr Asp Ser Ser Gly Tyr Tyr Phe Asp Tyr
            100                 105                 110 tgg ggc cga gga acc ctg gtc acc gtc tcg agt gga ggc ggc ggt tca       384
Trp Gly Arg Gly Thr Leu Val Thr Val Ser Ser Gly Gly Gly Gly Ser
        115                 120                 125 ggc gga ggt ggc tct ggc ggt ggc gga agt gca ctt tct tct gag ctg       432
Gly Gly Gly Gly Ser Gly Gly Gly Gly Ser Ala Leu Ser Ser Glu Leu
    130                 135                 140 act cag gac cct ttc gtg tct gtt gcc ttg gga cag aca gtc agg atc       480
Thr Gln Asp Pro Phe Val Ser Val Ala Leu Gly Gln Thr Val Arg Ile
145                 150                 155                 160 gca tgc cga gga gac agc ctc aga gat tct tat gca agt tgg tac cag       528
Ala Cys Arg Gly Asp Ser Leu Arg Asp Ser Tyr Ala Ser Trp Tyr Gln
                165                 170                 175 cag aag cca gga cag gcc cct cga ctt ctc gtc tat gga aac aat ctt       576
Gln Lys Pro Gly Gln Ala Pro Arg Leu Leu Val Tyr Gly Asn Asn Leu
            180                 185                 190 cgg ccc tcc ggg atc cct ggc cgg ttc tct ggc tcc agc tca gga gac       624
Arg Pro Ser Gly Ile Pro Gly Arg Phe Ser Gly Ser Ser Ser Gly Asp
        195                 200                 205 aca gct tcc ttg tcc atc act gag act cag gcg gga gat gag gct gac       672
Thr Ala Ser Leu Ser Ile Thr Glu Thr Gln Ala Gly Asp Glu Ala Asp
    210                 215                 220 tat tac tgc agt tcc cgg ggc aac agt acc tct cgc ctc tat gtc ttc       720
Tyr Tyr Cys Ser Ser Arg Gly Asn Ser Thr Ser Arg Leu Tyr Val Phe
225                 230                 235                 240 gga act ggg acc aag ctg acc gtc cta ggt                               750
Gly Thr Gly Thr Lys Leu Thr Val Leu Gly
                245                 250

<210> SEQ ID NO 215
<211> LENGTH: 735
<212> TYPE: DNA
<213> ORGANISM: Artificial sequence
<220> FEATURE:
```

<221> NAME/KEY: CDS
<222> LOCATION: (1)..(735)
<223> OTHER INFORMATION: Polynucleotide encoding GMCC106 scFv protein

<400> SEQUENCE: 215

```
cag gtg cag ctg cag gag tcg ggt cca gga ctg gtg aag cct tcg ggg        48
Gln Val Gln Leu Gln Glu Ser Gly Pro Gly Leu Val Lys Pro Ser Gly
1               5                   10                  15 acc ctg tcc ctc act tgc gct gtc tct gtt ggc tcc atc aac gaa agt        96
Thr Leu Ser Leu Thr Cys Ala Val Ser Val Gly Ser Ile Asn Glu Ser
            20                  25                  30 aac tgg tgg agt tgg gtt cgc cag tcc cca ggg aag gga ctg gag tgg       144
Asn Trp Trp Ser Trp Val Arg Gln Ser Pro Gly Lys Gly Leu Glu Trp
        35                  40                  45 att gga gaa atc tat cct act ggg acc acc aac tac aac ccg tcc ctg       192
Ile Gly Glu Ile Tyr Pro Thr Gly Thr Thr Asn Tyr Asn Pro Ser Leu
    50                  55                  60 gag agt cgg gtc acg ata tca gta gac aag tcc agg aac ctc ttc tcc       240
Glu Ser Arg Val Thr Ile Ser Val Asp Lys Ser Arg Asn Leu Phe Ser
65                  70                  75                  80 ctg aaa ctg aag tct gtg acc gcc gcg gac tcg gcc atg tat ttc tgt       288
Leu Lys Leu Lys Ser Val Thr Ala Ala Asp Ser Ala Met Tyr Phe Cys
                85                  90                  95 gcg aga gat cgg tgg gct ggt ggt ttt gat ctc tgg ggc aga ggg aca       336
Ala Arg Asp Arg Trp Ala Gly Gly Phe Asp Leu Trp Gly Arg Gly Thr
            100                 105                 110 atg gtc acc gtc tcg agt gga ggc ggt ggt tca ggc gga ggt ggc tct       384
Met Val Thr Val Ser Ser Gly Gly Gly Gly Ser Gly Gly Gly Gly Ser
        115                 120                 125 ggc ggt ggc gga agt gca cag tct gtg ttg acg cag ccg ccc tca gcg       432
Gly Gly Gly Gly Ser Ala Gln Ser Val Leu Thr Gln Pro Pro Ser Ala
    130                 135                 140 tct ggg acc ccc ggg cag agg gtc acc atc tct tgt tct gga agc agc       480
Ser Gly Thr Pro Gly Gln Arg Val Thr Ile Ser Cys Ser Gly Ser Ser
145                 150                 155                 160 tcc aac atc gga agt aat tct gta tac tgg tac cag cag ctc cca gga       528
Ser Asn Ile Gly Ser Asn Ser Val Tyr Trp Tyr Gln Gln Leu Pro Gly
                165                 170                 175 acg gcc ccc aaa ctc ctc atc tat agg aat aat cag cgg ccc tca ggg       576
Thr Ala Pro Lys Leu Leu Ile Tyr Arg Asn Asn Gln Arg Pro Ser Gly
            180                 185                 190 gtc cct gac cga ttc tct gct tcc aag tct ggc acc tca gcc tcc ctg       624
Val Pro Asp Arg Phe Ser Ala Ser Lys Ser Gly Thr Ser Ala Ser Leu
        195                 200                 205 gcc atc agt ggg ctc cgg tcc gag gat gag gct gat tat tac tgt gca       672
Ala Ile Ser Gly Leu Arg Ser Glu Asp Glu Ala Asp Tyr Tyr Cys Ala
    210                 215                 220 gca tgg gat gac agc ctg agt ggt ctg gtc ttc ggc gga ggg acc aag       720
Ala Trp Asp Asp Ser Leu Ser Gly Leu Val Phe Gly Gly Gly Thr Lys
225                 230                 235                 240 ctg acc gtc cta ggt                                                    735
Leu Thr Val Leu Gly
                245
```

<210> SEQ ID NO 216
<211> LENGTH: 750
<212> TYPE: DNA
<213> ORGANISM: Artificial sequence
<220> FEATURE:
<221> NAME/KEY: CDS
<222> LOCATION: (1)..(750)
<223> OTHER INFORMATION: Polynucleotide encoding GMCC107 scFv protein

<400> SEQUENCE: 216

```
cag gtc cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc agg acc tct gga tac acc ttc act gac cat      96
Ser Val Lys Val Ser Cys Arg Thr Ser Gly Tyr Thr Phe Thr Asp His
            20                  25                  30 tct atg cat tgg gtg cgc cag gcc ccc gga cag agg ttt gag tgg atg     144
Ser Met His Trp Val Arg Gln Ala Pro Gly Gln Arg Phe Glu Trp Met
        35                  40                  45 gga tgg atc ggc gct gac agt ggt tcc aca cag tat tca cgg aac ttc     192
Gly Trp Ile Gly Ala Asp Ser Gly Ser Thr Gln Tyr Ser Arg Asn Phe
    50                  55                  60 cag ggc aga ctc acc att ggc agg gac aca tcc gcg agc aca gtg tac     240
Gln Gly Arg Leu Thr Ile Gly Arg Asp Thr Ser Ala Ser Thr Val Tyr
65                  70                  75                  80 atg gag ctg acc agt ctg aga tct gaa gac acg gct gtc tat tac tgt     288
Met Glu Leu Thr Ser Leu Arg Ser Glu Asp Thr Ala Val Tyr Tyr Cys
                85                  90                  95 gcg aga gtg ggg gga ggt cag ggg tgg tac tcc ggc atg gac gtc tgg     336
Ala Arg Val Gly Gly Gly Gln Gly Trp Tyr Ser Gly Met Asp Val Trp
            100                 105                 110 ggc aga ggc acc ctg gtc acc gtc tcg agt gga ggc ggc ggt tca ggc     384
Gly Arg Gly Thr Leu Val Thr Val Ser Ser Gly Gly Gly Gly Ser Gly
        115                 120                 125 gga ggt ggc tct ggc ggt ggc gga agt gca cag gct gtg ctg act cag     432
Gly Gly Gly Ser Gly Gly Gly Gly Ser Ala Gln Ala Val Leu Thr Gln
    130                 135                 140 ccg tcc tca gtg tct ggg gcc cca ggg cag agg gtc acc atc tcc tgc     480
Pro Ser Ser Val Ser Gly Ala Pro Gly Gln Arg Val Thr Ile Ser Cys
145                 150                 155                 160 act ggg agc agc tcc aac atc ggg gca agt tat gat gta cac tgg tac     528
Thr Gly Ser Ser Ser Asn Ile Gly Ala Ser Tyr Asp Val His Trp Tyr
                165                 170                 175 cag cag ctt cca gga aca gcc ccc aaa ctc ctc atc tat aat aac aat     576
Gln Gln Leu Pro Gly Thr Ala Pro Lys Leu Leu Ile Tyr Asn Asn Asn
            180                 185                 190 aat cgg ccc tca ggg gtc cct gac cga ttc tct ggc tcc agg tct ggc     624
Asn Arg Pro Ser Gly Val Pro Asp Arg Phe Ser Gly Ser Arg Ser Gly
        195                 200                 205 acc tca gcc tcc ctg gcc atc act ggg ctc cag gct gag gat gag gct     672
Thr Ser Ala Ser Leu Ala Ile Thr Gly Leu Gln Ala Glu Asp Glu Ala
    210                 215                 220 gat tat tac tgc cac tcc tat gac agc aac ctg agt ggt gat gtc ttc     720
Asp Tyr Tyr Cys His Ser Tyr Asp Ser Asn Leu Ser Gly Asp Val Phe
225                 230                 235                 240 gga tct ggg acc aag ctg acc gtc cta ggt                             750
Gly Ser Gly Thr Lys Leu Thr Val Leu Gly
                245                 250
```

<210> SEQ ID NO 217
<211> LENGTH: 765
<212> TYPE: DNA
<213> ORGANISM: Artificial sequence
<220> FEATURE:
<221> NAME/KEY: CDS
<222> LOCATION: (1)..(765)
<223> OTHER INFORMATION: Polynucleotide encoding GMCC108 scFv protein

<400> SEQUENCE: 217

```
gaa gtg cag ctg gtg cag tct ggg gca gag gtg aag gag cct ggg gcc      48
Glu Val Gln Leu Val Gln Ser Gly Ala Glu Val Lys Glu Pro Gly Ala
1               5                   10                  15 tca gtg acc gtt tcc tgc aag gct tct gga tac acc ttc att agt tac      96
Ser Val Thr Val Ser Cys Lys Ala Ser Gly Tyr Thr Phe Ile Ser Tyr
                20                  25                  30 cac atg cac tgg gtt cga cag gcc cct gga caa ggg ctt gag tgg atg     144
His Met His Trp Val Arg Gln Ala Pro Gly Gln Gly Leu Glu Trp Met
            35                  40                  45 gga ata atc aat cct agt ggt ggt gac aca acc tac gca cag aag ttc     192
Gly Ile Ile Asn Pro Ser Gly Gly Asp Thr Thr Tyr Ala Gln Lys Phe
        50                  55                  60 cag ggc aga gtc acc atg acc agg gac acg tca acg agc aca gtt tac     240
Gln Gly Arg Val Thr Met Thr Arg Asp Thr Ser Thr Ser Thr Val Tyr
65                  70                  75                  80 atg gag ctg agg agc ctg aga ttt gag gac acg gcc agg tat tac tgt     288
Met Glu Leu Arg Ser Leu Arg Phe Glu Asp Thr Ala Arg Tyr Tyr Cys
                85                  90                  95 gcg aga gat cta aag ttc tac gat ttt cgg agt gga aag tat cag gac     336
Ala Arg Asp Leu Lys Phe Tyr Asp Phe Arg Ser Gly Lys Tyr Gln Asp
            100                 105                 110 tac gga atg gat gtc tgg ggc cag gga acc ctg gtc acc gtc tcg agt     384
Tyr Gly Met Asp Val Trp Gly Gln Gly Thr Leu Val Thr Val Ser Ser
        115                 120                 125 gga ggc ggc ggt tca ggc gga ggt ggc tct ggc ggt ggc gga agt gca     432
Gly Gly Gly Gly Ser Gly Gly Gly Gly Ser Gly Gly Gly Gly Ser Ala
130                 135                 140 cag tct gtg ctg act cag cca ccg tcg ctg tca gtg gcc cca gga cag     480
Gln Ser Val Leu Thr Gln Pro Pro Ser Leu Ser Val Ala Pro Gly Gln
145                 150                 155                 160 acg gcc agt att acc tgt ggg gga aac gac att gga act aaa agt gta     528
Thr Ala Ser Ile Thr Cys Gly Gly Asn Asp Ile Gly Thr Lys Ser Val
                165                 170                 175 cac tgg tac cag ctg aag cca ggc cag gcc cct gtg ttg gtc gtc tat     576
His Trp Tyr Gln Leu Lys Pro Gly Gln Ala Pro Val Leu Val Val Tyr
            180                 185                 190 gat aat aga gac cgg ccc tca ggg atc cct gag cga ttc tct ggc tcc     624
Asp Asn Arg Asp Arg Pro Ser Gly Ile Pro Glu Arg Phe Ser Gly Ser
        195                 200                 205 aac tct ggg aac acg gcc acc cta acc atc agc agg gtc gaa ggc ggg     672
Asn Ser Gly Asn Thr Ala Thr Leu Thr Ile Ser Arg Val Glu Gly Gly
210                 215                 220 gat gag gcc gac tat tat tgt cag gtg tgg gat agt agt att gat cat     720
Asp Glu Ala Asp Tyr Tyr Cys Gln Val Trp Asp Ser Ser Ile Asp His
225                 230                 235                 240 tcc gaa tat gtc ttc gga act ggg acc aag ctg acc gtc cta ggt         765
Ser Glu Tyr Val Phe Gly Thr Gly Thr Lys Leu Thr Val Leu Gly
                245                 250                 255

<210> SEQ ID NO 218
<211> LENGTH: 732
<212> TYPE: DNA
<213> ORGANISM: Artificial sequence
<220> FEATURE:
<221> NAME/KEY: CDS
<222> LOCATION: (1)..(732)
<223> OTHER INFORMATION: Polynucleotide encoding GMCC109 scFv protein

<400> SEQUENCE: 218 cag gtg cag ctg cag gag tcg ggg gga ggc ttg gta cag cct ggg ggg      48
Gln Val Gln Leu Gln Glu Ser Gly Gly Gly Leu Val Gln Pro Gly Gly
1               5                   10                  15
```

```
tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
        20                  25                  30 gcc atg agc tgg gtc cgc cag gct cca ggg aag ggg ctg gag tgg gtc     144
Ala Met Ser Trp Val Arg Gln Ala Pro Gly Lys Gly Leu Glu Trp Val
            35                  40                  45 tca gct att agt ggt agt ggt ggt agc aca tac tac gca gac tcc gtg     192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt     288
Leu Gln Met Asn Ser Leu Arg Ala Glu Asp Thr Ala Val Tyr Tyr Cys
                85                  90                  95 gcg aaa agt caa tgg agt ggg agc tac tac ggc tca ttt gac tac tgg     336
Ala Lys Ser Gln Trp Ser Gly Ser Tyr Tyr Gly Ser Phe Asp Tyr Trp
            100                 105                 110 ggc cgg ggg aca atg gtc acc gtc tcg agt gga ggc ggc ggt tca ggc     384
Gly Arg Gly Thr Met Val Thr Val Ser Ser Gly Gly Gly Gly Ser Gly
        115                 120                 125 gga ggt ggc tct ggc ggt ggc gga agt gca cag tct gtg ctg act cag     432
Gly Gly Gly Ser Gly Gly Gly Gly Ser Ala Gln Ser Val Leu Thr Gln
    130                 135                 140 cca ccc tca gtg tcc gtt tct cca gga cag aca gcc acc atc acc tgc     480
Pro Pro Ser Val Ser Val Ser Pro Gly Gln Thr Ala Thr Ile Thr Cys
145                 150                 155                 160 tct gga gac aaa ttg ggg gat aaa tat gtt tcc tgg tat cag aag aag     528
Ser Gly Asp Lys Leu Gly Asp Lys Tyr Val Ser Trp Tyr Gln Lys Lys
                165                 170                 175 cca gga cag gcc cct gtg ctg gtc atc tat caa gat gac aag cgg ccg     576
Pro Gly Gln Ala Pro Val Leu Val Ile Tyr Gln Asp Asp Lys Arg Pro
            180                 185                 190 tca ggg atc cct gag cga ttc tct ggc tcc aac tct ggg aac aca gcc     624
Ser Gly Ile Pro Glu Arg Phe Ser Gly Ser Asn Ser Gly Asn Thr Ala
        195                 200                 205 act ctg acc atc agc ggg acc cag gct atg gat gag ggt gac tat tac     672
Thr Leu Thr Ile Ser Gly Thr Gln Ala Met Asp Glu Gly Asp Tyr Tyr
    210                 215                 220 tgt cag gcg tgg gac aga agt gtg ata ttc ggc gga ggg acc aag gtc     720
Cys Gln Ala Trp Asp Arg Ser Val Ile Phe Gly Gly Gly Thr Lys Val
225                 230                 235                 240 acc gtc cta ggt                                                     732
Thr Val Leu Gly <210> SEQ ID NO 219
<211> LENGTH: 750
<212> TYPE: DNA
<213> ORGANISM: Artificial sequence
<220> FEATURE:
<221> NAME/KEY: CDS
<222> LOCATION: (1)..(750)
<223> OTHER INFORMATION: Polynucleotide encoding GMCC110 scFv protein

<400> SEQUENCE: 219 cag gtg cag ctg cag gag tcg ggc ccg gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt gcc tcc atc agt agt gga      96
Thr Leu Ser Leu Thr Cys Thr Val Ser Gly Ala Ser Ile Ser Ser Gly
            20                  25                  30
```

-continued

```
ggt tac cgc tgg atc tgg att cgc cag cac cca ggg cag ggg ctg gag      144
Gly Tyr Arg Trp Ile Trp Ile Arg Gln His Pro Gly Gln Gly Leu Glu
         35                  40                  45 tgg att ggg gac atc cat tac agt ggg agc acc cag tac aac ccg tcc      192
Trp Ile Gly Asp Ile His Tyr Ser Gly Ser Thr Gln Tyr Asn Pro Ser
 50                  55                  60 ctc aag agt cga gtt gcc ttg aca ctg gac agg tct aaa aac caa ttc      240
Leu Lys Ser Arg Val Ala Leu Thr Leu Asp Arg Ser Lys Asn Gln Phe
 65                  70                  75                  80 tcc ctg cag ctg agc tct gtg acg gcc gcg gac acg gcc gtc tac tat      288
Ser Leu Gln Leu Ser Ser Val Thr Ala Ala Asp Thr Ala Val Tyr Tyr
             85                  90                  95 tgt gcg aga gat ccg cgt gga cac acg tat ggt tat ggt tac tac ttt      336
Cys Ala Arg Asp Pro Arg Gly His Thr Tyr Gly Tyr Gly Tyr Tyr Phe
            100                 105                 110 gac tac tgg ggc aaa ggc acc ctg gtc acc gtc tcg agt gga ggc ggc      384
Asp Tyr Trp Gly Lys Gly Thr Leu Val Thr Val Ser Ser Gly Gly Gly
        115                 120                 125 ggt tca ggc gga ggt ggc tct ggc ggt ggc gga agt gca ctt tct tct      432
Gly Ser Gly Gly Gly Gly Ser Gly Gly Gly Gly Ser Ala Leu Ser Ser
130                 135                 140 gag ctg act cag gac cct gat gtg tct gtg gcc ttg gga cag aca gtc      480
Glu Leu Thr Gln Asp Pro Asp Val Ser Val Ala Leu Gly Gln Thr Val
145                 150                 155                 160 acg atc aca tgc caa gga gac aga ctc aga aga tat tat gca agc tgg      528
Thr Ile Thr Cys Gln Gly Asp Arg Leu Arg Arg Tyr Tyr Ala Ser Trp
                165                 170                 175 tac cag cag aag cca gga cag gcc cct gtg ctt gtc atc ttt cgt aaa      576
Tyr Gln Gln Lys Pro Gly Gln Ala Pro Val Leu Val Ile Phe Arg Lys
            180                 185                 190 aac aac cgg ccc tca ggg atc cca gac cga ttc tct ggc tcc agc tca      624
Asn Asn Arg Pro Ser Gly Ile Pro Asp Arg Phe Ser Gly Ser Ser Ser
        195                 200                 205 gga gac aca gct tcc ttg acc atc act ggg gct cag gcg gaa gat gag      672
Gly Asp Thr Ala Ser Leu Thr Ile Thr Gly Ala Gln Ala Glu Asp Glu
    210                 215                 220 gct gac tat tac tgt aac tca cgg gac acc agt ggt acc ctt tca ttc      720
Ala Asp Tyr Tyr Cys Asn Ser Arg Asp Thr Ser Gly Thr Leu Ser Phe
225                 230                 235                 240 ggc gga ggg acc cag ctc acc gtt tta agt                              750
Gly Gly Gly Thr Gln Leu Thr Val Leu Ser
                245                 250

<210> SEQ ID NO 220
<211> LENGTH: 735
<212> TYPE: DNA
<213> ORGANISM: Artificial sequence
<220> FEATURE:
<221> NAME/KEY: CDS
<222> LOCATION: (1)..(735)
<223> OTHER INFORMATION: Polynucleotide encoding GMCC112 scFv protein

<400> SEQUENCE: 220 cag gtc cag ctg gta cag tct ggg gga ggc ttg gta cag ccg ggg ggg       48
Gln Val Gln Leu Val Gln Ser Gly Gly Gly Leu Val Gln Pro Gly Gly
1               5                  10                  15 tcc ctg aga ctc tcc tgt gca gcc tct gga ttc agc ttt agt act tat       96
Ser Leu Arg Leu Ser Cys Ala Ala Ser Gly Phe Ser Phe Ser Thr Tyr
            20                  25                  30 gcc atg agt tgg gtc cgc cag gct cca ggg aag gga ctg gag tgg gtc      144
Ala Met Ser Trp Val Arg Gln Ala Pro Gly Lys Gly Leu Glu Trp Val
        35                  40                  45
```

```
                  35                  40                  45
tca ggc gtt agt gat ggt ggt gac aca ttc tac gca gac tcc gta agg        192
Ser Gly Val Ser Asp Gly Gly Asp Thr Phe Tyr Ala Asp Ser Val Arg
     50                  55                  60 ggc cgc ttc acc ctc tcc aga gac aac gcc aag aac acg ctg ttt ctg        240
Gly Arg Phe Thr Leu Ser Arg Asp Asn Ala Lys Asn Thr Leu Phe Leu
 65                  70                  75                  80 caa atg aac agc ctg aca gcc gag gac acg gcc aca tat tac tgt gcg        288
Gln Met Asn Ser Leu Thr Ala Glu Asp Thr Ala Thr Tyr Tyr Cys Ala
                 85                  90                  95 aaa gag ata gca aga att gga gtt cca aat ttc gac cac tgg ggc cag        336
Lys Glu Ile Ala Arg Ile Gly Val Pro Asn Phe Asp His Trp Gly Gln
            100                 105                 110 ggc acc ctg gtc acc gtc tcg agt gga ggc ggc ggt tca ggc gga ggt        384
Gly Thr Leu Val Thr Val Ser Ser Gly Gly Gly Gly Ser Gly Gly Gly
        115                 120                 125 ggc tct ggc ggt ggc gga agt gca ctt gaa acg aca ctc acg cag tct        432
Gly Ser Gly Gly Gly Gly Ser Ala Leu Glu Thr Thr Leu Thr Gln Ser
    130                 135                 140 ccg ggc acc ttg tct ttg tct cca ggg gac aga gcc acc ctc tcc tgc        480
Pro Gly Thr Leu Ser Leu Ser Pro Gly Asp Arg Ala Thr Leu Ser Cys
145                 150                 155                 160 agg gcc agt cag agt att aga aat aac gac gtc gcc tgg tac cag cag        528
Arg Ala Ser Gln Ser Ile Arg Asn Asn Asp Val Ala Trp Tyr Gln Gln
                165                 170                 175 aaa cct ggc cag gca ccc aga ctc ctc atc tat agt gca tcc agg cgc        576
Lys Pro Gly Gln Ala Pro Arg Leu Leu Ile Tyr Ser Ala Ser Arg Arg
            180                 185                 190 gcc act gac atc cca gac agg ttc agt ggc agt gcc tct ggg aca gac        624
Ala Thr Asp Ile Pro Asp Arg Phe Ser Gly Ser Ala Ser Gly Thr Asp
        195                 200                 205 ttc act ctc acc atc agc aga ctg gag cct gag gat ttt gcg atg tac        672
Phe Thr Leu Thr Ile Ser Arg Leu Glu Pro Glu Asp Phe Ala Met Tyr
    210                 215                 220 tac tgt cag cag tat ggc ggc tcg gcc tcc ttc ggc caa ggg aca cga        720
Tyr Cys Gln Gln Tyr Gly Gly Ser Ala Ser Phe Gly Gln Gly Thr Arg
225                 230                 235                 240 ctg gag att aaa cgt                                                     735
Leu Glu Ile Lys Arg
                245

<210> SEQ ID NO 221
<211> LENGTH: 750
<212> TYPE: DNA
<213> ORGANISM: Artificial sequence
<220> FEATURE:
<221> NAME/KEY: CDS
<222> LOCATION: (1)..(750)
<223> OTHER INFORMATION: Polynucleotide encoding GMCC114 scFv protein

<400> SEQUENCE: 221 gag gtg cag ctg gtg gag tcc ggg cct gag gtg aag aag cct ggg tcc         48
Glu Val Gln Leu Val Glu Ser Gly Pro Glu Val Lys Lys Pro Gly Ser
 1               5                  10                  15 tcg gtt aag gtc tcc tgc aag gct tct ggt gcc gcc gcc ttc agc agc         96
Ser Val Lys Val Ser Cys Lys Ala Ser Gly Ala Ala Ala Phe Ser Ser
             20                  25                  30 tat gca atc agc tgg gtg cgt cag gcc cct gga cga ggg ctt gag tgg        144
Tyr Ala Ile Ser Trp Val Arg Gln Ala Pro Gly Arg Gly Leu Glu Trp
         35                  40                  45 atg ggc ggc atc atc ccc atc tct gat aca cca aag tat gca cat aag        192
Met Gly Gly Ile Ile Pro Ile Ser Asp Thr Pro Lys Tyr Ala His Lys
```

```
Met Gly Gly Ile Ile Pro Ile Ser Asp Thr Pro Lys Tyr Ala His Lys
 50                  55                  60 ttc cag ggc aga gtc aca att acc gcg gac gaa tcc acg acc aca gtc      240
Phe Gln Gly Arg Val Thr Ile Thr Ala Asp Glu Ser Thr Thr Thr Val
 65                  70                  75                  80 ttc atg gag gtg agc ggc ctg aga tct gac gac acg gcc gtc tat tac      288
Phe Met Glu Val Ser Gly Leu Arg Ser Asp Asp Thr Ala Val Tyr Tyr
                 85                  90                  95 tgt gcg aca acc aca agg tat ggt tcg ggc act tat gat tac atg gac      336
Cys Ala Thr Thr Thr Arg Tyr Gly Ser Gly Thr Tyr Asp Tyr Met Asp
            100                 105                 110 gtc tgg ggc caa ggg aca atg gtc acc gtc tcg agt gga ggc ggc ggt      384
Val Trp Gly Gln Gly Thr Met Val Thr Val Ser Ser Gly Gly Gly Gly
        115                 120                 125 tca ggc gga ggt ggc tct ggc ggt ggc gga agt gca ctt tct tct gag      432
Ser Gly Gly Gly Gly Ser Gly Gly Gly Gly Ser Ala Leu Ser Ser Glu
    130                 135                 140 ctg act cag gac cct gct gtg tct gtg gcc ttg gga cag aca gtc agg      480
Leu Thr Gln Asp Pro Ala Val Ser Val Ala Leu Gly Gln Thr Val Arg
145                 150                 155                 160 atc aca tgc caa gga gac agc ctc aga agt tat tat gca agt tgg tat      528
Ile Thr Cys Gln Gly Asp Ser Leu Arg Ser Tyr Tyr Ala Ser Trp Tyr
                165                 170                 175 caa cag aag cca gga cag gcc ccg gta ctt gtc ttc tat ggt aaa aac      576
Gln Gln Lys Pro Gly Gln Ala Pro Val Leu Val Phe Tyr Gly Lys Asn
            180                 185                 190 aag cgg ccc tcg ggg atc cca gac cga ttc tcg ggc tcc acc tca gga      624
Lys Arg Pro Ser Gly Ile Pro Asp Arg Phe Ser Gly Ser Thr Ser Gly
        195                 200                 205 aac aca gct tcc ttg tcc atc acc ggg gct ctg gcg gat gat gag gcc      672
Asn Thr Ala Ser Leu Ser Ile Thr Gly Ala Leu Ala Asp Asp Glu Ala
    210                 215                 220 gac tat tac tgt cac tcc cgt gac acc agt ggt gcc cag att ctt ttc      720
Asp Tyr Tyr Cys His Ser Arg Asp Thr Ser Gly Ala Gln Ile Leu Phe
225                 230                 235                 240 ggc gga ggg acc aag ctg acc gtc cta ggt                              750
Gly Gly Gly Thr Lys Leu Thr Val Leu Gly
                245                 250

<210> SEQ ID NO 222
<211> LENGTH: 753
<212> TYPE: DNA
<213> ORGANISM: Artificial sequence
<220> FEATURE:
<221> NAME/KEY: CDS
<222> LOCATION: (1)..(753)
<223> OTHER INFORMATION: Polynucleotide encoding GMCC118 scFv protein

<400> SEQUENCE: 222 gag gtg cag ctg gtg cag tct ggg gga ggc ttg gta aag ccg ggg ggg       48
Glu Val Gln Leu Val Gln Ser Gly Gly Gly Leu Val Lys Pro Gly Gly
  1               5                  10                  15 tca ctt aga ctc tcc tgt aca gcc tct gga ttc agt ttc act aac gcc       96
Ser Leu Arg Leu Ser Cys Thr Ala Ser Gly Phe Ser Phe Thr Asn Ala
             20                  25                  30 tgg atg agc tgg gtc cgc cag gct cca ggg aag ggg ctg gag tgg gtt      144
Trp Met Ser Trp Val Arg Gln Ala Pro Gly Lys Gly Leu Glu Trp Val
         35                  40                  45 ggc cgt att aaa agc aga aat gat ggt ggg gca aca gac tac gct gca      192
Gly Arg Ile Lys Ser Arg Asn Asp Gly Gly Ala Thr Asp Tyr Ala Ala
 50                  55                  60
```

| | | |
|---|---|---|
| ccc gtg aaa ggc aga ttc acc atc tca aga gat gat tca aaa aac acg<br>Pro Val Lys Gly Arg Phe Thr Ile Ser Arg Asp Asp Ser Lys Asn Thr<br>65                            70                     75                    80 | 240 |
| ttg tat ctg caa atg aat agc ctg aaa acc gac gac aca gcc gta tac<br>Leu Tyr Leu Gln Met Asn Ser Leu Lys Thr Asp Asp Thr Ala Val Tyr<br>                     85                     90                     95 | 288 |
| tac tgt acc aca gat aac ttc cca tta cga ttt ttg gag tgg tta tcc<br>Tyr Cys Thr Thr Asp Asn Phe Pro Leu Arg Phe Leu Glu Trp Leu Ser<br>                100                    105                  110 | 336 |
| cat cct gac tac tgg ggc caa ggg aca atg gtc acc gtc tcg agt gga<br>His Pro Asp Tyr Trp Gly Gln Gly Thr Met Val Thr Val Ser Ser Gly<br>             115                    120                  125 | 384 |
| ggc ggc ggt tca ggc gga ggt ggc tct ggc ggt ggc gga agt gca cag<br>Gly Gly Gly Ser Gly Gly Gly Gly Ser Gly Gly Gly Gly Ser Ala Gln<br>130                     135                    140 | 432 |
| gct gtg ctg act cag ccg tcc tca gtg tcc gtg tcc cca gga cag aca<br>Ala Val Leu Thr Gln Pro Ser Ser Val Ser Val Ser Pro Gly Gln Thr<br>145                     150                    155                  160 | 480 |
| gtc acc atc acc tgc tct ggg gaa aaa ttg gac aat aaa tat att tcc<br>Val Thr Ile Thr Cys Ser Gly Glu Lys Leu Asp Asn Lys Tyr Ile Ser<br>                165                    170                  175 | 528 |
| tgg tat caa cag agg cca ggc cgg tcc cct atc ctg gtc att tat caa<br>Trp Tyr Gln Gln Arg Pro Gly Arg Ser Pro Ile Leu Val Ile Tyr Gln<br>180                     185                    190 | 576 |
| gat cgg aag cgg ccc tca ggg atc cct gag cga ttc tct ggc tcc aac<br>Asp Arg Lys Arg Pro Ser Gly Ile Pro Glu Arg Phe Ser Gly Ser Asn<br>195                     200                    205 | 624 |
| tcc ggg aac aca gcc act ctg acc atc acc ggg tcc cag cct ttg gat<br>Ser Gly Asn Thr Ala Thr Leu Thr Ile Thr Gly Ser Gln Pro Leu Asp<br>210                     215                    220 | 672 |
| gag gct gac tat tac tgt cag gcg tgg gac agc agc act gct tgg gag<br>Glu Ala Asp Tyr Tyr Cys Gln Ala Trp Asp Ser Ser Thr Ala Trp Glu<br>225                     230                    235                  240 | 720 |
| ttc ggc gga ggg acc aag ctg acc gtc cta ggt<br>Phe Gly Gly Gly Thr Lys Leu Thr Val Leu Gly<br>                245                    250 | 753 |

```
<210> SEQ ID NO 223
<211> LENGTH: 756
<212> TYPE: DNA
<213> ORGANISM: Artificial sequence
<220> FEATURE:
<221> NAME/KEY: CDS
<222> LOCATION: (1)..(756)
<223> OTHER INFORMATION: Polynucleotide encoding GMCC119 scFv protein

<400> SEQUENCE: 223
```

| | | |
|---|---|---|
| gaa gtg cag ctg gtg cag tct ggg cct gag gtg aag aag cca ggg gcc<br>Glu Val Gln Leu Val Gln Ser Gly Pro Glu Val Lys Lys Pro Gly Ala<br>1                   5                    10                    15 | 48 |
| tca gtg aag gtc tcc tgc aag gct tct aat tac acc ttc acc acc tac<br>Ser Val Lys Val Ser Cys Lys Ala Ser Asn Tyr Thr Phe Thr Thr Tyr<br>                    20                    25                    30 | 96 |
| gac atc agc tgg gtg cga cag gcc cct gga caa ggg ctt gag tgg atg<br>Asp Ile Ser Trp Val Arg Gln Ala Pro Gly Gln Gly Leu Glu Trp Met<br>                35                    40                  45 | 144 |
| gga tgg atc agc aca tat agt ggg aac aca aag tat gca cag aag ttc<br>Gly Trp Ile Ser Thr Tyr Ser Gly Asn Thr Lys Tyr Ala Gln Lys Phe<br>          50                    55                    60 | 192 |
| cag ggc aga gtc acc atg acc aga gac acg tcc acg agc gca gcc tac<br>Gln Gly Arg Val Thr Met Thr Arg Asp Thr Ser Thr Ser Ala Ala Tyr<br>65                     70                    75                  80 | 240 |

-continued

```
atg gag ctg agg aac ctg aga tct gac gac acg gcc gtt tat ttc tgt    288
Met Glu Leu Arg Asn Leu Arg Ser Asp Asp Thr Ala Val Tyr Phe Cys
            85                  90                  95 gcg aga gat atc cgt gtg tgg cgt ggt tcg ggc agt gtc cac tac ttc    336
Ala Arg Asp Ile Arg Val Trp Arg Gly Ser Gly Ser Val His Tyr Phe
        100                 105                 110 gac ccc tgg ggg cga ggg acc acg gtc acc gtc tcg agt gga ggc ggc    384
Asp Pro Trp Gly Arg Gly Thr Thr Val Thr Val Ser Ser Gly Gly Gly
    115                 120                 125 ggt tca ggc gga ggt ggc tct ggc ggt ggc gga agt gca caa tct gcc    432
Gly Ser Gly Gly Gly Gly Ser Gly Gly Gly Gly Ser Ala Gln Ser Ala
130                 135                 140 ctg act cag cct cgc tca gtg tcc ggg tct cct gga cag tca gtc acc    480
Leu Thr Gln Pro Arg Ser Val Ser Gly Ser Pro Gly Gln Ser Val Thr
145                 150                 155                 160 atc tcc tgc act gga acc agc aat gat gtt ggt ggt tat aac ttt gtc    528
Ile Ser Cys Thr Gly Thr Ser Asn Asp Val Gly Gly Tyr Asn Phe Val
                165                 170                 175 tcc tgg tac caa caa cac cca ggc aaa gcc ccc aaa ctc atg gtt tat    576
Ser Trp Tyr Gln Gln His Pro Gly Lys Ala Pro Lys Leu Met Val Tyr
            180                 185                 190 aat gtc agt aag cgg ccc tca ggg gtc cct gat cgc ttc tct ggc tcc    624
Asn Val Ser Lys Arg Pro Ser Gly Val Pro Asp Arg Phe Ser Gly Ser
        195                 200                 205 aag tct ggc aac acg gcc tcc ctg acc atc tct ggg ctc cag gct gag    672
Lys Ser Gly Asn Thr Ala Ser Leu Thr Ile Ser Gly Leu Gln Ala Glu
    210                 215                 220 gat gag gct gat tat tac tgc tcc tca tat gca cac agc tac acc ttg    720
Asp Glu Ala Asp Tyr Tyr Cys Ser Ser Tyr Ala His Ser Tyr Thr Leu
225                 230                 235                 240 gtc ttc ggc gga ggg acc aag gtc acc gtc cta ggt                    756
Val Phe Gly Gly Gly Thr Lys Val Thr Val Leu Gly
                245                 250
```

<210> SEQ ID NO 224
<211> LENGTH: 753
<212> TYPE: DNA
<213> ORGANISM: Artificial sequence
<220> FEATURE:
<221> NAME/KEY: CDS
<222> LOCATION: (1)..(753)
<223> OTHER INFORMATION: Polynucleotide encoding GMCC124 scFv protein

<400> SEQUENCE: 224

```
cag gtc acc ttg aag gag tct ggg gct gag gtg aag aag cct ggg gcc     48
Gln Val Thr Leu Lys Glu Ser Gly Ala Glu Val Lys Lys Pro Gly Ala
1               5                   10                  15 tca gtg aag gtt tcc tgc aag gct tct gga tac acc ttc aca gac aat     96
Ser Val Lys Val Ser Cys Lys Ala Ser Gly Tyr Thr Phe Thr Asp Asn
            20                  25                  30 gct cta cat tgg gtg cgt cag gcc ccc gga caa agg cca gag tgg atg    144
Ala Leu His Trp Val Arg Gln Ala Pro Gly Gln Arg Pro Glu Trp Met
        35                  40                  45 gca tgg atc aac act gcc aat gga aac aca aga tat tca caa aag ttc    192
Ala Trp Ile Asn Thr Ala Asn Gly Asn Thr Arg Tyr Ser Gln Lys Phe
    50                  55                  60 cag ggc aga ctc acc att acc agg gac aca tcc gcg agc aca gcc ttc    240
Gln Gly Arg Leu Thr Ile Thr Arg Asp Thr Ser Ala Ser Thr Ala Phe
65                  70                  75                  80 atg gat ctg agc agc cta aga tct gag gac acg gct gta tat tac tgt    288
Met Asp Leu Ser Ser Leu Arg Ser Glu Asp Thr Ala Val Tyr Tyr Cys
```

```
                    85                  90                  95
gcg agg cag aaa gcc tac aag aat tac tac tac tac ggt atg gac       336
Ala Arg Gln Lys Ala Tyr Lys Asn Tyr Tyr Tyr Tyr Gly Met Asp
            100                 105                 110 gtc tgg ggc caa ggc acc ctg gtc acc gtc tcg agt gga ggc ggt       384
Val Trp Gly Gln Gly Thr Leu Val Thr Val Ser Ser Gly Gly Gly
        115                 120                 125 tca ggc gga ggt ggc tct ggc ggt ggc gga agt gca cag tct gtc gtg   432
Ser Gly Gly Gly Gly Ser Gly Gly Gly Gly Ser Ala Gln Ser Val Val
130                 135                 140 acg cag ccg ccc tca gtg tct gcg gcc cca gga cag aag gtc acc atc   480
Thr Gln Pro Pro Ser Val Ser Ala Ala Pro Gly Gln Lys Val Thr Ile
145                 150                 155                 160 tcc tgc tct gga agc agc tcc aac att ggg aat aat tat gta tcc tgg   528
Ser Cys Ser Gly Ser Ser Ser Asn Ile Gly Asn Asn Tyr Val Ser Trp
            165                 170                 175 tac cag cag ctc cca gga aca gcc ccc aaa ctc ctc atc tat gaa aat   576
Tyr Gln Gln Leu Pro Gly Thr Ala Pro Lys Leu Leu Ile Tyr Glu Asn
        180                 185                 190 aat aag cga ccc tca gga att cct gac cga ttc tcg ggc tcc cag tct   624
Asn Lys Arg Pro Ser Gly Ile Pro Asp Arg Phe Ser Gly Ser Gln Ser
    195                 200                 205 ggc acg tca gcc acc ctg ggc atc tcc gga ctc cag act ggg gac gag   672
Gly Thr Ser Ala Thr Leu Gly Ile Ser Gly Leu Gln Thr Gly Asp Glu
210                 215                 220 gcc gat tat tac tgc gga aca tgg gat agc agc ctg cgt gct ggg gtg   720
Ala Asp Tyr Tyr Cys Gly Thr Trp Asp Ser Ser Leu Arg Ala Gly Val
225                 230                 235                 240 ttc ggc gga ggg acc aag ctg acc gtc cta ggt                       753
Phe Gly Gly Gly Thr Lys Leu Thr Val Leu Gly
                245                 250

<210> SEQ ID NO 225
<211> LENGTH: 741
<212> TYPE: DNA
<213> ORGANISM: Artificial sequence
<220> FEATURE:
<221> NAME/KEY: CDS
<222> LOCATION: (1)..(741)
<223> OTHER INFORMATION: Polynucleotide encoding GMCC125 scFv protein

<400> SEQUENCE: 225 gag gtg cag ctg gtg cag tct ggg gga ggc ttg gtc aag cct gga ggg   48
Glu Val Gln Leu Val Gln Ser Gly Gly Gly Leu Val Lys Pro Gly Gly
1               5                   10                  15 tcc ctg aga ctc tcc tgt gca gcc tct gga ttc agc ttc agt gac tac   96
Ser Leu Arg Leu Ser Cys Ala Ala Ser Gly Phe Ser Phe Ser Asp Tyr
            20                  25                  30 tcc atg cac tgg atc cgc cag gct cca ggg aag ggg ctg gag tgg ctt   144
Ser Met His Trp Ile Arg Gln Ala Pro Gly Lys Gly Leu Glu Trp Leu
        35                  40                  45 tca cac att ggt aca agt act tct tac aca aac tac gca gat tct gtg   192
Ser His Ile Gly Thr Ser Thr Ser Tyr Thr Asn Tyr Ala Asp Ser Val
    50                  55                  60 aag ggc cga ttc acc atc tcc aga gac aac gcc aag aac tct ttc tat   240
Lys Gly Arg Phe Thr Ile Ser Arg Asp Asn Ala Lys Asn Ser Phe Tyr
65                  70                  75                  80 ctc caa atg aac agc ctg aga gtc gac gac acg gct gtg tat ttc tgt   288
Leu Gln Met Asn Ser Leu Arg Val Asp Asp Thr Ala Val Tyr Phe Cys
            85                  90                  95 gcg agg gga ttc ggg ggc ctc cgg ggc tac ttt gac tac tgg ggc cag   336
```

|  |  |  |  |  |  |  |  |  |  |  |  |  |  |
|---|---|---|---|---|---|---|---|---|---|---|---|---|---|
| Ala | Arg | Gly | Phe | Gly | Gly | Leu | Arg | Gly | Tyr | Phe | Asp | Tyr | Trp | Gly | Gln |
|  |  |  | 100 |  |  |  |  | 105 |  |  |  |  | 110 |

```
ggc acc ctg gtc acc gtc tcg agt gga ggc ggc ggt tca ggc gga ggt      384
Gly Thr Leu Val Thr Val Ser Ser Gly Gly Gly Gly Ser Gly Gly Gly
        115                 120                 125 ggc tct ggc ggt ggc gga agt gca ctt tct tct gag ctg act cag gac      432
Gly Ser Gly Gly Gly Gly Ser Ala Leu Ser Ser Glu Leu Thr Gln Asp
130                 135                 140 cct gct gtg tct gtg gcc ttg gga cag aca gtc aaa atc aca tgc caa      480
Pro Ala Val Ser Val Ala Leu Gly Gln Thr Val Lys Ile Thr Cys Gln
145                 150                 155                 160 gga gac aga ctc cga aga ttt tat gca agc tgg tac cag cag aag cca      528
Gly Asp Arg Leu Arg Arg Phe Tyr Ala Ser Trp Tyr Gln Gln Lys Pro
                165                 170                 175 ggc cag gcc cct cta ctt ctc atc tat ggt aaa aat agt cgg ccc tca      576
Gly Gln Ala Pro Leu Leu Leu Ile Tyr Gly Lys Asn Ser Arg Pro Ser
            180                 185                 190 ggg atc ccg gac cga ttc tct ggc tcc acc tcg gga gcc aca gct tcc      624
Gly Ile Pro Asp Arg Phe Ser Gly Ser Thr Ser Gly Ala Thr Ala Ser
        195                 200                 205 ttg acc atc act ggg gct cag gcg gaa gac gag gct gat tat tac tgt      672
Leu Thr Ile Thr Gly Ala Gln Ala Glu Asp Glu Ala Asp Tyr Tyr Cys
210                 215                 220 aac tcc cgg gac agt tcc ggc agc ctc cat tct gtc ttc gga act ggg      720
Asn Ser Arg Asp Ser Ser Gly Ser Leu His Ser Val Phe Gly Thr Gly
225                 230                 235                 240 acc aag gtc acc gtc cta ggt                                          741
Thr Lys Val Thr Val Leu Gly
                245

<210> SEQ ID NO 226
<211> LENGTH: 738
<212> TYPE: DNA
<213> ORGANISM: Artificial sequence
<220> FEATURE:
<221> NAME/KEY: CDS
<222> LOCATION: (1)..(738)
<223> OTHER INFORMATION: Polynucleotide encoding GMCC126 scFv protein

<400> SEQUENCE: 226 cag gtg cag ctg cag gag tcg ggc cca gga ctg gtg aag cct tcg cag       48
Gln Val Gln Leu Gln Glu Ser Gly Pro Gly Leu Val Lys Pro Ser Gln
1               5                   10                  15 acc ctg tcc ctc tcc tgc gct gtt tct ggt ttt tcc gtc acc agt ggt       96
Thr Leu Ser Leu Ser Cys Ala Val Ser Gly Phe Ser Val Thr Ser Gly
            20                  25                  30 cac tac tgg ggc tgg atc cgg cag tcc cca ggg aag ggc ctg gag tgg      144
His Tyr Trp Gly Trp Ile Arg Gln Ser Pro Gly Lys Gly Leu Glu Trp
        35                  40                  45 att gga aat atc tat cat act ggg agc acc agg tac aat ccg tcc ctc      192
Ile Gly Asn Ile Tyr His Thr Gly Ser Thr Arg Tyr Asn Pro Ser Leu
    50                  55                  60 gag agt cga gtc tcc atg tca gta gac acg tcc aag aac cag ttc tcc      240
Glu Ser Arg Val Ser Met Ser Val Asp Thr Ser Lys Asn Gln Phe Ser
65                  70                  75                  80 ctg agg ttg act tct gtg acc gcc gca gac acg gcc atc tat tat tgt      288
Leu Arg Leu Thr Ser Val Thr Ala Ala Asp Thr Ala Ile Tyr Tyr Cys
                85                  90                  95 gcg aga gtg ggc cga ggg cag cat ctg gta cgg ggg gac ttt gac tac      336
Ala Arg Val Gly Arg Gly Gln His Leu Val Arg Gly Asp Phe Asp Tyr
            100                 105                 110
```

```
tgg ggc cga ggc acc ctg gtc acc gtc tcg agt gga ggc ggt gga tca        384
Trp Gly Arg Gly Thr Leu Val Thr Val Ser Ser Gly Gly Gly Gly Ser
            115                 120                 125 ggc gga ggt ggc tct ggc ggt ggc gga agt gca cag tct gtg ctg act        432
Gly Gly Gly Gly Ser Gly Gly Gly Gly Ser Ala Gln Ser Val Leu Thr
        130                 135                 140 cag cca ccc tca ata tcc gtg tcc cca gga cag aca gcc agc atc acc        480
Gln Pro Pro Ser Ile Ser Val Ser Pro Gly Gln Thr Ala Ser Ile Thr
145                 150                 155                 160 tgc tct gga gat gaa ttg ggg cat aag tat gct tcc tgg tat cag cag        528
Cys Ser Gly Asp Glu Leu Gly His Lys Tyr Ala Ser Trp Tyr Gln Gln
                165                 170                 175 aag cca ggc cag tcc cct gtg gtg gtc gtc tat caa gat aac aag cga        576
Lys Pro Gly Gln Ser Pro Val Val Val Val Tyr Gln Asp Asn Lys Arg
            180                 185                 190 ccc tca ggg atc cct gag cga ttc tct ggc tcc agt tct ggg aac aca        624
Pro Ser Gly Ile Pro Glu Arg Phe Ser Gly Ser Ser Ser Gly Asn Thr
        195                 200                 205 gcc act ctg acc atc agc ggg acc cag gct gtg gat gag gct gat tat        672
Ala Thr Leu Thr Ile Ser Gly Thr Gln Ala Val Asp Glu Ala Asp Tyr
    210                 215                 220 ttc tgt cag gcg tgg gac agc agc gct gtg gtc ttc ggc gga ggg acc        720
Phe Cys Gln Ala Trp Asp Ser Ser Ala Val Val Phe Gly Gly Gly Thr
225                 230                 235                 240 aag ctg acc gtc cta ggt                                                738
Lys Leu Thr Val Leu Gly
                245

<210> SEQ ID NO 227
<211> LENGTH: 726
<212> TYPE: DNA
<213> ORGANISM: Artificial sequence
<220> FEATURE:
<221> NAME/KEY: CDS
<222> LOCATION: (1)..(726)
<223> OTHER INFORMATION: Polynucleotide encoding GMCC127 scFv protein

<400> SEQUENCE: 227 cag gtc cag ctg gtg cag tct ggg gga ggt gtg gta cgg cct ggg ggg         48
Gln Val Gln Leu Val Gln Ser Gly Gly Gly Val Val Arg Pro Gly Gly
1               5                   10                  15 tcc ctg aga ctc tcc tgt gca gcc tct gga ttc acc ttt gat gat tat         96
Ser Leu Arg Leu Ser Cys Ala Ala Ser Gly Phe Thr Phe Asp Asp Tyr
            20                  25                  30 ggc atg agc tgg gtc cgc caa gct cca ggg aag ggg ctg gag tgg gtc        144
Gly Met Ser Trp Val Arg Gln Ala Pro Gly Lys Gly Leu Glu Trp Val
        35                  40                  45 tct ggt att aat tgg aat ggt ggt agc aca ggt tat gca gac tct gtg        192
Ser Gly Ile Asn Trp Asn Gly Gly Ser Thr Gly Tyr Ala Asp Ser Val
    50                  55                  60 aag ggc cga ttc acc atc tcc aga gac aac gcc aag aac tcc ctg tat        240
Lys Gly Arg Phe Thr Ile Ser Arg Asp Asn Ala Lys Asn Ser Leu Tyr
65                  70                  75                  80 ctg caa atg aac agt ctg aga gcc gag gac aca gcc gtg tat tac tgt        288
Leu Gln Met Asn Ser Leu Arg Ala Glu Asp Thr Ala Val Tyr Tyr Cys
                85                  90                  95 gca aga agg cgg tat gcg ttg gat tat tgg ggc cgg ggc acc ctg gtc        336
Ala Arg Arg Arg Tyr Ala Leu Asp Tyr Trp Gly Arg Gly Thr Leu Val
            100                 105                 110 acc gtc tcg agt gga ggc ggt tca ggc gga ggt ggc tct ggc ggt             384
Thr Val Ser Ser Gly Gly Gly Gly Ser Gly Gly Gly Gly Ser Gly Gly
        115                 120                 125
```

```
ggc gga agt gca ctt tct tct gag ctg act cag gac cct gct gtg tct    432
Gly Gly Ser Ala Leu Ser Ser Glu Leu Thr Gln Asp Pro Ala Val Ser
        130                 135                 140 gtg gcc ttg gga cag gca gtc agg atc aca tgc caa gga gac agt ctc    480
Val Ala Leu Gly Gln Ala Val Arg Ile Thr Cys Gln Gly Asp Ser Leu
145                 150                 155                 160 aga acc aat tat gca agc tgg tac cag cag agg cca gga cag gcc cct    528
Arg Thr Asn Tyr Ala Ser Trp Tyr Gln Gln Arg Pro Gly Gln Ala Pro
                165                 170                 175 gtt ctt gtc atc cgt ggt aac aac aac cgg ccc tca ggg atc cca gac    576
Val Leu Val Ile Arg Gly Asn Asn Asn Arg Pro Ser Gly Ile Pro Asp
            180                 185                 190 cga ttc tct ggc tcc aac tca gga gac aca gtt tcc ctg acc atc act    624
Arg Phe Ser Gly Ser Asn Ser Gly Asp Thr Val Ser Leu Thr Ile Thr
        195                 200                 205 ggg gct cag gcg gaa gat gag gct gac tat tat tgt aac tcc cgg gac    672
Gly Ala Gln Ala Glu Asp Glu Ala Asp Tyr Tyr Cys Asn Ser Arg Asp
    210                 215                 220 acc agt ggt tac cat tat gtc ttc gga act ggg acc aag ctg acc gtc    720
Thr Ser Gly Tyr His Tyr Val Phe Gly Thr Gly Thr Lys Leu Thr Val
225                 230                 235                 240 cta ggt                                                            726
Leu Gly

<210> SEQ ID NO 228
<211> LENGTH: 738
<212> TYPE: DNA
<213> ORGANISM: Artificial sequence
<220> FEATURE:
<221> NAME/KEY: CDS
<222> LOCATION: (1)..(738)
<223> OTHER INFORMATION: Polynucleotide encoding GMCC129 scFv protein

<400> SEQUENCE: 228 gag gtg cag ctg gtg gag acc ggg gga ggc ttg gca cag ccg ggg ggg    48
Glu Val Gln Leu Val Glu Thr Gly Gly Gly Leu Ala Gln Pro Gly Gly
1               5                   10                  15 tcc ctg aga ctc tcc tgt gaa gcc tct gga ttc acc ttt aat aac tat    96
Ser Leu Arg Leu Ser Cys Glu Ala Ser Gly Phe Thr Phe Asn Asn Tyr
            20                  25                  30 gcc atg agc tgg gtc cgc cag gct cca ggg aag ggg ctg gag tgg gtc    144
Ala Met Ser Trp Val Arg Gln Ala Pro Gly Lys Gly Leu Glu Trp Val
        35                  40                  45 tca ggt att agt att agt ggt tat agt aca ttc tac aca gac tcc gtg    192
Ser Gly Ile Ser Ile Ser Gly Tyr Ser Thr Phe Tyr Thr Asp Ser Val
    50                  55                  60 cag ggc cgg ttc acc atc tcc aga gac aat tcc aag aac acg ctg tat    240
Gln Gly Arg Phe Thr Ile Ser Arg Asp Asn Ser Lys Asn Thr Leu Tyr
65                  70                  75                  80 ttg caa atg aac agc ctg gga gtc gac gac acg gcc gta tat tac tgt    288
Leu Gln Met Asn Ser Leu Gly Val Asp Asp Thr Ala Val Tyr Tyr Cys
                85                  90                  95 gcg aaa cgc cgt gga gag ggc ggc gac ttt gac tac tgg ggc cgg ggc    336
Ala Lys Arg Arg Gly Glu Gly Gly Asp Phe Asp Tyr Trp Gly Arg Gly
            100                 105                 110 aca atg gtc acc gtc tcg agt gga ggc ggc ggt tca ggc gga ggt ggc    384
Thr Met Val Thr Val Ser Ser Gly Gly Gly Gly Ser Gly Gly Gly Gly
        115                 120                 125 tct ggc ggt ggc gga agt gca ctt tct tct gag ctg act cag gac cct    432
Ser Gly Gly Gly Gly Ser Ala Leu Ser Ser Glu Leu Thr Gln Asp Pro
    130                 135                 140
```

```
gct gtg tct gtg gcc ttg ggg cag aca gtc agg atc aca tgc caa gga    480
Ala Val Ser Val Ala Leu Gly Gln Thr Val Arg Ile Thr Cys Gln Gly
145                 150                 155                 160 gac agc ctc aga ggc tat tat gca agc tgg tac caa cag aag gca gga    528
Asp Ser Leu Arg Gly Tyr Tyr Ala Ser Trp Tyr Gln Gln Lys Ala Gly
                165                 170                 175 cag gcc cct gta ctt gtc atc tat ggt aag aac aac cgg ccc tca ggg    576
Gln Ala Pro Val Leu Val Ile Tyr Gly Lys Asn Asn Arg Pro Ser Gly
            180                 185                 190 atc cca gac cga ttc tct ggc tcc agc tca gga aac aca gct tcc ttg    624
Ile Pro Asp Arg Phe Ser Gly Ser Ser Ser Gly Asn Thr Ala Ser Leu
        195                 200                 205 acc atc act ggg gct cag gcg gaa gat gag gct gac tat tac tgt tac    672
Thr Ile Thr Gly Ala Gln Ala Glu Asp Glu Ala Asp Tyr Tyr Cys Tyr
    210                 215                 220 tcc cgg gac aga agt ggt aac cat cta gga atg ttc ggc gga ggg acc    720
Ser Arg Asp Arg Ser Gly Asn His Leu Gly Met Phe Gly Gly Gly Thr
225                 230                 235                 240 aag gtc acc gtc cta ggt                                            738
Lys Val Thr Val Leu Gly
                245

<210> SEQ ID NO 229
<211> LENGTH: 744
<212> TYPE: DNA
<213> ORGANISM: Artificial sequence
<220> FEATURE:
<221> NAME/KEY: CDS
<222> LOCATION: (1)..(744)
<223> OTHER INFORMATION: Polynucleotide encoding GMCC131 scFv protein

<400> SEQUENCE: 229 cag gtg cag ctg cag gag tcc ggc cca gga ctg gtg aag cct tcg gag     48
Gln Val Gln Leu Gln Glu Ser Gly Pro Gly Leu Val Lys Pro Ser Glu
1               5                   10                  15 acc ctg tcc ctc acc tgc agt gtc tct ggt ggc tcc atc aga agt cat     96
Thr Leu Ser Leu Thr Cys Ser Val Ser Gly Gly Ser Ile Arg Ser His
            20                  25                  30 tac tgg agt tgg atg cgg caa ccc cca ggg aag gga ctg gag tgg att    144
Tyr Trp Ser Trp Met Arg Gln Pro Pro Gly Lys Gly Leu Glu Trp Ile
        35                  40                  45 gga tac gtc tat tac act ggg agt acc aac tac aat ccg tcc ctc aag    192
Gly Tyr Val Tyr Tyr Thr Gly Ser Thr Asn Tyr Asn Pro Ser Leu Lys
    50                  55                  60 agt cga gtc acc atg tca gta gac acg tcc aag aac cag ttc tcg ctg    240
Ser Arg Val Thr Met Ser Val Asp Thr Ser Lys Asn Gln Phe Ser Leu
65                  70                  75                  80 aac ctg agc tct gtg acc gct gcg gac acg gcc att tat tac tgt gcg    288
Asn Leu Ser Ser Val Thr Ala Ala Asp Thr Ala Ile Tyr Tyr Cys Ala
                85                  90                  95 aga ttc cca tat agc agt ggc tcg aac ccg ctt gac tac tgg ggc cgg    336
Arg Phe Pro Tyr Ser Ser Gly Ser Asn Pro Leu Asp Tyr Trp Gly Arg
            100                 105                 110 gga acc ctg gtc acc gtc tcg agt gga ggc ggc ggt tca ggc gga ggt    384
Gly Thr Leu Val Thr Val Ser Ser Gly Gly Gly Gly Ser Gly Gly Gly
        115                 120                 125 ggc tct ggc ggt ggc gga agt gca cag tct gtg ctg acg cag ccg ccc    432
Gly Ser Gly Gly Gly Gly Ser Ala Gln Ser Val Leu Thr Gln Pro Pro
    130                 135                 140 tca gtg tct gcg gcc cca gga cag agg gtc acc atc tcc tgc act ggg    480
Ser Val Ser Ala Ala Pro Gly Gln Arg Val Thr Ile Ser Cys Thr Gly
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     | 145 |     |     |     | 150 |     |     |     | 155 |     |     |     | 160 |     |     |

```
agc agc tcc aac atc ggg gca cgt tat gat gta cac tgg tac cag cac     528
Ser Ser Ser Asn Ile Gly Ala Arg Tyr Asp Val His Trp Tyr Gln His
            165             170             175 ctg cca gga acc gcc ccc aaa ctc ctc atc tac ggt gac agc aat cga     576
Leu Pro Gly Thr Ala Pro Lys Leu Leu Ile Tyr Gly Asp Ser Asn Arg
        180             185             190 ccc tca ggg gtc cct gac cga ttc tct ggt tcc aag tct ggc acc tca     624
Pro Ser Gly Val Pro Asp Arg Phe Ser Gly Ser Lys Ser Gly Thr Ser
    195             200             205 gcc tcc ctg gcc atc act ggg ctc cag cct gag gat gag gct gat tat     672
Ala Ser Leu Ala Ile Thr Gly Leu Gln Pro Glu Asp Glu Ala Asp Tyr
210             215             220 tac tgc cag tcc tat gac agc agc ctg agt ggt gtg gta ttc ggc gga     720
Tyr Cys Gln Ser Tyr Asp Ser Ser Leu Ser Gly Val Val Phe Gly Gly
225             230             235             240 ggg acc aag gtc acc gtc cta ggt                                     744
Gly Thr Lys Val Thr Val Leu Gly
            245

<210> SEQ ID NO 230
<211> LENGTH: 735
<212> TYPE: DNA
<213> ORGANISM: Artificial sequence
<220> FEATURE:
<221> NAME/KEY: CDS
<222> LOCATION: (1)..(735)
<223> OTHER INFORMATION: Polynucleotide encoding GMCC136 scFv protein

<400> SEQUENCE: 230 gaa gtg cag ctg gtg cag tct ggg gga ggc ttg gta cag cct ggg ggg     48
Glu Val Gln Leu Val Gln Ser Gly Gly Gly Leu Val Gln Pro Gly Gly
1               5                   10                  15 tcc ctg aga ctc tcc tgt gca gcc tct gga ttc acc ttt agc agc tat     96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctt gag tgg gtc    144
Ala Met Ser Trp Val Arg Gln Ala Pro Gly Lys Gly Leu Glu Trp Val
        35                  40                  45 tca gct att agt ggt agt ggt ggt agc aca tac tcc gcc gac tcc gtg    192
Ser Ala Ile Ser Gly Ser Gly Gly Ser Thr Tyr Ser Ala Asp Ser Val
    50                  55                  60 aag ggc cgg ttc acc atc tcc aga gac aat tcc aag aac acg ctg tat    240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt    288
Leu Gln Met Asn Ser Leu Arg Ala Glu Asp Thr Ala Val Tyr Tyr Cys
                85                  90                  95 gcg aaa tgc tgg cgt agt ggt acc agc tgc ccg gac ggc tgg ggc aaa    336
Ala Lys Cys Trp Arg Ser Gly Thr Ser Cys Pro Asp Gly Trp Gly Lys
            100                 105                 110 ggg aca atg gtc acc gtc tcg agt gga ggc ggc ggt tca ggc gga ggt    384
Gly Thr Met Val Thr Val Ser Ser Gly Gly Gly Gly Ser Gly Gly Gly
        115                 120                 125 ggc tct ggc ggt ggc gga agt gca ctt gaa att gtg ttg acg cag tct    432
Gly Ser Gly Gly Gly Gly Ser Ala Leu Glu Ile Val Leu Thr Gln Ser
    130                 135                 140 cca gcc acc ctg tct gtg tct cca ggg gaa aga gcc acc ctc tcc tgc    480
Pro Ala Thr Leu Ser Val Ser Pro Gly Glu Arg Ala Thr Leu Ser Cys
145                 150                 155                 160 agg acc agt cag agt gtt ggc agc aag tta gcc tgg tac cag cag aaa    528
```

```
                                                         -continued

Arg Thr Ser Gln Ser Val Gly Ser Lys Leu Ala Trp Tyr Gln Gln Lys
            165                 170                 175 cct ggc cag gct ccc agg ctc ctc atc tat gat gca tcc acc ggg gcc          576
Pro Gly Gln Ala Pro Arg Leu Leu Ile Tyr Asp Ala Ser Thr Gly Ala
                180                 185                 190 act ggt gac cca gcc agg ttc agt ggc agt ggg tct ggg aca gag ttc          624
Thr Gly Asp Pro Ala Arg Phe Ser Gly Ser Gly Ser Gly Thr Glu Phe
                195                 200                 205 act ctc acc atc agc aac ctg cag tct gaa gat ctt gca att tat tac          672
Thr Leu Thr Ile Ser Asn Leu Gln Ser Glu Asp Leu Ala Ile Tyr Tyr
            210                 215                 220 tgt cag cag tat cat aag tgg ccg atc acc ttc ggc caa ggg aca cga          720
Cys Gln Gln Tyr His Lys Trp Pro Ile Thr Phe Gly Gln Gly Thr Arg
225                 230                 235                 240 ctg gag att aaa cgt                                                      735
Leu Glu Ile Lys Arg
                245

<210> SEQ ID NO 231
<211> LENGTH: 744
<212> TYPE: DNA
<213> ORGANISM: Artificial sequence
<220> FEATURE:
<221> NAME/KEY: CDS
<222> LOCATION: (1)..(744)
<223> OTHER INFORMATION: Polynucleotide encoding GMCC138 scFv protein

<400> SEQUENCE: 231 gag gtg cag ctg gtg gag acc ggc cca gga ctg gtg aag ccc tca cag           48
Glu Val Gln Leu Val Glu Thr Gly Pro Gly Leu Val Lys Pro Ser Gln
1               5                   10                  15 acc cta tcc ctc acc tgc act gtg tct ggt ggc tcc atc agc agt ggt           96
Thr Leu Ser Leu Thr Cys Thr Val Ser Gly Gly Ser Ile Ser Ser Gly
                20                  25                  30 ggt tat tac tgg agc tgg atc cgc cag gtc cca ggg aag ggc ctg gag          144
Gly Tyr Tyr Trp Ser Trp Ile Arg Gln Val Pro Gly Lys Gly Leu Glu
            35                  40                  45 tgg att ggg tac aac ttt tac aat ggg agc acg tac ttc aac ccg tcc          192
Trp Ile Gly Tyr Asn Phe Tyr Asn Gly Ser Thr Tyr Phe Asn Pro Ser
        50                  55                  60 ctc aag agt cga gct acc ata tca att gac acg act aag aac cag ttc          240
Leu Lys Ser Arg Ala Thr Ile Ser Ile Asp Thr Thr Lys Asn Gln Phe
65                  70                  75                  80 tcc ctg aag ttg agc tct gtg acc gcc gcg gac acg gcc gtc tat tat          288
Ser Leu Lys Leu Ser Ser Val Thr Ala Ala Asp Thr Ala Val Tyr Tyr
                85                  90                  95 tgt gcg agg ggt aat gga tat agg tat ggt cgg tgg ttc gac ccc tgg          336
Cys Ala Arg Gly Asn Gly Tyr Arg Tyr Gly Arg Trp Phe Asp Pro Trp
                100                 105                 110 ggc agg ggc acc ctg gtc acc gtc tcg agt gga ggc ggt tca ggc                384
Gly Arg Gly Thr Leu Val Thr Val Ser Ser Gly Gly Gly Ser Gly
            115                 120                 125 gga ggt ggc tct ggc ggt ggc gga agt gca ctt tcc tat gag ctg act          432
Gly Gly Gly Ser Gly Gly Gly Gly Ser Ala Leu Ser Tyr Glu Leu Thr
        130                 135                 140 cag cca ccc tcg gtg tca gtg tcc cca gga cag acg gcc agg atc acc          480
Gln Pro Pro Ser Val Ser Val Ser Pro Gly Gln Thr Ala Arg Ile Thr
145                 150                 155                 160 tgc tct gga gat gca ttg cca aag caa tat gct tat tgg tac cag cag          528
Cys Ser Gly Asp Ala Leu Pro Lys Gln Tyr Ala Tyr Trp Tyr Gln Gln
                165                 170                 175
```

```
aag cca ggc cag gcc cct gtg ctg gtg ata tct aaa gac agt gag agg    576
Lys Pro Gly Gln Ala Pro Val Leu Val Ile Ser Lys Asp Ser Glu Arg
        180                 185                 190 ccc tca ggg atc cct gag cga ttc tct ggc tcc agc tca ggg aca aca    624
Pro Ser Gly Ile Pro Glu Arg Phe Ser Gly Ser Ser Ser Gly Thr Thr
    195                 200                 205 gtc acg ttg acc atc agt gga gtc cag gca gaa gac gag gct gac tat    672
Val Thr Leu Thr Ile Ser Gly Val Gln Ala Glu Asp Glu Ala Asp Tyr
210                 215                 220 tac tgt caa tca gca gac agc agt ggt act tat tgg gtg ttc ggc gga    720
Tyr Cys Gln Ser Ala Asp Ser Ser Gly Thr Tyr Trp Val Phe Gly Gly
225                 230                 235                 240 ggg acc aag gtc acc gtc cta ggt                                    744
Gly Thr Lys Val Thr Val Leu Gly
                245

<210> SEQ ID NO 232
<211> LENGTH: 738
<212> TYPE: DNA
<213> ORGANISM: Artificial sequence
<220> FEATURE:
<221> NAME/KEY: CDS
<222> LOCATION: (1)..(738)
<223> OTHER INFORMATION: Polynucleotide encoding GMCC142 scFv protein

<400> SEQUENCE: 232 gag gtc cag ctg gtg cag tct gga gct gag gtg aag aag cct ggg gcc     48
Glu Val Gln Leu Val Gln Ser Gly Ala Glu Val Lys Lys Pro Gly Ala
1               5                   10                  15 tca gtg act att tcc tgc aag gca tct gga tac acc ttc acc gcc tac     96
Ser Val Thr Ile Ser Cys Lys Ala Ser Gly Tyr Thr Phe Thr Ala Tyr
            20                  25                  30 tat ata tac tgg gtg cga cag gcc cct gga caa ggg ctt gag tgg atg    144
Tyr Ile Tyr Trp Val Arg Gln Ala Pro Gly Gln Gly Leu Glu Trp Met
        35                  40                  45 gga atg agc aac cct aat ggt ggt tac aca gtg tac cca ccg aat ttc    192
Gly Met Ser Asn Pro Asn Gly Gly Tyr Thr Val Tyr Pro Pro Asn Phe
    50                  55                  60 ctg ggc aga gtc acc acg acc ccg gac acg tca acg aac aca ata tat    240
Leu Gly Arg Val Thr Thr Thr Pro Asp Thr Ser Thr Asn Thr Ile Tyr
65                  70                  75                  80 atg gag ctg aga agc ctg aga tct gaa gac acg gcc gtg tat tac tgt    288
Met Glu Leu Arg Ser Leu Arg Ser Glu Asp Thr Ala Val Tyr Tyr Cys
                85                  90                  95 gcg aga ggt cgg ggg cgg gcc ccc agc aat gct ttt gac ttc tgg ggc    336
Ala Arg Gly Arg Gly Arg Ala Pro Ser Asn Ala Phe Asp Phe Trp Gly
            100                 105                 110 cga gga acc ctg gtc acc gtc tcg agt gga ggc ggc ggt tca ggc gga    384
Arg Gly Thr Leu Val Thr Val Ser Ser Gly Gly Gly Gly Ser Gly Gly
        115                 120                 125 ggt ggc tct ggc ggt ggc gga agt gca ctt tct tct gag ctg act cag    432
Gly Gly Ser Gly Gly Gly Gly Ser Ala Leu Ser Ser Glu Leu Thr Gln
    130                 135                 140 gac cct gct gtg tct gtg gcc ttg gga cag aca gtc agg atc aca tgc    480
Asp Pro Ala Val Ser Val Ala Leu Gly Gln Thr Val Arg Ile Thr Cys
145                 150                 155                 160 caa gga gac agc ctc aaa ttc tat tat gca agc tgg tat caa cag aag    528
Gln Gly Asp Ser Leu Lys Phe Tyr Tyr Ala Ser Trp Tyr Gln Gln Lys
                165                 170                 175 cca gga cag gcc cct gta ctt gtc ctc cat ggt aaa aat aac cgg ccc    576
Pro Gly Gln Ala Pro Val Leu Val Leu His Gly Lys Asn Asn Arg Pro
            180                 185                 190
```

-continued

```
tca ggg atc cca gac cga ttc tct ggc tcc acc tca aga gac aca gct      624
Ser Gly Ile Pro Asp Arg Phe Ser Gly Ser Thr Ser Arg Asp Thr Ala
        195                 200                 205 tcc ttg acc atc act ggg act cag gcg gaa gat gag gct gac tat tac      672
Ser Leu Thr Ile Thr Gly Thr Gln Ala Glu Asp Glu Ala Asp Tyr Tyr
    210                 215                 220 tgt aac tcc cgg gac aac agt gac aac att gtc ttc gga act ggg acc      720
Cys Asn Ser Arg Asp Asn Ser Asp Asn Ile Val Phe Gly Thr Gly Thr
225                 230                 235                 240 aag ctg acc gtc cta ggt                                              738
Lys Leu Thr Val Leu Gly
                245

<210> SEQ ID NO 233
<211> LENGTH: 750
<212> TYPE: DNA
<213> ORGANISM: Artificial sequence
<220> FEATURE:
<221> NAME/KEY: CDS
<222> LOCATION: (1)..(750)
<223> OTHER INFORMATION: Polynucleotide encoding GMCC151 scFv protein
<220> FEATURE:
<221> NAME/KEY: misc_feature
<222> LOCATION: (601)
<223> OTHER INFORMATION: n equals a,t,g, or c

<400> SEQUENCE: 233 cag gtc cag ctg gtg cag tct ggg gga gga gtg gtc cag cct ggg agg       48
Gln Val Gln Leu Val Gln Ser Gly Gly Gly Val Val Gln Pro Gly Arg
1               5                   10                  15 tcc ctg aga ctc tcc tgc aca gcc tct gga ttc aac ctc ggt tcc cat       96
Ser Leu Arg Leu Ser Cys Thr Ala Ser Gly Phe Asn Leu Gly Ser His
            20                  25                  30 ggc atg cac tgg gtc cgc cag gct ccc ggc aag ggg ctg gag tgg gtg      144
Gly Met His Trp Val Arg Gln Ala Pro Gly Lys Gly Leu Glu Trp Val
        35                  40                  45 gca gtt ata gga ttt gat gga acg act aaa tat tat gtg gac tcc gtg      192
Ala Val Ile Gly Phe Asp Gly Thr Thr Lys Tyr Tyr Val Asp Ser Val
    50                  55                  60 aag ggc cga ttc acc atc tcc agg gac aac tcc agg aac acc cta tct      240
Lys Gly Arg Phe Thr Ile Ser Arg Asp Asn Ser Arg Asn Thr Leu Ser
65                  70                  75                  80 ctg caa atg aac agc ctg aga gct gag gac acg gct gtc tat tac tgt      288
Leu Gln Met Asn Ser Leu Arg Ala Glu Asp Thr Ala Val Tyr Tyr Cys
                85                  90                  95 gtg aga gaa gat tac tac tat gat agt agt ggt tat tac ttt gac tac      336
Val Arg Glu Asp Tyr Tyr Tyr Asp Ser Ser Gly Tyr Tyr Phe Asp Tyr
            100                 105                 110 tgg ggc cga gga acc ctg gtc acc gtc tcg agt gga ggc ggt tca          384
Trp Gly Arg Gly Thr Leu Val Thr Val Ser Ser Gly Gly Gly Ser
        115                 120                 125 ggc gga ggt ggc tct ggc ggt ggc gga agt gca ctt tct tct gag ctg      432
Gly Gly Gly Gly Ser Gly Gly Gly Gly Ser Ala Leu Ser Ser Glu Leu
    130                 135                 140 act cag gac cct ttc gtg tct gtt gcc ttg gga cag aca gtc agg atc      480
Thr Gln Asp Pro Phe Val Ser Val Ala Leu Gly Gln Thr Val Arg Ile
145                 150                 155                 160 gca tgc cga gga gac agc ctc aga gat tct tat gca agt tgg tac cag      528
Ala Cys Arg Gly Asp Ser Leu Arg Asp Ser Tyr Ala Ser Trp Tyr Gln
                165                 170                 175 cag aag cca gga cag gcc cct cga ctt ctc gtc tat gga aac aat ctt      576
Gln Lys Pro Gly Gln Ala Pro Arg Leu Leu Val Tyr Gly Asn Asn Leu
```

-continued

```
                       180                 185                 190
cgg ccc tcc ggg atc cct ggc cgg ntc tct ggc ttc agc tca gga gac      624
Arg Pro Ser Gly Ile Pro Gly Arg Xaa Ser Gly Phe Ser Ser Gly Asp
        195                 200                 205 acc agt tcc ctg gcc atc act gag act cag gcg gga gat gag gct gac      672
Thr Ser Ser Leu Ala Ile Thr Glu Thr Gln Ala Gly Asp Glu Ala Asp
        210                 215                 220 tat tac tgc agt tcc cgg ggc aac agt acc tct cgc ctc tat gtc ttc      720
Tyr Tyr Cys Ser Ser Arg Gly Asn Ser Thr Ser Arg Leu Tyr Val Phe
225                 230                 235                 240 gga act ggg acc aag ctg acc gtc cta ggt                              750
Gly Thr Gly Thr Lys Leu Thr Val Leu Gly
                    245                 250
```

<210> SEQ ID NO 234
<211> LENGTH: 250
<212> TYPE: PRT
<213> ORGANISM: homo sapiens

<400> SEQUENCE: 234

```
Met Pro Ala Ser Ser Pro Phe Leu Leu Ala Pro Lys Gly Pro Pro Gly
1               5                   10                  15
Asn Met Gly Gly Pro Val Arg Glu Pro Ala Leu Ser Val Ala Leu Trp
            20                  25                  30
Leu Ser Trp Gly Ala Ala Leu Gly Ala Val Ala Cys Ala Met Ala Leu
        35                  40                  45
Leu Thr Gln Gln Thr Glu Leu Gln Ser Leu Arg Arg Glu Val Ser Arg
    50                  55                  60
Leu Gln Gly Thr Gly Gly Pro Ser Gln Asn Gly Glu Gly Tyr Pro Trp
65                  70                  75                  80
Gln Ser Leu Pro Glu Gln Ser Ser Asp Ala Leu Glu Ala Trp Glu Asn
                85                  90                  95
Gly Glu Arg Ser Arg Lys Arg Ala Val Leu Thr Gln Lys Gln Lys
                100                 105                 110
Lys Gln His Ser Val Leu His Leu Val Pro Ile Asn Ala Thr Ser Lys
            115                 120                 125
Asp Asp Ser Asp Val Thr Glu Val Met Trp Gln Pro Ala Leu Arg Arg
        130                 135                 140
Gly Arg Gly Leu Gln Ala Gln Gly Tyr Gly Val Arg Ile Gln Asp Ala
145                 150                 155                 160
Gly Val Tyr Leu Leu Tyr Ser Gln Val Leu Phe Gln Asp Val Thr Phe
                165                 170                 175
Thr Met Gly Gln Val Val Ser Arg Glu Gly Gln Gly Arg Gln Glu Thr
            180                 185                 190
Leu Phe Arg Cys Ile Arg Ser Met Pro Ser His Pro Asp Arg Ala Tyr
        195                 200                 205
Asn Ser Cys Tyr Ser Ala Gly Val Phe His Leu His Gln Gly Asp Ile
    210                 215                 220
Leu Ser Val Ile Ile Pro Arg Ala Arg Ala Lys Leu Asn Leu Ser Pro
225                 230                 235                 240
His Gly Thr Phe Leu Gly Phe Val Lys Leu
                245                 250
```